(12) United States Patent
Bruno

(10) Patent No.: US 9,562,900 B2
(45) Date of Patent: Feb. 7, 2017

(54) METHODS AND COMPOSITIONS OF NUCLEIC ACID LIGANDS FOR DETECTION OF FOODBORNE AND WATERBORNE PATHOGENS

(75) Inventor: John G. Bruno, Boerne, TX (US)

(73) Assignee: OTC Biotechnologies, LLC, San Antonio, TX (US)

( * ) Notice: Subject to any disclaimer, the term of this patent is extended or adjusted under 35 U.S.C. 154(b) by 458 days.

(21) Appl. No.: 13/136,820

(22) Filed: Aug. 11, 2011

(65) Prior Publication Data

US 2012/0071639 A1    Mar. 22, 2012
US 2016/0258948 A9    Sep. 8, 2016

Related U.S. Application Data

(63) Continuation-in-part of application No. 12/378,515, filed on Feb. 17, 2009, now abandoned.

(60) Provisional application No. 61/372,649, filed on Aug. 23, 2010, provisional application No. 61/066,506, filed on Feb. 21, 2008, provisional application No. 61/132,147, filed on Jun. 16, 2008.

(51) Int. Cl.
*C07H 21/04* (2006.01)
*G01N 33/569* (2006.01)
*C12N 15/115* (2010.01)
*C12Q 1/68* (2006.01)

(52) U.S. Cl.
CPC ....... *G01N 33/56916* (2013.01); *C12N 15/115* (2013.01); *C12Q 1/689* (2013.01); *G01N 33/56922* (2013.01); *C12N 2310/16* (2013.01)

(58) Field of Classification Search
None
See application file for complete search history.

(56) References Cited

U.S. PATENT DOCUMENTS

2012/0123096 A1 *   5/2012   Bruno et al. .............. 530/363

\* cited by examiner

*Primary Examiner* — Robert A Zeman
(74) *Attorney, Agent, or Firm* — William H. Quirk; Jesse L. Frizzell; Rosenthal Pauerstein Sandoloski Agather LLP

(57) ABSTRACT

Specific DNA sequences for binding various foodborne and waterborne pathogens and biotoxins are described. Each of these sequences can function in varying assay and sensor formats with varying degrees of success.

4 Claims, 5 Drawing Sheets

METHODS AND COMPOSITIONS OF NUCLEIC ACID LIGANDS FOR DETECTION OF FOODBORNE AND WATERBORNE PATHOGENS

PRIORITY INFORMATION

This application is a continuation-in-part and claims the benefit of prior filed Non-Provisional U.S. patent application Ser. No. 12/378,515, filed Feb. 17, 2009, which claims the benefit of U.S. Provisional Application No. 61/132,147, filed on Jun. 16, 2008, and U.S. Provisional Application No. 61/066,506, filed on Feb. 21, 2008, and the present application also claims the benefit of its U.S. Provisional Application Ser. No. 61/372,649, filed on Aug. 23, 2010. By this reference, the full disclosures, including the claims and drawings, of U.S. patent application Ser. No. 12/378,515, as well as U.S. Provisional Application Nos. 61/372,649, 61/132,147, and 61/066,506, are incorporated herein as though now set forth in their entirety.

BACKGROUND OF THE INVENTION

Field of the Invention

The present invention pertains to the field of aptamer- and nucleic acid ligand (DNA and RNA ligand)-based diagnostics. More particularly, it relates to single-stranded Deoxyribonucleic acid ("DNA") and Ribonucleic acid ("RNA") ligand sequences, whether individual or linked together to form longer multiple binding site "receptors," that specifically target and bind to foodborne and waterborne pathogenic bacteria or parasites such as *Campylobacter jejuni*, pathogenic *Escherichia coli*, *Listeria monocytogenes*, *Salmonella enterica* serovar *Typhimurium* (formerly *S. typhimurium*), molds or other pathogenic fungi, *Cryptosporidium* and *Giardia* parasites and related toxins produced by some bacteria (e.g., Shiga or Vero toxins) and other virulence factors (intimins, adhesions, capsules, etc.) indicating the presence of the pathogens.

These individual or linked DNA ligand (aptamer) sequences represent valuable target analyte-responsive components of diagnostic devices or biosensors. A biosensor can be defined as any device that employs a biologically-derived molecule as the sensing component and transduces a target analyte binding event into a detectable physical signal (including, but not limited to, changes in light intensity, absorbance, emission, wavelength, color, electrical conduction, electrical resistance, or other electrical properties, etc). Once bonded with the target, these DNA ligand sequences can be used to qualitatively determine the presence of target analyte, as well as to quantify the target analyte amount, in a sample using a broad variety of assay types and diagnostic or sensor platforms including, but not limited to, affinity-based lateral flow test strips, membrane blotting, surface plasmon resonance ("SPR"), magnetic bead ("MB")-based capture, plastic-adherent sandwich assays ("PASA"), chemiluminescence ("CL"), electrochemiluminescence ("ECL"), radioisotopic, fluorescence intensity, including quantum dot ("QD") or other fluorescent nanoparticle ("FNP") of dye-based, fluorescence lifetime, and fluorescence polarization ("FP") assays or enzyme-linked (ELISA-like) microplate assays. ELISA-like assays refer to microwell or microplate assays similar to traditional "Enzyme-Linked Immunosorbent Assays" or "ELISA" in which an aptamer or nucleic acid ligand is substituted for the antibody component or components, but the other components such as peroxidase or alkaline phosphatase enzymes and color-producing substrates remain the same.

In addition, these DNA ligand sequences are valuable in competitive displacement assays which are not solely dependent on high affinity (strong attractive forces between a receptor and its ligand) or high avidity (high tensile or physical strength of receptor-ligand bonds) to produce sensitive detection (sub-nanoMolar or sub-nanogram levels), because the equilibrium constant (generally $K_a = 10^6$ to $10^8$ to enable competition) must allow reasonable displacement of previously bound target materials to detect a change at or below nanogram or nanoMolar levels. In a competitive displacement assay, labeled DNA ligand plus labeled analyte complexes compete with unlabeled analyte to bind with the labeled DNA. After allowing the labeled and unlabeled analytes to come to equilibrium with the labeled DNA, the unlabeled target analyte may be quantitatively assayed by fluorescence intensity or other methods. Such assays would include competitive displacement fluorescence resonance energy transfer ("FRET") assays or DNA ligand "beacon" FRET assays. Each of these types of assays and detection platforms has different applications in either central laboratories or as portable detectors to identify tainted foods and water either in the field (e.g. on farms or in water supplies) or in the food processing chain progressing toward the human or animal consumer.

Background Information

The DNA ligand sequences listed in Table 1 herein were derived by iterative cycles of affinity-based selection, washing, heated elution, and polymerase chain reaction ("PCR") amplification of bound DNA ligands from a randomized library using immobilized target analytes for affinity selection and PCR amplification followed by cloning and Sanger dideoxynucleotide DNA sequencing. Sanger dideoxynucleotide sequencing refers to DNA chain termination due to lack of a 3'-OH to link incoming bases with during DNA synthesis followed by automated fluorescence reading of the DNA sequence from an electrophoresis gel containing all of the terminated DNA fragments. DNA sequencing may be accomplished by PCR doped with dideoxynucleotides lacking hydroxyl groups at the 2' and 3' sugar ring positions and thereby disallowing chain formation. PCR refers to the enzymatic amplification or copying of DNA molecules with a thermo-stable DNA polymerase such as *Thermus aquaticus* polymerase ("Taq") with known "primer" regions or short oligonucleotides of known sequence that can hybridize to a longer target DNA sequence to enable priming of the chain reaction (exponential doubling of the DNA target copy number with each round of amplification). A randomized library can be chemically synthesized by linking together the four deoxynucleotide triphosphate bases (adenine; A, cytosine; C, guanine; G, and thymine; T) in equal amounts (25% each), so that a combinatorial oligonucleotide arises with sequence diversity equal to 4 raised to the nth power ($4^n$) where n is the desired length of the randomized region in bases. In other words, if position 1 in an oligonucleotide is allowed to consist of A, C, G, or T (diversity=4) by equal availability of all 4 bases and these 4 possibilities are multiplied by each base linking to 4 more possible bases at position 2, then this process yields 16 possible 2-base oligonucleotides (i.e., AA, AC, AG, AT, CA, CC, CG, CT, GA, GC, GG, GT, TA, TC, TG, TT) and so on for the entire chosen length (n) of the randomized region. This combinatorial progression displays immense diversity as a function of oligonucleotide chain length. For example, an oligonucleotide decamer of 10 base length could be expected to contain $4^n=4^{10}$ or 1,048,576 unique DNA sequences from which to chose or select by affinity one or more sequences that bind a given immobilized target analyte. The randomized oligonucleotide or DNA is designed to be flanked on either side by short primer regions of known and fixed sequences to enable PCR amplification (exponential copying) of the rare sequences that are selected from the random library by binding to the target after the non-binding members of the random library are washed away (not selected).

Additional assays, such as ELISA-like plate assays or fluorescence (intensity and FRET) assays, may be used to screen or verify the value of particular DNA and RNA ligands or aptamer sequences for detection of a given target analyte in a given assay format or type of biosensor. Some of the sequences operate (bind and transduce the binding signal) more effectively in affinity-based (ELISA-like or fluorescence intensity) assays, while other DNA ligand sequences against the same targets function better in competitive or other assays, thereby leading to more sensitive detection with lower limits of detection (sub-nanoMolar or sub-nanogram) and less cross-reactivity or more specificity for the target analyte. Specificity means the ability to selectively exclude molecules similar in structure to the true target analyte that may interfere with the assay and give false readings. All of the listed DNA ligand nucleotide sequences have potential applications in some type of assay format, because they have survived at least 5 rounds of affinity-based selection and enrichment (by PCR amplification), although some of the sequences will undoubtedly perform better in certain assay formats or configurations (in tubes, square cuvettes, membranes, or on biochips) than others.

Combinations of the DNA ligands whether in whole or in part (i.e., their binding sites of 5-10 or more nucleotides or bases) could be linked together in a linear or 2-dimensional or 3-dimensional fashion similar to dendrimers to bind multiple epitopes or binding sites on a complex target analyte (Ag or antigen). The advantage of linking aptamers or their shorter binding pockets, loops or binding sites is that the nascent linear, 2-D or 3-D aptamer construct will likely have improved affinity or "avidity" (tensile binding strength) making it more difficult to remove or dissociate from the target antigen. The linked aptamer complex will be likely to gain specificity as well since the probability of binding to multiple epitopes with any degree of success is multiplicative. Thus, the ability to bind to epitopes A, B and C equals the product of the probability of binding to A with high affinity times the probability of binding to B with high affinity times the probability of binding to C with high affinity and that probability is clearly much less than binding to only A, B, or C or any combination of the two epitopes therein. In this way, the specificity of aptamers or DNA ligands can be increased. This approach to binding site linkage emulates that of nature in that antibodies demonstrate linkage of their "hypervariable" (HV) regions on the antigen combining sites of the immunoglobulin light and heavy chains. In the HV regions, the variability of the 20 amino acid types is quite high and essentially represents a selection of one combination from a large combinatorial library in the protein realm. The trait of HV region linkage contributes to antibody affinity, avidity and specificity. Similarly, linking aptamers or aptamer binding sites for various epitopes in one, two or three dimensions will enhance larger aptamer or DNA ligand construct affinity, avidity, and selectivity or specificity.

All of the listed DNA ligand nucleotide sequences have potential utility in some assay format, although some of the candidate sequences will perform better in certain assay formats or configurations (in tubes, cuvettes, membranes, or on biochips) than others. Assays such as ELISA-like plate assays or fluorescence (intensity and FRET) assays, may be used to verify the utility of the DNA ligand sequences. Some of the sequences function more effectively in affinity-based (ELISA-like or fluorescence intensity) assays, while other DNA ligand sequences against the same bacterial targets or analytes function better in competitive FRET assays.

SUMMARY OF THE INVENTION

The present invention provides specific DNA sequence information as shown in Table 1 for nucleic acid ligands selected from randomized pools to bind targeted foodborne and waterborne pathogenic bacteria and toxins, which can be put into a composition useful in a variety of assay formats and sensor or diagnostic platforms to detect or quantify the targeted bacteria or toxin. While all of the candidate sequences have been shown to bind their cognate targets, some are shown to function more effectively in affinity-based assays versus fluorescence resonance energy transfer (FRET) or other assay formats that rely more on physical parameters other than affinity such as fluorophore-quencher proximity (i.e., the Förster distance). Therefore, all of the sequences are potentially valuable for detection or quantitative assays, but some may function better than others in particular assay formats.

DETAILED DESCRIPTION OF THE PREFERRED EMBODIMENTS

Figure 1:
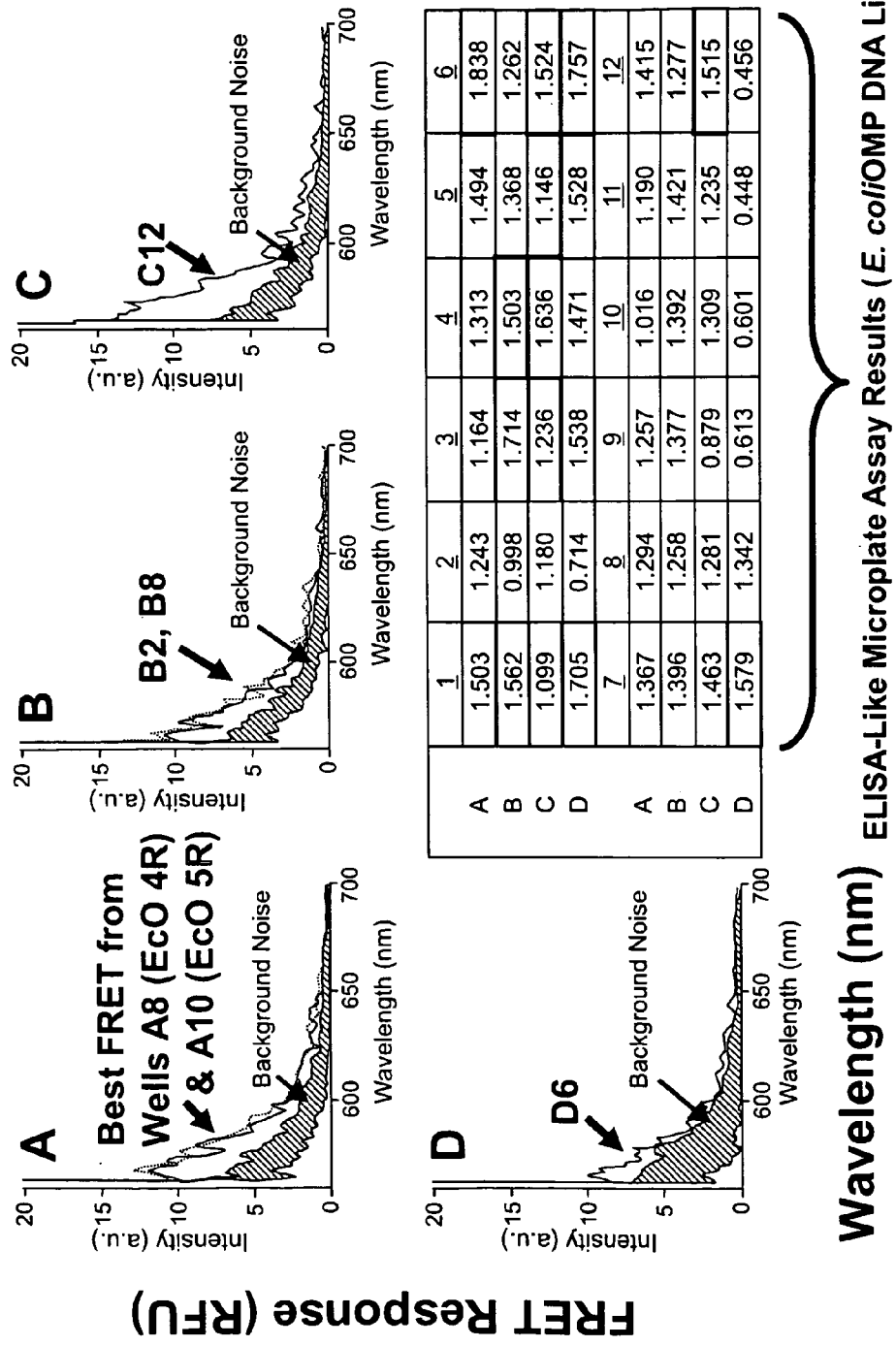
FIG. 1 is a graph and table comparing the FRET responses of specific DNA ligands.

There is no single preferred embodiment for use of the DNA aptamer ligand sequences or linked aptamer constructs identified herein. Rather, the sequences are useful to varying extents in a variety of assay formats and sensors or diagnostic devices chosen from at least the following list: lateral flow test strips, ELISA-like or enzyme-linked microplate assays, magnetic bead-based capture assays, ECL or other chemiluminescence assays, radioisotopic assays and a variety of fluorescence assays including, but not limited to, fluorescence intensity, fluorescence lifetime, FP assays, and FRET assays (both beacon and competitive FRET in round tubes, square or flat cuvettes, or immobilized on magnetic beads, other types of microbeads, or flat surfaces such as nitrocellulose, nylon, or other membranes or on glass or plastic DNA microarrays or "biochips."

While there may appear to be considerable variability among sequences that bind the same clinical analyte targets, "epitopes" or binding sites are usually quite small (e.g., 5-10 bases) and a single target may contain numerous individual binding sites or epitopes for multiple aptamer binding. In addition, however, there is often a common or consensus sequence or common segments of 5-10 or more nucleotides in a row within otherwise different aptamer sequences that can bind a specific target epitope that may dominate the other binding sites by being more physically accessible or having stronger electrostatic, hydrogen bonding, or other attractive forces (summation of van der Waals or other weak forces). Variations in nucleotide sequences around these consensus segments or common binding sequence segments may serve to modulate the binding segment's affinity or specificity or may have no effect at all.

DNA Ligand (Aptamer) Selection and Generation

General methods for developing DNA ligands or aptamers to the immobilized proteins, peptides, or small molecules (defined as less than 1,000 Daltons) are as follows. The protein, peptide or an amino-derivative of the small molecule (such as glucosamine in the case of D-glucose or dextrose) is then added to $2 \times 10^9$ tosyl-coated magnetic beads (MBs; e.g., Dynal brand from Invitrogen Corp. Carlsbad, Calif., 2.8 micron size) for 2 hours at 37° C. The tosyl group is a "leaving" group that allows the formation of a very stable covalent bond between primary amine groups in the target protein, peptide or amino-derivatized small molecule and therefore immobilizes the target on the surfaces of the MBs so that they can be used to probe the randomized DNA library for DNA ligands. Target molecule-conjugated MBs (or target-MBs) are collected for 2 minutes in a magnetic collection device using an external magnet and the supernate is carefully withdrawn with a pipette tip. Target-MBs are then resuspended by vortexing briefly in 1× Binding Buffer (1×BB; 0.5M NaCl, 10 mM Tris-HCl, and 1 mM $MgCl_2$, pH 7.5-7.6) and washed by agitation for 5 minutes. MBs are collected and washed three times in this manner and then resuspended in 1 ml of 1×BB.

MB-based DNA ligand or aptamer development is then performed using a template library sequence such as SEQ ID NO. 1209: 5'-ATCCGTCACACCTGCTCT-$N_{36}$-TGGTGT-TGGCTCCCGTAT-3' (present, for example, in SEQ ID NO's: 8, 10, 12, 14, 16, 18, 20, 22, 24, 26, 28, 30, 32, 35, 36, 38, 40, 42, 44, 46, 48, 50, 52, 54, 56, 58, 67-73, 82, 84, 86, 88, 90, 91, 93, 96, 98, 99, 101, 104, 105, 107, 110, 112, 113, 115, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224-231, 239-244, 251-258, 267-272, 279-283, 285, 286, 292, 295-300, 302, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404-412, 422, 424, 426, 428, 430, 432, 434, 436, 438, 440, 442, 444, 446, 448, 452, 456, 458, 460, 462, 464, 466, 468, 470, 472, 474, 476, 478, 480, 482, 484, 486, 488, 489, 491, 493, 495, 497, 499, 501, 503, 505, 507, 509, 511, 513, 515, 517, 519, 521, 523, 525, 527, 529, 531, 533, 535, 537, 539, 541, 543, 544, 547, 548, 551, 552, 557, 560, 562, 565, 567, 570, 571, 573, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650), where $N_{36}$ represents the randomized 36-base region of the DNA library (maximal sequence diversity=$4^{36}$ in theory). Primer sequences are SEQ ID NO. 1210: 5'-ATACGGGAGCCAACACCA-3' (designated forward); and SEQ ID NO. 1211: 5'-ATCCGTCACACCT-GCTCT-3' (designated reverse). The primer sequences (SEQ ID NO's.: 1210 and 1211) are used to prime the template and nascent strands for PCR, respectively. The random library is reconstituted in 500 µl of sterile nuclease-free water and heated to 95° C. for 5 minutes to ensure that the DNA library is completely single-stranded and linear. The hot DNA library solution is added to 110 µl of target MBs ($2 \times 10^8$ beads) with 600 µl of sterile 2× Binding Buffer (2×BB). The DNA library and target-MB suspension (1.2 ml) is mixed at room temperature (RT, approximately 25° C.) for 1 hour. Target-MBs with any bound DNA (round 1 aptamers) are magnetically collected. The DNA-target-MB complexes are washed three times in 400 µl of sterile 1×BB. Following the third wash, the DNA-target-MB pellet (about 75 µl) is used in a PCR reaction to amplify the bound DNA as follows. The MB pellet is split into 15 µl aliquots and added to five pre-made PCR tubes which contain most of the nonperishable ingredients of a PCR reaction beneath a wax seal. A total of 3 µl of 1:10 primer mix (10% forward primer plus 10% reverse primer) in nuclease-free deionized water or ~20 nanomoles of each primer per ml plus 1 µl (5 U) of Taq DNA polymerase and 5 µl of 2 mM $MgCl_2$ are added to each of the five tubes. PCR reactions are supplemented with 0.5 µl of E. coli single-strand binding protein (SSBP, Stratagene Inc., La Jolla, Calif.) to inhibit high molecular weight concatamer (end to end aggregates of the DNA ligands) formation. PCR is carried out as follows: an initial 95° C. phase for 5 minutes, followed by 20 cycles of 1 minute at 95° C., 1 minute at 53° C., and 1 minute at 72° C. followed by a 72° C. completion stage for 7 minutes, and refrigeration at 4° C. This constitutes the first of multiple rounds of MB-aptamer development. Iteration of the MB-aptamer development process is repeated until the desired affinity or assay sensitivity and specificity are achieved. Typically, 5-10 rounds of the MB-aptamer development process are required to achieve low ng/ml detection of target analytes. To begin the second round and all subsequent rounds, 4 complete tubes of the 5 original PCR rubes are heated to 95° C. for 5 minutes to release bound DNA from the target-MBs. The fifth tubes is always retained and refrigerated as a back-up for that round of the aptamer generation process. All available DNA (25 µl per tube) is siphoned out of the hot tubes without removing the target-MBs before the tubes cool significantly and the DNA is pooled. The 100 µl of hot DNA is added to 100 µl of fresh target-MBs in 200 µl of 2×BB and allowed to mix for 1 hr at RT. Thereafter, the selection and amplification process are repeated for 3-8 more rounds with checking for 72 bp aptamer PCR products by ethidium bromide-stained 2% agarose electrophoresis after each round. Following the last round of aptamer development, aptamers are cloned into chemically competent E. coli and are sequenced.

Screening of Aptamers for Highest Affinity, Lowest Cross-Reactivity and to Determine Lower Limit of Detection by Target Titration in ELISA-Like Plate Assay ("ELASA")

To evaluate, screen, and rank aptamers based on affinity against clinically relevant targets, an enzyme-linked plate assay is conducted by first immobilizing 100 µl of 1:10 diluted target (about 0.1 mg of total protein, peptide or small molecule) in 0.1M $NaHCO_3$ (pH 8.5) overnight at 4° C. in a covered polystyrene 96-well plate. The plate is decanted and washed three times in 250 µl of 1×BB. Each of the different 5'-biotinylated aptamers raised against the target is dissolved in 1×BB at 1.00 nmoles to 4.50 nmoles per 100 microliters and applied to their corresponding plate wells for 1 hour at room temperature (RT; ~25° C.) with gentle mixing on an orbital shaker. The plate is decanted and washed three times in 250 µl of 1×BB for at least 5 minutes per wash with gentle mixing. One hundred µl of a 1:2,000 dilution of streptavidin-peroxidase from a 5 mg/ml stock solution in 1×BB is added per well for 30 minutes at RT with gentle mixing. The plate is decanted and washed three times with 250 µl of 1×BB per well as before. One hundred µl of ABTS (2,2'-azino-bis(3-ethylbenzothiazoline-6-sulphonic acid) substrate with stabilized hydrogen peroxide is added per well for 10 minute at room temperature. Finally absorbance is quantified using a microplate reader with 405 nm optical filter.

Aptamer Beacons and Competitive FRET-Aptamer Assays

Once key aptamers have been identified by the commonality of their sequences or their secondary stem-loop structures, the assay developer decides upon secondary structure loops (potential binding pockets) to label with an F or Q. Secondary stem-loop structures are generated by Gibbs free energy minimization with common software. At this point, one can assess aptamer "beacon" potential in FRET analyte titration experiments. The suspected short aptamer beacon loop is synthesized again with a fluorophore (F) such as TYE 665 attached to the 5' end and quencher (Q) such as Iowa Black attached to the 3' end (or vice versa), purified by HPLC or other form of chromatography and assessed for fluorescence output or intensity as a function of different levels of the target analyte.

Alternatively, one may label the suspected binding loops internally and place an F or a Q somewhere in the midsection of the suspected loop other than the 3' or 5' end (i.e., intrachain FRET). Attachment of F or Q is usually accomplished via succinimide linkage of F- or Q-succinimides added to amino-modified aptamers at specifically chosen locations in the binding pockets. Primary amine linker moieties, such as UniLink™, can be added internally at the time of chemical synthesis of aptamers. Typically 1 mg or more of an aptamer sequence is synthesized with a primary amine linker moiety located at the approximate center of each loop structure (suspected binding pockets). Each of these internally amine-labeled aptamers is then labeled with 100 µl (0.1 mg) of F-succinimide (or alternatively Q-succinimide) for 2 hours in a 37° C. incubator, followed by purification through a 1×BB-equilibrated PD-10 (Sephadex G-25; GE Healthcare) column. In the meantime, an equal molar amount of amino-modified target molecule is labeled with 0.1 mg of spectrally matched Q-succinimide (to accept photons from F) at 37° C. for 2 hours and then washed three times by centrifugation at 14,000 rpm for 10 minutes per wash and resuspension in 1 ml of 1×BB. "Spectrally matched" means that most of the wavelengths of light emitted by F can be effectively absorbed by Q because its absorbance spectrum largely overlaps the emission spectrum of F. Naturally, if the aptamer is labeled with a Q-succinimide in the alternate form of the assay, the amino-target must be labeled with an appropriately matched F-succinimide to be quenched when bound to the Q-labeled aptamer. Pooled one ml fractions of purified F-labeled DNA aptamers are mixed with an equimolar amount of Q-labeled-aminotarget analyte (or vice versa in the alternate embodiment) for 30 minutes at RT with mixing in 1×BB and then purified through an appropriate size-exclusion chromatography column (according to molecular weight of the combined F-aptamer plus Q-target complex) to produce a "FRET complex" consisting of bound F-aptamer plus Q-labeled target.

Generally, the aptamer beacons or FRET-aptamer complexes are then diluted to a final concentration of 1-5 µg/ml in 1×BB and equally dispensed to polystyrene or methacrylate cuvettes in which 1 ml of unlabeled target at various concentrations in 1×BB or diluted blood, plasma, serum, saliva, aspirate or urine has been added already. Cuvettes are gently mixed for 15 to 20 minutes at RT prior to reading their fluorescence in the homogeneous beacon or competitive-displacement FRET assay formats using a spectrofluorometer having gratings to vary the excitation wavelength and emission scanning ability or handheld or otherwise portable fluorometer having a more restricted or fixed excitation and emission optical filter set with a range of wavelengths for excitation and emission.

Aptamer or Aptamer Binding Site Linkage in One or More Dimensions

The linkage of binding sites is beneficial in terms of enhancing receptor affinity, avidity (tensile binding strength), and selectivity versus complex targets with two or more distinct epitopes. This linkage can be sequential and linear (one-dimensional as in antibody heavy and light chain linkage of HV regions) or could be expanded into two or three dimensions much like DNA dendrimers or other more complex structures known to those skilled in the art. Linear linkage by chemical synthesis is quite facile, if one knows that aptamer DNA sequences or shorter (5-10 base) binding site sequences to be linked. One long sequence can be designed to incorporate the desired aptamers or binding sites with repetitive poly-adenine, poly-cytosine, poly-guanine, poly-thymine, poly-uridine, or other intervening sequences that are unlikely to bind the target. The length of the composite aptamer construct will be limited to about 200 bases by current chemical synthesis technology. However, biosynthesis or enzymatic synthesis by PCR or asymmetric PCR (producing predominately single-stranded DNA from a template) would not be so limited and should produce aptamer constructs up to 2,000 bases before the Taq polymerase falls off the template. In this way, very lengthy 2 kilobase aptamer constructs could be made from complementary DNA templates that would enable binding of different epitopes that are distal on the surface of relatively large objects such as whole bacterial or eukaryotic cells. Again, poly-A, C, G, T, or U or other linker nucleotide segments could be designed into the cDNA template and the resultant nascent strand to ligate aptamers or aptamer binding sites together into one contiguous linear chain.

For 2-D or 3-D linked aptamer structures a variety of linker chemistries are available, but the preferred embodiment is probably addition of a primary amine group somewhere in the mid-section of a larger multi-aptamer construct followed by covalent linkage of two or more such multi-aptamer constructs by means of bifunctional linkers such as low levels (≤1%) glutaraldehyde, carbodiimides, sulfo-EGS, sulfo-SMCC or other such bifunctional linkers familiar to those skilled in conjugate chemistry.

Referring to the figures, FIG. 1 is a comparison of ELISA-like affinity-based and competitive FRET assays using the same DNA ligands. It provides a graphical comparison of the same selected family of DNA ligands that bind *E. coli* OMPs in an ELISA-like affinity-based plate assay (data table in FIG. 1) with competitive FRET response spectra for the same population of DNA ligand sequences. It further is an illustration of how anti-*E. coli* OMP DNA ligands are useful in an ELISA-like assay format (tabled absorbance values) and how some candidate DNA ligand sequences show greater affinity than others (i.e., have higher absorbance values approaching 1.9) for the Crook's strain (ATCC 8739) of *E. coli*. The figure also demonstrates that some DNA ligand sequences with generally lower affinities (some of the shaded boxes in FIG. 1) from the same population yield a greater competitive FRET response to *E. coli* 8739 (i.e., are more useful in a FRET assay format, but not as useful for affinity-based assays like ELISA). The boxed values in the table of FIG. 1 show all of the highest affinity DNA ligand sequences or wells with absorbance values greater than 1.5. The shaded values indicate wells with the greatest competitive FRET responses (wells A8, A10, B2, B8, C12, and D6). It is clear from FIG. 1 that only two of the highest affinity DNA ligands in wells D6 and C12 also gave strong FRET responses, thereby illustrating the varied utility of different members of the same general DNA ligand family that binds *E. coli* OMPs.

Figure 2:
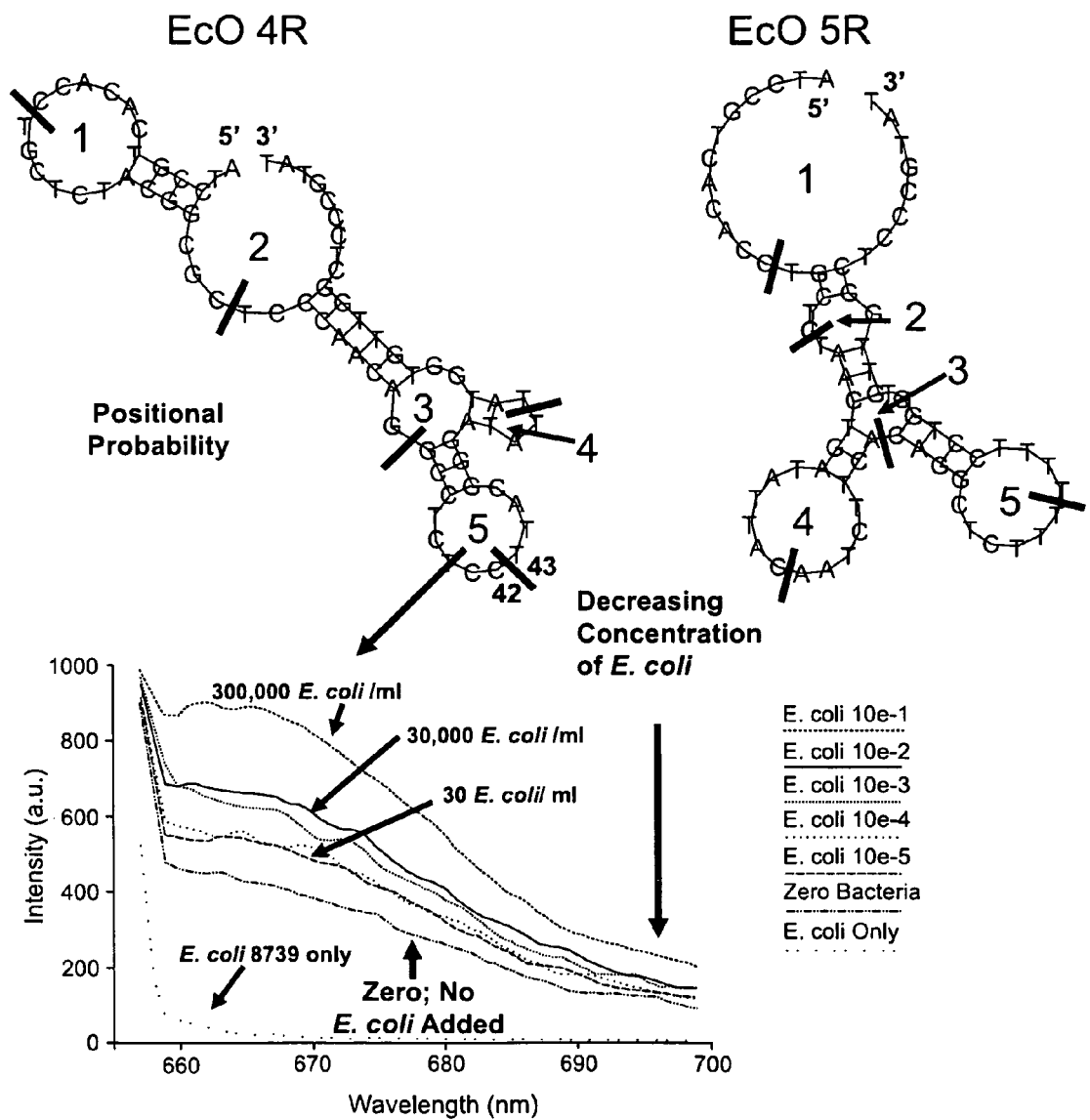
FIG. 2 shows the secondary structures of two DNA ligands which both bind *E. coli* strain ATCC 8739, but only one loop structure in the EcO 4R DNA ligand (SEQ ID No. 88) yielded competitive FRET as illustrated by the fluorescence spectra.

FIG. 2 shows the secondary structures of two DNA ligands (as determined by Vienna RNA free energy minimization software using DNA mathematical parameters at room temperature (25° C.)) shown to bind the OMPs of *E. coli* strain ATCC 8739 with moderate to high affinity by ELISA-like assay. However, only the loop or binding pocket of the DNA ligand designated EcO 4R (SEQ ID No. 88) was useful for competitive FRET as illustrated by the fluorescence spectra at the bottom of the figure when AlexaFluor 647-succinimide is used to label the putative binding pocket via a UniLink™ amine linker between bases 42 and 43 (numbered from the 5' end) and the fluorophore-labeled EcO 4R DNA molecules is bound to Black Hole Quencher (BHQ)-3-succinimide labeled *E. coli* ATCC 8739 and competed against decreasing levels or concentrations of unlabeled *E. coli* ATCC 8739 in neat buffer. None of the other loop structures in EcO 4R or EcO 5R (SEQ ID No. 90) DNA ligands were capable of producing a FRET response in this competitive FRET format.

Figure 3:
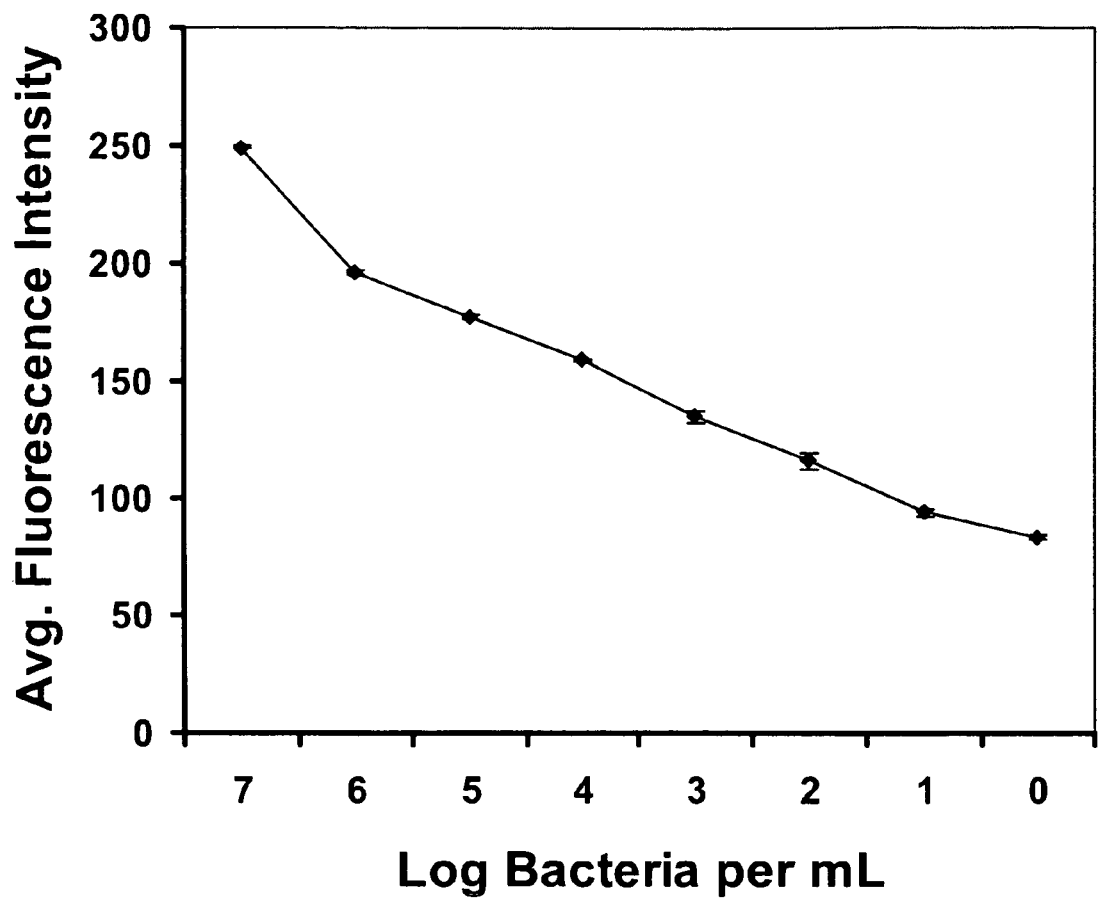
FIG. 3 is a graph plotting relative fluorescence intensity against the concentration of *Campylobacter jejuni* bacteria detected in chicken juice by plastic-adherent DNA sandwich assay.

FIG. 3 graphically illustrates an ultrasensitive detection of *Campylobacter jejuni* by a plastic-adherent sandwich assay. The graph plots relative fluorescence intensity against the concentration of the targeted, *Campylobacter jejuni*, bacteria detected in chicken juice down to a level of approximately 10 bacterial cells using a one-step plastic-adherent DNA ligand-MB/DNA ligand red QD (Q-dot 655 nm) sandwich assay. Five independent readings were taken per data point with the green (Rhodamine) channel of a fluorometer. The DNA ligand sequences may be used to detect as few as 2 live or dead *C. jejuni* bacterial cells (a well-known foodborne pathogen) in neat buffer and various food matrices including diluted whole milk and poultry rinsate.

In this assay, two different *C. jejuni* sequences (C2 and C3) from the SEQ ID NO's 1-6 were 5'-amine modified upon synthesis and attached to either 1,000 tosyl-M280 (2.8 micron diameter) Dynal (Invitrogen, Inc.) MB's or 0.24 picoliters of Q-dot 655 ITK reagent (Invitrogen, Inc.) per test. The C2 DNA ligand was used for capture on the surface of tosyl-MB's and the C3 DNA ligand was used as the reporter reagent after attachment to the Q-dot 655 ITK reagent via BS3 (bis-suberate bifunctional linker from Pierce Chemical Co.). The reagents were purified, mixed together and lyophilized in plastic cuvettes. The powered assays were later back-flushed with nitrogen and capped. Upon rehydration, the adherent one-step sandwich assays were used to detect live or dead *C. jejuni* cells with the very sensitive results depicted in FIG. 2 in chicken juice.

Figure 4:
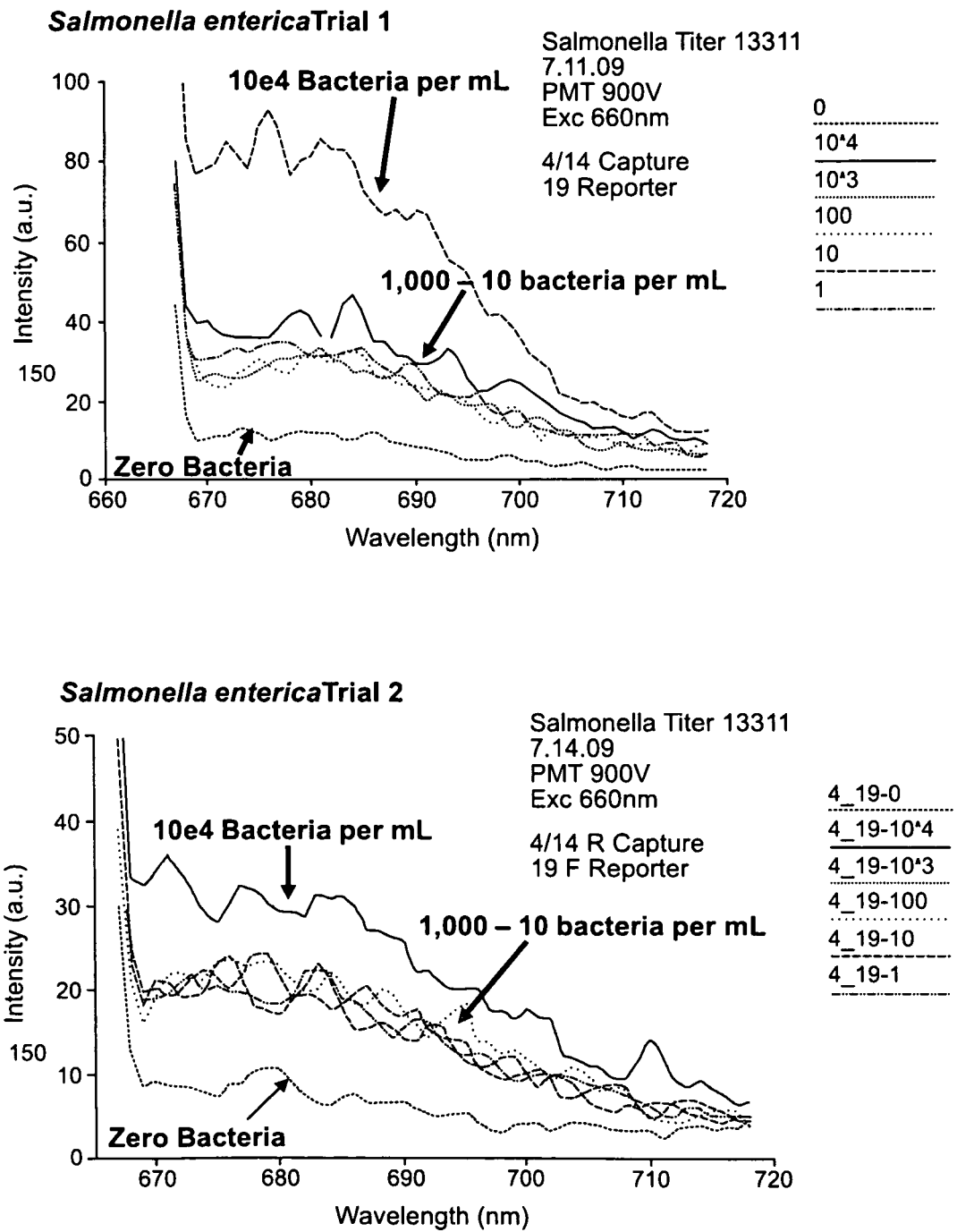
FIG. 4 shows graphs demonstrating detection of *Salmonella enterica* ATCC strain 13311 by plastic-adherent DNA sandwich assay.

FIG. 4 demonstrates sensitive detection of the targeted *Salmonella* species by plastic-adherent sandwich assay in the range of 10 to 1,000 bacteria per mL. The graphs show the detection of *Salmonella enterica* ATCC strain 13311 in two separate trials using specific DNA ligands in a plastic-adherent DNA ligand-MB plus DNA ligand-QD dot sandwich assay format in neat buffer The particular high affinity DNA ligand sequence used for MB conjugate formation and capture was Sal 4/14R and the DNA ligand used for QD coupling and reporting was designated Sal 19F and selected from SEQ ID NO's 81-218. However, other DNA ligands from the same family give similar affinity-based results and may be useful for detection of different species or strains of *Salmonella*.

Figure 5:
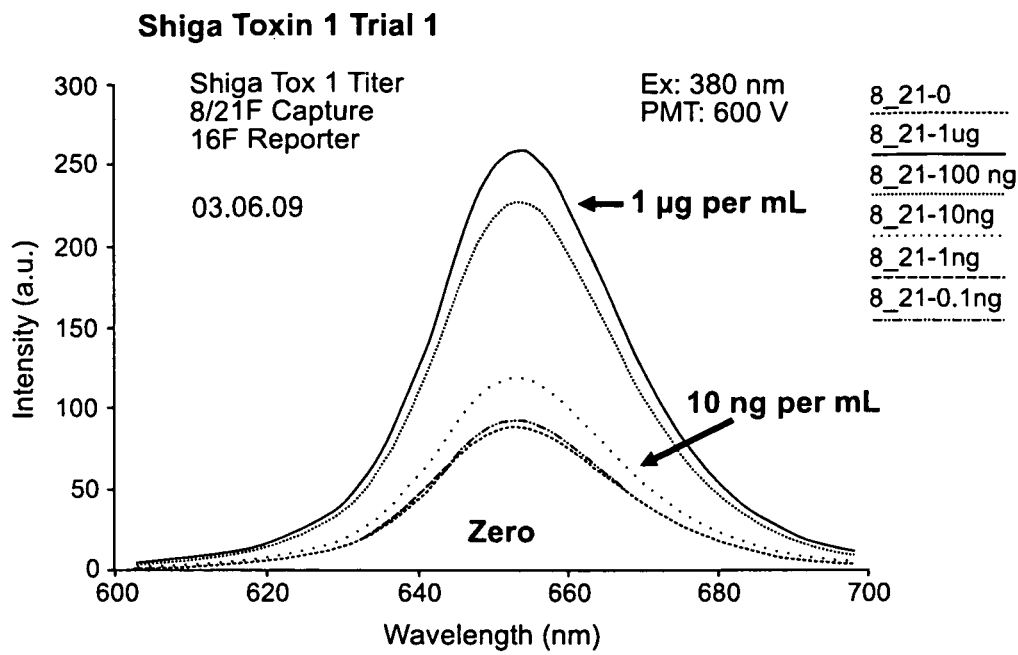
FIG. 5 shows graphs demonstrating detection of Shiga toxin type 1 by plastic-adherent DNA sandwich assay.
Figure 5:
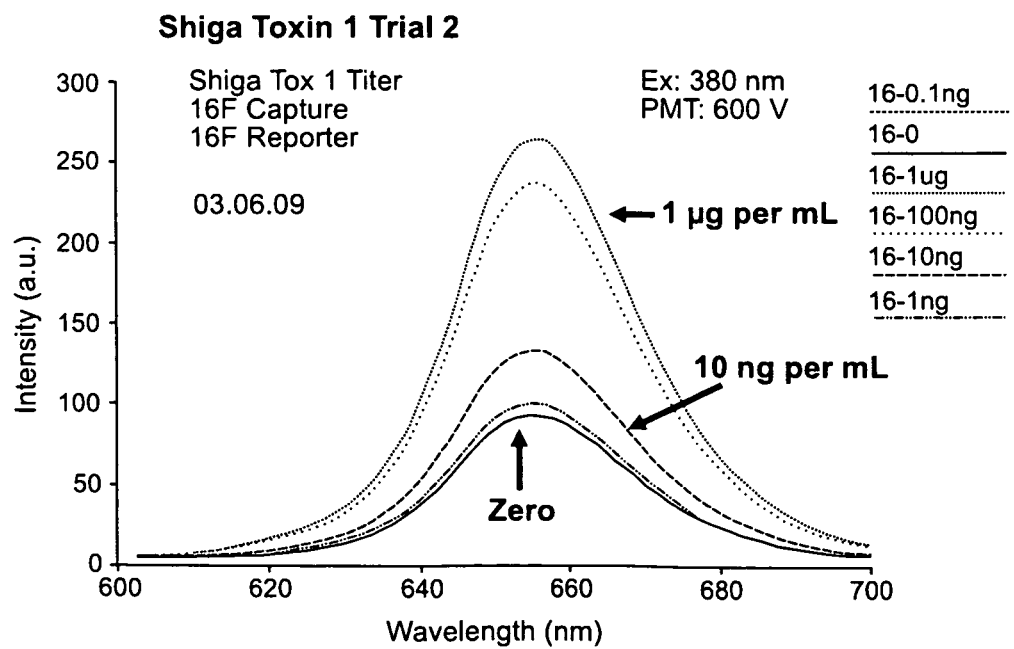

FIG. 5 demonstrates the ultrasensitive detection of *E. coli* Shiga toxins by plastic-adherent sandwich assay. The graphs show the detection of Shiga toxin type 1. from two separate trials using specific DNA ligands in a plastic-adherent DNA ligand-magnetic bead plus DNA ligand quantum dot sandwich assay format. Using the plastic-adherent aptamer-MB plus aptamer-QD conjugate sandwich assay described in FIGS. 3 and 4, similar ultrasensitive detection of Shiga or Shiga-like toxin 1 to a level of 10 ng per mL was achieved in neat buffer as shown in FIG. 5. The particular high affinity DNA ligand sequence used for MB conjugate formation and capture was Shiga 8/21F in one trial and 16F in the other and the DNA ligand used for QD coupling and reporting was designated Shiga 16F in both cases. All three of these DNA ligand sequences were selected from SEQ ID NO's 544-574. However, other DNA ligands from the same family give similar results and may be useful for detection of different species or strains of Shiga-like or Vero toxins.

Although the invention and DNA ligand sequences have been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

TABLE 1

DNA ligand Sequence ID Nos.

*Campylobacter jejuni* OMPs - Fresh bacteria

SEQ ID NO. 1 (C1) - CATCCGTCACACCTGCTCTGGGGAGGGTGGCGCCCGTCTCGGT
GGTGTTGGCTCCCGTATCA

SEQ ID NO. 2 (C2) - CATCCGTCACACCTGCTCTGGGATAGGGTCTCGTGCTAGATGTG
GTGTTGGCTCCCGTATCA

SEQ ID NO. 3 (C3) - CATCCGTCACACCTGCTCTGGACCGGCGCTTATTCCTGCTTGTG
GTGTTGGCTCCCGTATCA

SEQ ID NO. 4 (C4) - CATCCGTCACACCTGCTCTGGAGCTGATATTGGATGGTCCGGTG
GTGTTGGCTCCCGTATCA

TABLE 1-continued

DNA ligand Sequence ID Nos.

SEQ ID NO. 5 (C5) - CATCCGTCACACCTGCTCTGCCCAGAGCAGGTGTGACGGATGTG
GTGTTGGCTCCCGTATCA

SEQ ID NO. 6 (C6) - CATCCGTCACACCTGCTCTGCCGGACCATCCAATATCAGCTGTG
GTGTTGGCTCCCGTATCA

*Aged Campylobacter jejuni* (ACj; Greater than one month at 4° C.)

SEQ ID NO. 7 (ACj-1 For) - ATACGGGAGCCAACACCAGGACCAAAATAAATAATCAC
AATAAAAATGCTTCCTAGAGCAGGTGTGACGGAT

SEQ ID NO. 8 (ACj-1 Rev) - ATCCGTCACACCTGCTCTAGGAAGCATTTTTATTGTGAT
TATTTATTTTGGTCCTGGTGTTGGCTCCCGTAT

SEQ ID NO. 9 (ACj-2 For) - ATACGGGAGCCAACACCACGCCGGGCCATAGGCGTGTG
GTAGCATACTCGTACTAGAGCAGGTGTGACGGAT

SEQ ID NO. 10 (ACj-2 Rev) - ATCCGTCACACCTGCTCTAGTACGAGTATGCTACCACA
CGCCTATGGCCCGGCGTGGTGTTGGCTCCCGTAT

SEQ ID NO. 11 (ACj-3 For) - ATACGGGAGCCAACACCATAGTATAAAGACCCAATTG
ACAGACTATCCTAGGCTAGAGCAGGTGTGACGGAT

SEQ ID NO. 12 (ACj-3 Rev) - ATCCGTCACACCTGCTCTAGCCTAGGATAGTCTGTCAA
TTGGGTCTTTATACTATGGTGTTGGCTCCCGTAT

SEQ ID NO. 13 (ACj-4 For) - ATACGGGAGCCAACACCAAGAGGGGACAGAGGGTATA
AGACAACTATTCTCCCCAGAGCAGGTGTGACGGAT

SEQ ID NO. 14 (ACj-4 Rev) - ATCCGTCACACCTGCTCTGGGGAGAATAGTTGTCTTAT
ACCCTCTGTCCCCTCTTGGTGTTGGCTCCCGTAT

SEQ ID NO. 15 (ACj-7 For) - ATACGGGAGCCAACACCAGGCGGCCGCAACTTGGTCC
CCTCTTCATCCTCGGATAGAGCAGGTGTGACGGAT

SEQ ID NO. 16 (ACj-7 Rev) - ATCCGTCACACCTGCTCTATCCGAGGATGAAGAGGGG
ACCAAGTTGCGGCCGCCTGGTGTTGGCTCCCGTAT

SEQ ID NO. 17 (ACj-8 For (69)) - ATACGGGAGCCAACACCATAGTGTTGGACCAA
TACGGTAACGTGTCCTTGGAGAGCAGGTGTGACGGAT

SEQ ID NO. 18 (ACj-8 Rev (69)) - ATCCGTCACACCTGCTCTCCAAGGACACGTTA
CCGTATTGGTCCAACACTATGGTGTTGGCTCCCGTAT

SEQ ID NO. 19 (ACj-9 For) - ATACGGGAGCCAACACCACGCGATACAATGTGCTAAA
AAAGTTCGTGCCCCTGCAGAGCAGGTGTGACGGAT

SEQ ID NO. 20 (ACj-9 Rev) - ATCCGTCACACCTGCTCTGCAGGGGCACGAACTTTTTT
AGCACATTGTATCGCGTGGTGTTGGCTCCCGTAT

SEQ ID NO. 21 (ACj-10 For) - ATACGGGAGCCAACACCACGCCGAATAGTGTTCGTAT
GCCACCCGCACGTGTCTAGAGCAGGTGTGACGGAT

SEQ ID NO. 22 (ACj-10 Rev) - ATCCGTCACACCTGCTCTAGACACGTGCGGGTGGCAT
ACGAACACTATTCGGCGTGGTGTTGGCTCCCGTAT

SEQ ID NO. 23 (ACj-11 For) - ATACGGGAGCCAACACCAGGCATGACTAAAAAGGAT
AACCTAATCTCTTGTTCCAGAGCAGGTGTGACGGAT

SEQ ID NO. 24 (ACj-11 Rev) - ATCCGTCACACCTGCTCTGGAACAAGAGATTAGGTTA
TCCTTTTTAGTCATGCCTGGTGTTGGCTCCCGTAT

SEQ ID NO. 25 (ACj-15 For) - ATACGGGAGCCAACACCATACAGTCCACCGTATACTA
GTGGTACCCAGGCGTCGAGAGCAGGTGTGACGGAT

SEQ ID NO. 26 (ACj-15 Rev) - ATCCGTCACACCTGCTCTCGACGCCTGGGTACCACTA
GTATACGGTGGACTGTATGGTGTTGGCTCCCGTAT

SEQ ID NO. 27 (ACj-16 For) - ATACGGGAGCCAACACCAGGGGCGAACAGTTACCC
TTGGTCTGGACCACTGCCAGAGCAGGTGTGACGGAT

SEQ ID NO. 28 (ACj-16 Rev) - ATCCGTCACACCTGCTCTGGCAGTGGTCCAGACCAAG
GGTAACTGTTCGCCCCCTGGTGTTGGCTCCCGTAT

SEQ ID NO. 29 (ACj-17 For) - ATACGGGAGCCAACACCAGGGGCGTCGGGCCAGGCG
ACGGCCGCCGTTTCCGGCAGAGCAGGTGTGACGGAT

TABLE 1-continued

DNA ligand Sequence ID Nos.

SEQ ID NO. 30 (ACj-17 Rev) - ATCCGTCACACCTGCTCTGCCGGAAACGGCGGCCGTC
GCCTGGCCCGACGCCCCTGGTGTTGGCTCCCGTAT

SEQ ID NO. 31 (ACj-18 For) - ATACGGGAGCCAACACCACGGGCCGTCCCTGGCCCG
GGGGGGCGAAACGCGCTGAGAGCAGGTGTGACGGAT

SEQ ID NO. 32 (ACj-18 Rev) - ATCCGTCACACCTGCTCTCAGCGCGTTTCGCCCCCCC
GGGCCAGGGACGGCCCGTGGTGTTGGCTCCCGTAT

SEQ ID NO. 33 (ACj-19 For) - ATACGGGAGCCAACACCAGGCGATTACTAAGGGAAA
AAAGTGTAAAACCTACCCAGAGCAGGTGTGACGGAT

SEQ ID NO. 34 (ACj-19 Rev) - ATCCGTCACACCTGCTCTGGGTAGGTTTTACACTTTT
TTCCCTTAGTAATCGCCTGGTGTTGGCTCCCGTAT

SEQ ID NO. 35 (ACj-24 For) - ATACGGGAGCCAACACCACCACCCACTGGCCCGGTC
CGCGGCCGCGCGCGCCCCAGAGCAGGTGTGACGGAT

SEQ ID NO. 36 (ACj-24 Rev) - ATCCGTCACACCTGCTCTGGGGCGCGCGCGGCCGCG
GACCGGGCCAGTGGGTGGTGGTGTTGGCTCCCGTAT

SEQ ID NO. 37 (ACj-25 For) - ATACGGGAGCCAACACCAACGATATCCCTGACCAAA
GACGTTAAATGCTTCCATAGAGCAGGTGTGACGGAT

SEQ ID NO. 38 (ACj-25 Rev) - ATCCGTCACACCTGCTCTATGGAAGCATTTAACGTCT
TTGGTCAGGGATATCGTTGGTGTTGGCTCCCGTAT

SEQ ID NO. 39 (ACj-26 For) - ATACGGGAGCCAACACCAGGGCGGGGGTTGGCGAG
CAGGAATCGAGAGAGGTGAGAGCAGGTGTGACGGAT

SEQ ID NO. 40 (ACj-26 Rev) - ATCCGTCACACCTGCTCTCACCTCTCTCGATTCCTG
CTCGCCAACCCCCGCCCTGGTGTTGGCTCCCGTAT

SEQ ID NO. 41 (ACj-27 For) - ATACGGGAGCCAACACCAGATGCGCTTCCTGTAATGA
ACAGATCATATTTATGTAGAGCAGGTGTGACGGAT

SEQ ID NO. 42 (ACj-27 Rev) - ATCCGTCACACCTGCTCTACATAAATATGATCTGTTC
ATTACAGGAAGCGCATCTGGTGTTGGCTCCCGTAT

SEQ ID NO. 43 (ACj-28 For) - ATACGGGAGCCAACACCAAGGTAGGTTGCCGCAGGT
TGGCGACAAACCAGGTTGAGAGCAGGTGTGACGGAT

SEQ ID NO. 44 (ACj-28 Rev) - ATCCGTCACACCTGCTCTCAACCTGGTTTGTCGCCAA
CCTGCGGCAACCTACCTTGGTGTTGGCTCCCGTAT

SEQ ID NO. 45 (ACj-30 For (69)) - ATACGGGAGCCAACACCATAGTGTTGGACCA
ATACGGTAACGTGTCCTTGGAGAGCAGGTGTGACGGAT

SEQ ID NO. 46 (ACj-30 Rev (69)) - ATCCGTCACACCTGCTCTCCAAGGACACGTT
ACCGTATTGGTCCAACACTATGGTGTTGGCTCCCGTAT

SEQ ID NO. 47 (ACj-33 For) - ATACGGGAGCCAACACCACCCGGGTGGCGGGGTGGG
TGTGGGTCGACGTTCTGGAGAGCAGGTGTGACGGAT

SEQ ID NO. 48 (ACj-33 Rev) - ATCCGTCACACCTGCTCTCCAGAACGTCGACCCACAC
CCACCCCGCCACCCGGGTGGTGTTGGCTCCCGTAT

SEQ ID NO. 49 (ACj-34 For) - ATACGGGAGCCAACACCAGGGGGGGGTGGCCGCAGG
AAATATGCAGTCCACTATAGAGCAGGTGTGACGGAT

SEQ ID NO. 50 (ACj-34 Rev) - ATCCGTCACACCTGCTCTATAGTGGACTGCATATTTC
CTGCGGCCACCCCCCCCTGGTGTTGGCTCCCGTAT

SEQ ID NO. 51 (ACj-35 For) - ATACGGGAGCCAACACCACACACCGGGCCCGCCCCC
AGCGCCCCCCTACGCACAAGAGCAGGTGTGACGGAT

SEQ ID NO. 52 (ACj-35 Rev) - ATCCGTCACACCTGCTCTTGTGCGTAGGGGGCGCTG
GGGGCGGGCCCGGTGTGGTGTTGGCTCCCGTAT

SEQ ID NO. 53 (ACj-38 For) - ATACGGGAGCCAACACCATGAAGGAAACCTTGATAG
CAGGAATAGTCCATTCCCAGAGCAGGTGTGACGGAT

SEQ ID NO. 54 (ACj-38 Rev) - ATCCGTCACACCTGCTCTGGGAATGGACTATTCCTGC
TATCAAGGTTTCCTTCATGGTGTTGGCTCCCGTAT

SEQ ID NO. 55 (ACj-39 For) - ATACGGGAGCCAACACCACCCGGGTGGCGGGGTGGG
TGTGGGTCGACGTTCTGGAGAGCAGGTGTGACGGAT

TABLE 1-continued

DNA ligand Sequence ID Nos.

SEQ ID NO. 56 (ACj-39 Rev) - ATCCGTCACACCTGCTCTCCAGAACGTCGACCCACA
CCCACCCCGCCACCCGGGTGGTGTTGGCTCCCGTAT

SEQ ID NO. 57 (ACj-40 For) - ATACGGGAGCCAACACCACGCCCGCCGGCGACTCGC
TCCACTCCGTCCCGCTCCAGAGCAGGTGTGACGGAT

SEQ ID NO. 58 (ACj-40 Rev) - ATCCGTCACACCTGCTCTGGAGCGGGACGGAGTGGA
GCGAGTCGCCGGCGGGCGTGGTGTTGGCTCCCGTAT

*Enterococcus faecalis* Teichoic Acid (TA) DNA ligands

SEQ ID NO. 59 (TA5F) - CATTCACCACACCTCTGCTGGCTTGGCTAGCCTTGATGCTA
AACGACCCATAGTGTGGTGTCGTCCCGTATC

SEQ ID NO. 60 (TA5R) - GATACGGGACGACACCACACTATGGGTCGTTTAGCATCAA
GGCTAGCCAAGCCAGCAGAGGTGTGGTGAATG

SEQ ID NO. 61 (TA6F) - CATTCACCACACCTCTGCTGGAGGAGGAAGTGGTCTGGAG
TTACTTGACATAGTGTGGTGTCGTCCCGTATC

SEQ ID NO. 62 (TA6R) - GATACGGGACGACACCACACTATGTCAAGTAACTCCAGAC
CACTTCCTCCTCCAGCAGAGGTGTGGTGAATG

SEQ ID NO. 63 (TA7F) - CATTCACCACACCTCTGCTGGACGGAAACAATCCCCGGGTA
CGAGAATCAGGGTGTGGTGTCGTCCCGTATC

SEQ ID NO. 64 (TA7R) - GATACGGGACGACACCACACCCTGATTCTCGTACCCGGGGA
TTGTTTCCGTCCAGCAGAGGTGTGGTGAATG

SEQ ID NO. 65 (TA9F) - CATTCACCACACCTCTGCTGGAAACCTACCATTAATGAGAC
ATGATGCGGTGGTGTGGTGTCGTCCCGTATC

SEQ ID NO. 66 (TA9R) - GATACGGGACGACACCACACCACCGCATCATGTCTCATTAA
TGGTAGGTTTCCAGCAGAGGTGTGGTGAATG

*E. coli* O157 Lipopolysaccharide (LPS) DNA ligands

SEQ ID NO. 67 (E-5F) - ATCCGTCACACCTGCTCTGGTGGAATGGACTAAGCTAGCTAG
CGTTTTAAAAGGTGGTGTTGGCTCCCGTAT

SEQ ID NO. 68 (E-11F) - ATCCGTCACACCTGCTCTGTAAGGGGGGGAATCGCTTTCG
TCTTAAGATGACATGGTGTTGGCTCCCGTAT

SEQ ID NO. 69 (E-12F) - ATCCGTCACACCTGCTCTGCCGGACCATCCAATATCAGCTG
TGGTGTTGGCTCCCGTAT

SEQ ID NO. 70 (E-16F) - ATCCGTCACACCTGCTCTATCCGTCACGCCTGCTCTATCCG
TCACACCTGCTCTGGTGTTGGCTCCCGTAT

SEQ ID NO. 71 (E-17F) - ATCCGTCACACCTGCTCTATCAAATGTGCAGATATCAAGA
CGATTTGTACAAGATGGTGTTGGCTCCCGTAT

SEQ ID NO. 72 (E-18F) - ATCCGTCACACCTGCTCTGTAGATGGCAAGGCATAAGCGT
CCGGAACGATAGAATGGTGTTGGCTCCCGTAT

SEQ ID NO. 73 (E-19F) - ATCCGTCACACCTGCTCTGTAGATGGCAAGGCATAAGCGTC
CGGAACGATAGAATGGTGTTGGCTCCCGTAT

SEQ ID NO. 74 (E-5R) - ATACGGGAGCCAACACCACCTTTTAAAACGCTAGCTAGCTT
AGTCCATTCCACCAGAGCAGGTGTGACGGAT

SEQ ID NO. 75 (E-11R) - ATACGGGAGCCAACACCATGTCATCTTAAGACGAAAGCGA
TTCCCCCCCTTACAGAGCAGGTGTGACGGAT

SEQ ID NO. 76 (E-12R) - ATACGGGAGCCAACACCACAGCTGATATTGGATGGTCCGG
CAGAGCAGGTGTGACGGAT

SEQ ID NO. 77 (E-16R) - ATACGGGAGCCAACACCAGAGCAGGTGTGACGGATAGAGC
AGGCGTGACGGATAGAGCAGGTGTGACGGAT

SEQ ID NO. 78 (E-17R) - ATACGGGAGCCAACACCATCTTGTACAAATCGTCTTGATAT
CTGCACATTTGATAGAGCAGGTGTGACGGAT

SEQ ID NO. 79 (E-18R) - ATACGGGAGCCAACACCATTCTATCGTTCCGGACGCTTATG
CCTTGCCATCTACAGAGCAGGTGTGACGGAT

TABLE 1-continued

DNA ligand Sequence ID Nos.

SEQ ID NO. 80 (E-19R) - ATACGGGAGCCAACACCATTCTATCGTTCCGGACGCTTAT
GCCTTGCCATCTACAGAGCAGGTGTGACGGAT

*E. coli* Outer Membrane Proteins (OMPs) - Fresh Bacteria

SEQ ID NO. 81 (EcO-1F) - ATACGGGAGCCAACACCATGGTACAAGCAAACCAATAT
TAGGGCCCAGACATCGAGAGCAGGTGTGACGGAT

SEQ ID NO. 82 (EcO-1R) - ATCCGTCACACCTGCTCTCGATGTCTGGGCCCTAATATT
GGTTTGCTTGTACCATGGTGTTGGCTCCCGTAT

SEQ ID NO. 83 (EcO-2F) - ATACGGGAGCCAACACCATGATACCCTAAGGTAGGGGA
GGCCTAAGCGCCACGTAGAGCAGGTGTGACGGAT

SEQ ID NO. 84 (EcO-2R) - ATCCGTCACACCTGCTCTACGTGGCGCTTAGGCCTCCCC
TACCTTAGGGTATCATGGTGTTGGCTCCCGTAT

SEQ ID NO. 85 (EcO-3F) - ATACGGGAGCCAACACCACGCATCCCCCGCCGGGCCC
GCGCCCCGCTCGCAGACAGAGCAGGTGTGACGGAT

SEQ ID NO. 86 (EcO-3R) - ATCCGTCACACCTGCTCTGTCTGCGAGCGGGGCGCGGGC
CCGGCGGGGATGCGTGGTGTTGGCTCCCGTAT

SEQ ID NO. 87 (EcO-4F (73)) - ATACGGGAGCCAACACCATAATATGCCGTAAGGAG
AGGCCTGTTGGGAGCGCCGTAGAGCAGGTGTGACGGAT

SEQ ID NO. 88 (EcO-4R (73)) - ATCCGTCACACCTGCTCTACGGCGCTCCCAACAGGC
CTCTCCTTACGGCATATTATGGTGTTGGCTCCCGTAT

SEQ ID NO. 89 (EcO-5F) - ATACGGGAGCCAACACCAGGAAAAAAAGAGCCTGTGAA
GATTGTAATATCAGTTAGAGCAGGTGTGACGGAT

SEQ ID NO. 90 (EcO-5R) - ATCCGTCACACCTGCTCTAACTGATATTACAATCTTCAC
AGGCTCTTTTTTTCCTGGTGTTGGCTCCCGTAT

SEQ ID NO. 91 (EcO-7Fa) - ATCCGTCACACCTGCTCTCGGAGGTAGACTAGGATTGC
GGCGGGGGGTCAGGTATGGTGTTGGCTCCCGTAT

SEQ ID NO. 92 (EcO-7Fb) - ATACGGGAGCCAACACCACAAAAGCCTTACCTAACTGC
CAACAATGAATAGCAAGAGCAGGTGTGACGGAT

SEQ ID NO. 93 (EcO-7Ra) - ATCCGTCACACCTGCTCTTGCTATTCATTGTTGGCAGTT
AGGTAAGGCTTTTGTTGGTGTTGGCTCCCGTAT

SEQ ID NO. 94 (EcO-7Rb) - ATACGGGAGCCAACACCATACCTGACCCCCCGCCGCAA
TCCTAGTCTACCTCCGAGAGCAGGTGTGACGGAT

SEQ ID NO. 95 (EcO-8F) - ATACGGGAGCCAACACCACGACTAACACGACCGTTGGG
GGGGGCTCGCGCGGGCAGAGCAGGTGTGACGGAT

SEQ ID NO. 96 (EcO-8R) - ATCCGTCACACCTGCTCTGCCCGCGCGAGCCCCCCCCAA
CGGTCGTGTTAGTCGTGGTGTTGGCTCCCGTAT

SEQ ID NO. 97 (EcO-9F) - ATACGGGAGCCAACACCAGTCCCCGCCCAGCCGTGAGC
CGTACCCCCGCACACCAGAGCAGGTGTGACGGAT

SEQ ID NO. 98 (EcO-9R) - ATCCGTCACACCTGCTCTGGTGTGCGGGGTACGGCTCA
CGGCTGGGCGGGACTGGTGTTGGCTCCCGTAT

SEQ ID NO. 99 (EcO-10F) - ATCCGTCACACCTGCTCTCAAGGTTGGGCCTGCAAGAG
CAAAAACGGGGCGGGATGGTGTTGGCTCCCGTAT

SEQ ID NO. 100 (EcO-10R) - ATACGGGAGCCAACACCATCCCGCCCCGTTTTTGCTCT
TGCAGGCCCAACCTTGAGAGCAGGTGTGACGGAT

SEQ ID NO. 101 (EcO-11F) - ATCCGTCACACCTGCTCTACTTGGCTTGCGACTATTAT
TCACAGGGCCAAAGACTGGTGTTGGCTCCCGTAT

SEQ ID NO. 102 (EcO-11R) - ATACGGGAGCCAACACCAGTCTTTGGCCCTGTGAATA
ATAGTCGCAAGCCAAGTAGAGCAGGTGTGACGGAT

SEQ ID NO. 103 (EcO-12/37/60F (69)) - ATACGGGAGCCAACACCATAGTGTTGGA
CCAATACGGTAACGTGTCCTTGGAGAGCAGGTGTGACGGAT

SEQ ID NO. 104 (EcO-12/37/60R (69)) - ATCCGTCACACCTGCTCTCCAAGGACAC
GTTACCGTATTGGTCCAACACTATGGTGTTGGCTCCCGTAT

TABLE 1-continued

DNA ligand Sequence ID Nos.

SEQ ID NO. 105 (EcO-17F) - ATCCGTCACACCTGCTCTTGGAATGTCGGTGTTTTCC
AATTCCTTGGGTCGTGTGGTGTTGGCTCCCGTAT

SEQ ID NO. 106 (EcO-17R) - ATACGGGAGCCAACACCACACGACCCAAGGAATTGG
AAAAACACCGACATTCCAAGAGCAGGTGTGACGGAT

SEQ ID NO. 107 (EcO-18F) - ATCCGTCACACCTGCTCTGCGACGGCGACGCGGTCCG
GGCGGGGGTGGAGGACGTGGTGTTGGCTCCCGTAT

SEQ ID NO. 108 (EcO-18R) - ATACGGGAGCCAACACCACGTCCTCCACCCCCGCCCG
GACCGCGTCGCCGTCGCAGAGCAGGTGTGACGGAT

SEQ ID NO. 109 (EcO-19Fa) - ATACGGGAGCCAACACCAGAGGGTTCTAGGGTCACT
TCCATGAGAATGGCTCACAGAGCAGGTGTGACGGAT

SEQ ID NO. 110 (EcO-19Fb) - ATCCGTCACACCTGCTCTGGCCTGGGGACGCGAGGG
AGGCGGGGGAGTCGTGGTGGTGTTGGCTCCCGTAT

SEQ ID NO. 111 (EcO-19Ra) - ATACGGGAGCCAACACCACCACGACTCCCCCCGCCT
CCCTCGCGTCCCCAGGCCAGAGCAGGTGTGACGGAT

SEQ ID NO. 112 (EcO-19Rb) - ATCCGTCACACCTGCTCTGTGAGCCATTCTCATGGAA
GTGACCCTAGAACCCTCTGGTGTTGGCTCCCGTAT

SEQ ID NO. 113 (EcO-20F)ATCCGTCACACCTGCTCTCACAGGGCCTCTTACTATACA
GTTCTCCAGCGCTGCTGGTGTTGGCTCCCGTAT

SEQ ID NO. 114 (EcO-20R) - ATACGGGAGCCAACACCAGCAGCGCTGGAGAACTGTA
TAGTAAGAGGCCCTGTG GAGCAGGTGTGACGGAT

SEQ ID NO. 115 (EcO-21F) - ATCCGTCACACCTGCTCTGCACGGGCTCAGTTTGGCTT
TGTATCCTAAGAGAGATGGTGTTGGCTCCCGTAT

SEQ ID NO. 116 (EcO-21R) - ATACGGGAGCCAACACCATCTCTCTTAGGATACAAAG
CCAAACTGAGCCCGTGCAGAGCAGGTGTGACGGAT

SEQ ID NO. 117 (EcO-22F) - ATACGGGAGCCAACACCAGGGGTGGCGAACATGGTAT
AACTTGATAAGTGTGAAGAGCAGGTGTGACGGAT

SEQ ID NO. 118 (EcO-22R) - ATCCGTCACACCTGCTCTTCACACTTATCAAGTTATAC
CATGTTCGCCACCCCCTGGTGTTGGCTCCCGTAT

SEQ ID NO. 119 (EcO-23F) - ATACGGGAGCCAACACCACTCCGACACCGGCCGCCGG
CACCACCCACTCCCCCTAGAGCAGGTGTGACGGAT

SEQ ID NO. 120 (EcO-23R) - ATCCGTCACACCTGCTCTAGGGGGAGTGGGTGGTGCC
GGCGGCCGGTGTCGGAGTGGTGTTGGCTCCCGTAT

SEQ ID NO. 121 (EcO-24F) - ATACGGGAGCCAACACCATCCGGCGCGCCCTCCTCCC
CCACTGCTCCCCGCCCGAGAGCAGGTGTGACGGAT

SEQ ID NO. 122 (EcO-24R) - ATCCGTCACACCTGCTCTCGGGCGGGGAGCAGTGGGG
GAGGAGGGCGCGCCGGATGGTGTTGGCTCCCGTAT

SEQ ID NO. 123 (EcO-25F) - ATACGGGAGCCAACACCATACGCAGAGGTCCCCTACC
CAGGCCAGCCGGATGCCAGAGCAGGTGTGACGGAT

SEQ ID NO. 124 (EcO-25R) - ATCCGTCACACCTGCTCTGGCATCCGGCTGGCCTGGG
TAGGGGACCTCTGCGTATGGTGTTGGCTCCCGTAT

SEQ ID NO. 125 EcO-26 F - ATACGGGAGCCAACACCACGAGGATTACAACTTTATGC
GTGCAACCAGACACCAAGAGCAGGTGTGACGGAT

SEQ ID NO. 126 EcO-26 R - ATCCGTCACACCTGCTCTTGGTGTCTGGTTGCACGCATA
AAGTTGTAATCCTCGTGGTGTTGGCTCCCGTAT

SEQ ID NO. 127 EcO-27 F - ATACGGGAGCCAACACCATATAAACGAGGAAATAAAA
CTGCAGAACACTTCCTCAGAGCAGGTGTGACGGAT

SEQ ID NO. 128 EcO-27 R - ATCCGTCACACCTGCTCTGAGGAAGTGTTCTGCAGTTTT
ATTTCCTCGTTTATATGGTGTTGGCTCCCGTAT

SEQ ID NO. 129 EcO-28 F(71) - ATACGGGAGCCAACACCATCACGGCAATGTCCCGA
TAATGTCTTGCTTCAGCGAGAGCAGGTGTGACGGAT

SEQ ID NO. 130 EcO-28 R(71) - ATCCGTCACACCTGCTCTCGCTGAAGCAAGACATTA
TCGGGACATTGCCGTGATGGTGTTGGCTCCCGTAT

TABLE 1-continued

DNA ligand Sequence ID Nos.

SEQ ID NO. 131 EcO-29 F - ATACGGGAGCCAACACCAAGCAATCAGTATACCCACCC
GTCAAAAACATCATGCAGAGCAGGTGTGACGGAT

SEQ ID NO. 132 EcO-29 R - ATCCGTCACACCTGCTCTGCATGATGTTTTTGACGGGTG
GGTATACTGATTGCTTGGTGTTGGCTCCCGTAT

SEQ ID NO. 133 EcO-30 F - ATACGGGAGCCAACACCACGGCTTCTTGCGCCCCCCCG
CGCCCGCGCCCCCCCCAGAGCAGGTGTGACGGAT

SEQ ID NO. 134 EcO-30 R - ATCCGTCACACCTGCTCTGGGGGGGGCGCGGGCGCGG
GGGGGCGCAAGAAGCCGTGGTGTTGGCTCCCGTAT

SEQ ID NO. 135 EcO-31 F - ATACGGGAGCCAACACCAACGGAGGATGAAGAGATAA
AGTAAATATCCGGGGGCAGAGCAGGTGTGACGGAT

SEQ ID NO. 136 EcO-31 R - ATCCGTCACACCTGCTCTGCCCCCGGATATTTACTTTAT
CTCTTCATCCTCCGTTGGTGTTGGCTCCCGTAT

SEQ ID NO. 137 EcO-32 F - ATACGGGAGCCAACACCACCCGTGGCCTTCACCCAGCC
AGGGGCCCCGTCTCTGAGAGCAGGTGTGACGGAT

SEQ ID NO. 138 EcO-32 R - ATCCGTCACACCTGCTCTCAGAGACGGGGCCCCTGGCT
GGGTGAAGGCCACGGGTGGTGTTGGCTCCCGTAT

SEQ ID NO. 139 EcO-33 F - ATACGGGAGCCAACACCACACTACCGTCCCACCCCCTC
CCAGCTCCTCCGGCCGAGAGCAGGTGTGACGGAT

SEQ ID NO. 140 EcO-33 R - ATCCGTCACACCTGCTCTCGGCCGGAGGAGCTGGGAG
GGGGTGGGACGGTAGTGTGGTGTTGGCTCCCGTAT

SEQ ID NO. 141 EcO-34 F - ATACGGGAGCCAACACCAATCCCCCGCCTGCGACCGAT
GCACTCCCATATGTCGAGAGCAGGTGTGACGGAT

SEQ ID NO. 142 EcO-34 R - ATCCGTCACACCTGCTCTCGACATATGGGAGTGCATCG
G TCGCAGGCGGGGATTGGTGTTGGCTCCCGTAT

SEQ ID NO. 143 EcO-35 F - ATACGGGAGCCAACACCATACATGCCCAAGGTTTCGGG
TGAGGCTACCGTGAGTAGAGCAGGTGTGACGGAT

SEQ ID NO. 144 EcO-35 R - ATCCGTCACACCTGCTCTACTCACGGTAGCCTCACCCG
AAACCTTGGGCATGTATGGTGTTGGCTCCCGTAT

SEQ ID NO. 145 EcO-36 F - ATACGGGAGCCAACACCATTTATGTTTCATACTTTAAAC
TTGGTCGTTTGCGATAGAGCAGGTGTGACGGAT

SEQ ID NO. 146 EcO-36 R - ATCCGTCACACCTGCTCTATCGCAAACGACCAAGTTTA
AAGTATGAAACATAAATGGTGTTGGCTCCCGTAT

SEQ ID NO. 147 EcO-38 F - ATACGGGAGCCAACACCAGGCGTTTAATAATCGGAGCG
ACAAATTCTACGCTGTAGAGCAGGTGTGACGGAT

SEQ ID NO. 148 EcO-38 R - ATCCGTCACACCTGCTCTACAGCGTAGAATTTGTCGCT
CCGATTATTAAACGCCTGGTGTTGGCTCCCGTAT

SEQ ID NO. 149 EcO-40/41B F - ATACGGGAGCCAACACCACGGCAACTTCAAACCCA
AGACTAAGAAAAGCTCGTGAGAGCAGGTGTGACGGAT

SEQ ID NO. 150 EcO-40/41B R - ATCCGTCACACCTGCTCTCACGAGCTTTTCTTAGTC
TTGGGTTTGAAGTTGCCGTGGTGTTGGCTCCCGTAT

SEQ ID NO. 151 EcO-41A F - ATACGGGAGCCAACACCATTGTAGGCGGATATTAGAC
AAGACCGAATTCCATGGAGAGCAGGTGTGACGGAT

SEQ ID NO. 152 EcO-41A R - ATCCGTCACACCTGCTCTCCATGGAATTCGGTCTTGTC
TAATATCCGCCTACAATGGTGTTGGCTCCCGTAT

SEQ ID NO. 153 EcO-42/43A F - ATACGGGAGCCAACACCAGTAGGCTAAAGTGAGG
TTAATTATGTCGACAAGGCCAGAGCAGGTGTGACGGAT

SEQ ID NO. 154 EcO-42/43A R - ATCCGTCACACCTGCTCTGGCCTTGTCGACATAATT
AACCTCACTTTAGCCTACTGGTGTTGGCTCCCGTAT

SEQ ID NO. 155 EcO-43B F - ATACGGGAGCCAACACCACCTCGCCCAGACGCCGGG
CCCTCCCCGCCCCACCCCAGAGCAGGTGTGACGGAT

SEQ ID NO. 156 EcO-43B R - ATCCGTCACACCTGCTCTGGGGTGGGCGGGAGGG
CCCGGCGTCTGGGCGAGGTGGTGTTGGCTCCCGTAT

TABLE 1-continued

DNA ligand Sequence ID Nos.

SEQ ID NO. 157 EcO-44 F - ATACGGGAGCCAACACCAGGTATTGGAGCTATACACGT
TAACCACCGCTATTGCAGAGCAGGTGTGACGGAT

SEQ ID NO. 158 EcO-44 R - ATCCGTCACACCTGCTCTGCAATAGCGGTGGTTAACGT
GTATAGCTCCAATACCTGGTGTTGGCTCCCGTAT

SEQ ID NO. 159 EcO-45 F - ATACGGGAGCCAACACCACGCGGGGCGGGGGGCTGG
TCGCGCGGGCCTGGCGGAGAGCAGGTGTGACGGAT

SEQ ID NO. 160 EcO-45 F - ATCCGTCACACCTGCTCTCCGCCAGGCCCGCGCGACCA
GCCCCCCCGCCCCGCGTGGTGTTGGCTCCCGTAT

SEQ ID NO. 161 EcO-46 F - ATACGGGAGCCAACACCAAACATTGGAACAACAAACG
CTAATACACGATCGCATAGAGCAGGTGTGACGGAT

SEQ ID NO. 162 EcO-46 R - ATCCGTCACACCTGCTCTATGCGATCGTGTATTAGCGTT
TGTTGTTCCAATGTTTGGTGTTGGCTCCCGTAT

SEQ ID NO. 163 EcO-47 F - ATACGGGAGCCAACACCAATAGATGGATAAGGGGGA A
ACTGCCATTCGGTTAGTAGAGCAGGTGTGACGGAT

SEQ ID NO. 164 EcO-47 R - ATCCGTCACACCTGCTCTACTAACCGAATGGCAGTTTC
CCCCTTATCCATCTATTGGTGTTGGCTCCCGTAT

SEQ ID NO. 165 EcO-48 F - ATACGGGAGCCAACACCAACCAACGAAGAAGGGTCAG
ACAAAAAGGAGTTCTCGAGAGCAGGTGTGACGGAT

SEQ ID NO. 166 EcO-48 R - ATCCGTCACACCTGCTCTCGAGAACTCCTTTTTGTCTGA
CCCTTCTTCGTTGGTTGGTGTTGGCTCCCGTAT

SEQ ID NO. 167 EcO-49 F - ATACGGGAGCCAACACCACAACAGTCAGATTGCAACT
GAGTAGTACATACGTTAAGAGCAGGTGTGACGGAT

SEQ ID NO. 168 EcO-49 R - ATCCGTCACACCTGCTCTTAACGTATGTACTACTCAGTT
GCAATCTGACTGTTGTGGTGTTGGCTCCCGTAT

SEQ ID NO. 169 EcO-50 F - ATACGGGAGCCAACACCATAAACCAAGGGTGTAACAG
AAATGATGTGACCAGGCAGAGCAGGTGTGACGGAT

SEQ ID NO. 170 EcO-50 R - ATCCGTCACACCTGCTCTGCCTGGTCACATCATTTCTGT
TACACCCTTGGTTTATGGTGTTGGCTCCCGTAT

SEQ ID NO. 171 EcO-51 F - ATACGGGAGCCAACACCATCATTGCGACATTGAATTCA
GAAGGAGGAGTGGTGTAGAGCAGGTGTGACGGAT

SEQ ID NO. 172 EcO-51 R - ATCCGTCACACCTGCTCTACACCACTCCTCCTTCTGAAT
TCAATGTCGCAATGATGGTGTTGGCTCCCGTAT

SEQ ID NO. 173 EcO-52 F (71) - ATACGGGAGCCAACACCAGAGAATTACAACAGGTT
AAGTAGTGTGACGATCATAGAGCAGGTGTGACGGAT

SEQ ID NO. 174 EcO-52 R (71) - ATCCGTCACACCTGCTCTATGATCGTCACACTACT
TAACCTGTTGTAATTCTCTGGTGTTGGCTCCCGTAT

SEQ ID NO. 175 EcO-53 F - ATACGGGAGCCAACACCACGGCGGAACACATGGAACA
CCGAATAATGTGGCTTAAGAGCAGGTGTGACGGAT

SEQ ID NO. 176 EcO-53 R - ATCCGTCACACCTGCTCTTAAGCCACATTATTCGGTGTT
CCATGTGTTCCGCCGTGGTGTTGGCTCCCGTAT

SEQ ID NO. 177 EcO-54 F - ATACGGGAGCCAACACCAGCGTGGTGGACGTATAACAA
GACAGAAGTAACCCGTAGAGCAGGTGTGACGGAT

SEQ ID NO. 178 EcO-54 R - ATCCGTCACACCTGCTCTACGGGTTACTTCTGTCTTGTT
ATACGTCCACCACGCTGGTGTTGGCTCCCGTAT

SEQ ID NO. 179 EcO-55 R (71) - ATACGGGAGCCAACACCATGACAAACATCAATGCA
GCAAAGACTAGCAACGTGAGAGCAGGTGTGACGGAT

SEQ ID NO. 180 EcO-55 F (71) - ATCCGTCACACCTGCTCTCACGTTGCTAGTCTTTG
CTGCATTGATGTTTGTCATGGTGTTGGCTCCCGTAT

SEQ ID NO. 181 EcO-56 F (71) - ATACGGGAGCCAACACCAGCCGGCAATGGCTGAG
AGAGAATAGAGCGTGGTATAGAGCAGGTGTGACGGAT

SEQ ID NO. 182 EcO-56 R (71) - ATCCGTCACACCTGCTCTATACCACGCTCTATTCT
CTCTCAGCCATTGCCGGCTGGTGTTGGCTCCCGTAT

TABLE 1-continued

DNA ligand Sequence ID Nos.

SEQ ID NO. 183 EcO-57 F - ATACGGGAGCCAACACCAAGGGGCGGCGAGTCGTAG
CGTCGATAATACTGGACAGAGCAGGTGTGACGGAT

SEQ ID NO. 184 EcO-57 R - ATCCGTCACACCTGCTCTGTCCAGTATTATCGACGCTA
CGACTCGCCGCCCCTTGGTGTTGGCTCCCGTAT

SEQ ID NO. 185 EcO-58 F - ATACGGGAGCCAACACCAGCCCGGAGCCCTTCGTCTGC
CCGCAGTCCAGTGTATAGAGCAGGTGTGACGGAT

SEQ ID NO. 186 EcO-58 R - ATCCGTCACACCTGCTCTATACACTGGACTGCGGGCAG
ACGAAGGGCTCCGGGCTGGTGTTGGCTCCCGTAT

SEQ ID NO. 187 EcO-59 F - ATACGGGAGCCAACACCATCCGCGCCCCGCGGCATCC
GCTCACGCGTCCCGGCAGAGCAGGTGTGACGGAT

SEQ ID NO. 188 EcO-59 R - ATCCGTCACACCTGCTCTGCCGGGACGCGTGAGCGGAT
GCCGCGGGGCGCGGATGGTGTTGGCTCCCGTAT

SEQ ID NO. 189 EcO-60B F - ATACGGGAGCCAACACCATGCAGGACAAAGCGATGA
GATACGATCTACCGCTCGAGAGCAGGTGTGACGGAT

SEQ ID NO. 190 EcO-60B R - ATCCGTCACACCTGCTCTCGAGCGGTAGATCGTATCT
CATCGCTTTGTCCTGCATGGTGTTGGCTCCCGTAT

SEQ ID NO. 191 EcO-62 F - ATACGGGAGCCAACACCATGGAGAGGAAGACGGAAA
GTATGGAGTGGATGAAGGAGAGCAGGTGTGACGGAT

SEQ ID NO. 192 EcO-62 R - ATCCGTCACACCTGCTCTCCTTCATCCACTCCATACTTT
CCGTCTTCCTCTCCATGGTGTTGGCTCCCGTAT

SEQ ID NO. 193 EcO-63 F - ATACGGGAGCCAACACCACGAAGGAGTAAAGCATGCT
GTCCCTATGAGCTGGGAAGAGCAGGTGTGACGGAT

SEQ ID NO. 194 EcO-63 R - ATCCGTCACACCTGCTCTTCCCAGCTCATAGGGACAGC
ATGCTTTACTCCTTCGTGGTGTTGGCTCCCGTAT

SEQ ID NO. 195 EcO-64 F - ATACGGGAGCCAACACCACCCTGAGACATACCTAGTCA
AGTGGAACAGACAGGTAGAGCAGGTGTGACGGAT

SEQ ID NO. 196 EcO-64 R - ATCCGTCACACCTGCTCTACCTGTCTGTTCCACTTGACT
AGGTATGTCTCAGGGTGGTGTTGGCTCCCGTAT

SEQ ID NO. 197 EcO-65 F - ATACGGGAGCCAACACCAGTAGGGAGAAGTTCGAATG
AAAATACGCTACGAACAAGAGCAGGTGTGACGGAT

SEQ ID NO. 198 EcO-65 R - ATCCGTCACACCTGCTCTTGTTCGTAGCGTATTTTCATT
CGAACTTCTCCCTACTGGTGTTGGCTCCCGTAT

SEQ ID NO. 199 EcO-66 F - ATACGGGAGCCAACACCACTCCCTACCGGCTCTGCGGG
AAATATGTTTTGACCCAGAGCAGGTGTGACGGAT

SEQ ID NO. 200 EcO-66 R - ATCCGTCACACCTGCTCTGGGTCAAAACATATTTCCCG
CAGAGCCGGTAGGGAGTGGTGTTGGCTCCCGTAT

SEQ ID NO. 201 EcO-67 F - ATACGGGAGCCAACACCACCCGTGGCCTTCACCCAGCC
AGGGGCCCCGTCTCTGAGAGCAGGTGTGACGGAT

SEQ ID NO. 202 EcO-67 R - ATCCGTCACACCTGCTCTCAGAGACGGGCCCCTGGCT
GGGTGAAGGCCACGGGTGGTGTTGGCTCCCGTAT

SEQ ID NO. 203 EcO-68 F - ATACGGGAGCCAACACCACAAAGTCCTCCCCCCTGGGC
GCCTTCACCCCACTGCAGAGCAGGTGTGACGGAT

SEQ ID NO. 204 EcO-68 R - ATCCGTCACACCTGCTCTGCGGTGGGTGAAGGCGCCC
AGGGGGGAGGACTTTGTGGTGTTGGCTCCCGTAT

SEQ ID NO. 205 EcO-69 R - ATACGGGAGCCAACACCATGGTAGACAGCGTCGCCCT
GCCATCACTCCGGCCCCAGAGCAGGTGTGACGGAT

SEQ ID NO. 206 EcO-69 F - ATCCGTCACACCTGCTCTGGGGCCGGAGTGATGGCAGG
GCGACGCTGTCTACCATGGTGTTGGCTCCCGTAT

SEQ ID NO. 207 EcO-70 F - ATACGGGAGCCAACACCACGATCCCGGCGCGACGGAT
GTAAAATAAGTGTGCTCAGAGCAGGTGTGACGGAT

SEQ ID NO. 208 EcO-70 R - ATCCGTCACACCTGCTCTGAGCACACTTATTTTACATCC
GTCGCGCCGGGATCGTGGTGTTGGCTCCCGTAT

TABLE 1-continued

DNA ligand Sequence ID Nos.

SEQ ID NO. 209 EcO-71 F - ATACGGGAGCCAACACCAGGGAAGATATGCAACAGAT
GGTGGACCGTAGTATGGAGAGCAGGTGTGACGGAT

SEQ ID NO. 210 EcO-71 R - ATCCGTCACACCTGCTCTCCATACTACGGTCCACCATCT
GTTGCATATCTTCCCTGGTGTTGGCTCCCGTAT

SEQ ID NO. 211 EcO-72 F - ATACGGGAGCCAACACCACAGCAGGGTACTGTAGTGG
TGGGGGGCCGGTCCGGGAGAGCAGGTGTGACGGAT

SEQ ID NO. 212 EcO-72 R - ATCCGTCACACCTGCTCTCCCGGACCGGCCCCCCACCA
CTACAGTACCCTGCTGTGGTGTTGGCTCCCGTAT

SEQ ID NO. 213 EcO-73 F - ATACGGGAGCCAACACCAAGACGGACAGGGGACGTCG
GTGAAGCGACGGATTGGAGAGCAGGTGTGACGGAT

SEQ ID NO. 214 EcO-73 R - ATCCGTCACACCTGCTCTCCAATCCGTCGCTTCACCGA
CGTCCCCTGTCCGTCTTGGTGTTGGCTCCCGTAT

SEQ ID NO. 215 EcO-74 F - ATACGGGAGCCAACACCACACGAGCCAGGTAAAAGTA
AGCCACACAAAGTGCTCAGAGCAGGTGTGACGGAT

SEQ ID NO. 216 EcO-74 R - ATCCGTCACACCTGCTCTGAGCACTTTGTGTGGCTTACT
TTTACCTGGCTCGTGTGGTGTTGGCTCCCGTAT

SEQ ID NO. 217 EcO-75 F - ATACGGGAGCCAACACCACCACGCGACACCCCCTCCT
GTCCCCCGCCCGCTTCCAGAGCAGGTGTGACGGAT

SEQ ID NO. 218 EcO-75 R - ATCCGTCACACCTGCTCTGGAAGCGGGCGGGGGACAG
GAGGGGGTGTCGCGTGGTGGTGTTGGCTCCCGTAT

Aged *E. coli* (AEc; Greater than one month at 4° C.)

SEQ ID NO. 219 AEc-47F - ATACGGGAGCCAACACCATCGAGAAGCATTGATAACAA
AATTTAAACCCCTGCCAGAGCAGGTGTGACGGAT

SEQ ID NO. 220 AEc-47R - ATCCGTCACACCTGCTCTGGCAGGGGTTTAAATTTTGTT
ATCAATGCTTCTCGATGGTGTTGGCTCCCGTAT

SEQ ID NO. 221 AEc-48 F - ATACGGGAGCCAACACCATCGAGAAGCATTGATAACA
AAATTTAAACCCCTGCCAGAGCAGGTGTGACGGAT

SEQ ID NO. 222 AEc-48R - ATCCGTCACACCTGCTCTGGCAGGGGTTTAAATTTTGTT
ATCAATGCTTCTCGATGGTGTTGGCTCCCGTAT

SEQ ID NO. 223 AEc-49 F - ATACGGGAGCCAACACCAGGATCCGTAGAATGATTTA
AATAAACACGAACACATAGAGCAGGTGTGACGGAT

SEQ ID NO. 224 AEc-49R - ATCCGTCACACCTGCTCTATGTGTTCGTGTTTATTTAAA
TCATTCTACGGATCCTGGTGTTGGCTCCCGTAT

LPS Core Antigen DNA ligands

SEQ ID NO. 225 (Glucosamine(G)1F) - ATCCGTCACACCTGCTCTAATTAGGATACG
GGGCAACAGAACGAGAGGGGGGAATGGTGTTGGCTCCCGTAT SEQ ID NO. 226 (G2F) - ATCCGTCACACCTGCTCTCGGACCAGGTCAGACAAGCACAT
CGGATATCCGGCTGGTGTTGGCTCCCGTAT SEQ ID NO. 227 (G5F) - ATCCGTCACACCTGCTCTTGAGTCAAAGAGTTTAGGGAGGA
GCTAACATAACAGTGGTGTTGGCTCCCGTAT SEQ ID NO. 228 (G7F) - ATCCGTCACACCTGCTCTAACAACAATGCATCAGCGGGCTG
GGAACGCATGCGGTGGTGTTGGCTCCCGTAT SEQ ID NO. 229 (G8F) - ATCCGTCACACCTGCTCTGAACAGGTTATAAGCAGGAGTGA
TAGTTTCAGGATCTGGTGTTGGCTCCCGTAT SEQ ID NO. 230 (G9F) - ATCCGTCACACCTGCTCTCGGCGGCTCGCAAACCGAGTGGT
CAGCACCCGGGTTGGTGTTGGCTCCCGTAT SEQ ID NO. 231 (G10F) - ATCCGTCACACCTGCTCTGCGCAAGACGTAATCCACAAGA
CCGTGAAAACATAGTGGTGTTGGCTCCCGTAT SEQ ID NO. 232 (G1R) - ATACGGGAGCCAACACCATTCCCCCCTCTCGTTCTGTTGCC
CCGTATCCTAATTAGAGCAGGTGTGACGGAT SEQ ID NO. 233 (G2R) - ATACGGGAGCCAACACCAGCCGGATATCCGATGTGCTTGTC
TGACCTGGTCCGAGAGCAGGTGTGACGGAT TABLE 1-continued DNA ligand Sequence ID Nos.

SEQ ID NO. 234 (G5R) - ATACGGGAGCCAACACCACTGTTATGTTAGCTCCTCCCTAA
ACTCTTTGACTCAAGAGCAGGTGTGACGGAT

SEQ ID NO. 235 (G7R) - ATACGGGAGCCAACACCACCGCATGCGTTCCCAGCCCGCTG
ATGCATTGTTGTTAGAGCAGGTGTGACGGAT

SEQ ID NO. 236 (G8R) - ATACGGGAGCCAACACCAGATCCTGAAACTATCACTCCTG
CTTATAACCTGTTCAGAGCAGGTGTGACGGAT

SEQ ID NO. 237 (G9R) - ATACGGGAGCCAACACCAACCCGGGTGCTGACCACTCGGT
TTGCGAGCCGCCGAGAGCAGGTGTGACGGAT

SEQ ID NO. 238 (G10R) - ATACGGGAGCCAACACCACTATGTTTTCACGGTCTTGTGG
ATTACGTCTTGCGCAGAGCAGGTGTGACGGAT

SEQ ID NO. 239 (KDO (K) Antigen 2F) - ATCCGTCACACCTGCTCTAGGCGTAGTG
ACTAAGTCGCGCGAAAATCACAGCATTGGTGTTGGCTCCCGTAT SEQ ID NO. 240 (K5F) - ATCCGTCACACCTGCTCTCAGCGGCAGCTATACAGTGAGAA
CGGACTAGTGCGTTGGTGTTGGCTCCCGTAT SEQ ID NO. 241 (K7F) - ATCCGTCACACCTGCTCTGGCAAATAATACTAGCGATGATG
GATCTGGATAGACTGGTGTTGGCTCCCGTAT SEQ ID NO. 242 (K8F) - ATCCGTCACACCTGCTCTGGGGGTGCGACTTAGGGTAAGTG
GGAAAGACGATGCTGGTGTTGGCTCCCGTAT SEQ ID NO. 243 (K9F) - ATCCGTCACACCTGCTCTCAAGAGGAGATGAACCAATCTTA
GTCCGACAGGCGGTGGTGTTGGCTCCCGTAT SEQ ID NO. 244 (K10F) - ATCCGTCACACCTGCTCTGGCCCGGAATTGTCATGACGTC
ACCTACACCTCCTGTGGTGTTGGCTCCCGTAT SEQ ID NO. 245 (K2R) - ATACGGGAGCCAACACCAATGCTGTGATTTTCGCGCGACTT
AGTCACTACGCCTAGAGCAGGTGTGACGGAT SEQ ID NO. 246 (K5R) - ATACGGGAGCCAACACCAACGCACTAGTCCGTTCTCACTGT
ATAGCTGCCGCTGAGAGCAGGTGTGACGGAT SEQ ID NO. 247 (K7R) - ATACGGGAGCCAACACCAGTCTATCCAGATCCATCATCGC
TAGTATTATTTGCCAGAGCAGGTGTGACGGAT SEQ ID NO. 248 (K8R) - ATACGGGAGCCAACACCAGCATCGTCTTTCCCACTTACCCT
AAGTCGCACCCCCAGAGCAGGTGTGACGGAT SEQ ID NO. 249 (K9R) - ATACGGGAGCCAACACCACCGCCTGTCGGACTAAGATTGG
TTCATCTCCTCTTGAGAGCAGGTGTGACGGAT SEQ ID NO. 250 (K10R) - ATACGGGAGCCAACACCACAGGAGGTGTAGGTGACGTCA
TGACAATTCCGGGCCAGAGCAGGTGTGACGGAT SEQ ID NO. 251 (Whole LPS from E. coli O111:B4 (L)1F) - ATCCGTCAC
CCCTGCTCTCGTCGCTATGAAGTAACAAAGATAGGAGCAATCGGGTGGTGTTGGCTCCCGTAT SEQ ID NO. 252 (L3F) - ATCCGTCACACCTGCTCTAACGAAGACTGAAACCAAAGCAG
TGACAGTGCTGAATGGTGTTGGCTCCCGTAT SEQ ID NO. 253 (L4F) - ATCCGTCACACCTGCTCTCGGTGACAATAGCTCGATCAGCC
C AAAGTCGTCAGATGGTGTTGGCTCCCGTAT SEQ ID NO. 254 (L6F) - ATCCGTCACACCTGCTCTAACGAAATAGACCACAAATCGAT
ACTTTATGTTATTGGTGTTGGCTCCCGTAT (71)

SEQ ID NO. 255 (L7F) - ATCCGTCACACCTGCTCTGTCGAATGCTCTGCCTGGAAGAG
TTGTTAGCAGGGATGGTGTTGGCTCCCGTAT

SEQ ID NO. 256 (L8F) - ATCCGTCACACCTGCTCTTAAGCCGAGGGGTAAATCTAGGA
CAGGGGTCCATGATGGTGTTGGCTCCCGTAT

SEQ ID NO. 256 (L9F) - ATCCGTCACACCTGCTCTACTGGCCGGCTCAGCATGACTAA
GAAGGAAGTTATGTGGTGTTGGCTCCCGTAT

SEQ ID NO. 258 (L10F) - ATCCGTCACACCTGCTCTGGTACGAATCACAGGGGATGCT
GGAAGCTTGGCTCTTGGTGTTGGCTCCCGTAT

SEQ ID NO. 259 (L1R) - ATACGGGAGCCAACACCACCCGATTGCTCCTATCTTTGTTA
CTTCATAGCGACGAGAGCAGGGGTGACGGAT

TABLE 1-continued

DNA ligand Sequence ID Nos.

SEQ ID NO. 260 (L3R) - ATACGGGAGCCAACACCATTCAGCACTGTCACTGCTTTGGT
TTCAGTCTTCGTTAGAGCAGGTGTGACGGAT

SEQ ID NO. 261 (L4R) - ATACGGGAGCCAACACCATCTGACGACTTTGGGCTGATCGA
GCTATTGTCACCGAGAGCAGGTGTGACGGAT

SEQ ID NO. 262 (L6R) - ATACGGGAGCCAACACCAATAACATAAAGTATCGATTTGTG
GTCTATTTCGTTAGAGCAGGTGTGACGGAT

SEQ ID NO. 263 (L7R) - ATACGGGAGCCAACACCATCCCTGCTAACAACTCTTCCAGG
CAGAGCATTCGACAGAGCAGGTGTGACGGAT

SEQ ID NO. 264 (L8R) - ATACGGGAGCCAACACCATCATGGACCCCTGTCCTAGATTT
ACCCCTCGGCTTAAGAGCAGGTGTGACGGAT

SEQ ID NO. 265 (L9R) - ATACGGGAGCCAACACCACATAACTTCCTTCTTAGTCATGC
TGAGCCGGCCAGTAGAGCAGGTGTGACGGAT

SEQ ID NO. 266 (L10R) - ATACGGGAGCCAACACCAAGAGCCAAGCTTCCAGCATCCC
CTGTGATTCGTACCAGAGCAGGTGTGACGGAT

SEQ ID NO. 267 (Rough (Ra or R) Core LPS Antigens R1F) - ATCCGTC
ACACCTGCTCTCCGCACGTAGGACCACTTTGGTACACGCTCCCGTAGTGGTGTTGGCTCCCGTAT SEQ ID NO. 268 (R5F) - ATCCGTCACACCTGCTCTACGGATGAACGAAGATTTTAAAG
TCAAGCTAATGCATGGTGTTGGCTCCCGTAT SEQ ID NO. 269 (R6F) - ATCCGTCACACCTGCTCTGTAGTGAAGAGTCCGCAGTCCAC
GCTGTTCAACTCATGGTGTTGGCTCCCGTAT SEQ ID NO. 270 (R7F) - ATCCGTCACACCTGCTCTACCGGCTGGCACGGTTATGTGTGA
CGGGCGAAGATATGGTGTTGGCTCCCGTAT SEQ ID NO. 271 (R9F) - ATCCGTCACACCTGCTCTGCGTGTGGAGCGCCTAGGTGAGT
GGTGTTGGCTCCCGTAT SEQ ID NO. 272 (R10F) - ATCCGTCACACCTGCTCTGATGTCCCTTTGAAGAGTTCCAT
GACGCTGGCTCCTTGGTGTTGGCTCCCGTAT SEQ ID NO. 273 (R1R) - ATACGGGAGCCAACACCACTACGGGAGCGTGTACCAAAGT
GGTCCTACGTGCGGAGAGCAGGTGTGACGGAT SEQ ID NO. 274 (R5R) - ATACGGGAGCCAACACCATGCATTAGCTTGACTTTAAAATC
TTCGTTCATCCGTAGAGCAGGTGTGACGGAT SEQ ID NO. 275 (R6R) - ATACGGGAGCCAACACCATGAGTTGAACAGCGTGGACTGC
GGACTCTTCACTACAGAGCAGGTGTGACGGAT SEQ ID NO. 276 (R7R) - ATACGGGAGCCAACACCATATCTTCGCCCGTCACACATAAC
CGTGCCAGCCGGTAGAGCAGGTGTGACGGAT SEQ ID NO. 277 (R9R) - ATACGGGAGCCAACACCACTCACCTAGGCGCTCCACACGC
AGAGCAGGTGTGACGGAT SEQ ID NO. 278 (R10R) - ATACGGGAGCCAACACCAAGGAGCCAGCGTCATGGAACTC
TTCAAAGGGACATCAGAGCAGGTGTGACGGAT Listeriolysin (A surface protein on *Listeria monocytogenes*) DNA
ligands SEQ ID NO. 279 (LO-10F) - ATCCGTCACACCTGCTCTGCCGGACCATCCAATATCAGC
TGTGGTGTTGGCTCCCGTAT SEQ ID NO. 280 (LO-11F) - ATCCGTCACACCTGCTCTGGTGGAATGGACTAAGCTAGC
TAGCGTTTTAAAAGGTGGTGTTGGCTCCCGTAT SEQ ID NO. 281 (LO-13F) - ATCCGTCACACCTGCTCTTAAAGTAGAGGCTGTTCTCCA
GACGTCGCAGGAGGATGGTGTTGGCTCCCGTAT SEQ ID NO. 282 (LO-15F) - ATCCGTCACACCTGCTCTGTAGATGGCAAGGCATAAGCG
TCCGGAACGATAGAATGGTGTTGGCTCCCGTAT SEQ ID NO. 283 (LO-16F) - ATCCGTCACACCTGCTCTGTAGATGGCAAGGCATAAGCG
TCCGGAACGATAGAATGGTGTTGGCTCCCGTAT SEQ ID NO. 284 (LO-17F) - ATACGGGAGCCAACACCACAGCTGATATTGGATGGTCC
GGCAGAGCAGGTGTGACGGAT TABLE 1-continued DNA ligand Sequence ID Nos.

SEQ ID NO. 285 (LO-19F) - ATCCGTCACACCTGCTCTTGGGCAGGAGCGAGAGACTCT
AATGGTAAGCAAGAATGGTGTTGGCTCCCGTAT

SEQ ID NO. 286 (LO-20F) - ATCCGTCACACCTGCTCTCCAACAAGGCGACCGACCGCA
TGCAGATAGCCAGGTTGGTGTTGGCTCCCGTAT

SEQ ID NO. 287 (LO-10R) - ATACGGGAGCCAACACCACAGCTGATATTGGATGGTCC
GGCAGAGCAGGTGTGACGGAT

SEQ ID NO. 288 (LO-11R) - ATACGGGAGCCAACACCACCTTTTAAAACGCTAGCTAG
CTTAGTCCATTCCACCAGAGCAGGTGTGACGGAT

SEQ ID NO. 289 (LO-13R) - ATACGGGAGCCAACACCATCCTCCTGCGACGTCTGGAGA
ACAGCCTCTACTTTAAGAGCAGGTGTGACGGAT

SEQ ID NO. 290 (LO-15R) - ATACGGGAGCCAACACCATTCTATCGTTCCGGACGCTTA
TGCCTTGCCATCTACAGAGCAGGTGTGACGGAT

SEQ ID NO. 291 (LO-16R) - ATACGGGAGCCAACACCATTCTATCGTTCCGGACGCTTA
TGCCTTGCCATCTACAGAGCAGGTGTGACGGAT

SEQ ID NO. 292 (LO-17R) - ATCCGTCACACCTGCTCTGCCGGACCATCCAATATCAGC
TGTGGTGTTGGCTCCCGTAT

SEQ ID NO. 293 (LO-19R) - ATACGGGAGCCAACACCATTCTTGCTTACCATTAGAGTC
TCTCGCTCCTGCCCAAGAGCAGGTGTGACGGAT

SEQ ID NO. 294 (LO-20R) - ATACGGGAGCCAACACCAACCTGGCTATCTGCATGCGGT
CGGTCGCCTTGTTGGAGAGCAGGTGTGACGGAT

Listeriolysin (Alternate form of Listeria surface protein
designated "Pest-Free") DNA ligands SEQ ID NO. 295 (LP-3F) - ATCCGTCACACCTGCTCTGTAGATGGCAAGGCATAAGCGT
CCGGAACGATAGAATGGTGTTGGCTCCCGTAT SEQ ID NO. 296 (LP-11F) - ATCCGTCACACCTGCTCTAACCAAAAGGGTAGGAGACCA
AGCTAGCGATTTGGATGGTGTTGGCTCCCGTAT SEQ ID NO. 297 (LP-13F) - ATCCGTCACACCTGCTCTGCCGGACCATCCAATATCAGCT
GTGGTGTTGGCTCCCGTAT SEQ ID NO. 298 (LP-14F) - ATCCGTCACACCTGCTCTGAAGCCTAACGGAGAAGATGG
CCCTACTGCCGTAGGTGGTGTTGGCTCCCGTAT SEQ ID NO. 299 (LP-15F) - ATCCGTCACACCTGCTCTACTAAACAAGGGCAAACTGTA
AACACAGTAGGGGCGTGGTGTTGGCTCCCGTAT SEQ ID NO. 300 (LP-17F) - ATCCGTCACACCTGCTCTGGTGTTGGCTCCCGTATAGCTT
GGCTCCCGTATGGTGTTGGCTCCCGTAT SEQ ID NO. 301 (LP-18F) - TCCGTCACACCTGCTCTGTCGCGATGATGAGCAGCAGCG
CAGGAGGGAGGGGTGGTGTTGGCTCCCGTAT SEQ ID NO. 302 (LP-20F) - ATCCGTCACACCTGCTCTGATCAGGGAAGACGCCAACAC
TGGTGTTGGCTCCCGTAT SEQ ID NO. 303 (LP-3R) - ATACGGGAGCCAACACCATTCTATCGTTCCGGACGCTTA
TGCCTTGCCATCTACAGAGCAGGTGTGACGGAT SEQ ID NO. 304 (LP-11R) - ATACGGGAGCCAACACCATCCAAATCGCTAGCTTGGTC
TCCTACCCTTTTGGTTAGAGCAGGTGTGACGGAT SEQ ID NO. 305 (LP-13R) - ATACGGGAGCCAACACCACAGCTGATATTGGATGGTCCG
GCAGAGCAGGTGTGACGGAT SEQ ID NO. 306 (LP-14R) - ATACGGGAGCCAACACCACCTACGGCAGTAGGGCCATC
TTCTCCGTTAGGCTTCAGAGCAGGTGTGACGGAT SEQ ID NO. 307 (LP-15R) - ATACGGGAGCCAACACCACGCCCCTACTGTGTTTACAG
TTTGCCCTTGTTTAGTAGAGCAGGTGTGACGGAT SEQ ID NO. 308 (LP-17R) - ATACGGGAGCCAACACCATACGGGAGCCAAGCTATACG
GGAGCCAACACCAGAGCAGGTGTGACGGAT SEQ ID NO. 309 (LP-18R) - ATACGGGAGCCAACACCACCCCCTCCCTCCTGCGCTGCT
GCTCATCATCGCGACAGAGCAGGTGTGACGGAT TABLE 1-continued DNA ligand Sequence ID Nos.

SEQ ID NO. 310 (LP-20R) - ATACGGGAGCCAACACCAGTGTTGGCGTCTTCCCTGATC
AGAGCAGGTGTGACGGAT

*Listeria monocytogenes* Whole Cell (LmW)

SEQ ID NO. 311 LmW-2 F - ATACGGGAGCCAACACCAATACCTGTAAAAGTCTGAG
AAGTGGAGTAACCTAGAGAGCAGGTGTGACGGAT (71)

SEQ ID NO. 312 LmW-2 R - ATCCGTCACACCTGCTCTCTAGGTTACTCCACTTCTCA
GACTTTTACAGGTATTGGTGTTGGCTCCCGTAT (71)

SEQ ID NO. 313 LmW-3 F - ATACGGGAGCCAACACCACCGACCAACAGTAATAGCC
TAAAAGAGTTATGCGCTAGAGCAGGTGTGACGGAT

SEQ ID NO. 314 LmW-3 R - ATCCGTCACACCTGCTCTAGCGCATAACTCTTTTAGGCT
ATTACTGTTGGTCGGTGGTGTTGGCTCCCGTAT

SEQ ID NO. 315 LmW-5 F - ATACGGGAGCCAACACCAGGTGGACTATATATGAAGTT
AGTGAGCTTTAACAGGAGAGCAGGTGTGACGGAT

SEQ ID NO. 316 LmW-5 R - ATCCGTCACACCTGCTCTCCTGTTAAAGCTCACTAACT
TCATATATAGTCCACCTGGTGTTGGCTCCCGTAT

SEQ ID NO. 317 LmW-8 F - ATACGGGAGCCAACACCACAGGAGAGGCAGTAAAAG
GGTTGGCTGCCTGGGTAGAGAGCAGGTGTGACGGAT

SEQ ID NO. 318 LmW-8 R - ATCCGTCACACCTGCTCTCTACCCAGGCAGCCAACCCT
TTTACTGCCTCTCCTGTGGTGTTGGCTCCCGTAT

SEQ ID NO. 319 LmW-9 F - ATACGGGAGCCAACACCATTAGCAAGGTAAGAACAGT
TTTAATACATGCCTTCCAGAGCAGGTGTGACGGAT

SEQ ID NO. 320 LmW-9 R - ATCCGTCACACCTGCTCTGGAAGGCATGTATTAAAACT
GTTCTTACCTTGCTAATGGTGTTGGCTCCCGTAT

SEQ ID NO. 321 LmW-10 F - ATACGGGAGCCAACACCATAACAAATAACCACCCTC
AATGCTAGATAGTGGCTTAGAGCAGGTGTGACGGAT

SEQ ID NO. 322 LmW-10 R - ATCCGTCACACCTGCTCTAAGCCACTATCTAGCATTGA
GGGTGGTTATTTGTTATGGTGTTGGCTCCCGTAT

SEQ ID NO. 323 LmW-11 F - ATACGGGAGCCAACACCAGGAACATGATAAGTGAGA
AGTGCGACGTTAGCTTATAGAGCAGGTGTGACGGAT

SEQ ID NO. 324 LmW-11 R - ATCCGTCACACCTGCTCTATAAGCTAACGTCGCACTTC
TCACTTATCATGTTCCTGGTGTTGGCTCCCGTAT

SEQ ID NO. 325 LmW-12 F - ATACGGGAGCCAACACCAAAAGGGTGTTCATACGGA
ATGTAGATCGCCTAAGTGAGAGCAGGTGTGACGGAT

SEQ ID NO. 326 LmW-12 R - ATCCGTCACACCTGCTCTCACTTAGGCGATCTACATTC
CGTATGAACACCCTTTTGGTGTTGGCTCCCGTAT

SEQ ID NO. 327 LmW-13 F - ATACGGGAGCCAACACCATGAGCACCGGCAAACGCG
TAGGTTAAGCTACATGACAGAGCAGGTGTGACGGAT

SEQ ID NO. 328 LmW-13 R - ATCCGTCACACCTGCTCTGTCATGTAGCTTAACCTACG
CGTTTGCCGGTGCTCATGGTGTTGGCTCCCGTAT

SEQ ID NO. 329 LmW-14 F - ATACGGGAGCCAACACCATGATTAGATACTGCCTAGC
TGTGTGCTCGTTGGGGGAGAGCAGGTGTGACGGAT

SEQ ID NO. 330 LmW-14 R - ATCCGTCACACCTGCTCTCCCCCAACGAGCACACAGC
TAGGCAGTATCTAATCATGGTGTTGGCTCCCGTAT

SEQ ID NO. 331 LmW-19 F - ATACGGGAGCCAACACCAGGAGGAAGGTCAGCGTTC
TTCACGTGGCTAGGGGCAGAGCAGGTGTGACGGAT

SEQ ID NO. 332 LmW-19 R - ATCCGTCACACCTGCTCTGCCCCCTAGCCACGTGAAG
AACGCTGACCTTCCTCCTGGTGTTGGCTCCCGTAT

SEQ ID NO. 333 LmW-22 F - ATACGGGAGCCAACACCAACTGAGCTATATCTAGATC
GACTTACACATACACGTAGAGCAGGTGTGACGGAT

SEQ ID NO. 334 LmW-22 R - ATCCGTCACACCTGCTCTACGTGTATGTGTAAGTCGAT
CTAGATATAGCTCAGTTGGTGTTGGCTCCCGTAT

TABLE 1-continued

DNA ligand Sequence ID Nos.

SEQ ID NO. 335 LmW-23 F - ATACGGGAGCCAACACCAGAGACGTGTGAAGTCCAG
G CAGGGTGCCTTCTGTCGAGAGCAGGTGTGACGGAT

SEQ ID NO. 336 LmW-23 R - ATCCGTCACACCTGCTCTCGACAGAAGGCACCCTGCC
TGGACTTCACACGTCTCTGGTGTTGGCTCCCGTAT

SEQ ID NO. 337 LmW-24 F - ATACGGGAGCCAACACCATCAAGTGGTGAGCGCCTCG
TCGGGAACTGCCGTGCGAGAGCAGGTGTGACGGAT

SEQ ID NO. 338 LmW-24 R - ATCCGTCACACCTGCTCTCGCACGGCAGTTCCCGACG
AGGCGCTCACCACTTGATGGTGTTGGCTCCCGTAT

SEQ ID NO. 339 LmW-25 F - ATACGGGAGCCAACACCACCGCTGAAACCTCTCCGCC
GTCCCGCCCTCCTCCCCAGAGCAGGTGTGACGGAT

SEQ ID NO. 340 LmW-25 R - ATCCGTCACACCTGCTCTGGGGAGGAGGGCGGGACGG
CGGAGAGGTTTCAGCGGTGGTGTTGGCTCCCGTAT

SEQ ID NO. 341 LmW-27 F - ATACGGGAGCCAACACCAGGAGATGGTAGCACTAAA
ATACGACGTATGCTGTGTAGAGCAGGTGTGACGGAT

SEQ ID NO. 342 LmW-27 R - ATCCGTCACACCTGCTCTACACAGCATACGTCGTATTT
TAGTGCTACCATCTCCTGGTGTTGGCTCCCGTAT

SEQ ID NO. 343 LmW-28 F - ATACGGGAGCCAACACCAAATCGACCGGACTAATCCT
GTGACTCCCCTATGTCTAGAGCAGGTGTGACGGAT

SEQ ID NO. 344 LmW-28 R - ATCCGTCACACCTGCTCTAGACATAGGGGAGTCACAG
G ATTAGTCCGGTCGATTTGGTGTTGGCTCCCGTAT

SEQ ID NO. 345 LmW-30 F - ATACGGGAGCCAACACCAAATTCAATTGCGCACGTAA
GAATAGATAGGCTGACCAGAGCAGGTGTGACGGAT

SEQ ID NO. 346 LmW-30 R - ATCCGTCACACCTGCTCTGGTCAGCCTATCTATTCTTA
CGTGCGCAATTGAATTTGGTGTTGGCTCCCGTAT

SEQ ID NO. 347 LmW-31 F - ATACGGGAGCCAACACCACACACAGAGCGCCATGGA
CTCAGTCAGATGTGATGTAGAGCAGGTGTGACGGAT

SEQ ID NO. 348 LmW-31 R - ATCCGTCACACCTGCTCTACATCACATCTGACTGAGT
CCATGGCGCTCTGTGTGTGGTGTTGGCTCCCGTAT

SEQ ID NO. 349 LmW-32 F - ATACGGGAGCCAACACCATCCAATGAGGCCATGGACC
GGTAAACTCGGACGCGCAGAGCAGGTGTGACGGAT

SEQ ID NO. 350 LmW-32 R - ATCCGTCACACCTGCTCTGCGCGTCCGAGTTTACCGGT
CCATGGCCTCATTGGATGGTGTTGGCTCCCGTAT

SEQ ID NO. 351 LmW-33 F - ATACGGGAGCCAACACCAACCCCGGTACCATCCGAC
ACCACGAGCACCCGGACGAGAGCAGGTGTGACGGAT

SEQ ID NO. 352 LmW-33 R - ATCCGTCACACCTGCTCTCGTCCGGGTGCTCGTGGTGT
CGGATGGTACCGGGGTTGGTGTTGGCTCCCGTAT

SEQ ID NO. 353 LmW-34 F - ATACGGGAGCCAACACCAAGGCGAAACTATTCACAG
AGACTGATCCAGCAAGGTAGAGCAGGTGTGACGGAT

SEQ ID NO. 354 LmW-34 R - ATCCGTCACACCTGCTCTACCTTGCTGGATCAGTCTCT
GTGAATAGTTTCGCCTTGGTGTTGGCTCCCGTAT

SEQ ID NO. 355 LmW-35 F - ATACGGGAGCCAACACCAAACACATAGTCGTGGCAG
AACGAATACTTAGCGCGGAGAGCAGGTGTGACGGAT

SEQ ID NO. 356 LmW-35 R - ATCCGTCACACCTGCTCTCCGCGCTAAGTATTCGTTCT
GCCACGACTATGTGTTTGGTGTTGGCTCCCGTAT

SEQ ID NO. 357 LmW-36 F - ATACGGGAGCCAACACCAACACGATCGACGGCGCTT
GGTCCCTTACAACCCTGCAGAGCAGGTGTGACGGAT

SEQ ID NO. 358 LmW-36 R - ATCCGTCACACCTGCTCTGCAGGGTTGTAAGGGACCA
AGCGCCGTCGATCGTGTTGGTGTTGGCTCCCGTAT

SEQ ID NO. 359 LmW-37 F - ATACGGGAGCCAACACCAAACCAGGACTCTGTCGCTC
TAAACATGACCATCGATAGAGCAGGTGTGACGGAT

SEQ ID NO. 360 LmW-37 R - ATCCGTCACACCTGCTCTATCGATGGTCATGTTTAGA
GCGACAGAGTCCTGGTTTGGTGTTGGCTCCCGTAT

TABLE 1-continued

DNA ligand Sequence ID Nos.

SEQ ID NO. 361 LmW-39 F - ATACGGGAGCCAACACCACAACCACTGTAGGCTCAT
GTAACTACCCGTTGTTGAGAGCAGGTGTGACGGAT (71)

SEQ ID NO. 362 LmW-39 R - ATCCGTCACACCTGCTCTCAACAACGGGTAGTTACAT
GAGCCTACAGTGGTTGTGGTGTTGGCTCCCGTAT (71)

SEQ ID NO. 363 LmW-40 F - ATACGGGAGCCAACACCAGGGGACAAGCAGAACCGA
ACAGATTGCAACGTATCCAGAGCAGGTGTGACGGAT

SEQ ID NO. 364 LmW-40 R - ATCCGTCACACCTGCTCTGGATACGTTGCAATCTGTTC
GGTTCTGCTTGTCCCCTGGTGTTGGCTCCCGTAT

SEQ ID NO. 365 LmW-41 F - ATACGGGAGCCAACACCAGCGCTTGAACAACATAAT
GCCGCCCAAGACCTTGACAGAGCAGGTGTGACGGAT

SEQ ID NO. 366 LmW-41 R - ATCCGTCACACCTGCTCTGTCAAGGTCTTGGGCGGCA
TTATGTTGTTCAAGCGCTGGTGTTGGCTCCCGTAT

SEQ ID NO. 367 LmW-42 F - ATACGGGAGCCAACACCACAGTGCCTAGACTTTTACA
ATGAACCAATTGCTGGAAGAGCAGGTGTGACGGAT

SEQ ID NO. 368 LmW-42 R - ATCCGTCACACCTGCTCTTCCAGCAATTGGTTCATTGT
AAAAGTCTAGGCACTGTGGTGTTGGCTCCCGTAT

SEQ ID NO. 369 LmW-43 F - ATACGGGAGCCAACACCACCCACTCTCCCCCCGCTCC
CGCTCCCCCGCTCCGCGAGAGCAGGTGTGACGGAT

SEQ ID NO. 370 LmW-43 R - ATCCGTCACACCTGCTCTCGCGGAGCGGGGAGCGGG
AGCGGGGGAGAGTGGGTGGTGTTGGCTCCCGTAT

SEQ ID NO. 371 LmW-44 F - ATACGGGAGCCAACACCATCTAACAATCATACACTTG
GAAGGTGACTGTCCTGGAGAGCAGGTGTGACGGAT

SEQ ID NO. 372 LmW-44 R - ATCCGTCACACCTGCTCTCCAGGACAGTCACCTTCCA
AGTGTATGATTGTTAGATGGTGTTGGCTCCCGTAT

SEQ ID NO. 373 LmW-46 F - ATACGGGAGCCAACACCATGTCAGGACCTCCATCGCC
CGGGCCCGCCGCCGCTGAGAGCAGGTGTGACGGAT

SEQ ID NO. 374 LmW-46 R - ATCCGTCACACCTGCTCTCAGCGGCGGCGGGCCCGGG
CGATGGAGGTCCTGACATGGTGTTGGCTCCCGTAT

SEQ ID NO. 375 LmW-47 F - ATACGGGAGCCAACACCAGGCGACAGCCTGTGCGAGT
AAGATTGAATGGTAGGTAGAGCAGGTGTGACGGAT

SEQ ID NO. 376 LmW-47 R - ATCCGTCACACCTGCTCTACCTACCATTCAATCTTACT
CGCACAGGCTGTCGCCTGGTGTTGGCTCCCGTAT

SEQ ID NO. 377 LmW-49 F - ATACGGGAGCCAACACCATCTGTGTCAGTCTGGCCTG
TTTTTTATTCTCCGCGGAGAGCAGGTGTGACGGAT

SEQ ID NO. 378 LmW-49 R - ATCCGTCACACCTGCTCTCCGCGGAGAATAAAAAACA
GGCCAGACTGACACAGATGGTGTTGGCTCCCGTAT

SEQ ID NO. 379 LmW-50 F - ATACGGGAGCCAACACCAGCCAGGAAAACTATGAGG
CAAAAACACGATCCGGGTAGAGCAGGTGTGACGGAT

SEQ ID NO. 380 LmW-50 R - ATCCGTCACACCTGCTCTACCCGGATCGTGTTTTGCC
TCATAGTTTTCCTGGCTGGTGTTGGCTCCCGTAT

N-acetyl-glucosamine (NAG) Component of Bacterial Peptidoglycan
and Fungal Chitin SEQ ID NO. 381 NAG 13F - ATACGGGAGCCAACACCATAGAAGTATGTTGTTATTCTA
TGGAAATAAAACGACAGAGCAGGTGTGACGGAT SEQ ID NO. 382 NAG 13R - ATCCGTCACACCTGCTCTGTCGTTTTATTTCCATAGAATA
ACAACATACTTCTATGGTGTTGGCTCCCGTAT SEQ ID NO. 383 NAG 14F - ATACGGGAGCCAACACCATCCCGTTGTGATCAGAGAGC
ATGAAATGATGTTTTGAGAGCAGGTGTGACGGAT SEQ ID NO. 384 NAG 14R - ATCCGTCACACCTGCTCTCAAAACATCATTTCATGCTCT
CTGATCACAACGGGATGGTGTTGGCTCCCGTAT SEQ ID NO. 385 NAG 18F - ATACGGGAGCCAACACCATGCATGGGACCTGTTATCCTA
ACAAGCTGTCAAGGCAGAGCAGGTGTGACGGAT TABLE 1-continued DNA ligand Sequence ID Nos.

SEQ ID NO. 386 NAG 18R - ATCCGTCACACCTGCTCTGCCTTGACAGCTTGTTAGGAT
AACAGGTCCCATGCATGGTGTTGGCTCCCGTAT

SEQ ID NO. 387 NAG 20F - ATACGGGAGCCAACACCACAAAACGTTCCGAGGGAGTA
AGCACTTAATAATGTAGAGCAGGTGTGACGGAT (71)

SEQ ID NO. 388 NAG 20R - ATCCGTCACACCTGCTCTACATTATTAAGTGCTTACTCCC
TCGGAACGTTTTGTGGTGTTGGCTCCCGTAT (71)

SEQ ID NO. 389 NAG 21F - ATACGGGAGCCAACACCACGTCTTATAGATGTCTGTATT
GTTTATCGCTCGCCCAGAGCAGGTGTGACGGAT

SEQ ID NO. 390 NAG 21R - ATCCGTCACACCTGCTCTGGGCGAGCGATAAACAATACA
GACATCTATAAGACGTGGTGTTGGCTCCCGTAT

SEQ ID NO. 391 NAG 22F - ATACGGGAGCCAACACCACCATCTCTGGTGATAACCAGT
GATCTTAACTATAGCAGAGCAGGTGTGACGGAT

SEQ ID NO. 392 NAG 22R - ATCCGTCACACCTGCTCTGCTATAGTTAAGATCACTGGT
TATCACCAGAGATGGTGGTGTTGGCTCCCGTAT

SEQ ID NO. 393 NAG 23F - ATACGGGAGCCAACACCACCACCTCACTACAGTGATCTT
TTGCTCTGAATAGCCAGAGCAGGTGTGACGGAT

SEQ ID NO. 394 NAG 23R - ATCCGTCACACCTGCTCTGGCTATTCAGAGCAAAAGATC
ACTGTAGTGAGGTGGTGGTGTTGGCTCCCGTAT

SEQ ID NO. 395 NAG 25F - ATACGGGAGCCAACACCATGTCTCTTAGGATACAAAGCC
AAACTGAGCCCGTGCAGAGCAGGTGTGACGGAT

SEQ ID NO. 396 NAG 25R - ATCCGTCACACCTGCTCTGCACGGGCTCAGTTTGGCTTT
GTATCCTAAGAGACATGGTGTTGGCTCCCGTAT

SEQ ID NO. 397 NAG 26F - ATACGGGAGCCAACACCACCTCCAATAGCCAAAAGAAA
TCGCCAACTAACGGCAAGAGCAGGTGTGACGGAT

SEQ ID NO. 398 NAG 26R - ATCCGTCACACCTGCTCTTGCCGTTAGTTGGCGATTTCTT
TTGGCTATTGGAGGTGGTGTTGGCTCCCGTAT

SEQ ID NO. 399 NAG 30F - ATACGGGAGCCAACACCATCACTACTTTTATAATTTCATT
CTTCTGGCGTCCCTAGAGCAGGTGTGACGGAT

SEQ ID NO. 400 NAG 30R - ATCCGTCACACCTGCTCTAGGGACGCCAGAAGAATGAA
ATTATAAAAGTAGTGATGGTGTTGGCTCCCGTAT

N-acetyl-muramic acid (NAM) Component of Bacterial Peptidoglycan

SEQ ID NO. 401 NAM 23F - ATACGGGAGCCAACACCAACTGCCCACGCCGCGACCCC
GCGGCGCACCCAACCAAGAGCAGGTGTGACGGAT

SEQ ID NO. 402 NAM 23R - ATCCGTCACACCTGCTCTTGGTTGGGTGCGCCGCGGGG
TCGCGGCGTGGGCAGTTGGTGTTGGCTCCCGTAT

SEQ ID NO. 403 NAM 31F - ATACGGGAGCCAACACCAACGGTTACCAGGCGTGTTAA
GGATATATGCTGAACCAGAGCAGGTGTGACGGAT

SEQ ID NO. 404 NAM 31R - ATCCGTCACACCTGCTCTGGTTCAGCATATATCCTTAAC
ACGCCTGGTAACCGTTGGTGTTGGCTCCCGTAT

*Salmonella typhimurium* lipopolysaccharide (LPS) DNA ligands

SEQ ID NO. 405 (St-7F) - ATCCGTCACACCTGCTCTGTCCAAAGGCTACGCGTTAACGT
GGTGTTGGCTCCCGTAT

SEQ ID NO. 406 (St-10F) - ATCCGTCACACCTGCTCTGGAGCAATATGGTGGAGAAACG
TGGTGTTGGCTCCCGTAT

SEQ ID NO. 407 (St-11F) - ATCCGTCACACCTGCTCTGCCGGACCATCCAATATCAGCT
GTGGTGTTGGCTCCCGTAT

SEQ ID NO. 408 (St-15F) - ATCCGTCACACCTGCTCTGAACAGGATAGGGATTAGCGAG
TCAACTAAGCAGCATGGTGTTGGCTCCCGTAT

SEQ ID NO. 409 (St-16F) - ATCCGTCACACCTGCTCTGGCGGACAGGAAATAAGAATG
AACGCAAAATTTATCTGGTGTTGGCTCCCGTAT

SEQ ID NO. 410 (St-18F) - ATCCGTCACACCTGCTCTACGCAACGCGACAGGAACATTC
ATTATAGAATGTGTTGGTGTTGGCTCCCGTAT

TABLE 1-continued

DNA ligand Sequence ID Nos.

SEQ ID NO. 411 (St-19F) - ATCCGTCACACCTGCTCTCGGCTGCAATGCGGGAGAGTAG
GGGGGAACCAAACCTGGTGTTGGCTCCCGTAT

SEQ ID NO. 412 (St-20F) - ATCCGTCACACCTGCTCTATGACTGGAACACGGGTATCGA
TGATTAGATGTCCTTGGTGTTGGCTCCCGTAT

SEQ ID NO. 413 (St-7R) - ATACGGGAGCCAACACCACGTTAACGCGTAGCCTTTGGAC
AGAGCAGGTGTGACGGAT

SEQ ID NO. 414 (St-10R) - ATACGGGAGCCAACACCACGTTTCTCCACCATATTGCTCC
AGAGCAGGTGTGACGGAT

SEQ ID NO. 415 (St-11R) - ATACGGGAGCCAACACCACAGCTGATATTGGATGGTCCG
GCAGAGCAGGTGTGACGGAT

SEQ ID NO. 416 (St-15R) - ATACGGGAGCCAACACCATGCTGCTTAGTTGACTCGCTAA
TCCCTATCCTGTTCAGAGCAGGTGTGACGGAT

SEQ ID NO. 417 (St-16R) - ATACGGGAGCCAACACCAGATAAATTTTGCGTTCATTCTT
ATTTCCTGTCCGCCAGAGCAGGTGTGACGGAT

SEQ ID NO. 418 (St-18R) - ATACGGGAGCCAACACCAACACATTCTATAATGAATGTT
CCTGTCGCGTTGCGTAGAGCAGGTGTGACGGAT

SEQ ID NO. 419 (St-19R) - ATACGGGAGCCAACACCAGGTTTGGTTCCCCCCTACTCTC
CCGCATTGCAGCCGAGAGCAGGTGTGACGGAT

SEQ ID NO. 420 (St-20R) - ATACGGGAGCCAACACCAAGGACATCTAATCATCGATAC
CCGTGTTCCAGTCATAGAGCAGGTGTGACGGAT

*S. typhimurium* (*S. enterica* serovar *Typhimurium* type 13311)
OMPs - Fresh Bacteria SEQ ID NO. 421 (StO-2F) - ATACGGGAGCCAACACCAGATAAATTTTGCGTTCATTCT
TATTTCCTGTCCGCCAGAGCAGGTGTGACGGAT SEQ ID NO. 422 (StO-2R) - ATCCGTCACACCTGCTCTGGCGGACAGGAAATAAGAAT
GAACGCAAAATTTATCTGGTGTTGGCTCCCGTAT SEQ ID NO. 423 (StO-4F) - ATACGGGAGCCAACACCAGATAAATTTTGGTTCATTCTT
ATTTCCTGTCCGCCAGAGCAGGTGTGACGGAT (71)

SEQ ID NO. 424 (StO-4R) - ATCCGTCACACCTGCTCTGGCGGACAGGAAATAAGAAT
GAACCAAAATTTATCTGGTGTTGGCTCCCGTAT (71)

SEQ ID NO. 425 (StO-5F) - ATACGGGAGCCAACACCACGGGGCTACCAGCACCGTCA
CCCCTCATTCTGCCACAGAGCAGGTGTGACGGAT

SEQ ID NO. 426 (StO-5R) - ATCCGTCACACCTGCTCTGTGGCAGAATGAGGGGTGAC
GGTGCTGGTAGCCCCGTGGTGTTGGCTCCCGTAT

SEQ ID NO. 427 (StO-6F) - ATACGGGAGCCAACACCAAAAGATGGAAAACACTGGAA
GGAAAATGCGGTCAGAGCAGGTGTGACGGAT (69)

SEQ ID NO. 429 (StO-6R) - ATCCGTCACACCTGCTCTGACCGCATTTTCCTTCCAGTGT
TTTCCATCTTTTGGTGTTGGCTCCCGTAT (69)

SEQ ID NO. 429 (StO-7F) - ATACGGGAGCCAACACCACCGGGCCGATGGGCACCAGG
AACTCTCGGACGAGTGAGAGCAGGTGTGACGGAT

SEQ ID NO. 430 (StO-7R) - ATCCGTCACACCTGCTCTCACTCGTCCGAGAGTTCCTGG
TGCCCATCGGCCCGGTGGTGTTGGCTCCCGTAT

SEQ ID NO. 431 (StO-8F) - ATACGGGAGCCAACACCACAGCTGATATTGGATGGTCC
GGCAGAGCAGGTGTGACGGAT (59)

SEQ ID NO. 432 (StO-8R) - ATCCGTCACACCTGCTCTGCCGGACCATCCAATATCAGC
TGTGGTGTTGGCTCCCGTAT (59)

SEQ ID NO. 433 (StO-9F) - ATACGGGAGCCAACACCAGTCGAAAGGCGGCCGTCCAG
TCGAGTGATTTGACCTAGAGCAGGTGTGACGGAT

SEQ ID NO. 434 (StO-9R) - ATCCGTCACACCTGCTCTAGGTCAAATCACTCGACTGGA
CGGCCGCCTTTCGACTGGTGTTGGCTCCCGTAT

SEQ ID NO. 435 (StO-10F) - ATACGGGAGCCAACACCACGGGGCGTGCCGTCAAAAG
ACCGAGATGTGGCTGCGAGAGCAGGTGTGACGGAT

TABLE 1-continued

DNA ligand Sequence ID Nos.

SEQ ID NO. 436 (StO-10R) - ATCCGTCACACCTGCTCTCGCAGCCACATCTCGGTCTT
TTGACGGCACGCCCCGTGGTGTTGGCTCCCGTAT

SEQ ID NO. 437 (StO-11/13F) - ATACGGGAGCCAACACCACTAACTTGTTGCTGATCT
TATCCAGAGCAGGTGTGACGGAT (59)

SEQ ID NO. 438 (StO-11/13R) - ATCCGTCACACCTGCTCTGGATAAGATCAGCAACAA
GTTAGTGGTGTTGGCTCCCGTAT (59)

SEQ ID NO. 439 (StO-12F) - ATACGGGAGCCAACACCATTTAGCGTAGGGCTCGCTTA
T CATTTCTCATTCCCTAGAGCAGGTGTGACGGAT

SEQ ID NO. 440 (StO-12R) - ATCCGTCACACCTGCTCTAGGGAATGAGAAATGATAAG
CGAGCCCTACGCTAAATGGTGTTGGCTCCCGTAT

SEQ ID NO. 441 (StO-14F) - ATACGGGAGCCAACACCACCGCAACCCAAATCTCTACA
CGGATTATCGTCGAGCAGAGCAGGTGTGACGGAT

SEQ ID NO. 442 (StO-14R) - ATCCGTCACACCTGCTCTGCTCGACGATAATCCGTGTA
GAGATTTGGGTTGCGGTGGTGTTGGCTCCCGTAT

SEQ ID NO. 443 (StO-16F) - ATACGGGAGCCAACACCAACACATTCTATAATGAATGT
TCCTGTCGCGTTGCGTAGAGCAGGTGTGACGGAT

SEQ ID NO. 444 (StO-16R) - ATCCGTCACACCTGCTCTACGCAACGCGACAGGAACAT
TCATTATAGAATGTGTTGGTGTTGGCTCCCGTAT

SEQ ID NO. 445 (StO-17F) - ATACGGGAGCCAACACCAGCCTACCCCCCTGTACGAG
GGCCGCAACCACGTAGAGAGCAGGTGTGACGGAT

SEQ ID NO. 446 (StO-17R) - ATCCGTCACACCTGCTCTCTACGTGGTTGCGGCCCTCGT
ACAGGGGGGTAGGCTGGTGTTGGCTCCCGTAT

SEQ ID NO. 447 (StO-18F) - ATACGGGAGCCAACACCACATCTAGCACGAGACCCTAT
CCCAGAGCAGGTGTGACGGAT (59)

SEQ ID NO. 448 (StO-18R) - ATCCGTCACACCTGCTCTGGGATAGGGTCTCGTGCTAG
ATGTGGTGTTGGCTCCCGTAT (59)

SEQ ID NO. 449 (StO-19F) - ATACGGGAGCCAACACCAACAGCGACTCGAGTCTGAC
GACTCGCGGGGCAAATGAGAGCAGGTGTGACGGAT

SEQ ID NO. 450 (StO-19R) - ATCCGTCACACCTGCTCTCATTTGCCCCGCGAGTCGTC
AGACTCGAGTCGCTGTTGGTGTTGGCTCCCGTAT

SEQ ID NO. 451 (StO-20/24F) - ATACGGGAGCCAACACCATAGTGTTGGGCCAATACG
GTAACGTGTCCTTGGAGAGCAGGTGTGACGGAT (69)

SEQ ID NO. 452 (StO-20/24R) - ATCCGTCACACCTGCTCTCCAAGGACACGTTACCGT
ATTGGCCCAACACTATGGTGTTGGCTCCCGTAT (69)

SEQ ID NO. 453 (StO-21F) - ATACGGGAGCCAACACCACTAAGGAGAGGTCGCGACA
GACTCTTCTGGTCAAGGAGAGCAGGTGTGACGGAT

SEQ ID NO. 454 (StO-21R) - ATCCGTCACACCTGCTCTCCTTGACCAGAAGAGTCTGT
CGCGACCTCTCCTTAGTGGTGTTGGCTCCCGTATG

SEQ ID NO. 455 (StO-22F) - ATACGGGAGCCAACACCAACTTCGACTCAAAGAAGTCC
ACGTGAGACTGGTGGAAGAGCAGGTGTGACGGAT

SEQ ID NO. 456 (StO-22R) - ATCCGTCACACCTGCTCTTCCACCAGTCTCACGTGGAC
TTCTTTGAGTCGAAGTTGGTGTTGGCTCCCGTAT

SEQ ID NO. 457 (StO-23F) - ATACGGGAGCCAACACCACCCGGGGAGACCCGCACGG
GCGCACAATCCTTGTCGAGAGCAGGTGTGACGGAT

SEQ ID NO. 458 (StO-23R) - ATCCGTCACACCTGCTCTCGACAAGGATTGTGCGCCCG
TGCGGGTCTCCCCGGGTGGTGTTGGCTCCCGTAT

SEQ ID NO. 459 (StO-25F) - ATACGGGAGCCAACACCAGCTGGACCAAACTACGCCC
ATTGTGGGGGTCCCCGGAGAGCAGGTGTGACGGAT

TABLE 1-continued

DNA ligand Sequence ID Nos.

SEQ ID NO. 460 (StO-25R) - ATCCGTCACACCTGCTCTCCGGGGACCCCCACAATGGG
CGTAGTTTGGTCCAGCTGGTGTTGGCTCCCGTAT

*S. typhimurium* (*S. enterica* serovar *Typhimurium* type 13311)
Whole Cell DNA Ligands SEQ ID NO. 461 StW-4/14/24/26/39/72 F - ATACGGGAGCCAACACCATAGTGTT
GGGCCAATACGGTAACGTGTCCTTGGAGAGCAGGTGTGACGGAT (69)

SEQ ID NO. 462 StW-4/14/24/26/39/72 R - ATCCGTCACACCTGCTCTCCAAGGAC
ACGTTACCGTATTGGCCCAACACTATGGTGTTGGCTCCCGTAT (69)

SEQ ID NO. 463 StW-7 F - ATACGGGAGCCAACACCAGTGGGACCTACGGCCTTTGG
CCCGCTGTTACAACGTAGAGCAGGTGTGACGGAT

SEQ ID NO. 464 StW-7 R - ATCCGTCACACCTGCTCTACGTTGTAACAGCGGGCCAAA
GGCCGTAGGTCCCACTGGTGTTGGCTCCCGTAT

SEQ ID NO. 465 StW-9 F - ATACGGGAGCCAACACCACTTACGCATCAGCCACTCGA
GAGACGGCGTTATGGCAGAGCAGGTGTGACGGAT

SEQ ID NO. 466 StW-9 R - ATCCGTCACACCTGCTCTGCCATAACGCCGTCTCTCGAG
TGGCTGATGCGTAAGTGGTGTTGGCTCCCGTAT

SEQ ID NO. 467 StW-11 F - ATACGGGAGCCAACACCACTATAGGGTGTAGCTGATC
CGCTCCCTTCTCCCAGGAGAGCAGGTGTGACGGAT

SEQ ID NO. 468 StW-11 R - ATCCGTCACACCTGCTCTCCTGGGAGAAGGGAGCGGAT
CAGCTACACCCTATAGTGGTGTTGGCTCCCGTAT

SEQ ID NO. 469 StW-12 F - ATACGGGAGCCAACACCAGAACACCTAGAGACTAGTT
CGTGTCGGCCCAGCGTGAGAGCAGGTGTGACGGAT

SEQ ID NO. 470 StW-12 R - ATCCGTCACACCTGCTCTCACGCTGGGCCGACACGAAC
TAGTCTCTAGGTGTTCTGGTGTTGGCTCCCGTAT

SEQ ID NO. 471 StW-16 F - ATACGGGAGCCAACACCATAAGAACCACCATTCCGCGT
TCGCCTCCCGAGGTGTAGAGCAGGTGTGACGGAT

SEQ ID NO. 472 StW-16 R - ATCCGTCACACCTGCTCTACACCTCGGGAGGCGAACGC
GGAATGGTGGTTCTTATGGTGTTGGCTCCCGTAT

SEQ ID NO. 473 StW-19 F - ATACGGGAGCCAACACCAGGCCATAGGCAATTTCATAT
AGCAACTGGTGAGCGTAGAGCAGGTGTGACGGAT

SEQ ID NO. 474 StW-19 R - ATCCGTCACACCTGCTCTACGCTCACCAGTTGCTATAT
GAAATTGCCTATGGCCTGGTGTTGGCTCCCGTAT

SEQ ID NO. 475 StW-20 F - ATACGGGAGCCAACACCAACAGAAGTCGACCCTGGTA
ATCATGCTCTCTCACGGAGAGCAGGTGTGACGGAT

SEQ ID NO. 476 StW-20 R - ATCCGTCACACCTGCTCTCCGTGAGAGCATGATTAC
CAGGGTCGACTTCTGTTGGTGTTGGCTCCCGTAT

SEQ ID NO. 477 StW-22 F - ATACGGGAGCCAACACCACCAACACCTGGAGAACTTG
AAACGCAGATGGTCCCCAGAGCAGGTGTGACGGAT

SEQ ID NO. 478 StW-22 R - ATCCGTCACACCTGCTCTGGGGACCATCTGCGTTTCAA
GTTCTCCAGGTGTTGGTGGTGTTGGCTCCCGTAT

SEQ ID NO. 479 StW-23 F - ATACGGGAGCCAACACCAGGTAGCGACATGACAGTAC
CACTTACAGGACGTGCCAGAGCAGGTGTGACGGAT

SEQ ID NO. 480 StW-23 R - ATCCGTCACACCTGCTCTGGCACGTCCTGTAAGTGGTA
CTGTCATGTCGCTACCTGGTGTTGGCTCCCGTAT

SEQ ID NO. 481 StW-25 F - ATACGGGAGCCAACACCAATGACGTAAACACAAACGG
CGGACCCAATCGTGTTCAGAGCAGGTGTGACGGAT

SEQ ID NO. 482 StW-25 R - ATCCGTCACACCTGCTCTGAACACGATTGGGTCCGCCG
TTTGTGTTTACGTCATTGGTGTTGGCTCCCGTAT

SEQ ID NO. 483 StW-27 F - ATACGGGAGCCAACACCATGCTCCAGCATATTGATTAA
TGCCAAGAGTTGGAACAGAGCAGGTGTGACGGAT

SEQ ID NO. 484 StW-27 R - ATCCGTCACACCTGCTCTGTTCCAACTCTTGGCATTAAT
CAATATGCTGGAGCATGGTGTTGGCTCCCGTAT

TABLE 1-continued

DNA ligand Sequence ID Nos.

SEQ ID NO. 485 StW-29 F - ATACGGGAGCCAACACCATGTGGTTCAGATGCGCCATA
TCTAGACGGTCTCTGTAGAGCAGGTGTGACGGAT

SEQ ID NO. 486 StW-29 R - ATCCGTCACACCTGCTCTACAGAGACCGTCTAGATATG
GCGCATCTGAACCACATGGTGTTGGCTCCCGTAT

SEQ ID NO. 487 StW-30 F - ATACGGGAGCCAACACCAAACCCCATTCTGTCACAGCG
CCACCCAACGAGTGTTAGAGCAGGTGTGACGGAT

SEQ ID NO. 488 StW-30 R - ATCCGTCACACCTGCTCTAACACTCGTTGGGTGGCGCT
GTGACAGAATGGGGTTTGGTGTTGGCTCCCGTAT

SEQ ID NO. 489 StW-34 F - ATACGGGAGCCAACACCAGCCGGTATCGGTGCTGAGGG
CCTTGGCTTGGCTCTGAGAGCAGGTGTGACGGAT

SEQ ID NO. 489 StW-34 R - ATCCGTCACACCTGCTCTCAGAGCCAAGCCAAGGCCCT
CAGCACCGATACCGGCTGGTGTTGGCTCCCGTAT

SEQ ID NO. 490 StW-36 F - ATACGGGAGCCAACACCATGGCGACCTAATCAGCCGGA
CAGTGCTCCTCAACGTAGAGCAGGTGTGACGGAT

SEQ ID NO. 491 StW-36 R - ATCCGTCACACCTGCTCTACGTTGAGGAGCACTGTCCG
GCTGATTAGGTCGCCATGGTGTTGGCTCCCGTAT

SEQ ID NO. 492 StW-38 F - ATACGGGAGCCAACACCATGGAGACAGGGGGAACGAC
AGCGGCGGTTGCGGGGCAGAGCAGGTGTGACGGA

SEQ ID NO. 493 StW-38 R - ATCCGTCACACCTGCTCTGCCCCGCAACCGCCGCTGTC
GTTCCCCCTGTCTCCATGGTGTTGGCTCCCGTAT

SEQ ID NO. 494 StW-40 F - ATACGGGAGCCAACACCAATAGCCGGCCGAAATCCCTT
TGGGATGGTCATACCGAGAGCAGGTGTGACGGAT

SEQ ID NO. 495 StW-40 R - ATCCGTCACACCTGCTCTCGGTATGACCATCCCAAAGG
GATTTCGGCCGGCTATTGGTGTTGGCTCCCGTAT

SEQ ID NO. 496 StW-42 F - ATACGGGAGCCAACACCACCGAATGTGCTGCAAGACT
AATCTGGATGGCCATGCAGAGCAGGTGTGACGGAT

SEQ ID NO. 497 StW-42 R - ATCCGTCACACCTGCTCTGCATGGCCATCCAGATTAGTC
TTGCAGCACATTCGGTGGTGTTGGCTCCCGTAT

SEQ ID NO. 498 StW-43 F - ATACGGGAGCCAACACCAAATCGAGTTCGTGACAGTTG
GGCAGATACCGAGTCCAGAGCAGGTGTGACGGAT

SEQ ID NO. 499 StW-43 R - ATCCGTCACACCTGCTCTGGACTCGGTATCTGCCCAAC
TGTCACGAACTCGATTTGGTGTTGGCTCCCGTAT

SEQ ID NO. 500 StW-45 F - ATACGGGAGCCAACACCAGGGTCCACGCTACACGGATC
AAGTCTAGCTGGTTGTAGAGCAGGTGTGACGGAT

SEQ ID NO. 501 StW-45 R - ATCCGTCACACCTGCTCTACAACCAGCTAGACTTGATC
CGTGTAGCGTGGACCCTGGTGTTGGCTCCCGTAT

SEQ ID NO. 502 StW-47 F - ATACGGGAGCCAACACCATCCCACAAGGCTCGTGTTAG
GCCTCCAATGCTCTCGAGAGCAGGTGTGACGGAT

SEQ ID NO. 503 StW-47 R - ATCCGTCACACCTGCTCTCGAGAGCATTGGAGGCCTAA
CACGAGCCTTGTGGGATGGTGTTGGCTCCCGTAT

SEQ ID NO. 504 StW-48 F - ATACGGGAGCCAACACCAGGCCCCGAGAAATTATCGAT
AGTGGTTTCTCGCCCTAGAGCAGGTGTGACGGAT

SEQ ID NO. 505 StW-48 R - ATCCGTCACACCTGCTCTAGGGCGAGAAACCACTATCG
ATAATTTCTCGGGGCCTGGTGTTGGCTCCCGTAT

SEQ ID NO. 506 StW-49 F - ATACGGGAGCCAACACCACACCCGGATGCGATTAAGAA
GTTACTGCCTTGCGGGAGAGCAGGTGTGACGGAT

SEQ ID NO. 507 StW-49 R - ATCCGTCACACCTGCTCTCCCGCAAGGCAGTAACTTCTT
AATCGCATCCGGGTGTGGTGTTGGCTCCCGTAT

SEQ ID NO. 508 StW-50 F - ATACGGGAGCCAACACCATGCCATGCACTTGGTTCCGA
ACGTTCGCGTCATTGCAGAGCAGGTGTGACGGAT

SEQ ID NO. 509 StW-50 R - ATCCGTCACACCTGCTCTGCAATGACGCGAACGTTCGG
AACCAAGTGCATGGCATGGTGTTGGCTCCCGTAT

TABLE 1-continued

DNA ligand Sequence ID Nos.

SEQ ID NO. 510 StW-56 F - ATACGGGAGCCAACACCACCAAAAAAAGCTGTGACCG
GAAGGTGCTGCTGACGTAGAGCAGGTGTGACGGAT

SEQ ID NO. 511 StW-56 R - ATCCGTCACACCTGCTCTACGTCAGCAGCACCTTCCGGT
CACAGCTTTTTTTGGTGGTGTTGGCTCCCGTAT

SEQ ID NO. 512 StW-58 F - ATACGGGAGCCAACACCAAGCTACCATCCACCTAACAG
GACTACGCGAATTGCAAGAGCAGGTGTGACGGAT

SEQ ID NO. 513 StW-58 R - ATCCGTCACACCTGCTCTTGCAATTCGCGTAGTCCTGTT
AGGTGGATGGTAGCTTGGTGTTGGCTCCCGTAT

SEQ ID NO. 514 StW-61 F - ATACGGGAGCCAACACCACAAGCAGGAATAAGCGCCG
GTCCAGAGCAGGTGTGACGGAT (59)

SEQ ID NO. 515 StW-61 R - ATCCGTCACACCTGCTCTGGACCGGCGCTTATTCCTGCT
TGTGGTGTTGGCTCCCGTAT (59)

SEQ ID NO. 516 StW-62 F - ATACGGGAGCCAACACCACATGGACCGGCAACCTCAG
AAGTAGCAAACCACCATAGAGCAGGTGTGACGGAT

SEQ ID NO. 517 StW-62 R - ATCCGTCACACCTGCTCTATGGTGGTTTGCTACTTCTGA
GGTTGCCGGTCCATGTGGTGTTGGCTCCCGTAT

SEQ ID NO. 518 StW-65 F - ATACGGGAGCCAACACCATGTCCAAACCATTCTCGGAC
CTCCCTCAGTGGCGGCAGAGCAGGTGTGACGGAT

SEQ ID NO. 519 StW-65 R - ATCCGTCACACCTGCTCTGCCGCCACTGAGGGAGGTCC
GAGAATGGTTTGGACATGGTGTTGGCTCCCGTAT

SEQ ID NO. 520 StW-66 F - ATACGGGAGCCAACACCAGTCCGTTATGACATGTCCGG
ACCCGTACGCGTGTCAAGAGCAGGTGTGACGGAT

SEQ ID NO. 521 StW-66 R - ATCCGTCACACCTGCTCTTGACACGCGTACGGGTCCGG
ACATGTCATAACGGACTGGTGTTGGCTCCCGTAT

SEQ ID NO. 522 StW-67 F - ATACGGGAGCCAACACCATCCGCTCACATGATGCTGTA
CGATGGCCGCGTGCAAAGAGCAGGTGTGACGGAT

SEQ ID NO. 523 StW-67 R - ATCCGTCACACCTGCTCTTTGCACGCGGCCATCGTACA
GCATCATGTGAGCGGATGGTGTTGGCTCCCGTAT

SEQ ID NO. 524 StW-68 F - ATACGGGAGCCAACACCACGTCGCATATACCCCGAGAA
GGTAGATCGTGGACTAGAGCAGGTGTGACGGAT (71)

SEQ ID NO. 525 StW-68 R - ATCCGTCACACCTGCTCTAGTCCACGATCTACCTTCTCG
GGGTATATGCGACGTGGTGTTGGCTCCCGTAT (71)

SEQ ID NO. 526 StW-69 F - ATACGGGAGCCAACACCACGAGGACCTAGACTTGTCCG
ACATCACAGTGTGCGAGAGCAGGTGTGACGGAT (71)

SEQ ID NO. 527 StW-69 R - ATCCGTCACACCTGCTCTCGCACACTGTGATGTCGGAC
AAGTCTAGGTCCTCGTGGTGTTGGCTCCCGTAT (71)

SEQ ID NO. 528 StW-70 F - ATACGGGAGCCAACACCACAGCTGATATTGGATGGTCC
GGCAGAGCAGGTGTGACGGAT (59)

SEQ ID NO. 529 StW-70 R - ATCCGTCACACCTGCTCTGCCGGACCATCCAATATCAG
CTGTGGTGTTGGCTCCCGTAT (59)

SEQ ID NO. 530 StW-71 F - ATACGGGAGCCAACACCACGGGACCATCAGCCTCAACT
TCCTACAAGGCCTACTAGAGCAGGTGTGACGGAT

SEQ ID NO. 531 StW-71 R - ATCCGTCACACCTGCTCTAGTAGGCCTTGTAGGAAGTT
GAGGCTGATGGTCCCGTGGTGTTGGCTCCCGTAT

SEQ ID NO. 532 StW-73 F - ATACGGGAGCCAACACCAATGGACAAAGGCAATAGCG
TCAATTGAAGTCAGACCAGAGCAGGTGTGACGGAT

SEQ ID NO. 533 StW-73 R - ATCCGTCACACCTGCTCTGGTCTGACTTCAATTGACGCT
ATTGCCTTTGTCCATTGGTGTTGGCTCCCGTAT

SEQ ID NO. 534 StW-74 F - ATACGGGAGCCAACACCAACTGAACTCATGAAGCACG
ATTGTTGCCCCACGTGCAGAGCAGGTGTGACGGAT

SEQ ID NO. 535 StW-74 R - ATCCGTCACACCTGCTCTGCACGTGGGGCAACAATCGT
GCTTCATGAGTTCAGTTGGTGTTGGCTCCCGTAT

TABLE 1-continued

DNA ligand Sequence ID Nos.

SEQ ID NO. 536 StW-76 F - ATACGGGAGCCAACACCAATCCCTAGCAAGTAAGCTGG
TGGAGCTAGTACACGTAGAGCAGGTGTGACGGAT

SEQ ID NO. 537 StW-76 R - ATCCGTCACACCTGCTCTACGTGTACTAGCTCCACCAGC
TTACTTGCTAGGGATTGGTGTTGGCTCCCGTAT

SEQ ID NO. 538 StW-78 F - ATACGGGAGCCAACACCACACCGAAAGCCGGAACGAT
AGGGTACAGCTGGGTGTAGAGCAGGTGTGACGGAT

SEQ ID NO. 539 StW-78 R - ATCCGTCACACCTGCTCTACACCCAGCTGTACCCTATC
GTTCCGGCTTTCGGTGTGGTGTTGGCTCCCGTAT

SEQ ID NO. 540 StW-79 F - ATACGGGAGCCAACACCAAGGGCGAACTAGCATCACC
TCGGTCGCTCATAGGCCAGAGCAGGTGTGACGGAT

SEQ ID NO. 541 StW-79 R - ATCCGTCACACCTGCTCTGGCCTATGAGCGACCGAGGT
GATGCTAGTTCGCCCTTGGTGTTGGCTCCCGTAT

SEQ ID NO. 542 StW-80 F - ATACGGGAGCCAACACCACAGGGCGACGTAAGCTCCG
TCCAGAGGATGTCAGTAGAGCAGGTGTGACGGAT (71)

SEQ ID NO. 543 StW-80 R - ATCCGTCACACCTGCTCTACTGACATCCTCTGGACGGA
GCTTACGTCGCCCTGTGGTGTTGGCTCCCGTAT (71)

Shiga-like Toxin type 1; Stx-1

SEQ ID NO. 544 (SH-2F) - ATCCGTCACACCTGCTCTGGAGACATTAAAAACCGGAG
TTTATTTATACCTTTCTGGTGTTGGCTCCCGTAT

SEQ ID NO. 545 (SH-2R) - ATACGGGAGCCAACACCAGAAAGGTATAAATAAACTCC
GGTTTTTAATGTCTCCAGAGCAGGTGTGACGGAT

SEQ ID NO. 546 (SH-3F (59)) - ATACGGGAGCCAACACCACTAACTTGTTGCTGATCT
TATCCAGAGCAGGTGTGACGGAT

SEQ ID NO. 547 (SH-3R (59)) - ATCCGTCACACCTGCTCTGGATAAGATCAGCAACAA
GTTAGTGGTGTTGGCTCCCGTAT

SEQ ID NO. 548 (SH-4F (58)) - ATCCGTCACACCTGCTCTGCATGGA-
GAGTTTTTTGGT
CAGTGGTGTTGGCTCCCGTAT

SEQ ID NO. 549 (SH-4R (58)) - ATACGGGAGCCAACACCACTGACCAAAAAACTCTC
CATGCAGAGCAGGTGTGACGGAT

SEQ ID NO. 550 (SH-6F (58)) - ATACGGGAGCCAACACCACGTTAACGCGTAGCCTTT
GGACAGAGCAGGTGTGACGGAT

SEQ ID NO. 551 (SH-6R (58)) - ATCCGTCACACCTGCTCTGTCCAAAGGCTACGCGTT
AACGTGGTGTTGGCTCCCGTAT

SEQ ID NO. 552 (SH-8/21/23/24/25F (59)) - ATCCGTCACACCTGCTCTGCCGG
ACCATCCAATATCAGCTGTGGTGTTGGCTCCCGTAT

SEQ ID NO. 553 (SH-8/21/23/24/25 Rev (59)) - ATACGGGAGCCAACACCACA
GCTGATATTGGATGGTCCGGCAGAGCAGGTGTGACGGAT

SEQ ID NO. 554 (SH-9F) - ATCCGTCACACCTGCTCTCGTCCGTCATTAAGTTCGGAG
GCTGGCGGGTTGCGTTGGTGTTGGCTCCCGTAT

SEQ ID NO. 555 (SH-9R) - ATACGGGAGCCAACACCAACGCAACCCGCCAGCCTCCG
AACTTAATGACGGACGAGAGCAGGTGTGACGGAT

SEQ ID NO. 556 (SH-10F) - ATACGGGAGCCAACACCATTCTATCGTTCCGGACGCTT
ATGCCTTGCCATCTACAGAGCAGGTGTGACGGAT

SEQ ID NO. 557 (SH-10R) - ATCCGTCACACCTGCTCTGTAGATGGCAAGGCATAAGC
GTCCGGAACGATAGAATGGTGTTGGCTCCCGTAT

SEQ ID NO. 558 (SH-11F) - TCCGTCACACCTGCTCTAACTCTTACTACTTTGTTGCTA
TCACATTCAACTGTTGGTGTTGGCTCCCGTAT

SEQ ID NO. 559 (SH-11R) - ATACGGGAGCCAACACCAACAGTTGAATGTGATAGCA
ACAAAGTAGTAAGAGTTAGAGCAGGTGTGACGGAT

SEQ ID NO. 560 (SH-12 F(58)) - ATCCGTCACACCTGCTCTGGCCTTTCACCAAGCG
TCCTTGTGGTGTTGGCTCCCGTAT

TABLE 1-continued

| DNA ligand Sequence ID Nos. |
|---|
| SEQ ID NO. 561 (SH-12R (58)) - ATACGGGAGCCAACACCACAAGGACGCTTGGTGAA AGGCCAGAGCAGGTGTGACGGAT |
| SEQ ID NO. 562 (SH-16F (58)) - ATCCGTCACACCTGCTCTGGCACCGAGCACGGGAA CCCAGTGGTGTTGGCTCCCGTAT |
| SEQ ID NO. 563 (SH-16R (58)) - ATACGGGAGCCAACACCACTGGGTTCCCGTGCTCG GTGCCAGAGCAGGTGTGACGGAT |
| SEQ ID NO. 564 (SH-17F (69)) - ATACGGGAGCCAACACCATAGTGTTGGGCCAATAC GGTAACGTGTCCTTGGAGAGCAGGTGTGACGGAT |
| SEQ ID NO. 565 (SH-17R (69)) - ATCCGTCACACCTGCTCTCCAAGGACACGTTACCG TATTGGCCCAACACTATGGTGTTGGCTCCCGTAT |
| SEQ ID NO. 567 (SH-18F) - ATCCGTCACACCTGCTCTACCCGATGCCGCCCCGGGATT GTTGTATGACCATCTTGGTGTTGGCTCCCGTAT |
| SEQ ID NO. 568 (SH-18R) - ATACGGGAGCCAACACCAAGATGGTCATACAACAATC CCGGGGCGGCATCGGGTAGAGCAGGTGTGACGGAT |
| SEQ ID NO. 569 (SH-19F) - ATACGGGAGCCAACACCACCCCATGAGTACACGTGAAC GGACACAGCCTCCGGCAGAGCAGGTGTGACGGAT |
| SEQ ID NO. 570 (SH-19R) - ATCCGTCACACCTGCTCTGCCGGAGGCTGTGTCCGTTC ACGTGTACTCATGGGGTGGTGTTGGCTCCCGTAT |
| SEQ ID NO. 571 (SH-20F) - ATCCGTCACACCTGCTCTTAACCATTCATTTCTTTTGTG GTATGACCGTTCGCCTGGTGTTGGCTCCCGTAT |
| SEQ ID NO. 572 (SH-20R) - ATACGGGAGCCAACACCAGGCGAACGGTCATACCACA AAAGAAATGAATGGTTAAGAGCAGGTGTGACGGAT |
| SEQ ID NO. 573 (SH-22F (58)) - ATCCGTCACACCTGCTCTGGGGCTCTTTTCGTTA ACCAGGTGGTGTTGGCTCCCGTAT |
| SEQ ID NO. 574 (SH-22R (58)) - ATACGGGAGCCAACACCACCTGGTTAACGAAAAGA GCCCCAGAGCAGGTGTGACGGAT |
| Shiga-like toxin 2; Stx-2 |
| SEQ ID NO. 575 S2-1 F - ATACGGGAGCCAACACCAGGCGACCAAGTTTGAATCACC ACAATCGTGACGGTGAGAGCAGGTGTGACGGAT |
| SEQ ID NO. 576 S2-1 R - ATCCGTCACACCTGCTCTCACCGTCACGATTGTGGTGATTC AAACTTGGTCGCCTGGTGTTGGCTCCCGTAT |
| SEQ ID NO. 577 S2-2 F - ATACGGGAGCCAACACCACCATCACATCTTGGCCCGGTAC CCTGGATACTAGCCAGAGCAGGTGTGACGGAT |
| SEQ ID NO. 578 S2-2 R - ATCCGTCACACCTGCTCTGGCTAGTATCCAGGGTACCGGG CCAAGATGTGATGGTGGTGTTGGCTCCCGTAT |
| SEQ ID NO. 579 S2-3 F - ATACGGGAGCCAACACCAGCACTAGCTCGGGTAACGGGG ACATTAGAGTTTGCCAGAGCAGGTGTGACGGAT |
| SEQ ID NO. 580 S2-3 R - ATCCGTCACACCTGCTCTGGCAAACTCTAATGTCCCCGTT ACCCGAGCTAGTGCTGGTGTTGGCTCCCGTAT |
| SEQ ID NO. 581 S2-4 F - ATACGGGAGCCAACACCAAAGCCCACCGCGCCCAGATCT ACAAGACTTCCAACTAGAGCAGGTGTGACGGAT |
| SEQ ID NO. 582 S2-4 R - ATCCGTCACACCTGCTCTAGTTGGAAGTCTTGTAGATCTG GGCGCGGTGGGCTTTGGTGTTGGCTCCCGTAT |
| SEQ ID NO. 583 S2-5 F - ATACGGGAGCCAACACCATCTTTGTCACTCTGGATTAGGT TAATCCACTGAAACAGAGCAGGTGTGACGGAT |
| SEQ ID NO. 584 S2-5 R - ATCCGTCACACCTGCTCTGTTTCAGTGGATTAACCTAATC CAGAGTGACAAAGATGGTGTTGGCTCCCGTAT |
| SEQ ID NO. 585 S2-7 F - ATACGGGAGCCAACACCACGAACCCGGGATTCTAGCAATT GTCCCCCTCGAGCGAGAGCAGGTGTGACGGAT |
| SEQ ID NO. 586 S2-7 R - ATCCGTCACACCTGCTCTCGCTCGAGGGGGACAATTGCTA GAATCCCGGGTTCGTGGTGTTGGCTCCCGTAT |

TABLE 1-continued

DNA ligand Sequence ID Nos.

SEQ ID NO. 587 S2-8 F - ATACGGGAGCCAACACCAATGATTAATAGAACCCCCTAT
GACCTGGCCGCTGGGAGAGCAGGTGTGACGGAT

SEQ ID NO. 588 S2-8 R - ATCCGTCACACCTGCTCTCCCAGCGGCCAGGTCATAGGGG
GTTCTATTAATCATTGGTGTTGGCTCCCGTAT

SEQ ID NO. 589 S2-9 F - ATACGGGAGCCAACACCATGGTCGGATAGCATGTCCATG
TTGTCGGGTTTAACAAGAGCAGGTGTGACGGAT

SEQ ID NO. 590 S2-9 R - ATCCGTCACACCTGCTCTTGTTAAACCCGACAACATGGAC
ATGCTATCCGACCATGGTGTTGGCTCCCGTAT

SEQ ID NO. 591 S2-10 F - ATACGGGAGCCAACACCAGGGGAATCTTGCTTGCGTAGC
GACGCATAATGACGTAGAGCAGGTGTGACGGAT

SEQ ID NO. 592 S2-10 R - ATCCGTCACACCTGCTCTACGTCATTATGCGTCGCTACG
CAAGCAAGATTCCCCTGGTGTTGGCTCCCGTAT

SEQ ID NO. 593 S2-12 F - ATACGGAGCCAACACCATGAAGTGGACAAATGTGCGTT
CCCCTGACGTACCGGAGAGCAGGTGTGACGGAT

SEQ ID NO. 594 S2-12 R - ATCCGTCACACCTGCTCTCCGGTACGTCAGGGGAACGCA
CATTTGTCCACTTCATGGTGTTGGCTCCCGTA

SEQ ID NO. 595 S2-13 F - ATACGGGAGCCAACACCACCATTTAGTGTTAGACTAAGT
GATATCGAGTCGAGGAGAGCAGGTGTGACGGAT

SEQ ID NO. 596 S2-13 R - ATCCGTCACACCTGCTCTCCTCGACTCGATATCACTTAGT
CTAACACTAAATGGTGGTGTTGGCTCCCGTAT

SEQ ID NO. 597 S2-14 F - ATACGGGAGCCAACACCACTTCCACTTTTTCGCCTAATT
GCCTGTTGCATGGTAAGAGCAGGTGTGACGGAT

SEQ ID NO. 598 S2-14 R - ATCCGTCACACCTGCTCTTACCATGCAACAGGCAATTAG
GCGAAAAAGTGGAAGTGGTGTTGGCTCCCGTAT

SEQ ID NO. 599 S2-14.1 F - ATACGGGAGCCAACACCAGGCGATGTCCTAAAGTCTTT
AAGGCGAATATAGTTGAGAGCAGGTGTGACGGAT

SEQ ID NO. 600 S2-14.1 R - ATCCGTCACACCTGCTCTCAACTATATTCGCCTTAAAGA
CTTTAGGACATCGCCTGGTGTTGGCTCCCGTAT

SEQ ID NO. 601 S2-15 F - ATACGGGAGCCAACACCACCCCCCCCTCCGTGGGCCGCT
CCCCTCGGCCGGGCCAGAGCAGGTGTGACGGAT

SEQ ID NO. 602 S2-15 R - ATCCGTCACACCTGCTCTGGCCCGGCCGAGGGGAGCGGC
CCACGGAGGGGGGGTGGTGTTGGCTCCCGTAT

SEQ ID NO. 603 S2-16 F - ATACGGGAGCCAACACCATCCCGTGAAGCAACGACAATA
CAAGACGAGCGAAGGAGAGCAGGTGTGACGGAT

SEQ ID NO. 604 S2-16 R - ATCCGTCACACCTGCTCTCCTTCGCTCGTCTTGTATTGTC
GTTGCTTCACGGGATGGTGTTGGCTCCCGTAT

SEQ ID NO. 605 S2-17 F - ATACGGGAGCCAACACCACGCGACTTCTTCAACAGATAC
AGAGCGCTTGGGGCCAGAGCAGGTGTGACGGAT

SEQ ID NO. 606 S2-17 R - ATCCGTCACACCTGCTCTGGCCCCAAGCGCTCTGTATCT
GTTGAAGAAGTCGCGTGGTGTTGGCTCCCGTAT

SEQ ID NO. 607 S2-18 F - ATACGGGAGCCAACACCAGGAAATGGTACCTAAGAAAT
GAGAACTTTGACGCACAGAGCAGGTGTGACGGAT

SEQ ID NO. 607 S2-18 R - ATCCGTCACACCTGCTCTGTGCGTCAAAGTTCTCATTTCT
TAGGTACCATTTCCTGGTGTTGGCTCCCGTAT

SEQ ID NO. 609 S2-19 F - ATACGGGAGCCAACACCATTAAAGTTAATCTTACACGTT
TCCGACTTCCATTTGAGAGCAGGTGTGACGGAT

SEQ ID NO. 610 S2-19 R - ATCCGTCACACCTGCTCTCAAATGGAAGTCGGAAACGTG
TAAGATTAACTTTAATGGTGTTGGCTCCCGTAT

SEQ ID NO. 611 S2-20 F - ATACGGGAGCCAACACCAAGGAGTCCGTCTACGTTTTAC
GAGCTAAGGCCTTTGAGAGCAGGTGTGACGGAT

SEQ ID NO. 612 S2-20 R - ATCCGTCACACCTGCTCTCAAAGGCCTTAGCTCGTAAAA
CGTAGACGGACTCCTTGGTGTTGGCTCCCGTAT

TABLE 1-continued

DNA ligand Sequence ID Nos.

*Cryptosporidium parvum* oocysts (CP)

SEQ ID NO. 613 CP 12F - ATACGGGAGCCAACACCATAATGAAGCGATGTAGCGAGTT
TTTGAAAGGGACACAGAGCAGGTGTGACGGAT

SEQ ID NO. 614 CP12R - ATCCGTCACACCTGCTCTGTGTCCCTTTCAAAAACTCGCTA
CATCGCTTCATTATGGTGTTGGCTCCCGTAT

SEQ ID NO. 615 CP 13F - ATACGGGAGCCAACACCATTTAGTCCATAGCTTCAGCGCT
TCCACCTCCTTAACAGAGCAGGTGTGACGGAT

SEQ ID NO. 616 CP 13R - ATCCGTCACACCTGCTCTGTTAAGGAGGTGGAAGCGCTGA
AGCTATGGACTAAATGGTGTTGGCTCCCGTAT

SEQ ID NO. 617 CP 15F - ATACGGGAGCCAACACCACCCGTTTTTGATCTAATGAGGA
TACAATATTCGTCTAGAGCAGGTGTGACGGAT

SEQ ID NO. 618 CP 15R - ATCCGTCACACCTGCTCTAGACGAATATTGTATCCTCATTA
GATCAAAAACGGGTGGTGTTGGCTCCCGTAT

SEQ ID NO. 619 CP 16F - ATACGGGAGCCAACACCACCGGGTCCCCGTGATCTAGGAC
AACACGGCGGTTGGAGAGCAGGTGTGACGGAT

SEQ ID NO. 620 CP 16R - ATCCGTCACACCTGCTCTCCAACCGCCGTGTTGTCCTAGAT
CACGGGGACCCGGTGGTGTTGGCTCCCGTAT

SEQ ID NO. 621 CP 17F - ATACGGGAGCCAACACCAGTTCAGGCATACATGATGTGGG
TTCTTATTCCGTGCAGAGCAGGTGTGACGGAT

SEQ ID NO. 622 CP 17R - ATCCGTCACACCTGCTCTGCACGGAATAAGAACCCACATC
ATGTATGCCTGAACTGGTGTTGGCTCCCGTAT

SEQ ID NO. 623 CP18F - ATACGGGAGCCAACACCAGGCAGCCCGGTCCCGGACTAAC
AACCGCGGTACCCAAGAGCAGGTGTGACGGAT

SEQ ID NO. 624 CP18R - ATCCGTCACACCTGCTCTTGGGTACCGCGGTTGTTAGTCCG
GGACCGGGCTGCCTGGTGTTGGCTCCCGTAT

SEQ ID NO. 625 CP20F - ATACGGGAGCCAACACCATTCAGGGCTTTTGTGTATGCAC
TCCAGCTATCAGACAGAGCAGGTGTGACGGAT

SEQ ID NO. 626 CP20R - ATCCGTCACACCTGCTCTGTCTGATAGCTGGAGTGCATACA
CAAAAGCCCTGAATGGTGTTGGCTCCCGTAT

SEQ ID NO. 627 CP 21F - ATACGGGAGCCAACACCAAGGGACGGCAGGTTCGCAGCT
GCGTCATCTTTCTTCAGAGCAGGTGTGACGGAT

SEQ ID NO. 628 CP 21R - ATCCGTCACACCTGCTCTGAAGAAAGATGACGCAGCTGCG
AACCTGCCGTCCCTTGGTGTTGGCTCCCGTAT

SEQ ID NO. 629 CP 22F (71) - ATACGGGAGCCAACACCACGAGGACTTAGACTTGTCC
GACATCACAGTGTGCGAGAGCAGGTGTGACGGAT

SEQ ID NO. 630 CP 22R (71) - ATCCGTCACACCTGCTCTCGCACACTGTGATGTCGG
ACAAGTCTAAGTCCTCGTGGTGTTGGCTCCCGTAT

SEQ ID NO. 631 CP 23F - ATACGGGAGCCAACACCACTTCCCTGTCCTTCCCTCAGTG
AGGCCTGTCTCCTCAGAGCAGGTGTGACGGAT

SEQ ID NO. 632 CP 23R - ATCCGTCACACCTGCTCTGAGGAGACAGGCCTCACTGAGG
GAAGGACAGGGAAGTGGTGTTGGCTCCCGTAT

SEQ ID NO. 633 CP 24F - ATACGGGAGCCAACACCAGGAGATGTTCGTGTAATAGGGG
GTTACACCCGGTCGAGAGCAGGTGTGACGGAT

SEQ ID NO. 634 CP 24R - ATCCGTCACACCTGCTCTCGACCGGGTGTAACCCCCTATTA
CACGAACATCTCCTGGTGTTGGCTCCCGTAT

SEQ ID NO. 635 CP 25F - ATACGGGAGCCAACACCATCGCTCAAGTTCTTCATTACTCC
TATCGCTTCCGCTAGAGCAGGTGTGACGGAT

SEQ ID NO. 636 CP 25R - ATCCGTCACACCTGCTCTAGCGGAAGCGATAGGAGTAATG
AAGAACTTGAGCGATGGTGTTGGCTCCCGTAT

*Giardia* (UDP-N-acetylgalactosamine Surface Antigen; Gi)

SEQ ID NO. 637 Gi 22F - ATACGGGAGCCAACACCATTCTACTCCCAGGTATGTCTCTG
GGCCCCCCCGGCCAGAGCAGGTGTGACGGAT

TABLE 1-continued

DNA ligand Sequence ID Nos.

SEQ ID NO. 638 Gi 22R - ATCCGTCACACCTGCTCTGGCCGGGGGGCCCAGAGACAT
ACCTGGGAGTAGAATGGTGTTGGCTCCCGTAT

SEQ ID NO. 639 Gi 25F - ATACGGGAGCCAACACCAACAACATAGCCCTGGCACGAC
AGTGGCATACCAGGCAGAGCAGGTGTGACGGAT

SEQ ID NO. 640 Gi 25R - ATCCGTCACACCTGCTCTGCCTGGTATGCCACTGTCGTGCC
AGGGCTATGTTGTTGGTGTTGGCTCCCGTAT

SEQ ID NO. 641 Gi 30F - ATACGGGAGCCAACACCACGTAATGATGTGCACCTCTCTC
CGACTGTTTCTCGTAGAGCAGGTGTGACGGAT

SEQ ID NO. 642 Gi 30R - ATCCGTCACACCTGCTCTACGAGAAACAGTCGGAGAGAGG
TGCACATCATTACGTGGTGTTGGCTCCCGTAT

SEQ ID NO. 643 Gi-33F - ATACGGGAGCCAACACCACATCTTATTCGTCCCCAGTCCT
TTGGTCTCCTGCTCAGAGCAGGTGTGACGGAT

SEQ ID NO. 644 Gi-33R - TCCGTCACACCTGCTCTGAGCAGGAGACCAAAGGACTG
GGGACGAATAAGATGTGGTGTTGGCTCCCGTAT

SEQ ID NO. 645 Gi-37F - ATACGGGAGCCAACACCACCTGCTGATTTCCTATAATCC
GGCCCATACCTTAGGAGAGCAGGTGTGACGGAT

SEQ ID NO. 646 Gi-37R - ATCCGTCACACCTGCTCTCCTAAGGTATGGGCCGGATTA
TAGGAAATCAGCAGGTGGTGTTGGCTCCCGTAT

SEQ ID NO. 647 Gi-38F - ATACGGGAGCCAACACCATAAGAGTCCTCTAAGGTCGCT
TATTTTTAACCCCTAAGAGCAGGTGTGACGGAT

SEQ ID NO. 648 Gi-38R - ATCCGTCACACCTGCTCTTAGGGGTTAAAAATAAGCGAC
CTTAGAGGACTCTTATGGTGTTGGCTCCCGTAT

SEQ ID NO. 649 Gi-40F - ATACGGGAGCCAACACCATCCCCACACCCTCGTTCCGACC
GCTAGAATCCCCGAAGAGCAGGTGTGACGGAT

SEQ ID NO. 650 Gi-40R - ATCCGTCACACCTGCTCTTCGGGGATTCTAGCGGTCGGAA
CGAGGGTGTGGGATGGTGTTGGCTCCCGTAT

---

I claim:

1. A DNA ligand comprising the nucleic acid sequence of SEQ ID NO: 86.

2. A composition comprising the DNA ligand of claim 1.

3. The DNA ligand of claim 1, wherein said DNA ligand is attached to a membrane or a plastic or glass biochip to be used in an assay.

4. The DNA ligand of claim 1, wherein said DNA ligand is in a tube or a cuvette to be used in an assay.

* * * * *

SEQUENCE LISTING

<160> NUMBER OF SEQ ID NOS: 1211

<210> SEQ ID NO 1
<211> LENGTH: 136
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t

<400> SEQUENCE: 1
catccgtcac acctgctctg gggagggtgg cgcccgtctc ggtggtgttg gctcccgtat    60
casdncdnaa rtcacatccg tcacacctgc tctgggatag ggtctcgtgc tagatgtggt   120
gttggctccc gtatca                                                   136

<210> SEQ ID NO 2
<211> LENGTH: 62
<212> TYPE: DNA
<213> ORGANISM: Artificial Sequence
<220> FEATURE:

<223> OTHER INFORMATION: chemically synthesized

<400> SEQUENCE: 2
catccgtcac acctgctctg gaccggcgct tattcctgct tgtggtgttg gctcccgtat    60
ca                                                                  62

<210> SEQ ID NO 3
<211> LENGTH: 62
<212> TYPE: DNA
<213> ORGANISM: Artificial Sequence
<220> FEATURE:
<223> OTHER INFORMATION: chemically synthesized

<400> SEQUENCE: 3
catccgtcac acctgctctg gagctgatat tggatggtcc ggtggtgttg gctcccgtat    60
ca                                                                  62

<210> SEQ ID NO 4
<211> LENGTH: 62
<212> TYPE: DNA
<213> ORGANISM: Artificial Sequence
<220> FEATURE:
<223> OTHER INFORMATION: chemically synthesized

<400> SEQUENCE: 4
catccgtcac acctgctctg cccagagcag gtgtgacgga tgtggtgttg gctcccgtat    60
ca                                                                  62

<210> SEQ ID NO 5
<211> LENGTH: 62
<212> TYPE: DNA
<213> ORGANISM: Artificial Sequence
<220> FEATURE:
<223> OTHER INFORMATION: chemically synthesized

<400> SEQUENCE: 5
catccgtcac acctgctctg ccggaccatc caatatcagc tgtggtgttg gctcccgtat    60
ca                                                                  62

<210> SEQ ID NO 6
<211> LENGTH: 72
<212> TYPE: DNA
<213> ORGANISM: Artificial Sequence
<220> FEATURE:
<223> OTHER INFORMATION: chemically synthesized

<400> SEQUENCE: 6
atacgggagc caacaccagg accaaaataa ataatcacaa taaaaatgct tcctagagca    60
ggtgtgacgg at                                                       72

<210> SEQ ID NO 7
<211> LENGTH: 72
<212> TYPE: DNA
<213> ORGANISM: Artificial Sequence
<220> FEATURE:
<223> OTHER INFORMATION: chemically synthesized

<400> SEQUENCE: 7
atccgtcaca cctgctctag gaagcatttt tattgtgatt atttattttg gtcctggtgt    60
tggctcccgt at                                                       72

```
<210> SEQ ID NO 8
<211> LENGTH: 72
<212> TYPE: DNA
<213> ORGANISM: Artificial Sequence
<220> FEATURE:
<223> OTHER INFORMATION: chemically synthesized

<400> SEQUENCE: 8
atacgggagc caacaccacg ccgggccata ggcgtgtggt agcatactcg tactagagca      60
ggtgtgacgg at                                                         72

<210> SEQ ID NO 9
<211> LENGTH: 72
<212> TYPE: DNA
<213> ORGANISM: Artificial Sequence
<220> FEATURE:
<223> OTHER INFORMATION: chemically synthesized

<400> SEQUENCE: 9
atccgtcaca cctgctctag tacgagtatg ctaccacacg cctatggccc ggcgtggtgt      60
tggctcccgt at                                                         72

<210> SEQ ID NO 10
<211> LENGTH: 72
<212> TYPE: DNA
<213> ORGANISM: Artificial Sequence
<220> FEATURE:
<223> OTHER INFORMATION: chemically synthesized

<400> SEQUENCE: 10
atacgggagc caacaccata gtataaagac ccaattgaca gactatccta ggctagagca      60
ggtgtgacgg at                                                         72

<210> SEQ ID NO 11
<211> LENGTH: 72
<212> TYPE: DNA
<213> ORGANISM: Artificial Sequence
<220> FEATURE:
<223> OTHER INFORMATION: chemically synthesized

<400> SEQUENCE: 11
atccgtcaca cctgctctag cctaggatag tctgtcaatt gggtctttat actatggtgt      60
tggctcccgt at                                                         72

<210> SEQ ID NO 12
<211> LENGTH: 72
<212> TYPE: DNA
<213> ORGANISM: Artificial Sequence
<220> FEATURE:
<223> OTHER INFORMATION: chemically synthesized

<400> SEQUENCE: 12
atacgggagc caacaccaag aggggacaga gggtataaga caactattct ccccagagca      60
ggtgtgacgg at                                                         72

<210> SEQ ID NO 13
<211> LENGTH: 72
<212> TYPE: DNA
<213> ORGANISM: Artificial Sequence
<220> FEATURE:
<223> OTHER INFORMATION: chemically synthesized

<400> SEQUENCE: 13
```

```
atccgtcaca cctgctctgg ggagaatagt tgtcttatac cctctgtccc ctcttggtgt    60
tggctcccgt at                                                       72
```

<210> SEQ ID NO 14
<211> LENGTH: 72
<212> TYPE: DNA
<213> ORGANISM: Artificial Sequence
<220> FEATURE:
<223> OTHER INFORMATION: chemically synthesized

<400> SEQUENCE: 14

```
atacgggagc caacaccagg cggccgcaac ttggtcccct cttcatcctc ggatagagca    60
ggtgtgacgg at                                                       72
```

<210> SEQ ID NO 15
<211> LENGTH: 72
<212> TYPE: DNA
<213> ORGANISM: Artificial Sequence
<220> FEATURE:
<223> OTHER INFORMATION: chemically synthesized

<400> SEQUENCE: 15

```
atccgtcaca cctgctctat ccgaggatga agaggggacc aagttgcggc cgcctggtgt    60
tggctcccgt at                                                       72
```

<210> SEQ ID NO 16
<211> LENGTH: 69
<212> TYPE: DNA
<213> ORGANISM: Artificial Sequence
<220> FEATURE:
<223> OTHER INFORMATION: chemically synthesized

<400> SEQUENCE: 16

```
atacgggagc caacaccata gtgttggacc aatacggtaa cgtgtccttg gagagcaggt    60
gtgacggat                                                           69
```

<210> SEQ ID NO 17
<211> LENGTH: 69
<212> TYPE: DNA
<213> ORGANISM: Artificial Sequence
<220> FEATURE:
<223> OTHER INFORMATION: chemically synthesized

<400> SEQUENCE: 17

```
atccgtcaca cctgctctcc aaggacacgt taccgtattg gtccaacact atggtgttgg    60
ctcccgtat                                                           69
```

<210> SEQ ID NO 18
<211> LENGTH: 72
<212> TYPE: DNA
<213> ORGANISM: Artificial Sequence
<220> FEATURE:
<223> OTHER INFORMATION: chemically synthesized

<400> SEQUENCE: 18

```
atacgggagc caacaccacg cgatacaatg tgctaaaaaa gttcgtgccc ctgcagagca    60
ggtgtgacgg at                                                       72
```

<210> SEQ ID NO 19
<211> LENGTH: 72
<212> TYPE: DNA
<213> ORGANISM: Artificial Sequence

```
<220> FEATURE:
<223> OTHER INFORMATION: chemically synthesized

<400> SEQUENCE: 19
atccgtcaca cctgctctgc aggggcacga acttttttag cacattgtat cgcgtggtgt    60
tggctcccgt at                                                        72

<210> SEQ ID NO 20
<211> LENGTH: 72
<212> TYPE: DNA
<213> ORGANISM: Artificial Sequence
<220> FEATURE:
<223> OTHER INFORMATION: chemically synthesized

<400> SEQUENCE: 20
atacgggagc caacaccacg ccgaatagtg ttcgtatgcc acccgcacgt gtctagagca    60
ggtgtgacgg at                                                        72

<210> SEQ ID NO 21
<211> LENGTH: 72
<212> TYPE: DNA
<213> ORGANISM: Artificial Sequence
<220> FEATURE:
<223> OTHER INFORMATION: chemically synthesized

<400> SEQUENCE: 21
atccgtcaca cctgctctag acacgtgcgg gtggcatacg aacactattc ggcgtggtgt    60
tggctcccgt at                                                        72

<210> SEQ ID NO 22
<211> LENGTH: 72
<212> TYPE: DNA
<213> ORGANISM: Artificial Sequence
<220> FEATURE:
<223> OTHER INFORMATION: chemically synthesized

<400> SEQUENCE: 22
atacgggagc caacaccagg catgactaaa aaggataacc taatctcttg ttccagagca    60
ggtgtgacgg at                                                        72

<210> SEQ ID NO 23
<211> LENGTH: 72
<212> TYPE: DNA
<213> ORGANISM: Artificial Sequence
<220> FEATURE:
<223> OTHER INFORMATION: chemically synthesized

<400> SEQUENCE: 23
atccgtcaca cctgctctgg aacaagagat taggttatcc tttttagtca tgcctggtgt    60
tggctcccgt at                                                        72

<210> SEQ ID NO 24
<211> LENGTH: 72
<212> TYPE: DNA
<213> ORGANISM: Artificial Sequence
<220> FEATURE:
<223> OTHER INFORMATION: chemically synthesized

<400> SEQUENCE: 24
atacgggagc caacaccata cagtccaccg tatactagtg gtacccaggc gtcgagagca    60
ggtgtgacgg at                                                        72
```

<210> SEQ ID NO 25
<211> LENGTH: 72
<212> TYPE: DNA
<213> ORGANISM: Artificial Sequence
<220> FEATURE:
<223> OTHER INFORMATION: chemically synthesized

<400> SEQUENCE: 25
atccgtcaca cctgctctcg acgcctgggt accactagta tacggtggac tgtatggtgt    60
tggctcccgt at    72

<210> SEQ ID NO 26
<211> LENGTH: 72
<212> TYPE: DNA
<213> ORGANISM: Artificial Sequence
<220> FEATURE:
<223> OTHER INFORMATION: chemically synthesized

<400> SEQUENCE: 26
atacgggagc caacaccagg gggcgaacag ttacccttgg tctggaccac tgccagagca    60
ggtgtgacgg at    72

<210> SEQ ID NO 27
<211> LENGTH: 72
<212> TYPE: DNA
<213> ORGANISM: Artificial Sequence
<220> FEATURE:
<223> OTHER INFORMATION: chemically synthesized

<400> SEQUENCE: 27
atccgtcaca cctgctctgg cagtggtcca gaccaagggt aactgttcgc ccctggtgt    60 tggctcccgt at    72

<210> SEQ ID NO 28
<211> LENGTH: 72
<212> TYPE: DNA
<213> ORGANISM: Artificial Sequence
<220> FEATURE:
<223> OTHER INFORMATION: chemically synthesized

<400> SEQUENCE: 28
atacgggagc caacaccagg ggcgtcgggc caggcgacgg ccgccgtttc cggcagagca    60
ggtgtgacgg at    72

<210> SEQ ID NO 29
<211> LENGTH: 72
<212> TYPE: DNA
<213> ORGANISM: Artificial Sequence
<220> FEATURE:
<223> OTHER INFORMATION: chemically synthesized

<400> SEQUENCE: 29
atccgtcaca cctgctctgc cggaaacggc ggccgtcgcc tggcccgacg ccctggtgt    60 tggctcccgt at    72

<210> SEQ ID NO 30
<211> LENGTH: 72
<212> TYPE: DNA
<213> ORGANISM: Artificial Sequence
<220> FEATURE:
<223> OTHER INFORMATION: chemically synthesized

<400> SEQUENCE: 30

```
atacgggagc aacaccacg ggccgtccct ggcccggggg ggcgaaacgc gctgagagca    60
ggtgtgacgg at                                                      72

<210> SEQ ID NO 31
<211> LENGTH: 72
<212> TYPE: DNA
<213> ORGANISM: Artificial Sequence
<220> FEATURE:
<223> OTHER INFORMATION: chemically synthesized

<400> SEQUENCE: 31
atccgtcaca cctgctctca gcgcgtttcg ccccccggg ccaggacgg cccgtggtgt     60 tggctcccgt at                                                      72

<210> SEQ ID NO 32
<211> LENGTH: 72
<212> TYPE: DNA
<213> ORGANISM: Artificial Sequence
<220> FEATURE:
<223> OTHER INFORMATION: chemically synthesized

<400> SEQUENCE: 32
atacgggagc caacaccagg cgattactaa gggaaaaaag tgtaaaacct acccagagca   60
ggtgtgacgg at                                                      72

<210> SEQ ID NO 33
<211> LENGTH: 72
<212> TYPE: DNA
<213> ORGANISM: Artificial Sequence
<220> FEATURE:
<223> OTHER INFORMATION: chemically synthesized

<400> SEQUENCE: 33
atccgtcaca cctgctctgg gtaggtttta cacttttttc ccttagtaat cgcctggtgt   60
tggctcccgt at                                                      72

<210> SEQ ID NO 34
<211> LENGTH: 72
<212> TYPE: DNA
<213> ORGANISM: Artificial Sequence
<220> FEATURE:
<223> OTHER INFORMATION: chemically synthesized

<400> SEQUENCE: 34
atacgggagc caacaccacc acccactggc ccggtccgcg gccgcgcgcg ccccagagca   60
ggtgtgacgg at                                                      72

<210> SEQ ID NO 35
<211> LENGTH: 72
<212> TYPE: DNA
<213> ORGANISM: Artificial Sequence
<220> FEATURE:
<223> OTHER INFORMATION: chemically synthesized

<400> SEQUENCE: 35
atccgtcaca cctgctctgg ggcgcgcgcg gccgcggacc gggccagtgg gtggtggtgt   60
tggctcccgt at                                                      72

<210> SEQ ID NO 36
<211> LENGTH: 72
<212> TYPE: DNA
```

```
<213> ORGANISM: Artificial Sequence
<220> FEATURE:
<223> OTHER INFORMATION: chemically synthesized

<400> SEQUENCE: 36
atacgggagc caacaccaac gatatccctg accaaagacg ttaaatgctt ccatagagca    60
ggtgtgacgg at                                                        72

<210> SEQ ID NO 37
<211> LENGTH: 72
<212> TYPE: DNA
<213> ORGANISM: Artificial Sequence
<220> FEATURE:
<223> OTHER INFORMATION: chemically synthesized

<400> SEQUENCE: 37
atccgtcaca cctgctctat ggaagcattt aacgtctttg gtcaggata tcgttggtgt     60 tggctcccgt at                                                        72

<210> SEQ ID NO 38
<211> LENGTH: 72
<212> TYPE: DNA
<213> ORGANISM: Artificial Sequence
<220> FEATURE:
<223> OTHER INFORMATION: chemically synthesized

<400> SEQUENCE: 38
atacgggagc caacaccagg gcgggggtt ggcgagcagg aatcgagaga ggtgagagca     60
ggtgtgacgg at                                                        72

<210> SEQ ID NO 39
<211> LENGTH: 72
<212> TYPE: DNA
<213> ORGANISM: Artificial Sequence
<220> FEATURE:
<223> OTHER INFORMATION: chemically synthesized

<400> SEQUENCE: 39
atccgtcaca cctgctctca cctctctcga ttcctgctcg ccaaccccc gccctggtgt     60 tggctcccgt at                                                        72

<210> SEQ ID NO 40
<211> LENGTH: 72
<212> TYPE: DNA
<213> ORGANISM: Artificial Sequence
<220> FEATURE:
<223> OTHER INFORMATION: chemically synthesized

<400> SEQUENCE: 40
atacgggagc caacaccaga tgcgcttcct gtaatgaaca gatcatattt atgtagagca    60
ggtgtgacgg at                                                        72

<210> SEQ ID NO 41
<211> LENGTH: 72
<212> TYPE: DNA
<213> ORGANISM: Artificial Sequence
<220> FEATURE:
<223> OTHER INFORMATION: chemically synthesized

<400> SEQUENCE: 41
atccgtcaca cctgctctac ataaatatga tctgttcatt acaggaagcg catctggtgt    60
tggctcccgt at                                                        72
```

<210> SEQ ID NO 42
<211> LENGTH: 72
<212> TYPE: DNA
<213> ORGANISM: Artificial Sequence
<220> FEATURE:
<223> OTHER INFORMATION: chemically synthesized

<400> SEQUENCE: 42
atacgggagc caacaccaag gtaggttgcc gcaggttggc gacaaaccag gttgagagca      60
ggtgtgacgg at                                                         72

<210> SEQ ID NO 43
<211> LENGTH: 72
<212> TYPE: DNA
<213> ORGANISM: Artificial Sequence
<220> FEATURE:
<223> OTHER INFORMATION: chemically synthesized

<400> SEQUENCE: 43
atccgtcaca cctgctctca acctggtttg tcgccaacct gcggcaacct accttggtgt     60
tggctcccgt at                                                         72

<210> SEQ ID NO 44
<211> LENGTH: 69
<212> TYPE: DNA
<213> ORGANISM: Artificial Sequence
<220> FEATURE:
<223> OTHER INFORMATION: chemically synthesized

<400> SEQUENCE: 44
atacgggagc caacaccata gtgttggacc aatacggtaa cgtgtccttg gagagcaggt     60
gtgacggat                                                             69

<210> SEQ ID NO 45
<211> LENGTH: 69
<212> TYPE: DNA
<213> ORGANISM: Artificial Sequence
<220> FEATURE:
<223> OTHER INFORMATION: chemically synthesized

<400> SEQUENCE: 45
atccgtcaca cctgctctcc aaggacacgt taccgtattg gtccaacact atggtgttgg     60
ctcccgtat                                                             69

<210> SEQ ID NO 46
<211> LENGTH: 72
<212> TYPE: DNA
<213> ORGANISM: Artificial Sequence
<220> FEATURE:
<223> OTHER INFORMATION: chemically synthesized

<400> SEQUENCE: 46
atacgggagc caacaccacc cgggtggcgg ggtgggtgtg ggtcgacgtt ctggagagca     60
ggtgtgacgg at                                                         72

<210> SEQ ID NO 47
<211> LENGTH: 72
<212> TYPE: DNA
<213> ORGANISM: Artificial Sequence
<220> FEATURE:
<223> OTHER INFORMATION: chemically synthesized

<400> SEQUENCE: 47
atccgtcaca cctgctctcc agaacgtcga cccacaccca ccccgccacc cgggtggtgt    60
tggctcccgt at                                                        72

<210> SEQ ID NO 48
<211> LENGTH: 72
<212> TYPE: DNA
<213> ORGANISM: Artificial Sequence
<220> FEATURE:
<223> OTHER INFORMATION: chemically synthesized

<400> SEQUENCE: 48
atacgggagc caacaccagg gggggtggc cgcaggaaat atgcagtcca ctatagagca    60
ggtgtgacgg at                                                        72

<210> SEQ ID NO 49
<211> LENGTH: 72
<212> TYPE: DNA
<213> ORGANISM: Artificial Sequence
<220> FEATURE:
<223> OTHER INFORMATION: chemically synthesized

<400> SEQUENCE: 49
atccgtcaca cctgctctat agtggactgc atatttcctg cggccacccc ccctggtgt    60 tggctcccgt at                                                        72

<210> SEQ ID NO 50
<211> LENGTH: 72
<212> TYPE: DNA
<213> ORGANISM: Artificial Sequence
<220> FEATURE:
<223> OTHER INFORMATION: chemically synthesized

<400> SEQUENCE: 50
atacgggagc caacaccaca caccgggccc gccccagcg cccccctacg cacaagagca    60
ggtgtgacgg at                                                        72

<210> SEQ ID NO 51
<211> LENGTH: 72
<212> TYPE: DNA
<213> ORGANISM: Artificial Sequence
<220> FEATURE:
<223> OTHER INFORMATION: chemically synthesized

<400> SEQUENCE: 51
atccgtcaca cctgctcttg tgcgtagggg ggcgctgggg gcgggcccgg tgtgtggtgt    60
tggctcccgt at                                                        72

<210> SEQ ID NO 52
<211> LENGTH: 72
<212> TYPE: DNA
<213> ORGANISM: Artificial Sequence
<220> FEATURE:
<223> OTHER INFORMATION: chemically synthesized

<400> SEQUENCE: 52
atacgggagc caacaccatg aaggaaacct tgatagcagg aatagtccat tcccagagca    60
ggtgtgacgg at                                                        72

<210> SEQ ID NO 53
<211> LENGTH: 72

```
<212> TYPE: DNA
<213> ORGANISM: Artificial Sequence
<220> FEATURE:
<223> OTHER INFORMATION: chemically synthesized

<400> SEQUENCE: 53
atccgtcaca cctgctctgg gaatggacta ttcctgctat caaggtttcc ttcatggtgt    60
tggctcccgt at                                                        72

<210> SEQ ID NO 54
<211> LENGTH: 72
<212> TYPE: DNA
<213> ORGANISM: Artificial Sequence
<220> FEATURE:
<223> OTHER INFORMATION: chemically synthesized

<400> SEQUENCE: 54
atacgggagc caacaccacc cgggtggcgg ggtgggtgtg ggtcgacgtt ctggagagca    60
ggtgtgacgg at                                                        72

<210> SEQ ID NO 55
<211> LENGTH: 72
<212> TYPE: DNA
<213> ORGANISM: Artificial Sequence
<220> FEATURE:
<223> OTHER INFORMATION: chemically synthesized

<400> SEQUENCE: 55
atccgtcaca cctgctctcc agaacgtcga cccacaccca cccgccaccc gggtggtgt     60 tggctcccgt at                                                        72

<210> SEQ ID NO 56
<211> LENGTH: 72
<212> TYPE: DNA
<213> ORGANISM: Artificial Sequence
<220> FEATURE:
<223> OTHER INFORMATION: chemically synthesized

<400> SEQUENCE: 56
atacgggagc caacaccacg cccgccggcg actcgctcca ctccgtcccg ctccagagca    60
ggtgtgacgg at                                                        72

<210> SEQ ID NO 57
<211> LENGTH: 72
<212> TYPE: DNA
<213> ORGANISM: Artificial Sequence
<220> FEATURE:
<223> OTHER INFORMATION: chemically synthesized

<400> SEQUENCE: 57
atccgtcaca cctgctctgg agcgggacgg agtggagcga gtcgccggcg ggcgtggtgt    60
tggctcccgt at                                                        72

<210> SEQ ID NO 58
<211> LENGTH: 72
<212> TYPE: DNA
<213> ORGANISM: Artificial Sequence
<220> FEATURE:
<223> OTHER INFORMATION: chemically synthesized

<400> SEQUENCE: 58
cattcaccac acctctgctg gcttggctag ccttgatgct aaacgaccca tagtgtggtg    60
```

```
tcgtcccgta tc                                                          72

<210> SEQ ID NO 59
<211> LENGTH: 72
<212> TYPE: DNA
<213> ORGANISM: Artificial Sequence
<220> FEATURE:
<223> OTHER INFORMATION: chemically synthesized

<400> SEQUENCE: 59
gatacgggac gacaccacac tatgggtcgt ttagcatcaa ggctagccaa gccagcagag      60
gtgtggtgaa tg                                                          72

<210> SEQ ID NO 60
<211> LENGTH: 72
<212> TYPE: DNA
<213> ORGANISM: Artificial Sequence
<220> FEATURE:
<223> OTHER INFORMATION: chemically synthesized

<400> SEQUENCE: 60
cattcaccac acctctgctg gaggaggaag tggtctggag ttacttgaca tagtgtggtg      60
tcgtcccgta tc                                                          72

<210> SEQ ID NO 61
<211> LENGTH: 72
<212> TYPE: DNA
<213> ORGANISM: Artificial Sequence
<220> FEATURE:
<223> OTHER INFORMATION: chemically synthesized

<400> SEQUENCE: 61
gatacgggac gacaccacac tatgtcaagt aactccagac cacttcctcc tccagcagag      60
gtgtggtgaa tg                                                          72

<210> SEQ ID NO 62
<211> LENGTH: 72
<212> TYPE: DNA
<213> ORGANISM: Artificial Sequence
<220> FEATURE:
<223> OTHER INFORMATION: chemically synthesized

<400> SEQUENCE: 62
cattcaccac acctctgctg gacggaaaca atccccgggt acgagaatca gggtgtggtg      60
tcgtcccgta tc                                                          72

<210> SEQ ID NO 63
<211> LENGTH: 72
<212> TYPE: DNA
<213> ORGANISM: Artificial Sequence
<220> FEATURE:
<223> OTHER INFORMATION: chemically synthesized

<400> SEQUENCE: 63
gatacgggac gacaccacac cctgattctc gtacccgggg attgtttccg tccagcagag      60
gtgtggtgaa tg                                                          72

<210> SEQ ID NO 64
<211> LENGTH: 72
<212> TYPE: DNA
<213> ORGANISM: Artificial Sequence
<220> FEATURE:
<223> OTHER INFORMATION: chemically synthesized
```

<400> SEQUENCE: 64
cattcaccac acctctgctg gaaacctacc attaatgaga catgatgcgg tggtgtggtg    60
tcgtcccgta tc    72

<210> SEQ ID NO 65
<211> LENGTH: 72
<212> TYPE: DNA
<213> ORGANISM: Artificial Sequence
<220> FEATURE:
<223> OTHER INFORMATION: chemically synthesized

<400> SEQUENCE: 65
gatacgggac gacaccacac caccgcatca tgtctcatta atggtaggtt tccagcagag    60
gtgtggtgaa tg    72

<210> SEQ ID NO 66
<211> LENGTH: 72
<212> TYPE: DNA
<213> ORGANISM: Artificial Sequence
<220> FEATURE:
<223> OTHER INFORMATION: chemically synthesized

<400> SEQUENCE: 66
atccgtcaca cctgctctgg tggaatggac taagctagct agcgttttaa aaggtggtgt    60
tggctcccgt at    72

<210> SEQ ID NO 67
<211> LENGTH: 72
<212> TYPE: DNA
<213> ORGANISM: Artificial Sequence
<220> FEATURE:
<223> OTHER INFORMATION: chemically synthesized

<400> SEQUENCE: 67
atccgtcaca cctgctctgt aaggggggg aatcgctttc gtcttaagat gacatggtgt    60
tggctcccgt at    72

<210> SEQ ID NO 68
<211> LENGTH: 59
<212> TYPE: DNA
<213> ORGANISM: Artificial Sequence
<220> FEATURE:
<223> OTHER INFORMATION: chemically synthesized

<400> SEQUENCE: 68
atccgtcaca cctgctctgc cggaccatcc aatatcagct gtggtgttgg ctcccgtat    59

<210> SEQ ID NO 69
<211> LENGTH: 71
<212> TYPE: DNA
<213> ORGANISM: Artificial Sequence
<220> FEATURE:
<223> OTHER INFORMATION: chemically synthesized

<400> SEQUENCE: 69
atccgtcaca cctgctctat ccgtcacgcc tgctctatcc gtcacacctg ctctggtgtt    60
ggctcccgta t    71

<210> SEQ ID NO 70
<211> LENGTH: 72
<212> TYPE: DNA

<213> ORGANISM: Artificial Sequence
<220> FEATURE:
<223> OTHER INFORMATION: chemically synthesized

<400> SEQUENCE: 70
atccgtcaca cctgctctat caaatgtgca gatatcaaga cgatttgtac aagatggtgt    60
tggctcccgt at                                                        72

<210> SEQ ID NO 71
<211> LENGTH: 72
<212> TYPE: DNA
<213> ORGANISM: Artificial Sequence
<220> FEATURE:
<223> OTHER INFORMATION: chemically synthesized

<400> SEQUENCE: 71
atccgtcaca cctgctctgt agatggcaag gcataagcgt ccggaacgat agaatggtgt    60
tggctcccgt at                                                        72

<210> SEQ ID NO 72
<211> LENGTH: 72
<212> TYPE: DNA
<213> ORGANISM: Artificial Sequence
<220> FEATURE:
<223> OTHER INFORMATION: chemically synthesized

<400> SEQUENCE: 72
atccgtcaca cctgctctgt agatggcaag gcataagcgt ccggaacgat agaatggtgt    60
tggctcccgt at                                                        72

<210> SEQ ID NO 73
<211> LENGTH: 72
<212> TYPE: DNA
<213> ORGANISM: Artificial Sequence
<220> FEATURE:
<223> OTHER INFORMATION: chemically synthesized

<400> SEQUENCE: 73
atacgggagc caacaccacc ttttaaaacg ctagctagct tagtccattc caccagagca    60
ggtgtgacgg at                                                        72

<210> SEQ ID NO 74
<211> LENGTH: 72
<212> TYPE: DNA
<213> ORGANISM: Artificial Sequence
<220> FEATURE:
<223> OTHER INFORMATION: chemically synthesized

<400> SEQUENCE: 74
atacgggagc caacaccatg tcatcttaag acgaaagcga ttcccccccc ttacagagca    60
ggtgtgacgg at                                                        72

<210> SEQ ID NO 75
<211> LENGTH: 59
<212> TYPE: DNA
<213> ORGANISM: Artificial Sequence
<220> FEATURE:
<223> OTHER INFORMATION: chemically synthesized

<400> SEQUENCE: 75
atacgggagc caacaccaca gctgatattg gatggtccgg cagagcaggt gtgacggat    59

```
<210> SEQ ID NO 76
<211> LENGTH: 71
<212> TYPE: DNA
<213> ORGANISM: Artificial Sequence
<220> FEATURE:
<223> OTHER INFORMATION: chemically synthesized

<400> SEQUENCE: 76
atacgggagc caacaccaga gcaggtgtga cggatagagc aggcgtgacg gatagagcag      60
gtgtgacgga t                                                          71

<210> SEQ ID NO 77
<211> LENGTH: 72
<212> TYPE: DNA
<213> ORGANISM: Artificial Sequence
<220> FEATURE:
<223> OTHER INFORMATION: chemically synthesized

<400> SEQUENCE: 77
atacgggagc caacaccatc ttgtacaaat cgtcttgata tctgcacatt tgatagagca     60
ggtgtgacgg at                                                         72

<210> SEQ ID NO 78
<211> LENGTH: 72
<212> TYPE: DNA
<213> ORGANISM: Artificial Sequence
<220> FEATURE:
<223> OTHER INFORMATION: chemically synthesized

<400> SEQUENCE: 78
atacgggagc caacaccatt ctatcgttcc ggacgcttat gccttgccat ctacagagca     60
ggtgtgacgg at                                                         72

<210> SEQ ID NO 79
<211> LENGTH: 72
<212> TYPE: DNA
<213> ORGANISM: Artificial Sequence
<220> FEATURE:
<223> OTHER INFORMATION: chemically synthesized

<400> SEQUENCE: 79
atacgggagc caacaccatt ctatcgttcc ggacgcttat gccttgccat ctacagagca     60
ggtgtgacgg at                                                         72

<210> SEQ ID NO 80
<211> LENGTH: 72
<212> TYPE: DNA
<213> ORGANISM: Artificial Sequence
<220> FEATURE:
<223> OTHER INFORMATION: chemically synthesized

<400> SEQUENCE: 80
atacgggagc caacaccatg gtacaagcaa accaatatta gggcccagac atcgagagca     60
ggtgtgacgg at                                                         72

<210> SEQ ID NO 81
<211> LENGTH: 72
<212> TYPE: DNA
<213> ORGANISM: Artificial Sequence
<220> FEATURE:
<223> OTHER INFORMATION: chemically synthesized

<400> SEQUENCE: 81
```

```
atccgtcaca cctgctctcg atgtctgggc cctaatattg gtttgcttgt accatggtgt    60
tggctcccgt at                                                        72
```

<210> SEQ ID NO 82
<211> LENGTH: 72
<212> TYPE: DNA
<213> ORGANISM: Artificial Sequence
<220> FEATURE:
<223> OTHER INFORMATION: chemically synthesized

<400> SEQUENCE: 82

```
atacgggagc caacaccatg atacccctaag gtaggggagg cctaagcgcc acgtagagca    60
ggtgtgacgg at                                                        72
```

<210> SEQ ID NO 83
<211> LENGTH: 72
<212> TYPE: DNA
<213> ORGANISM: Artificial Sequence
<220> FEATURE:
<223> OTHER INFORMATION: chemically synthesized

<400> SEQUENCE: 83

```
atccgtcaca cctgctctac gtggcgctta ggcctcccct accttagggt atcatggtgt    60
tggctcccgt at                                                        72
```

<210> SEQ ID NO 84
<211> LENGTH: 72
<212> TYPE: DNA
<213> ORGANISM: Artificial Sequence
<220> FEATURE:
<223> OTHER INFORMATION: chemically synthesized

<400> SEQUENCE: 84

```
atacgggagc caacaccacg catccccgc cgggcccgcg ccccgctcgc agacagagca     60
ggtgtgacgg at                                                        72
```

<210> SEQ ID NO 85
<211> LENGTH: 72
<212> TYPE: DNA
<213> ORGANISM: Artificial Sequence
<220> FEATURE:
<223> OTHER INFORMATION: chemically synthesized

<400> SEQUENCE: 85

```
atccgtcaca cctgctctgt ctgcgagcgg ggcgcgggcc cggcggggga tgcgtggtgt    60
tggctcccgt at                                                        72
```

<210> SEQ ID NO 86
<211> LENGTH: 73
<212> TYPE: DNA
<213> ORGANISM: Artificial Sequence
<220> FEATURE:
<223> OTHER INFORMATION: chemically synthesized

<400> SEQUENCE: 86

```
atacgggagc caacaccata atatgccgta aggagaggcc tgttgggagc gccgtagagc    60
aggtgtgacg gat                                                       73
```

<210> SEQ ID NO 87
<211> LENGTH: 73
<212> TYPE: DNA
<213> ORGANISM: Artificial Sequence
<220> FEATURE:
<223> OTHER INFORMATION: chemically synthesized

<400> SEQUENCE: 87
atccgtcaca cctgctctac ggcgctccca acaggcctct ccttacggca tattatggtg    60
ttggctcccg tat                                                       73

<210> SEQ ID NO 88
<211> LENGTH: 72
<212> TYPE: DNA
<213> ORGANISM: Artificial Sequence
<220> FEATURE:
<223> OTHER INFORMATION: chemically synthesized

<400> SEQUENCE: 88
atacgggagc caacaccagg aaaaaaagag cctgtgaaga ttgtaatatc agttagagca    60
ggtgtgacgg at                                                        72

<210> SEQ ID NO 89
<211> LENGTH: 71
<212> TYPE: DNA
<213> ORGANISM: Artificial Sequence
<220> FEATURE:
<223> OTHER INFORMATION: chemically synthesized

<400> SEQUENCE: 89
atccgtcaca cctgctctaa ctgatattac aatcttcaca ggctcttttt ttcctggtgt    60
ggctcccgta t                                                         71

<210> SEQ ID NO 90
<211> LENGTH: 72
<212> TYPE: DNA
<213> ORGANISM: Artificial Sequence
<220> FEATURE:
<223> OTHER INFORMATION: chemically synthesized

<400> SEQUENCE: 90
atccgtcaca cctgctctcg gaggtagact aggattgcgg cggggggtca ggtatggtgt    60
tggctcccgt at                                                        72

<210> SEQ ID NO 91
<211> LENGTH: 71
<212> TYPE: DNA
<213> ORGANISM: Artificial Sequence
<220> FEATURE:
<223> OTHER INFORMATION: chemically synthesized

<400> SEQUENCE: 91
atacgggagc caacaccaca aaagccttac ctaactgcca acaatgaata gcaagagcag    60
gtgtgacgga t                                                         71

<210> SEQ ID NO 92
<211> LENGTH: 72
<212> TYPE: DNA
<213> ORGANISM: Artificial Sequence
<220> FEATURE:
<223> OTHER INFORMATION: chemically synthesized

<400> SEQUENCE: 92
atccgtcaca cctgctcttg ctattcattg ttggcagtta ggtaaggctt ttgttggtgt    60
tggctcccgt at                                                        72

```
<210> SEQ ID NO 93
<211> LENGTH: 72
<212> TYPE: DNA
<213> ORGANISM: Artificial Sequence
<220> FEATURE:
<223> OTHER INFORMATION: chemically synthesized

<400> SEQUENCE: 93
atacgggagc caacaccata cctgaccccc cgccgcaatc ctagtctacc tccgagagca      60
ggtgtgacgg at                                                         72

<210> SEQ ID NO 94
<211> LENGTH: 72
<212> TYPE: DNA
<213> ORGANISM: Artificial Sequence
<220> FEATURE:
<223> OTHER INFORMATION: chemically synthesized

<400> SEQUENCE: 94
atacgggagc caacaccacg actaacacga ccgttggggg gggctcgcgc gggcagagca      60
ggtgtgacgg at                                                         72

<210> SEQ ID NO 95
<211> LENGTH: 72
<212> TYPE: DNA
<213> ORGANISM: Artificial Sequence
<220> FEATURE:
<223> OTHER INFORMATION: chemically synthesized

<400> SEQUENCE: 95
atccgtcaca cctgctctgc ccgcgcgagc cccccccaac ggtcgtgtta gtcgtggtgt      60
tggctcccgt at                                                         72

<210> SEQ ID NO 96
<211> LENGTH: 72
<212> TYPE: DNA
<213> ORGANISM: Artificial Sequence
<220> FEATURE:
<223> OTHER INFORMATION: chemically synthesized

<400> SEQUENCE: 96
atacgggagc caacaccagt ccccgcccag ccgtgagccg taccccgca caccagagca       60 ggtgtgacgg at                                                         72

<210> SEQ ID NO 97
<211> LENGTH: 72
<212> TYPE: DNA
<213> ORGANISM: Artificial Sequence
<220> FEATURE:
<223> OTHER INFORMATION: chemically synthesized

<400> SEQUENCE: 97
atccgtcaca cctgctctgg tgtgcggggg tacggctcac ggctgggcgg ggactggtgt      60
tggctcccgt at                                                         72

<210> SEQ ID NO 98
<211> LENGTH: 72
<212> TYPE: DNA
<213> ORGANISM: Artificial Sequence
<220> FEATURE:
<223> OTHER INFORMATION: chemically synthesized

<400> SEQUENCE: 98
```

-continued

```
atccgtcaca cctgctctca aggttgggcc tgcaagagca aaaacggggc gggatggtgt    60
tggctcccgt at                                                         72
```

<210> SEQ ID NO 99
<211> LENGTH: 72
<212> TYPE: DNA
<213> ORGANISM: Artificial Sequence
<220> FEATURE:
<223> OTHER INFORMATION: chemically synthesized

<400> SEQUENCE: 99

```
atacgggagc caacaccatc ccgccccgtt tttgctcttg caggcccaac cttgagagca    60
ggtgtgacgg at                                                         72
```

<210> SEQ ID NO 100
<211> LENGTH: 72
<212> TYPE: DNA
<213> ORGANISM: Artificial Sequence
<220> FEATURE:
<223> OTHER INFORMATION: chemically synthesized

<400> SEQUENCE: 100

```
atccgtcaca cctgctctac ttggcttgcg actattattc acagggccaa agactggtgt    60
tggctcccgt at                                                         72
```

<210> SEQ ID NO 101
<211> LENGTH: 72
<212> TYPE: DNA
<213> ORGANISM: Artificial Sequence
<220> FEATURE:
<223> OTHER INFORMATION: chemically synthesized

<400> SEQUENCE: 101

```
atacgggagc caacaccagt ctttggccct gtgaataata gtcgcaagcc aagtagagca    60
ggtgtgacgg at                                                         72
```

<210> SEQ ID NO 102
<211> LENGTH: 69
<212> TYPE: DNA
<213> ORGANISM: Artificial Sequence
<220> FEATURE:
<223> OTHER INFORMATION: chemically synthesized

<400> SEQUENCE: 102

```
atacgggagc caacaccata gtgttggacc aatacggtaa cgtgtccttg gagagcaggt    60
gtgacggat                                                             69
```

<210> SEQ ID NO 103
<211> LENGTH: 69
<212> TYPE: DNA
<213> ORGANISM: Artificial Sequence
<220> FEATURE:
<223> OTHER INFORMATION: chemically synthesized

<400> SEQUENCE: 103

```
atccgtcaca cctgctctcc aaggacacgt taccgtattg gtccaacact atggtgttgg    60
ctcccgtat                                                             69
```

<210> SEQ ID NO 104
<211> LENGTH: 72
<212> TYPE: DNA

```
<213> ORGANISM: Artificial Sequence
<220> FEATURE:
<223> OTHER INFORMATION: chemically synthesized

<400> SEQUENCE: 104
atccgtcaca cctgctcttg gaatgtcggt gtttttccaa ttccttgggt cgtgtggtgt    60
tggctcccgt at                                                       72

<210> SEQ ID NO 105
<211> LENGTH: 72
<212> TYPE: DNA
<213> ORGANISM: Artificial Sequence
<220> FEATURE:
<223> OTHER INFORMATION: chemically synthesized

<400> SEQUENCE: 105
atacgggagc caacaccaca cgacccaagg aattggaaaa acaccgacat tccaagagca    60
ggtgtgacgg at                                                       72

<210> SEQ ID NO 106
<211> LENGTH: 72
<212> TYPE: DNA
<213> ORGANISM: Artificial Sequence
<220> FEATURE:
<223> OTHER INFORMATION: chemically synthesized

<400> SEQUENCE: 106
atccgtcaca cctgctctgc gacggcgacg cggtccgggc ggggggtggag gacgtggtgt    60 tggctcccgt at                                                       72

<210> SEQ ID NO 107
<211> LENGTH: 72
<212> TYPE: DNA
<213> ORGANISM: Artificial Sequence
<220> FEATURE:
<223> OTHER INFORMATION: chemically synthesized

<400> SEQUENCE: 107
atacgggagc caacaccacg tcctccaccc ccgcccggac cgcgtcgccg tcgcagagca    60
ggtgtgacgg at                                                       72

<210> SEQ ID NO 108
<211> LENGTH: 72
<212> TYPE: DNA
<213> ORGANISM: Artificial Sequence
<220> FEATURE:
<223> OTHER INFORMATION: chemically synthesized

<400> SEQUENCE: 108
atacgggagc caacaccaga gggttctagg gtcacttcca tgagaatggc tcacagagca    60
ggtgtgacgg at                                                       72

<210> SEQ ID NO 109
<211> LENGTH: 72
<212> TYPE: DNA
<213> ORGANISM: Artificial Sequence
<220> FEATURE:
<223> OTHER INFORMATION: chemically synthesized

<400> SEQUENCE: 109
atccgtcaca cctgctctgg cctggggacg cgagggaggc gggggagtc gtggtggtgt    60 tggctcccgt at                                                       72
```

<210> SEQ ID NO 110
<211> LENGTH: 72
<212> TYPE: DNA
<213> ORGANISM: Artificial Sequence
<220> FEATURE:
<223> OTHER INFORMATION: chemically synthesized

<400> SEQUENCE: 110
atacgggagc caacaccacc acgactcccc ccgcctccct cgcgtcccca ggccagagca    60
ggtgtgacgg at    72

<210> SEQ ID NO 111
<211> LENGTH: 72
<212> TYPE: DNA
<213> ORGANISM: Artificial Sequence
<220> FEATURE:
<223> OTHER INFORMATION: chemically synthesized

<400> SEQUENCE: 111
atccgtcaca cctgctctgt gagccattct catggaagtg accctagaac cctctggtgt    60
tggctcccgt at    72

<210> SEQ ID NO 112
<211> LENGTH: 72
<212> TYPE: DNA
<213> ORGANISM: Artificial Sequence
<220> FEATURE:
<223> OTHER INFORMATION: chemically synthesized

<400> SEQUENCE: 112
atccgtcaca cctgctctca cagggcctct tactatacag ttctccagcg ctgctggtgt    60
tggctcccgt at    72

<210> SEQ ID NO 113
<211> LENGTH: 72
<212> TYPE: DNA
<213> ORGANISM: Artificial Sequence
<220> FEATURE:
<223> OTHER INFORMATION: chemically synthesized

<400> SEQUENCE: 113
atacgggagc caacaccagc agcgctggag aactgtatag taagaggccc tgtgagagca    60
ggtgtgacgg at    72

<210> SEQ ID NO 114
<211> LENGTH: 72
<212> TYPE: DNA
<213> ORGANISM: Artificial Sequence
<220> FEATURE:
<223> OTHER INFORMATION: chemically synthesized

<400> SEQUENCE: 114
atccgtcaca cctgctctgc acgggctcag tttggctttg tatcctaaga gagatggtgt    60
tggctcccgt at    72

<210> SEQ ID NO 115
<211> LENGTH: 72
<212> TYPE: DNA
<213> ORGANISM: Artificial Sequence
<220> FEATURE:
<223> OTHER INFORMATION: chemically synthesized

```
<400> SEQUENCE: 115
atacgggagc caacaccatc tctcttagga tacaaagcca aactgagccc gtgcagagca    60
ggtgtgacgg at                                                        72

<210> SEQ ID NO 116
<211> LENGTH: 71
<212> TYPE: DNA
<213> ORGANISM: Artificial Sequence
<220> FEATURE:
<223> OTHER INFORMATION: chemically synthesized

<400> SEQUENCE: 116
atacgggagc caacaccagg ggtggcgaac atggtataac ttgataagtg tgaagagcag    60
gtgtgacgga t                                                         71

<210> SEQ ID NO 117
<211> LENGTH: 72
<212> TYPE: DNA
<213> ORGANISM: Artificial Sequence
<220> FEATURE:
<223> OTHER INFORMATION: chemically synthesized

<400> SEQUENCE: 117
atccgtcaca cctgctcttc acacttatca agttatacca tgttcgccac ccctggtgt    60 tggctcccgt at                                                        72

<210> SEQ ID NO 118
<211> LENGTH: 72
<212> TYPE: DNA
<213> ORGANISM: Artificial Sequence
<220> FEATURE:
<223> OTHER INFORMATION: chemically synthesized

<400> SEQUENCE: 118
atacgggagc caacaccact ccgacaccgg ccgccggcac cacccactcc ccctagagca    60
ggtgtgacgg at                                                        72

<210> SEQ ID NO 119
<211> LENGTH: 72
<212> TYPE: DNA
<213> ORGANISM: Artificial Sequence
<220> FEATURE:
<223> OTHER INFORMATION: chemically synthesized

<400> SEQUENCE: 119
atccgtcaca cctgctctag ggggagtggg tggtgccggc ggccggtgtc ggagtggtgt    60
tggctcccgt at                                                        72

<210> SEQ ID NO 120
<211> LENGTH: 72
<212> TYPE: DNA
<213> ORGANISM: Artificial Sequence
<220> FEATURE:
<223> OTHER INFORMATION: chemically synthesized

<400> SEQUENCE: 120
atacgggagc caacaccatc cggcgcgccc tcctccccca ctgctccccg cccgagagca    60
ggtgtgacgg at                                                        72

<210> SEQ ID NO 121
<211> LENGTH: 72
```

```
<212> TYPE: DNA
<213> ORGANISM: Artificial Sequence
<220> FEATURE:
<223> OTHER INFORMATION: chemically synthesized

<400> SEQUENCE: 121
atccgtcaca cctgctctcg ggcggggagc agtgggggag gagggcgcgc cggatggtgt      60
tggctcccgt at                                                          72

<210> SEQ ID NO 122
<211> LENGTH: 72
<212> TYPE: DNA
<213> ORGANISM: Artificial Sequence
<220> FEATURE:
<223> OTHER INFORMATION: chemically synthesized

<400> SEQUENCE: 122
atacgggagc caacaccata cgcagaggtc ccctacccag gccagccgga tgccagagca      60
ggtgtgacgg at                                                          72

<210> SEQ ID NO 123
<211> LENGTH: 72
<212> TYPE: DNA
<213> ORGANISM: Artificial Sequence
<220> FEATURE:
<223> OTHER INFORMATION: chemically synthesized

<400> SEQUENCE: 123
atccgtcaca cctgctctgg catccggctg gcctgggtag gggacctctg cgtatggtgt      60
tggctcccgt at                                                          72

<210> SEQ ID NO 124
<211> LENGTH: 72
<212> TYPE: DNA
<213> ORGANISM: Artificial Sequence
<220> FEATURE:
<223> OTHER INFORMATION: chemically synthesized

<400> SEQUENCE: 124
atacgggagc caacaccacg aggattacaa ctttatgcgt gcaaccagac accaagagca      60
ggtgtgacgg at                                                          72

<210> SEQ ID NO 125
<211> LENGTH: 72
<212> TYPE: DNA
<213> ORGANISM: Artificial Sequence
<220> FEATURE:
<223> OTHER INFORMATION: chemically synthesized

<400> SEQUENCE: 125
atccgtcaca cctgctcttg gtgtctggtt gcacgcataa agttgtaatc ctcgtggtgt      60
tggctcccgt at                                                          72

<210> SEQ ID NO 126
<211> LENGTH: 72
<212> TYPE: DNA
<213> ORGANISM: Artificial Sequence
<220> FEATURE:
<223> OTHER INFORMATION: chemically synthesized

<400> SEQUENCE: 126
atacgggagc caacaccata taaacgagga aataaaactg cagaacactt cctcagagca      60
```
ggtgtgacgg at                                                          72

<210> SEQ ID NO 127
<211> LENGTH: 72
<212> TYPE: DNA
<213> ORGANISM: Artificial Sequence
<220> FEATURE:
<223> OTHER INFORMATION: chemically synthesized

<400> SEQUENCE: 127
atccgtcaca cctgctctga ggaagtgttc tgcagtttta tttcctcgtt tatatggtgt      60
tggctcccgt at                                                          72

<210> SEQ ID NO 128
<211> LENGTH: 71
<212> TYPE: DNA
<213> ORGANISM: Artificial Sequence
<220> FEATURE:
<223> OTHER INFORMATION: chemically synthesized

<400> SEQUENCE: 128
atacgggagc caacaccatc acggcaatgt cccgataatg tcttgcttca gcgagagcag      60
gtgtgacgga t                                                           71

<210> SEQ ID NO 129
<211> LENGTH: 71
<212> TYPE: DNA
<213> ORGANISM: Artificial Sequence
<220> FEATURE:
<223> OTHER INFORMATION: chemically synthesized

<400> SEQUENCE: 129
atccgtcaca cctgctctcg ctgaagcaag acattatcgg gacattgccg tgatggtgtt      60
ggctcccgta t                                                           71

<210> SEQ ID NO 130
<211> LENGTH: 72
<212> TYPE: DNA
<213> ORGANISM: Artificial Sequence
<220> FEATURE:
<223> OTHER INFORMATION: chemically synthesized

<400> SEQUENCE: 130
atacgggagc caacaccaag caatcagtat acccacccgt caaaaacatc atgcagagca      60
ggtgtgacgg at                                                          72

<210> SEQ ID NO 131
<211> LENGTH: 72
<212> TYPE: DNA
<213> ORGANISM: Artificial Sequence
<220> FEATURE:
<223> OTHER INFORMATION: chemically synthesized

<400> SEQUENCE: 131
atccgtcaca cctgctctgc atgatgtttt tgacgggtgg gtatactgat tgcttggtgt      60
tggctcccgt at                                                          72

<210> SEQ ID NO 132
<211> LENGTH: 72
<212> TYPE: DNA
<213> ORGANISM: Artificial Sequence
<220> FEATURE:
<223> OTHER INFORMATION: chemically synthesized

<400> SEQUENCE: 132
atacgggagc caacaccacg gcttcttgcg cccccccgcg cccgcgcccc ccccagagca    60
ggtgtgacgg at                                                       72

<210> SEQ ID NO 133
<211> LENGTH: 72
<212> TYPE: DNA
<213> ORGANISM: Artificial Sequence
<220> FEATURE:
<223> OTHER INFORMATION: chemically synthesized

<400> SEQUENCE: 133
atccgtcaca cctgctctgg ggggggcgcg ggcgcggggg ggcgcaagaa gccgtggtgt    60
tggctcccgt at                                                       72

<210> SEQ ID NO 134
<211> LENGTH: 72
<212> TYPE: DNA
<213> ORGANISM: Artificial Sequence
<220> FEATURE:
<223> OTHER INFORMATION: chemically synthesized

<400> SEQUENCE: 134
atacgggagc caacaccaac ggaggatgaa gagataaagt aaatatccgg gggcagagca    60
ggtgtgacgg at                                                       72

<210> SEQ ID NO 135
<211> LENGTH: 72
<212> TYPE: DNA
<213> ORGANISM: Artificial Sequence
<220> FEATURE:
<223> OTHER INFORMATION: chemically synthesized

<400> SEQUENCE: 135
atccgtcaca cctgctctgc ccccggatat ttactttatc tcttcatcct ccgttggtgt    60
tggctcccgt at                                                       72

<210> SEQ ID NO 136
<211> LENGTH: 72
<212> TYPE: DNA
<213> ORGANISM: Artificial Sequence
<220> FEATURE:
<223> OTHER INFORMATION: chemically synthesized

<400> SEQUENCE: 136
atacgggagc caacaccacc cgtggccttc acccagccag ggccccgtc tctgagagca     60 ggtgtgacgg at                                                       72

<210> SEQ ID NO 137
<211> LENGTH: 72
<212> TYPE: DNA
<213> ORGANISM: Artificial Sequence
<220> FEATURE:
<223> OTHER INFORMATION: chemically synthesized

<400> SEQUENCE: 137
atccgtcaca cctgctctca gagacggggc ccctggctgg gtgaaggcca cgggtggtgt    60
tggctcccgt at                                                       72

<210> SEQ ID NO 138

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 138
atacgggagc caacaccaca ctaccgtccc accccctccc agctcctccg gccgagagca     60
ggtgtgacgg at                                                        72

<210> SEQ ID NO 139
<211> LENGTH: 72
<212> TYPE: DNA
<213> ORGANISM: Artificial Sequence
<220> FEATURE:
<223> OTHER INFORMATION: chemically synthesized

<400> SEQUENCE: 139
atccgtcaca cctgctctcg gccggaggag ctgggagggg gtgggacggt agtgtggtgt     60
tggctcccgt at                                                        72

<210> SEQ ID NO 140
<211> LENGTH: 72
<212> TYPE: DNA
<213> ORGANISM: Artificial Sequence
<220> FEATURE:
<223> OTHER INFORMATION: chemically synthesized

<400> SEQUENCE: 140
atacgggagc caacaccaat cccccgcctg cgaccgatgc actcccatat gtcgagagca     60
ggtgtgacgg at                                                        72

<210> SEQ ID NO 141
<211> LENGTH: 72
<212> TYPE: DNA
<213> ORGANISM: Artificial Sequence
<220> FEATURE:
<223> OTHER INFORMATION: chemically synthesized

<400> SEQUENCE: 141
atccgtcaca cctgctctcg acatatggga gtgcatcggt cgcaggcggg ggattggtgt     60
tggctcccgt at                                                        72

<210> SEQ ID NO 142
<211> LENGTH: 72
<212> TYPE: DNA
<213> ORGANISM: Artificial Sequence
<220> FEATURE:
<223> OTHER INFORMATION: chemically synthesized

<400> SEQUENCE: 142
atacgggagc caacaccata catgcccaag gtttcgggtg aggctaccgt gagtagagca     60
ggtgtgacgg at                                                        72

<210> SEQ ID NO 143
<211> LENGTH: 72
<212> TYPE: DNA
<213> ORGANISM: Artificial Sequence
<220> FEATURE:
<223> OTHER INFORMATION: chemically synthesized

<400> SEQUENCE: 143
atccgtcaca cctgctctac tcacggtagc ctcacccgaa accttgggca tgtatggtgt     60
```
tggctcccgt at                                                          72

<210> SEQ ID NO 144
<211> LENGTH: 72
<212> TYPE: DNA
<213> ORGANISM: Artificial Sequence
<220> FEATURE:
<223> OTHER INFORMATION: chemically synthesized

<400> SEQUENCE: 144
atacgggagc caacaccatt tatgtttcat actttaaact tggtcgtttg cgatagagca      60
ggtgtgacgg at                                                          72

<210> SEQ ID NO 145
<211> LENGTH: 72
<212> TYPE: DNA
<213> ORGANISM: Artificial Sequence
<220> FEATURE:
<223> OTHER INFORMATION: chemically synthesized

<400> SEQUENCE: 145
atccgtcaca cctgctctat cgcaaacgac caagtttaaa gtatgaaaca taaatggtgt      60
tggctcccgt at                                                          72

<210> SEQ ID NO 146
<211> LENGTH: 72
<212> TYPE: DNA
<213> ORGANISM: Artificial Sequence
<220> FEATURE:
<223> OTHER INFORMATION: chemically synthesized

<400> SEQUENCE: 146
atacgggagc caacaccagg cgtttaataa tcggagcgac aaattctacg ctgtagagca      60
ggtgtgacgg at                                                          72

<210> SEQ ID NO 147
<211> LENGTH: 72
<212> TYPE: DNA
<213> ORGANISM: Artificial Sequence
<220> FEATURE:
<223> OTHER INFORMATION: chemically synthesized

<400> SEQUENCE: 147
atccgtcaca cctgctctac agcgtagaat ttgtcgctcc gattattaaa cgcctggtgt      60
tggctcccgt at                                                          72

<210> SEQ ID NO 148
<211> LENGTH: 72
<212> TYPE: DNA
<213> ORGANISM: Artificial Sequence
<220> FEATURE:
<223> OTHER INFORMATION: chemically synthesized

<400> SEQUENCE: 148
atacgggagc caacaccacg gcaacttcaa acccaagact aagaaaagct cgtgagagca      60
ggtgtgacgg at                                                          72

<210> SEQ ID NO 149
<211> LENGTH: 72
<212> TYPE: DNA
<213> ORGANISM: Artificial Sequence
<220> FEATURE:

```
<223> OTHER INFORMATION: chemically synthesized

<400> SEQUENCE: 149
atccgtcaca cctgctctca cgagcttttc ttagtcttgg gtttgaagtt gccgtggtgt    60
tggctcccgt at                                                       72

<210> SEQ ID NO 150
<211> LENGTH: 72
<212> TYPE: DNA
<213> ORGANISM: Artificial Sequence
<220> FEATURE:
<223> OTHER INFORMATION: chemically synthesized

<400> SEQUENCE: 150
atacgggagc caacaccatt gtaggcggat attagacaag accgaattcc atggagagca    60
ggtgtgacgg at                                                       72

<210> SEQ ID NO 151
<211> LENGTH: 72
<212> TYPE: DNA
<213> ORGANISM: Artificial Sequence
<220> FEATURE:
<223> OTHER INFORMATION: chemically synthesized

<400> SEQUENCE: 151
atccgtcaca cctgctctcc atggaattcg gtcttgtcta atatccgcct acaatggtgt    60
tggctcccgt at                                                       72

<210> SEQ ID NO 152
<211> LENGTH: 72
<212> TYPE: DNA
<213> ORGANISM: Artificial Sequence
<220> FEATURE:
<223> OTHER INFORMATION: chemically synthesized

<400> SEQUENCE: 152
atacgggagc caacaccagt aggctaaagt gaggttaatt atgtcgacaa ggccagagca    60
ggtgtgacgg at                                                       72

<210> SEQ ID NO 153
<211> LENGTH: 72
<212> TYPE: DNA
<213> ORGANISM: Artificial Sequence
<220> FEATURE:
<223> OTHER INFORMATION: chemically synthesized

<400> SEQUENCE: 153
atccgtcaca cctgctctgg ccttgtcgac ataattaacc tcactttagc ctactggtgt    60
tggctcccgt at                                                       72

<210> SEQ ID NO 154
<211> LENGTH: 72
<212> TYPE: DNA
<213> ORGANISM: Artificial Sequence
<220> FEATURE:
<223> OTHER INFORMATION: chemically synthesized

<400> SEQUENCE: 154
atacgggagc caacaccacc tcgcccagac gccgggccct cccgccccca cccagagca    60 ggtgtgacgg at                                                       72
```

```
<210> SEQ ID NO 155
<211> LENGTH: 72
<212> TYPE: DNA
<213> ORGANISM: Artificial Sequence
<220> FEATURE:
<223> OTHER INFORMATION: chemically synthesized

<400> SEQUENCE: 155
atccgtcaca cctgctctgg ggtggggcgg ggagggcccg gcgtctgggc gaggtggtgt      60
tggctcccgt at                                                         72

<210> SEQ ID NO 156
<211> LENGTH: 72
<212> TYPE: DNA
<213> ORGANISM: Artificial Sequence
<220> FEATURE:
<223> OTHER INFORMATION: chemically synthesized

<400> SEQUENCE: 156
atacgggagc caacaccagg tattggagct atacacgtta accaccgcta ttgcagagca      60
ggtgtgacgg at                                                         72

<210> SEQ ID NO 157
<211> LENGTH: 72
<212> TYPE: DNA
<213> ORGANISM: Artificial Sequence
<220> FEATURE:
<223> OTHER INFORMATION: chemically synthesized

<400> SEQUENCE: 157
atccgtcaca cctgctctgc aatagcggtg gttaacgtgt atagctccaa tacctggtgt      60
tggctcccgt at                                                         72

<210> SEQ ID NO 158
<211> LENGTH: 72
<212> TYPE: DNA
<213> ORGANISM: Artificial Sequence
<220> FEATURE:
<223> OTHER INFORMATION: chemically synthesized

<400> SEQUENCE: 158
atacgggagc caacaccacg cggggcgggg gggctggtcg cgcgggcctg gcggagagca      60
ggtgtgacgg at                                                         72

<210> SEQ ID NO 159
<211> LENGTH: 72
<212> TYPE: DNA
<213> ORGANISM: Artificial Sequence
<220> FEATURE:
<223> OTHER INFORMATION: chemically synthesized

<400> SEQUENCE: 159
atccgtcaca cctgctctcc gccaggcccg cgcgaccagc cccccgcccc gcgtggtgt       60 tggctcccgt at                                                         72

<210> SEQ ID NO 160
<211> LENGTH: 72
<212> TYPE: DNA
<213> ORGANISM: Artificial Sequence
<220> FEATURE:
<223> OTHER INFORMATION: chemically synthesized

<400> SEQUENCE: 160
```
atacgggagc caacaccaaa cattggaaca acaaacgcta atacacgatc gcatagagca    60
ggtgtgacgg at    72

<210> SEQ ID NO 161
<211> LENGTH: 72
<212> TYPE: DNA
<213> ORGANISM: Artificial Sequence
<220> FEATURE:
<223> OTHER INFORMATION: chemically synthesized

<400> SEQUENCE: 161
atccgtcaca cctgctctat gcgatcgtgt attagcgttt gttgttccaa tgtttggtgt    60
tggctcccgt at    72

<210> SEQ ID NO 162
<211> LENGTH: 72
<212> TYPE: DNA
<213> ORGANISM: Artificial Sequence
<220> FEATURE:
<223> OTHER INFORMATION: chemically synthesized

<400> SEQUENCE: 162
atacgggagc caacaccaat agatggataa gggggaaact gccattcggt tagtagagca    60
ggtgtgacgg at    72

<210> SEQ ID NO 163
<211> LENGTH: 72
<212> TYPE: DNA
<213> ORGANISM: Artificial Sequence
<220> FEATURE:
<223> OTHER INFORMATION: chemically synthesized

<400> SEQUENCE: 163
atccgtcaca cctgctctac taaccgaatg gcagtttccc ccttatccat ctattggtgt    60
tggctcccgt at    72

<210> SEQ ID NO 164
<211> LENGTH: 72
<212> TYPE: DNA
<213> ORGANISM: Artificial Sequence
<220> FEATURE:
<223> OTHER INFORMATION: chemically synthesized

<400> SEQUENCE: 164
atacgggagc caacaccaac caacgaagaa gggtcagaca aaaggagtt ctcgagagca    60 ggtgtgacgg at    72

<210> SEQ ID NO 165
<211> LENGTH: 72
<212> TYPE: DNA
<213> ORGANISM: Artificial Sequence
<220> FEATURE:
<223> OTHER INFORMATION: chemically synthesized

<400> SEQUENCE: 165
atccgtcaca cctgctctcg agaactcctt tttgtctgac ccttcttcgt tggttggtgt    60
tggctcccgt at    72

<210> SEQ ID NO 166
<211> LENGTH: 72
<212> TYPE: DNA
<213> ORGANISM: Artificial Sequence

```
<220> FEATURE:
<223> OTHER INFORMATION: chemically synthesized

<400> SEQUENCE: 166
atacgggagc caacaccaca acagtcagat tgcaactgag tagtacatac gttaagagca    60
ggtgtgacgg at                                                       72

<210> SEQ ID NO 167
<211> LENGTH: 72
<212> TYPE: DNA
<213> ORGANISM: Artificial Sequence
<220> FEATURE:
<223> OTHER INFORMATION: chemically synthesized

<400> SEQUENCE: 167
atccgtcaca cctgctctta acgtatgtac tactcagttg caatctgact gttgtggtgt    60
tggctcccgt at                                                       72

<210> SEQ ID NO 168
<211> LENGTH: 72
<212> TYPE: DNA
<213> ORGANISM: Artificial Sequence
<220> FEATURE:
<223> OTHER INFORMATION: chemically synthesized

<400> SEQUENCE: 168
atacgggagc caacaccata aaccaagggt gtaacagaaa tgatgtgacc aggcagagca    60
ggtgtgacgg at                                                       72

<210> SEQ ID NO 169
<211> LENGTH: 72
<212> TYPE: DNA
<213> ORGANISM: Artificial Sequence
<220> FEATURE:
<223> OTHER INFORMATION: chemically synthesized

<400> SEQUENCE: 169
atccgtcaca cctgctctgc ctggtcacat catttctgtt acacccttgg tttatggtgt    60
tggctcccgt at                                                       72

<210> SEQ ID NO 170
<211> LENGTH: 72
<212> TYPE: DNA
<213> ORGANISM: Artificial Sequence
<220> FEATURE:
<223> OTHER INFORMATION: chemically synthesized

<400> SEQUENCE: 170
atacgggagc caacaccatc attgcgacat tgaattcaga aggaggagtg gtgtagagca    60
ggtgtgacgg at                                                       72

<210> SEQ ID NO 171
<211> LENGTH: 72
<212> TYPE: DNA
<213> ORGANISM: Artificial Sequence
<220> FEATURE:
<223> OTHER INFORMATION: chemically synthesized

<400> SEQUENCE: 171
atccgtcaca cctgctctac accactcctc cttctgaatt caatgtcgca atgatggtgt    60
tggctcccgt at                                                       72
```

<210> SEQ ID NO 172
<211> LENGTH: 71
<212> TYPE: DNA
<213> ORGANISM: Artificial Sequence
<220> FEATURE:
<223> OTHER INFORMATION: chemically synthesized

<400> SEQUENCE: 172
atacgggagc caacaccaga gaattacaac aggttaagta gtgtgacgat catagagcag    60
gtgtgacgga t                                                        71

<210> SEQ ID NO 173
<211> LENGTH: 71
<212> TYPE: DNA
<213> ORGANISM: Artificial Sequence
<220> FEATURE:
<223> OTHER INFORMATION: chemically synthesized

<400> SEQUENCE: 173
atccgtcaca cctgctctat gatcgtcaca ctacttaacc tgttgtaatt ctctggtgtt    60
ggctcccgta t                                                        71

<210> SEQ ID NO 174
<211> LENGTH: 72
<212> TYPE: DNA
<213> ORGANISM: Artificial Sequence
<220> FEATURE:
<223> OTHER INFORMATION: chemically synthesized

<400> SEQUENCE: 174
atacgggagc caacaccacg gcggaacaca tggaacaccg aataatgtgg cttaagagca    60
ggtgtgacgg at                                                       72

<210> SEQ ID NO 175
<211> LENGTH: 72
<212> TYPE: DNA
<213> ORGANISM: Artificial Sequence
<220> FEATURE:
<223> OTHER INFORMATION: chemically synthesized

<400> SEQUENCE: 175
atccgtcaca cctgctctta agccacatta ttcggtgttc catgtgttcc gccgtggtgt    60
tggctcccgt at                                                       72

<210> SEQ ID NO 176
<211> LENGTH: 72
<212> TYPE: DNA
<213> ORGANISM: Artificial Sequence
<220> FEATURE:
<223> OTHER INFORMATION: chemically synthesized

<400> SEQUENCE: 176
atacgggagc caacaccagc gtggtggacg tataacaaga cagaagtaac ccgtagagca    60
ggtgtgacgg at                                                       72

<210> SEQ ID NO 177
<211> LENGTH: 72
<212> TYPE: DNA
<213> ORGANISM: Artificial Sequence
<220> FEATURE:
<223> OTHER INFORMATION: chemically synthesized

<400> SEQUENCE: 177

```
atccgtcaca cctgctctac gggttacttc tgtcttgtta tacgtccacc acgctggtgt    60
tggctcccgt at                                                        72

<210> SEQ ID NO 178
<211> LENGTH: 71
<212> TYPE: DNA
<213> ORGANISM: Artificial Sequence
<220> FEATURE:
<223> OTHER INFORMATION: chemically synthesized

<400> SEQUENCE: 178
atacgggagc caacaccatg acaaacatca atgcagcaaa gactagcaac gtgagagcag    60
gtgtgacgga t                                                         71

<210> SEQ ID NO 179
<211> LENGTH: 71
<212> TYPE: DNA
<213> ORGANISM: Artificial Sequence
<220> FEATURE:
<223> OTHER INFORMATION: chemically synthesized

<400> SEQUENCE: 179
atccgtcaca cctgctctca cgttgctagt ctttgctgca ttgatgtttg tcatggtgtt    60
ggctcccgta t                                                         71

<210> SEQ ID NO 180
<211> LENGTH: 71
<212> TYPE: DNA
<213> ORGANISM: Artificial Sequence
<220> FEATURE:
<223> OTHER INFORMATION: chemically synthesized

<400> SEQUENCE: 180
atacgggagc caacaccagc cggcaatggc tgagagagaa tagagcgtgg tatagagcag    60
gtgtgacgga t                                                         71

<210> SEQ ID NO 181
<211> LENGTH: 71
<212> TYPE: DNA
<213> ORGANISM: Artificial Sequence
<220> FEATURE:
<223> OTHER INFORMATION: chemically synthesized

<400> SEQUENCE: 181
atccgtcaca cctgctctat accacgctct attctctctc agccattgcc ggctggtgtt    60
ggctcccgta t                                                         71

<210> SEQ ID NO 182
<211> LENGTH: 72
<212> TYPE: DNA
<213> ORGANISM: Artificial Sequence
<220> FEATURE:
<223> OTHER INFORMATION: chemically synthesized

<400> SEQUENCE: 182
atacgggagc caacaccaag ggggcggcga gtcgtagcgt cgataatact ggacagagca    60
ggtgtgacgg at                                                        72

<210> SEQ ID NO 183
<211> LENGTH: 72
<212> TYPE: DNA
```

<213> ORGANISM: Artificial Sequence
<220> FEATURE:
<223> OTHER INFORMATION: chemically synthesized

<400> SEQUENCE: 183
atccgtcaca cctgctctgt ccagtattat cgacgctacg actcgccgcc cccttggtgt    60
tggctcccgt at    72

<210> SEQ ID NO 184
<211> LENGTH: 72
<212> TYPE: DNA
<213> ORGANISM: Artificial Sequence
<220> FEATURE:
<223> OTHER INFORMATION: chemically synthesized

<400> SEQUENCE: 184
atacgggagc caacaccagc ccggagccct tcgtctgccc gcagtccagt gtatagagca    60
ggtgtgacgg at    72

<210> SEQ ID NO 185
<211> LENGTH: 72
<212> TYPE: DNA
<213> ORGANISM: Artificial Sequence
<220> FEATURE:
<223> OTHER INFORMATION: chemically synthesized

<400> SEQUENCE: 185
atccgtcaca cctgctctat acactggact gcgggcagac gaagggctcc gggctggtgt    60
tggctcccgt at    72

<210> SEQ ID NO 186
<211> LENGTH: 72
<212> TYPE: DNA
<213> ORGANISM: Artificial Sequence
<220> FEATURE:
<223> OTHER INFORMATION: chemically synthesized

<400> SEQUENCE: 186
atacgggagc caacaccatc cgcgcccccg cggcatccgc tcacgcgtcc cggcagagca    60
ggtgtgacgg at    72

<210> SEQ ID NO 187
<211> LENGTH: 72
<212> TYPE: DNA
<213> ORGANISM: Artificial Sequence
<220> FEATURE:
<223> OTHER INFORMATION: chemically synthesized

<400> SEQUENCE: 187
atccgtcaca cctgctctgc cgggacgcgt gagcggatgc cgcggggcg cggatggtgt    60 tggctcccgt at    72

<210> SEQ ID NO 188
<211> LENGTH: 72
<212> TYPE: DNA
<213> ORGANISM: Artificial Sequence
<220> FEATURE:
<223> OTHER INFORMATION: chemically synthesized

<400> SEQUENCE: 188
atacgggagc caacaccatg caggacaaag cgatgagata cgatctaccg ctcgagagca    60
ggtgtgacgg at    72

<210> SEQ ID NO 189
<211> LENGTH: 72
<212> TYPE: DNA
<213> ORGANISM: Artificial Sequence
<220> FEATURE:
<223> OTHER INFORMATION: chemically synthesized

<400> SEQUENCE: 189
atccgtcaca cctgctctcg agcggtagat cgtatctcat cgctttgtcc tgcatggtgt    60
tggctcccgt at    72

<210> SEQ ID NO 190
<211> LENGTH: 72
<212> TYPE: DNA
<213> ORGANISM: Artificial Sequence
<220> FEATURE:
<223> OTHER INFORMATION: chemically synthesized

<400> SEQUENCE: 190
atacgggagc caacaccatg gagaggaaga cggaaagtat ggagtggatg aaggagagca    60
ggtgtgacgg at    72

<210> SEQ ID NO 191
<211> LENGTH: 72
<212> TYPE: DNA
<213> ORGANISM: Artificial Sequence
<220> FEATURE:
<223> OTHER INFORMATION: chemically synthesized

<400> SEQUENCE: 191
atccgtcaca cctgctctcc ttcatccact ccatactttc cgtcttcctc tccatggtgt    60
tggctcccgt at    72

<210> SEQ ID NO 192
<211> LENGTH: 72
<212> TYPE: DNA
<213> ORGANISM: Artificial Sequence
<220> FEATURE:
<223> OTHER INFORMATION: chemically synthesized

<400> SEQUENCE: 192
atacgggagc caacaccacg aaggagtaaa gcatgctgtc cctatgagct gggaagagca    60
ggtgtgacgg at    72

<210> SEQ ID NO 193
<211> LENGTH: 72
<212> TYPE: DNA
<213> ORGANISM: Artificial Sequence
<220> FEATURE:
<223> OTHER INFORMATION: chemically synthesized

<400> SEQUENCE: 193
atccgtcaca cctgctcttc ccagctcata gggacagcat gctttactcc ttcgtggtgt    60
tggctcccgt at    72

<210> SEQ ID NO 194
<211> LENGTH: 72
<212> TYPE: DNA
<213> ORGANISM: Artificial Sequence
<220> FEATURE:
<223> OTHER INFORMATION: chemically synthesized

```
<400> SEQUENCE: 194
atacgggagc caacaccacc ctgagacata cctagtcaag tggaacagac aggtagagca    60
ggtgtgacgg at                                                        72

<210> SEQ ID NO 195
<211> LENGTH: 72
<212> TYPE: DNA
<213> ORGANISM: Artificial Sequence
<220> FEATURE:
<223> OTHER INFORMATION: chemically synthesized

<400> SEQUENCE: 195
atccgtcaca cctgctctac ctgtctgttc cacttgacta ggtatgtctc agggtggtgt    60
tggctcccgt at                                                        72

<210> SEQ ID NO 196
<211> LENGTH: 72
<212> TYPE: DNA
<213> ORGANISM: Artificial Sequence
<220> FEATURE:
<223> OTHER INFORMATION: chemically synthesized

<400> SEQUENCE: 196
atacgggagc caacaccagt agggagaagt tcgaatgaaa atacgctacg aacaagagca    60
ggtgtgacgg at                                                        72

<210> SEQ ID NO 197
<211> LENGTH: 72
<212> TYPE: DNA
<213> ORGANISM: Artificial Sequence
<220> FEATURE:
<223> OTHER INFORMATION: chemically synthesized

<400> SEQUENCE: 197
atccgtcaca cctgctcttg ttcgtagcgt attttcattc gaacttctcc ctactggtgt    60
tggctcccgt at                                                        72

<210> SEQ ID NO 198
<211> LENGTH: 72
<212> TYPE: DNA
<213> ORGANISM: Artificial Sequence
<220> FEATURE:
<223> OTHER INFORMATION: chemically synthesized

<400> SEQUENCE: 198
atacgggagc caacaccact ccctaccggc tctgcgggaa atatgttttg acccagagca    60
ggtgtgacgg at                                                        72

<210> SEQ ID NO 199
<211> LENGTH: 72
<212> TYPE: DNA
<213> ORGANISM: Artificial Sequence
<220> FEATURE:
<223> OTHER INFORMATION: chemically synthesized

<400> SEQUENCE: 199
atccgtcaca cctgctctgg gtcaaaacat atttcccgca gagccggtag ggagtggtgt    60
tggctcccgt at                                                        72

<210> SEQ ID NO 200
<211> LENGTH: 72
```

```
<212> TYPE: DNA
<213> ORGANISM: Artificial Sequence
<220> FEATURE:
<223> OTHER INFORMATION: chemically synthesized

<400> SEQUENCE: 200
atacgggagc caacaccacc cgtggccttc acccagccag gggccccgtc tctgagagca      60
ggtgtgacgg at                                                          72

<210> SEQ ID NO 201
<211> LENGTH: 72
<212> TYPE: DNA
<213> ORGANISM: Artificial Sequence
<220> FEATURE:
<223> OTHER INFORMATION: chemically synthesized

<400> SEQUENCE: 201
atccgtcaca cctgctctca gagacggggc cctggctgg gtgaaggcca cgggtggtgt       60
tggctcccgt at                                                          72

<210> SEQ ID NO 202
<211> LENGTH: 72
<212> TYPE: DNA
<213> ORGANISM: Artificial Sequence
<220> FEATURE:
<223> OTHER INFORMATION: chemically synthesized

<400> SEQUENCE: 202
atacgggagc caacaccaca aagtcctccc ccctgggcgc cttcaccca ctgcagagca       60 ggtgtgacgg at                                                          72

<210> SEQ ID NO 203
<211> LENGTH: 72
<212> TYPE: DNA
<213> ORGANISM: Artificial Sequence
<220> FEATURE:
<223> OTHER INFORMATION: chemically synthesized

<400> SEQUENCE: 203
atccgtcaca cctgctctgc ggtggggtga aggcgcccag ggggaggac tttgtggtgt       60 tggctcccgt at                                                          72

<210> SEQ ID NO 204
<211> LENGTH: 72
<212> TYPE: DNA
<213> ORGANISM: Artificial Sequence
<220> FEATURE:
<223> OTHER INFORMATION: chemically synthesized

<400> SEQUENCE: 204
atacgggagc caacaccatg gtagacagcg tcgccctgcc atcactccgg ccccagagca     60
ggtgtgacgg at                                                          72

<210> SEQ ID NO 205
<211> LENGTH: 72
<212> TYPE: DNA
<213> ORGANISM: Artificial Sequence
<220> FEATURE:
<223> OTHER INFORMATION: chemically synthesized

<400> SEQUENCE: 205
atccgtcaca cctgctctgg ggccggagtg atggcagggc gacgctgtct accatggtgt      60
```
tggctcccgt at                                                            72

<210> SEQ ID NO 206
<211> LENGTH: 72
<212> TYPE: DNA
<213> ORGANISM: Artificial Sequence
<220> FEATURE:
<223> OTHER INFORMATION: chemically synthesized

<400> SEQUENCE: 206
atacgggagc caacaccacg atcccggcgc gacggatgta aataagtgt gctcagagca        60 ggtgtgacgg at                                                            72

<210> SEQ ID NO 207
<211> LENGTH: 72
<212> TYPE: DNA
<213> ORGANISM: Artificial Sequence
<220> FEATURE:
<223> OTHER INFORMATION: chemically synthesized

<400> SEQUENCE: 207
atccgtcaca cctgctctga gcacacttat tttacatccg tcgcgccggg atcgtggtgt        60
tggctcccgt at                                                            72

<210> SEQ ID NO 208
<211> LENGTH: 72
<212> TYPE: DNA
<213> ORGANISM: Artificial Sequence
<220> FEATURE:
<223> OTHER INFORMATION: chemically synthesized

<400> SEQUENCE: 208
atacgggagc caacaccagg gaagatatgc aacagatggt ggaccgtagt atggagagca        60
ggtgtgacgg at                                                            72

<210> SEQ ID NO 209
<211> LENGTH: 72
<212> TYPE: DNA
<213> ORGANISM: Artificial Sequence
<220> FEATURE:
<223> OTHER INFORMATION: chemically synthesized

<400> SEQUENCE: 209
atccgtcaca cctgctctcc atactacggt ccaccatctg ttgcatatct tccctggtgt        60
tggctcccgt at                                                            72

<210> SEQ ID NO 210
<211> LENGTH: 72
<212> TYPE: DNA
<213> ORGANISM: Artificial Sequence
<220> FEATURE:
<223> OTHER INFORMATION: chemically synthesized

<400> SEQUENCE: 210
atacgggagc caacaccaca gcagggtact gtagtggtgg ggggccggtc cgggagagca        60
ggtgtgacgg at                                                            72

<210> SEQ ID NO 211
<211> LENGTH: 72
<212> TYPE: DNA
<213> ORGANISM: Artificial Sequence
<220> FEATURE:
<223> OTHER INFORMATION: chemically synthesized

<400> SEQUENCE: 211
atccgtcaca cctgctctcc cggaccggcc ccccaccact acagtaccct gctgtggtgt        60
tggctcccgt at                                                            72

<210> SEQ ID NO 212
<211> LENGTH: 72
<212> TYPE: DNA
<213> ORGANISM: Artificial Sequence
<220> FEATURE:
<223> OTHER INFORMATION: chemically synthesized

<400> SEQUENCE: 212
atacgggagc caacaccaag acggacaggg gacgtcggtg aagcgacgga ttggagagca        60
ggtgtgacgg at                                                            72

<210> SEQ ID NO 213
<211> LENGTH: 72
<212> TYPE: DNA
<213> ORGANISM: Artificial Sequence
<220> FEATURE:
<223> OTHER INFORMATION: chemically synthesized

<400> SEQUENCE: 213
atccgtcaca cctgctctcc aatccgtcgc ttcaccgacg tccctgtcc gtcttggtgt         60 tggctcccgt at                                                            72

<210> SEQ ID NO 214
<211> LENGTH: 72
<212> TYPE: DNA
<213> ORGANISM: Artificial Sequence
<220> FEATURE:
<223> OTHER INFORMATION: chemically synthesized

<400> SEQUENCE: 214
atacgggagc caacaccaca cgagccaggt aaaagtaagc cacacaaagt gctcagagca        60
ggtgtgacgg at                                                            72

<210> SEQ ID NO 215
<211> LENGTH: 72
<212> TYPE: DNA
<213> ORGANISM: Artificial Sequence
<220> FEATURE:
<223> OTHER INFORMATION: chemically synthesized

<400> SEQUENCE: 215
atccgtcaca cctgctctga gcactttgtg tggcttactt ttacctggct cgtgtggtgt        60
tggctcccgt at                                                            72

<210> SEQ ID NO 216
<211> LENGTH: 72
<212> TYPE: DNA
<213> ORGANISM: Artificial Sequence
<220> FEATURE:
<223> OTHER INFORMATION: chemically synthesized

<400> SEQUENCE: 216
atacgggagc caacaccacc acgcgacacc ccctcctgtc ccccgcccgc ttccagagca        60
ggtgtgacgg at                                                            72

<210> SEQ ID NO 217

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 217
atccgtcaca cctgctctgg aagcgggcgg gggacaggag ggggtgtcgc gtggtggtgt    60
tggctcccgt at                                                       72

<210> SEQ ID NO 218
<211> LENGTH: 72
<212> TYPE: DNA
<213> ORGANISM: Artificial Sequence
<220> FEATURE:
<223> OTHER INFORMATION: chemically synthesized

<400> SEQUENCE: 218
atacgggagc caacaccatc gagaagcatt gataacaaaa tttaaacccc tgccagagca    60
ggtgtgacgg at                                                       72

<210> SEQ ID NO 219
<211> LENGTH: 72
<212> TYPE: DNA
<213> ORGANISM: Artificial Sequence
<220> FEATURE:
<223> OTHER INFORMATION: chemically synthesized

<400> SEQUENCE: 219
atccgtcaca cctgctctgg cagggsgttta aattttgtta tcaatgcttc tcgatggtgt    60
tggctcccgt at                                                       72

<210> SEQ ID NO 220
<211> LENGTH: 72
<212> TYPE: DNA
<213> ORGANISM: Artificial Sequence
<220> FEATURE:
<223> OTHER INFORMATION: chemically synthesized

<400> SEQUENCE: 220
atacgggagc caacaccatc gagaagcatt gataacaaaa tttaaacccc tgccagagca    60
ggtgtgacgg at                                                       72

<210> SEQ ID NO 221
<211> LENGTH: 72
<212> TYPE: DNA
<213> ORGANISM: Artificial Sequence
<220> FEATURE:
<223> OTHER INFORMATION: chemically synthesized

<400> SEQUENCE: 221
atccgtcaca cctgctctgg cagggsgttta aattttgtta tcaatgcttc tcgatggtgt    60
tggctcccgt at                                                       72

<210> SEQ ID NO 222
<211> LENGTH: 72
<212> TYPE: DNA
<213> ORGANISM: Artificial Sequence
<220> FEATURE:
<223> OTHER INFORMATION: chemically synthesized

<400> SEQUENCE: 222
atacgggagc caacaccagg atccgtagaa tgatttaaat aaacacgaac acatagagca    60
```
ggtgtgacgg at                                                          72

<210> SEQ ID NO 223
<211> LENGTH: 72
<212> TYPE: DNA
<213> ORGANISM: Artificial Sequence
<220> FEATURE:
<223> OTHER INFORMATION: chemically synthesized

<400> SEQUENCE: 223
atccgtcaca cctgctctat gtgttcgtgt ttatttaaat cattctacgg atcctggtgt      60
tggctcccgt at                                                          72

<210> SEQ ID NO 224
<211> LENGTH: 72
<212> TYPE: DNA
<213> ORGANISM: Artificial Sequence
<220> FEATURE:
<223> OTHER INFORMATION: chemically synthesized

<400> SEQUENCE: 224
atccgtcaca cctgctctaa ttaggatacg gggcaacaga acgagagggg ggaatggtgt      60
tggctcccgt at                                                          72

<210> SEQ ID NO 225
<211> LENGTH: 71
<212> TYPE: DNA
<213> ORGANISM: Artificial Sequence
<220> FEATURE:
<223> OTHER INFORMATION: chemically synthesized

<400> SEQUENCE: 225
atccgtcaca cctgctctcg gaccaggtca gacaagcaca tcggatatcc ggctggtgtt      60
ggctcccgta t                                                           71

<210> SEQ ID NO 226
<211> LENGTH: 72
<212> TYPE: DNA
<213> ORGANISM: Artificial Sequence
<220> FEATURE:
<223> OTHER INFORMATION: chemically synthesized

<400> SEQUENCE: 226
atccgtcaca cctgctcttg agtcaaagag tttagggagg agctaacata acagtggtgt      60
tggctcccgt at                                                          72

<210> SEQ ID NO 227
<211> LENGTH: 72
<212> TYPE: DNA
<213> ORGANISM: Artificial Sequence
<220> FEATURE:
<223> OTHER INFORMATION: chemically synthesized

<400> SEQUENCE: 227
atccgtcaca cctgctctaa caacaatgca tcagcgggct gggaacgcat gcggtggtgt      60
tggctcccgt at                                                          72

<210> SEQ ID NO 228
<211> LENGTH: 72
<212> TYPE: DNA
<213> ORGANISM: Artificial Sequence
<220> FEATURE:

<223> OTHER INFORMATION: chemically synthesized

<400> SEQUENCE: 228
atccgtcaca cctgctctga acaggttata agcaggagtg atagtttcag gatctggtgt    60
tggctcccgt at    72

<210> SEQ ID NO 229
<211> LENGTH: 71
<212> TYPE: DNA
<213> ORGANISM: Artificial Sequence
<220> FEATURE:
<223> OTHER INFORMATION: chemically synthesized

<400> SEQUENCE: 229
atccgtcaca cctgctctcg gcggctcgca aaccgagtgg tcagcacccg ggttggtgtt    60
ggctcccgta t    71

<210> SEQ ID NO 230
<211> LENGTH: 72
<212> TYPE: DNA
<213> ORGANISM: Artificial Sequence
<220> FEATURE:
<223> OTHER INFORMATION: chemically synthesized

<400> SEQUENCE: 230
atccgtcaca cctgctctgc gcaagacgta atccacaaga ccgtgaaaac atagtggtgt    60
tggctcccgt at    72

<210> SEQ ID NO 231
<211> LENGTH: 72
<212> TYPE: DNA
<213> ORGANISM: Artificial Sequence
<220> FEATURE:
<223> OTHER INFORMATION: chemically synthesized

<400> SEQUENCE: 231
atacgggagc caacaccatt cccccctctc gttctgttgc cccgtatcct aattagagca    60
ggtgtgacgg at    72

<210> SEQ ID NO 232
<211> LENGTH: 71
<212> TYPE: DNA
<213> ORGANISM: Artificial Sequence
<220> FEATURE:
<223> OTHER INFORMATION: chemically synthesized

<400> SEQUENCE: 232
atacgggagc caacaccagc cggatatccg atgtgcttgt ctgacctggt ccgagagcag    60
gtgtgacgga t    71

<210> SEQ ID NO 233
<211> LENGTH: 72
<212> TYPE: DNA
<213> ORGANISM: Artificial Sequence
<220> FEATURE:
<223> OTHER INFORMATION: chemically synthesized

<400> SEQUENCE: 233
atacgggagc caacaccact gttatgttag ctcctcccta aactctttga ctcaagagca    60
ggtgtgacgg at    72

```
<210> SEQ ID NO 234
<211> LENGTH: 72
<212> TYPE: DNA
<213> ORGANISM: Artificial Sequence
<220> FEATURE:
<223> OTHER INFORMATION: chemically synthesized

<400> SEQUENCE: 234
atacgggagc caacaccacc gcatgcgttc ccagcccgct gatgcattgt tgttagagca      60
ggtgtgacgg at                                                         72

<210> SEQ ID NO 235
<211> LENGTH: 72
<212> TYPE: DNA
<213> ORGANISM: Artificial Sequence
<220> FEATURE:
<223> OTHER INFORMATION: chemically synthesized

<400> SEQUENCE: 235
atacgggagc caacaccaga tcctgaaact atcactcctg cttataacct gttcagagca      60
ggtgtgacgg at                                                         72

<210> SEQ ID NO 236
<211> LENGTH: 71
<212> TYPE: DNA
<213> ORGANISM: Artificial Sequence
<220> FEATURE:
<223> OTHER INFORMATION: chemically synthesized

<400> SEQUENCE: 236
atacgggagc caacaccaac ccgggtgctg accactcggt ttgcgagccg ccagagcag       60 gtgtgacgga t                                                          71

<210> SEQ ID NO 237
<211> LENGTH: 72
<212> TYPE: DNA
<213> ORGANISM: Artificial Sequence
<220> FEATURE:
<223> OTHER INFORMATION: chemically synthesized

<400> SEQUENCE: 237
atacgggagc caacaccact atgttttcac ggtcttgtgg attacgtctt gcgcagagca      60
ggtgtgacgg at                                                         72

<210> SEQ ID NO 238
<211> LENGTH: 72
<212> TYPE: DNA
<213> ORGANISM: Artificial Sequence
<220> FEATURE:
<223> OTHER INFORMATION: chemically synthesized

<400> SEQUENCE: 238
atccgtcaca cctgctctag gcgtagtgac taagtcgcgc gaaaatcaca gcattggtgt      60
tggctcccgt at                                                         72

<210> SEQ ID NO 239
<211> LENGTH: 72
<212> TYPE: DNA
<213> ORGANISM: Artificial Sequence
<220> FEATURE:
<223> OTHER INFORMATION: chemically synthesized

<400> SEQUENCE: 239
```

```
atccgtcaca cctgctctca gcggcagcta tacagtgaga acggactagt gcgttggtgt      60
tggctcccgt at                                                          72

<210> SEQ ID NO 240
<211> LENGTH: 72
<212> TYPE: DNA
<213> ORGANISM: Artificial Sequence
<220> FEATURE:
<223> OTHER INFORMATION: chemically synthesized

<400> SEQUENCE: 240
atccgtcaca cctgctctgg caaataatac tagcgatgat ggatctggat agactggtgt      60
tggctcccgt at                                                          72

<210> SEQ ID NO 241
<211> LENGTH: 72
<212> TYPE: DNA
<213> ORGANISM: Artificial Sequence
<220> FEATURE:
<223> OTHER INFORMATION: chemically synthesized

<400> SEQUENCE: 241
atccgtcaca cctgctctgg gggtgcgact tagggtaagt gggaaagacg atgctggtgt      60
tggctcccgt at                                                          72

<210> SEQ ID NO 242
<211> LENGTH: 72
<212> TYPE: DNA
<213> ORGANISM: Artificial Sequence
<220> FEATURE:
<223> OTHER INFORMATION: chemically synthesized

<400> SEQUENCE: 242
atccgtcaca cctgctctca agaggagatg aaccaatctt agtccgacag gcggtggtgt      60
tggctcccgt at                                                          72

<210> SEQ ID NO 243
<211> LENGTH: 72
<212> TYPE: DNA
<213> ORGANISM: Artificial Sequence
<220> FEATURE:
<223> OTHER INFORMATION: chemically synthesized

<400> SEQUENCE: 243
atccgtcaca cctgctctgg cccggaattg tcatgacgtc acctacacct cctgtggtgt      60
tggctcccgt at                                                          72

<210> SEQ ID NO 244
<211> LENGTH: 72
<212> TYPE: DNA
<213> ORGANISM: Artificial Sequence
<220> FEATURE:
<223> OTHER INFORMATION: chemically synthesized

<400> SEQUENCE: 244
atacgggagc caacaccaat gctgtgattt tcgcgcgact tagtcactac gcctagagca      60
ggtgtgacgg at                                                          72

<210> SEQ ID NO 245
<211> LENGTH: 72
<212> TYPE: DNA
<213> ORGANISM: Artificial Sequence
```

```
<220> FEATURE:
<223> OTHER INFORMATION: chemically synthesized

<400> SEQUENCE: 245
atacgggagc caacaccaac gcactagtcc gttctcactg tatagctgcc gctgagagca    60
ggtgtgacgg at                                                       72

<210> SEQ ID NO 246
<211> LENGTH: 72
<212> TYPE: DNA
<213> ORGANISM: Artificial Sequence
<220> FEATURE:
<223> OTHER INFORMATION: chemically synthesized

<400> SEQUENCE: 246
atacgggagc caacaccagt ctatccagat ccatcatcgc tagtattatt tgccagagca    60
ggtgtgacgg at                                                       72

<210> SEQ ID NO 247
<211> LENGTH: 72
<212> TYPE: DNA
<213> ORGANISM: Artificial Sequence
<220> FEATURE:
<223> OTHER INFORMATION: chemically synthesized

<400> SEQUENCE: 247
atacgggagc caacaccagc atcgtctttc ccacttaccc taagtcgcac ccccagagca    60
ggtgtgacgg at                                                       72

<210> SEQ ID NO 248
<211> LENGTH: 72
<212> TYPE: DNA
<213> ORGANISM: Artificial Sequence
<220> FEATURE:
<223> OTHER INFORMATION: chemically synthesized

<400> SEQUENCE: 248
atacgggagc caacaccacc gcctgtcgga ctaagattgg ttcatctcct cttgagagca    60
ggtgtgacgg at                                                       72

<210> SEQ ID NO 249
<211> LENGTH: 72
<212> TYPE: DNA
<213> ORGANISM: Artificial Sequence
<220> FEATURE:
<223> OTHER INFORMATION: chemically synthesized

<400> SEQUENCE: 249
atacgggagc caacaccaca ggaggtgtag gtgacgtcat gacaattccg ggccagagca    60
ggtgtgacgg at                                                       72

<210> SEQ ID NO 250
<211> LENGTH: 72
<212> TYPE: DNA
<213> ORGANISM: Artificial Sequence
<220> FEATURE:
<223> OTHER INFORMATION: chemically synthesized

<400> SEQUENCE: 250
atccgtcacc cctgctctcg tcgctatgaa gtaacaaaga taggagcaat cgggtggtgt    60
tggctcccgt at                                                       72
```

```
<210> SEQ ID NO 251
<211> LENGTH: 72
<212> TYPE: DNA
<213> ORGANISM: Artificial Sequence
<220> FEATURE:
<223> OTHER INFORMATION: chemically synthesized

<400> SEQUENCE: 251
atccgtcaca cctgctctaa cgaagactga aaccaaagca gtgacagtgc tgaatggtgt      60
tggctcccgt at                                                          72

<210> SEQ ID NO 252
<211> LENGTH: 72
<212> TYPE: DNA
<213> ORGANISM: Artificial Sequence
<220> FEATURE:
<223> OTHER INFORMATION: chemically synthesized

<400> SEQUENCE: 252
atccgtcaca cctgctctcg gtgacaatag ctcgatcagc ccaaagtcgt cagatggtgt      60
tggctcccgt at                                                          72

<210> SEQ ID NO 253
<211> LENGTH: 71
<212> TYPE: DNA
<213> ORGANISM: Artificial Sequence
<220> FEATURE:
<223> OTHER INFORMATION: chemically synthesized

<400> SEQUENCE: 253
atccgtcaca cctgctctaa cgaaatagac cacaaatcga tactttatgt tattggtgtt      60
ggctcccgta t                                                           71

<210> SEQ ID NO 254
<211> LENGTH: 72
<212> TYPE: DNA
<213> ORGANISM: Artificial Sequence
<220> FEATURE:
<223> OTHER INFORMATION: chemically synthesized

<400> SEQUENCE: 254
atccgtcaca cctgctctgt cgaatgctct gcctggaaga gttgttagca gggatggtgt      60
tggctcccgt at                                                          72

<210> SEQ ID NO 255
<211> LENGTH: 72
<212> TYPE: DNA
<213> ORGANISM: Artificial Sequence
<220> FEATURE:
<223> OTHER INFORMATION: chemically synthesized

<400> SEQUENCE: 255
atccgtcaca cctgctctta agccgagggg taaatctagg acagggtcc atgatggtgt       60 tggctcccgt at                                                          72

<210> SEQ ID NO 256
<211> LENGTH: 72
<212> TYPE: DNA
<213> ORGANISM: Artificial Sequence
<220> FEATURE:
<223> OTHER INFORMATION: chemically synthesized

<400> SEQUENCE: 256
```

```
atccgtcaca cctgctctac tggccggctc agcatgacta agaaggaagt tatgtggtgt      60
tggctcccgt at                                                         72

<210> SEQ ID NO 257
<211> LENGTH: 72
<212> TYPE: DNA
<213> ORGANISM: Artificial Sequence
<220> FEATURE:
<223> OTHER INFORMATION: chemically synthesized

<400> SEQUENCE: 257
atccgtcaca cctgctctgg tacgaatcac aggggatgct ggaagcttgg ctcttggtgt      60
tggctcccgt at                                                         72

<210> SEQ ID NO 258
<211> LENGTH: 72
<212> TYPE: DNA
<213> ORGANISM: Artificial Sequence
<220> FEATURE:
<223> OTHER INFORMATION: chemically synthesized

<400> SEQUENCE: 258
atacgggagc caacaccacc cgattgctcc tatctttgtt acttcatagc gacgagagca      60
ggggtgacgg at                                                         72

<210> SEQ ID NO 259
<211> LENGTH: 72
<212> TYPE: DNA
<213> ORGANISM: Artificial Sequence
<220> FEATURE:
<223> OTHER INFORMATION: chemically synthesized

<400> SEQUENCE: 259
atacgggagc caacaccatt cagcactgtc actgctttgg tttcagtctt cgttagagca      60
ggtgtgacgg at                                                         72

<210> SEQ ID NO 260
<211> LENGTH: 72
<212> TYPE: DNA
<213> ORGANISM: Artificial Sequence
<220> FEATURE:
<223> OTHER INFORMATION: chemically synthesized

<400> SEQUENCE: 260
atacgggagc caacaccatc tgacgacttt gggctgatcg agctattgtc accgagagca      60
ggtgtgacgg at                                                         72

<210> SEQ ID NO 261
<211> LENGTH: 71
<212> TYPE: DNA
<213> ORGANISM: Artificial Sequence
<220> FEATURE:
<223> OTHER INFORMATION: chemically synthesized

<400> SEQUENCE: 261
atacgggagc caacaccaat aacataaagt atcgatttgt ggtctatttc gttagagcag      60
gtgtgacgga t                                                          71

<210> SEQ ID NO 262
<211> LENGTH: 72
<212> TYPE: DNA
```

<213> ORGANISM: Artificial Sequence
<220> FEATURE:
<223> OTHER INFORMATION: chemically synthesized

<400> SEQUENCE: 262
atacgggagc caacaccatc cctgctaaca actcttccag gcagagcatt cgacagagca     60
ggtgtgacgg at                                                         72

<210> SEQ ID NO 263
<211> LENGTH: 72
<212> TYPE: DNA
<213> ORGANISM: Artificial Sequence
<220> FEATURE:
<223> OTHER INFORMATION: chemically synthesized

<400> SEQUENCE: 263
atacgggagc caacaccatc atggacccct gtcctagatt taccccctcgg cttaagagca    60 ggtgtgacgg at                                                         72

<210> SEQ ID NO 264
<211> LENGTH: 72
<212> TYPE: DNA
<213> ORGANISM: Artificial Sequence
<220> FEATURE:
<223> OTHER INFORMATION: chemically synthesized

<400> SEQUENCE: 264
atacgggagc caacaccaca taacttcctt cttagtcatg ctgagccggc cagtagagca     60
ggtgtgacgg at                                                         72

<210> SEQ ID NO 265
<211> LENGTH: 72
<212> TYPE: DNA
<213> ORGANISM: Artificial Sequence
<220> FEATURE:
<223> OTHER INFORMATION: chemically synthesized

<400> SEQUENCE: 265
atacgggagc caacaccaag agccaagctt ccagcatccc ctgtgattcg taccagagca     60
ggtgtgacgg at                                                         72

<210> SEQ ID NO 266
<211> LENGTH: 72
<212> TYPE: DNA
<213> ORGANISM: Artificial Sequence
<220> FEATURE:
<223> OTHER INFORMATION: chemically synthesized

<400> SEQUENCE: 266
atccgtcaca cctgctctcc gcacgtagga ccactttggt acacgctccc gtagtggtgt     60
tggctcccgt at                                                         72

<210> SEQ ID NO 267
<211> LENGTH: 72
<212> TYPE: DNA
<213> ORGANISM: Artificial Sequence
<220> FEATURE:
<223> OTHER INFORMATION: chemically synthesized

<400> SEQUENCE: 267
atccgtcaca cctgctctac ggatgaacga agattttaaa gtcaagctaa tgcatggtgt     60
tggctcccgt at                                                         72

<210> SEQ ID NO 268
<211> LENGTH: 72
<212> TYPE: DNA
<213> ORGANISM: Artificial Sequence
<220> FEATURE:
<223> OTHER INFORMATION: chemically synthesized

<400> SEQUENCE: 268
atccgtcaca cctgctctgt agtgaagagt ccgcagtcca cgctgttcaa ctcatggtgt    60
tggctcccgt at                                                       72

<210> SEQ ID NO 269
<211> LENGTH: 72
<212> TYPE: DNA
<213> ORGANISM: Artificial Sequence
<220> FEATURE:
<223> OTHER INFORMATION: chemically synthesized

<400> SEQUENCE: 269
atccgtcaca cctgctctac cggctggcac ggttatgtgt gacgggcgaa gatatggtgt    60
tggctcccgt at                                                       72

<210> SEQ ID NO 270
<211> LENGTH: 58
<212> TYPE: DNA
<213> ORGANISM: Artificial Sequence
<220> FEATURE:
<223> OTHER INFORMATION: chemically synthesized

<400> SEQUENCE: 270
atccgtcaca cctgctctgc gtgtggagcg cctaggtgag tggtgttggc tcccgtat     58

<210> SEQ ID NO 271
<211> LENGTH: 72
<212> TYPE: DNA
<213> ORGANISM: Artificial Sequence
<220> FEATURE:
<223> OTHER INFORMATION: chemically synthesized

<400> SEQUENCE: 271
atccgtcaca cctgctctga tgtcccttttg aagagttcca tgacgctggc tccttggtgt    60
tggctcccgt at                                                       72

<210> SEQ ID NO 272
<211> LENGTH: 72
<212> TYPE: DNA
<213> ORGANISM: Artificial Sequence
<220> FEATURE:
<223> OTHER INFORMATION: chemically synthesized

<400> SEQUENCE: 272
atacgggagc caacaccact acgggagcgt gtaccaaagt ggtcctacgt gcggagagca    60
ggtgtgacgg at                                                       72

<210> SEQ ID NO 273
<211> LENGTH: 72
<212> TYPE: DNA
<213> ORGANISM: Artificial Sequence
<220> FEATURE:
<223> OTHER INFORMATION: chemically synthesized

<400> SEQUENCE: 273

```
atacgggagc caacaccatg cattagcttg actttaaaat cttcgttcat ccgtagagca    60
ggtgtgacgg at                                                       72
```

<210> SEQ ID NO 274
<211> LENGTH: 72
<212> TYPE: DNA
<213> ORGANISM: Artificial Sequence
<220> FEATURE:
<223> OTHER INFORMATION: chemically synthesized

<400> SEQUENCE: 274

```
atacgggagc caacaccatg agttgaacag cgtggactgc ggactcttca ctacagagca    60
ggtgtgacgg at                                                       72
```

<210> SEQ ID NO 275
<211> LENGTH: 72
<212> TYPE: DNA
<213> ORGANISM: Artificial Sequence
<220> FEATURE:
<223> OTHER INFORMATION: chemically synthesized

<400> SEQUENCE: 275

```
atacgggagc caacaccata tcttcgcccg tcacacataa ccgtgccagc cggtagagca    60
ggtgtgacgg at                                                       72
```

<210> SEQ ID NO 276
<211> LENGTH: 58
<212> TYPE: DNA
<213> ORGANISM: Artificial Sequence
<220> FEATURE:
<223> OTHER INFORMATION: chemically synthesized

<400> SEQUENCE: 276

```
atacgggagc caacaccact cacctaggcg ctccacacgc agagcaggtg tgacggat      58
```

<210> SEQ ID NO 277
<211> LENGTH: 72
<212> TYPE: DNA
<213> ORGANISM: Artificial Sequence
<220> FEATURE:
<223> OTHER INFORMATION: chemically synthesized

<400> SEQUENCE: 277

```
atacgggagc caacaccaag gagccagcgt catggaactc ttcaaaggga catcagagca    60
ggtgtgacgg at                                                       72
```

<210> SEQ ID NO 278
<211> LENGTH: 59
<212> TYPE: DNA
<213> ORGANISM: Artificial Sequence
<220> FEATURE:
<223> OTHER INFORMATION: chemically synthesized

<400> SEQUENCE: 278

```
atccgtcaca cctgctctgc cggaccatcc aatatcagct gtggtgttgg ctcccgtat     59
```

<210> SEQ ID NO 279
<211> LENGTH: 72
<212> TYPE: DNA
<213> ORGANISM: Artificial Sequence
<220> FEATURE:
<223> OTHER INFORMATION: chemically synthesized

<400> SEQUENCE: 279

-continued

```
atccgtcaca cctgctctgg tggaatggac taagctagct agcgttttaa aaggtggtgt    60
tggctcccgt at                                                         72

<210> SEQ ID NO 280
<211> LENGTH: 72
<212> TYPE: DNA
<213> ORGANISM: Artificial Sequence
<220> FEATURE:
<223> OTHER INFORMATION: chemically synthesized

<400> SEQUENCE: 280
atccgtcaca cctgctctta aagtagaggc tgttctccag acgtcgcagg aggatggtgt    60
tggctcccgt at                                                         72

<210> SEQ ID NO 281
<211> LENGTH: 72
<212> TYPE: DNA
<213> ORGANISM: Artificial Sequence
<220> FEATURE:
<223> OTHER INFORMATION: chemically synthesized

<400> SEQUENCE: 281
atccgtcaca cctgctctgt agatggcaag gcataagcgt ccggaacgat agaatggtgt    60
tggctcccgt at                                                         72

<210> SEQ ID NO 282
<211> LENGTH: 72
<212> TYPE: DNA
<213> ORGANISM: Artificial Sequence
<220> FEATURE:
<223> OTHER INFORMATION: chemically synthesized

<400> SEQUENCE: 282
atccgtcaca cctgctctgt agatggcaag gcataagcgt ccggaacgat agaatggtgt    60
tggctcccgt at                                                         72

<210> SEQ ID NO 283
<211> LENGTH: 59
<212> TYPE: DNA
<213> ORGANISM: Artificial Sequence
<220> FEATURE:
<223> OTHER INFORMATION: chemically synthesized

<400> SEQUENCE: 283
atacgggagc caacaccaca gctgatattg gatggtccgg cagagcaggt gtgacggat     59

<210> SEQ ID NO 284
<211> LENGTH: 72
<212> TYPE: DNA
<213> ORGANISM: Artificial Sequence
<220> FEATURE:
<223> OTHER INFORMATION: chemically synthesized

<400> SEQUENCE: 284
atccgtcaca cctgctcttg ggcaggagcg agagactcta atggtaagca agaatggtgt    60
tggctcccgt at                                                         72

<210> SEQ ID NO 285
<211> LENGTH: 72
<212> TYPE: DNA
<213> ORGANISM: Artificial Sequence
<220> FEATURE:
```

<223> OTHER INFORMATION: chemically synthesized

<400> SEQUENCE: 285
atccgtcaca cctgctctcc aacaaggcga ccgaccgcat gcagatagcc aggttggtgt    60
tggctcccgt at    72

<210> SEQ ID NO 286
<211> LENGTH: 59
<212> TYPE: DNA
<213> ORGANISM: Artificial Sequence
<220> FEATURE:
<223> OTHER INFORMATION: chemically synthesized

<400> SEQUENCE: 286
atacgggagc caacaccaca gctgatattg gatggtccgg cagagcaggt gtgacggat    59

<210> SEQ ID NO 287
<211> LENGTH: 72
<212> TYPE: DNA
<213> ORGANISM: Artificial Sequence
<220> FEATURE:
<223> OTHER INFORMATION: chemically synthesized

<400> SEQUENCE: 287
atacgggagc caacaccacc ttttaaaacg ctagctagct tagtccattc caccagagca    60
ggtgtgacgg at    72

<210> SEQ ID NO 288
<211> LENGTH: 72
<212> TYPE: DNA
<213> ORGANISM: Artificial Sequence
<220> FEATURE:
<223> OTHER INFORMATION: chemically synthesized

<400> SEQUENCE: 288
atacgggagc caacaccatc ctcctgcgac gtctggagaa cagcctctac tttaagagca    60
ggtgtgacgg at    72

<210> SEQ ID NO 289
<211> LENGTH: 72
<212> TYPE: DNA
<213> ORGANISM: Artificial Sequence
<220> FEATURE:
<223> OTHER INFORMATION: chemically synthesized

<400> SEQUENCE: 289
atacgggagc caacaccatt ctatcgttcc ggacgcttat gccttgccat ctacagagca    60
ggtgtgacgg at    72

<210> SEQ ID NO 290
<211> LENGTH: 72
<212> TYPE: DNA
<213> ORGANISM: Artificial Sequence
<220> FEATURE:
<223> OTHER INFORMATION: chemically synthesized

<400> SEQUENCE: 290
atacgggagc caacaccatt ctatcgttcc ggacgcttat gccttgccat ctacagagca    60
ggtgtgacgg at    72

<210> SEQ ID NO 291
<211> LENGTH: 59

```
<212> TYPE: DNA
<213> ORGANISM: Artificial Sequence
<220> FEATURE:
<223> OTHER INFORMATION: chemically synthesized

<400> SEQUENCE: 291
atccgtcaca cctgctctgc cggaccatcc aatatcagct gtggtgttgg ctcccgtat       59

<210> SEQ ID NO 292
<211> LENGTH: 72
<212> TYPE: DNA
<213> ORGANISM: Artificial Sequence
<220> FEATURE:
<223> OTHER INFORMATION: chemically synthesized

<400> SEQUENCE: 292
atacgggagc caacaccatt cttgcttacc attagagtct ctcgctcctg cccaagagca      60
ggtgtgacgg at                                                          72

<210> SEQ ID NO 293
<211> LENGTH: 72
<212> TYPE: DNA
<213> ORGANISM: Artificial Sequence
<220> FEATURE:
<223> OTHER INFORMATION: chemically synthesized

<400> SEQUENCE: 293
atacgggagc caacaccaac ctggctatct gcatgcggtc ggtcgccttg ttggagagca      60
ggtgtgacgg at                                                          72

<210> SEQ ID NO 294
<211> LENGTH: 72
<212> TYPE: DNA
<213> ORGANISM: Artificial Sequence
<220> FEATURE:
<223> OTHER INFORMATION: chemically synthesized

<400> SEQUENCE: 294
atccgtcaca cctgctctgt agatggcaag gcataagcgt ccggaacgat agaatggtgt      60
tggctcccgt at                                                          72

<210> SEQ ID NO 295
<211> LENGTH: 72
<212> TYPE: DNA
<213> ORGANISM: Artificial Sequence
<220> FEATURE:
<223> OTHER INFORMATION: chemically synthesized

<400> SEQUENCE: 295
atccgtcaca cctgctctaa ccaaaagggt aggagaccaa gctagcgatt tggatggtgt      60
tggctcccgt at                                                          72

<210> SEQ ID NO 296
<211> LENGTH: 59
<212> TYPE: DNA
<213> ORGANISM: Artificial Sequence
<220> FEATURE:
<223> OTHER INFORMATION: chemically synthesized

<400> SEQUENCE: 296
atccgtcaca cctgctctgc cggaccatcc aatatcagct gtggtgttgg ctcccgtat       59

<210> SEQ ID NO 297
```

<211> LENGTH: 72
<212> TYPE: DNA
<213> ORGANISM: Artificial Sequence
<220> FEATURE:
<223> OTHER INFORMATION: chemically synthesized

<400> SEQUENCE: 297
atccgtcaca cctgctctga agcctaacgg agaagatggc cctactgccg taggtggtgt    60
tggctcccgt at                                                        72

<210> SEQ ID NO 298
<211> LENGTH: 72
<212> TYPE: DNA
<213> ORGANISM: Artificial Sequence
<220> FEATURE:
<223> OTHER INFORMATION: chemically synthesized

<400> SEQUENCE: 298
atccgtcaca cctgctctac taaacaaggg caaactgtaa acacagtagg ggcgtggtgt    60
tggctcccgt at                                                        72

<210> SEQ ID NO 299
<211> LENGTH: 68
<212> TYPE: DNA
<213> ORGANISM: Artificial Sequence
<220> FEATURE:
<223> OTHER INFORMATION: chemically synthesized

<400> SEQUENCE: 299
atccgtcaca cctgctctgg tgttggctcc cgtatagctt ggctcccgta tggtgttggc    60
tcccgtat                                                             68

<210> SEQ ID NO 300
<211> LENGTH: 72
<212> TYPE: DNA
<213> ORGANISM: Artificial Sequence
<220> FEATURE:
<223> OTHER INFORMATION: chemically synthesized

<400> SEQUENCE: 300
atccgtcaca cctgctctgt cgcgatgatg agcagcagcg caggagggag ggggtggtgt    60
tggctcccgt at                                                        72

<210> SEQ ID NO 301
<211> LENGTH: 57
<212> TYPE: DNA
<213> ORGANISM: Artificial Sequence
<220> FEATURE:
<223> OTHER INFORMATION: chemically synthesized

<400> SEQUENCE: 301
atccgtcaca cctgctctga tcagggaaga cgccaacact ggtgttggct cccgtat       57

<210> SEQ ID NO 302
<211> LENGTH: 72
<212> TYPE: DNA
<213> ORGANISM: Artificial Sequence
<220> FEATURE:
<223> OTHER INFORMATION: chemically synthesized

<400> SEQUENCE: 302
atacgggagc caacaccatt ctatcgttcc ggacgcttat gccttgccat ctacagagca    60
ggtgtgacgg at                                                        72

<210> SEQ ID NO 303
<211> LENGTH: 72
<212> TYPE: DNA
<213> ORGANISM: Artificial Sequence
<220> FEATURE:
<223> OTHER INFORMATION: chemically synthesized

<400> SEQUENCE: 303
atacgggagc caacaccatc caaatcgcta gcttggtctc ctacccttt ggttagagca    60 ggtgtgacgg at    72

<210> SEQ ID NO 304
<211> LENGTH: 59
<212> TYPE: DNA
<213> ORGANISM: Artificial Sequence
<220> FEATURE:
<223> OTHER INFORMATION: chemically synthesized

<400> SEQUENCE: 304
atacgggagc caacaccaca gctgatattg gatggtccgg cagagcaggt gtgacggat    59

<210> SEQ ID NO 305
<211> LENGTH: 72
<212> TYPE: DNA
<213> ORGANISM: Artificial Sequence
<220> FEATURE:
<223> OTHER INFORMATION: chemically synthesized

<400> SEQUENCE: 305
atacgggagc caacaccacc tacggcagta gggccatctt ctccgttagg cttcagagca    60
ggtgtgacgg at    72

<210> SEQ ID NO 306
<211> LENGTH: 72
<212> TYPE: DNA
<213> ORGANISM: Artificial Sequence
<220> FEATURE:
<223> OTHER INFORMATION: chemically synthesized

<400> SEQUENCE: 306
atacgggagc caacaccacg ccctactgt gtttacagtt tgcccttgtt tagtagagca    60
ggtgtgacgg at    72

<210> SEQ ID NO 307
<211> LENGTH: 68
<212> TYPE: DNA
<213> ORGANISM: Artificial Sequence
<220> FEATURE:
<223> OTHER INFORMATION: chemically synthesized

<400> SEQUENCE: 307
atacgggagc caacaccata cgggagccaa gctatacggg agccaacacc agagcaggtg    60
tgacggat    68

<210> SEQ ID NO 308
<211> LENGTH: 72
<212> TYPE: DNA
<213> ORGANISM: Artificial Sequence
<220> FEATURE:
<223> OTHER INFORMATION: chemically synthesized

<400> SEQUENCE: 308

```
atacgggagc caacaccacc ccctccctcc tgcgctgctg ctcatcatcg cgacagagca    60
ggtgtgacgg at                                                       72
```

<210> SEQ ID NO 309
<211> LENGTH: 57
<212> TYPE: DNA
<213> ORGANISM: Artificial Sequence
<220> FEATURE:
<223> OTHER INFORMATION: chemically synthesized

<400> SEQUENCE: 309

```
atacgggagc caacaccagt gttggcgtct tccctgatca gagcaggtgt gacggat      57
```

<210> SEQ ID NO 310
<211> LENGTH: 71
<212> TYPE: DNA
<213> ORGANISM: Artificial Sequence
<220> FEATURE:
<223> OTHER INFORMATION: chemically synthesized

<400> SEQUENCE: 310

```
atacgggagc caacaccaat acctgtaaaa gtctgagaag tggagtaacc tagagagcag   60
gtgtgacgga t                                                        71
```

<210> SEQ ID NO 311
<211> LENGTH: 71
<212> TYPE: DNA
<213> ORGANISM: Artificial Sequence
<220> FEATURE:
<223> OTHER INFORMATION: chemically synthesized

<400> SEQUENCE: 311

```
atccgtcaca cctgctctct aggttactcc acttctcaga cttttacagg tattggtgtt   60
ggctcccgta t                                                        71
```

<210> SEQ ID NO 312
<211> LENGTH: 72
<212> TYPE: DNA
<213> ORGANISM: Artificial Sequence
<220> FEATURE:
<223> OTHER INFORMATION: chemically synthesized

<400> SEQUENCE: 312

```
atacgggagc caacaccacc gaccaacagt aatagcctaa aagagttatg cgctagagca   60
ggtgtgacgg at                                                       72
```

<210> SEQ ID NO 313
<211> LENGTH: 72
<212> TYPE: DNA
<213> ORGANISM: Artificial Sequence
<220> FEATURE:
<223> OTHER INFORMATION: chemically synthesized

<400> SEQUENCE: 313

```
atccgtcaca cctgctctag cgcataactc ttttaggcta ttactgttgg tcggtggtgt   60
tggctcccgt at                                                       72
```

<210> SEQ ID NO 314
<211> LENGTH: 72
<212> TYPE: DNA
<213> ORGANISM: Artificial Sequence
<220> FEATURE:
<223> OTHER INFORMATION: chemically synthesized

<400> SEQUENCE: 314
atacgggagc caacaccagg tggactatat atgaagttag tgagctttaa caggagagca      60
ggtgtgacgg at                                                          72

<210> SEQ ID NO 315
<211> LENGTH: 72
<212> TYPE: DNA
<213> ORGANISM: Artificial Sequence
<220> FEATURE:
<223> OTHER INFORMATION: chemically synthesized

<400> SEQUENCE: 315
atccgtcaca cctgctctcc tgttaaagct cactaacttc atatatagtc cacctggtgt      60
tggctcccgt at                                                          72

<210> SEQ ID NO 316
<211> LENGTH: 72
<212> TYPE: DNA
<213> ORGANISM: Artificial Sequence
<220> FEATURE:
<223> OTHER INFORMATION: chemically synthesized

<400> SEQUENCE: 316
atacgggagc caacaccaca ggagaggcag taaaagggtt ggctgcctgg gtagagagca      60
ggtgtgacgg at                                                          72

<210> SEQ ID NO 317
<211> LENGTH: 72
<212> TYPE: DNA
<213> ORGANISM: Artificial Sequence
<220> FEATURE:
<223> OTHER INFORMATION: chemically synthesized

<400> SEQUENCE: 317
atccgtcaca cctgctctct acccaggcag ccaacccttt tactgcctct cctgtggtgt      60
tggctcccgt at                                                          72

<210> SEQ ID NO 318
<211> LENGTH: 72
<212> TYPE: DNA
<213> ORGANISM: Artificial Sequence
<220> FEATURE:
<223> OTHER INFORMATION: chemically synthesized

<400> SEQUENCE: 318
atacgggagc caacaccatt agcaaggtaa gaacagtttt aatacatgcc ttccagagca      60
ggtgtgacgg at                                                          72

<210> SEQ ID NO 319
<211> LENGTH: 72
<212> TYPE: DNA
<213> ORGANISM: Artificial Sequence
<220> FEATURE:
<223> OTHER INFORMATION: chemically synthesized

<400> SEQUENCE: 319
atccgtcaca cctgctctgg aaggcatgta ttaaaactgt tcttaccttg ctaatggtgt      60
tggctcccgt at                                                          72

<210> SEQ ID NO 320

<211> LENGTH: 72
<212> TYPE: DNA
<213> ORGANISM: Artificial Sequence
<220> FEATURE:
<223> OTHER INFORMATION: chemically synthesized

<400> SEQUENCE: 320
atacgggagc caacaccata acaaataacc accctcaatg ctagatagtg gcttagagca    60
ggtgtgacgg at                                                       72

<210> SEQ ID NO 321
<211> LENGTH: 72
<212> TYPE: DNA
<213> ORGANISM: Artificial Sequence
<220> FEATURE:
<223> OTHER INFORMATION: chemically synthesized

<400> SEQUENCE: 321
atccgtcaca cctgctctaa gccactatct agcattgagg gtggttattt gttatggtgt    60
tggctcccgt at                                                       72

<210> SEQ ID NO 322
<211> LENGTH: 72
<212> TYPE: DNA
<213> ORGANISM: Artificial Sequence
<220> FEATURE:
<223> OTHER INFORMATION: chemically synthesized

<400> SEQUENCE: 322
atacgggagc caacaccagg aacatgataa gtgagaagtg cgacgttagc ttatagagca    60
ggtgtgacgg at                                                       72

<210> SEQ ID NO 323
<211> LENGTH: 72
<212> TYPE: DNA
<213> ORGANISM: Artificial Sequence
<220> FEATURE:
<223> OTHER INFORMATION: chemically synthesized

<400> SEQUENCE: 323
atccgtcaca cctgctctat aagctaacgt cgcacttctc acttatcatg ttcctggtgt    60
tggctcccgt at                                                       72

<210> SEQ ID NO 324
<211> LENGTH: 72
<212> TYPE: DNA
<213> ORGANISM: Artificial Sequence
<220> FEATURE:
<223> OTHER INFORMATION: chemically synthesized

<400> SEQUENCE: 324
atacgggagc caacaccaaa agggtgttca tacggaatgt agatcgccta agtgagagca    60
ggtgtgacgg at                                                       72

<210> SEQ ID NO 325
<211> LENGTH: 72
<212> TYPE: DNA
<213> ORGANISM: Artificial Sequence
<220> FEATURE:
<223> OTHER INFORMATION: chemically synthesized

<400> SEQUENCE: 325
atccgtcaca cctgctctca cttaggcgat ctacattccg tatgaacacc cttttggtgt    60
tggctcccgt at                                                              72

<210> SEQ ID NO 326
<211> LENGTH: 72
<212> TYPE: DNA
<213> ORGANISM: Artificial Sequence
<220> FEATURE:
<223> OTHER INFORMATION: chemically synthesized

<400> SEQUENCE: 326
atacgggagc caacaccatg agcaccggca aacgcgtagg ttaagctaca tgacagagca      60
ggtgtgacgg at                                                              72

<210> SEQ ID NO 327
<211> LENGTH: 72
<212> TYPE: DNA
<213> ORGANISM: Artificial Sequence
<220> FEATURE:
<223> OTHER INFORMATION: chemically synthesized

<400> SEQUENCE: 327
atccgtcaca cctgctctgt catgtagctt aacctacgcg tttgccggtg ctcatggtgt      60
tggctcccgt at                                                              72

<210> SEQ ID NO 328
<211> LENGTH: 72
<212> TYPE: DNA
<213> ORGANISM: Artificial Sequence
<220> FEATURE:
<223> OTHER INFORMATION: chemically synthesized

<400> SEQUENCE: 328
atacgggagc caacaccatg attagatact gcctagctgt gtgctcgttg ggggagagca      60
ggtgtgacgg at                                                              72

<210> SEQ ID NO 329
<211> LENGTH: 72
<212> TYPE: DNA
<213> ORGANISM: Artificial Sequence
<220> FEATURE:
<223> OTHER INFORMATION: chemically synthesized

<400> SEQUENCE: 329
atccgtcaca cctgctctcc cccaacgagc acacagctag gcagtatcta atcatggtgt      60
tggctcccgt at                                                              72

<210> SEQ ID NO 330
<211> LENGTH: 158
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t

<400> SEQUENCE: 330
atacgggagc caacaccagg aggaaggtca gcgttcttca cgtggctagg gggcagagca      60

```
ggtgtgacgg atsdnmwrdn aartcaatcc gtcacacctg ctctgccccc tagccacgtg    120
aagaacgctg accttcctcc tggtgttggc tcccgtat                           158

<210> SEQ ID NO 331
<211> LENGTH: 72
<212> TYPE: DNA
<213> ORGANISM: Artificial Sequence
<220> FEATURE:
<223> OTHER INFORMATION: chemically synthesized

<400> SEQUENCE: 331
atacgggagc caacaccaac tgagctatat ctagatcgac ttacacatac acgtagagca    60
ggtgtgacgg at                                                       72

<210> SEQ ID NO 332
<211> LENGTH: 72
<212> TYPE: DNA
<213> ORGANISM: Artificial Sequence
<220> FEATURE:
<223> OTHER INFORMATION: chemically synthesized

<400> SEQUENCE: 332
atccgtcaca cctgctctac gtgtatgtgt aagtcgatct agatatagct cagttggtgt    60
tggctcccgt at                                                       72

<210> SEQ ID NO 333
<211> LENGTH: 72
<212> TYPE: DNA
<213> ORGANISM: Artificial Sequence
<220> FEATURE:
<223> OTHER INFORMATION: chemically synthesized

<400> SEQUENCE: 333
atacgggagc caacaccaga gacgtgtgaa gtccaggcag ggtgccttct gtcgagagca    60
ggtgtgacgg at                                                       72

<210> SEQ ID NO 334
<211> LENGTH: 72
<212> TYPE: DNA
<213> ORGANISM: Artificial Sequence
<220> FEATURE:
<223> OTHER INFORMATION: chemically synthesized

<400> SEQUENCE: 334
atccgtcaca cctgctctcg acagaaggca ccctgcctgg acttcacacg tctctggtgt    60
tggctcccgt at                                                       72

<210> SEQ ID NO 335
<211> LENGTH: 72
<212> TYPE: DNA
<213> ORGANISM: Artificial Sequence
<220> FEATURE:
<223> OTHER INFORMATION: chemically synthesized

<400> SEQUENCE: 335
atacgggagc caacaccatc aagtggtgag cgcctcgtcg ggaactgccg tgcgagagca    60
ggtgtgacgg at                                                       72

<210> SEQ ID NO 336
<211> LENGTH: 72
<212> TYPE: DNA
<213> ORGANISM: Artificial Sequence
```

```
<220> FEATURE:
<223> OTHER INFORMATION: chemically synthesized

<400> SEQUENCE: 336
atccgtcaca cctgctctcg cacggcagtt cccgacgagg cgctcaccac ttgatggtgt    60
tggctcccgt at                                                       72

<210> SEQ ID NO 337
<211> LENGTH: 72
<212> TYPE: DNA
<213> ORGANISM: Artificial Sequence
<220> FEATURE:
<223> OTHER INFORMATION: chemically synthesized

<400> SEQUENCE: 337
atacgggagc caacaccacc gctgaaacct ctccgccgtc ccgccctcct ccccagagca    60
ggtgtgacgg at                                                       72

<210> SEQ ID NO 338
<211> LENGTH: 72
<212> TYPE: DNA
<213> ORGANISM: Artificial Sequence
<220> FEATURE:
<223> OTHER INFORMATION: chemically synthesized

<400> SEQUENCE: 338
atccgtcaca cctgctctgg ggaggagggc gggacggcgg agaggtttca gcggtggtgt    60
tggctcccgt at                                                       72

<210> SEQ ID NO 339
<211> LENGTH: 72
<212> TYPE: DNA
<213> ORGANISM: Artificial Sequence
<220> FEATURE:
<223> OTHER INFORMATION: chemically synthesized

<400> SEQUENCE: 339
atacgggagc caacaccagg agatggtagc actaaaatac gacgtatgct gtgtagagca    60
ggtgtgacgg at                                                       72

<210> SEQ ID NO 340
<211> LENGTH: 72
<212> TYPE: DNA
<213> ORGANISM: Artificial Sequence
<220> FEATURE:
<223> OTHER INFORMATION: chemically synthesized

<400> SEQUENCE: 340
atccgtcaca cctgctctac acagcatacg tcgtatttta gtgctaccat ctcctggtgt    60
tggctcccgt at                                                       72

<210> SEQ ID NO 341
<211> LENGTH: 72
<212> TYPE: DNA
<213> ORGANISM: Artificial Sequence
<220> FEATURE:
<223> OTHER INFORMATION: chemically synthesized

<400> SEQUENCE: 341
atacgggagc caacaccaaa tcgaccggac taatcctgtg actcccctat gtctagagca    60
ggtgtgacgg at                                                       72
```

<210> SEQ ID NO 342
<211> LENGTH: 72
<212> TYPE: DNA
<213> ORGANISM: Artificial Sequence
<220> FEATURE:
<223> OTHER INFORMATION: chemically synthesized

<400> SEQUENCE: 342
atccgtcaca cctgctctag acataggcga gtcacaggat tagtccggtc gatttggtgt    60
tggctcccgt at    72

<210> SEQ ID NO 343
<211> LENGTH: 72
<212> TYPE: DNA
<213> ORGANISM: Artificial Sequence
<220> FEATURE:
<223> OTHER INFORMATION: chemically synthesized

<400> SEQUENCE: 343
atacgggagc caacaccaaa ttcaattgcg cacgtaagaa tagataggct gaccagagca    60
ggtgtgacgg at    72

<210> SEQ ID NO 344
<211> LENGTH: 72
<212> TYPE: DNA
<213> ORGANISM: Artificial Sequence
<220> FEATURE:
<223> OTHER INFORMATION: chemically synthesized

<400> SEQUENCE: 344
atccgtcaca cctgctctgg tcagcctatc tattcttacg tgcgcaattg aatttggtgt    60
tggctcccgt at    72

<210> SEQ ID NO 345
<211> LENGTH: 72
<212> TYPE: DNA
<213> ORGANISM: Artificial Sequence
<220> FEATURE:
<223> OTHER INFORMATION: chemically synthesized

<400> SEQUENCE: 345
atacgggagc caacaccaca cacagagcgc catggactca gtcagatgtg atgtagagca    60
ggtgtgacgg at    72

<210> SEQ ID NO 346
<211> LENGTH: 72
<212> TYPE: DNA
<213> ORGANISM: Artificial Sequence
<220> FEATURE:
<223> OTHER INFORMATION: chemically synthesized

<400> SEQUENCE: 346
atccgtcaca cctgctctac atcacatctg actgagtcca tggcgctctg tgtgtggtgt    60
tggctcccgt at    72

<210> SEQ ID NO 347
<211> LENGTH: 72
<212> TYPE: DNA
<213> ORGANISM: Artificial Sequence
<220> FEATURE:
<223> OTHER INFORMATION: chemically synthesized

<400> SEQUENCE: 347

```
atacgggagc caacaccatc caatgaggcc atggaccggt aaactcggac gcgcagagca    60
ggtgtgacgg at                                                       72

<210> SEQ ID NO 348
<211> LENGTH: 72
<212> TYPE: DNA
<213> ORGANISM: Artificial Sequence
<220> FEATURE:
<223> OTHER INFORMATION: chemically synthesized

<400> SEQUENCE: 348
atccgtcaca cctgctctgc gcgtccgagt ttaccggtcc atggcctcat tggatggtgt    60
tggctcccgt at                                                       72

<210> SEQ ID NO 349
<211> LENGTH: 72
<212> TYPE: DNA
<213> ORGANISM: Artificial Sequence
<220> FEATURE:
<223> OTHER INFORMATION: chemically synthesized

<400> SEQUENCE: 349
atacgggagc caacaccaac cccggtacca tccgacacca cgagcacccg gacgagagca    60
ggtgtgacgg at                                                       72

<210> SEQ ID NO 350
<211> LENGTH: 72
<212> TYPE: DNA
<213> ORGANISM: Artificial Sequence
<220> FEATURE:
<223> OTHER INFORMATION: chemically synthesized

<400> SEQUENCE: 350
atccgtcaca cctgctctcg tccgggtgct cgtggtgtcg gatggtaccg gggttggtgt    60
tggctcccgt at                                                       72

<210> SEQ ID NO 351
<211> LENGTH: 72
<212> TYPE: DNA
<213> ORGANISM: Artificial Sequence
<220> FEATURE:
<223> OTHER INFORMATION: chemically synthesized

<400> SEQUENCE: 351
atacgggagc caacaccaag gcgaaactat tcacagagac tgatccagca aggtagagca    60
ggtgtgacgg at                                                       72

<210> SEQ ID NO 352
<211> LENGTH: 72
<212> TYPE: DNA
<213> ORGANISM: Artificial Sequence
<220> FEATURE:
<223> OTHER INFORMATION: chemically synthesized

<400> SEQUENCE: 352
atccgtcaca cctgctctac cttgctggat cagtctctgt gaatagtttc gccttggtgt    60
tggctcccgt at                                                       72

<210> SEQ ID NO 353
<211> LENGTH: 72
<212> TYPE: DNA
```

```
<213> ORGANISM: Artificial Sequence
<220> FEATURE:
<223> OTHER INFORMATION: chemically synthesized

<400> SEQUENCE: 353
atacgggagc caacaccaaa cacatagtcg tggcagaacg aatacttagc gcggagagca    60
ggtgtgacgg at                                                       72

<210> SEQ ID NO 354
<211> LENGTH: 72
<212> TYPE: DNA
<213> ORGANISM: Artificial Sequence
<220> FEATURE:
<223> OTHER INFORMATION: chemically synthesized

<400> SEQUENCE: 354
atccgtcaca cctgctctcc gcgctaagta ttcgttctgc cacgactatg tgtttggtgt    60
tggctcccgt at                                                       72

<210> SEQ ID NO 355
<211> LENGTH: 72
<212> TYPE: DNA
<213> ORGANISM: Artificial Sequence
<220> FEATURE:
<223> OTHER INFORMATION: chemically synthesized

<400> SEQUENCE: 355
atacgggagc caacaccaac acgatcgacg gcgcttggtc ccttacaacc ctgcagagca    60
ggtgtgacgg at                                                       72

<210> SEQ ID NO 356
<211> LENGTH: 72
<212> TYPE: DNA
<213> ORGANISM: Artificial Sequence
<220> FEATURE:
<223> OTHER INFORMATION: chemically synthesized

<400> SEQUENCE: 356
atccgtcaca cctgctctgc agggttgtaa gggaccaagc gccgtcgatc gtgttggtgt    60
tggctcccgt at                                                       72

<210> SEQ ID NO 357
<211> LENGTH: 72
<212> TYPE: DNA
<213> ORGANISM: Artificial Sequence
<220> FEATURE:
<223> OTHER INFORMATION: chemically synthesized

<400> SEQUENCE: 357
atacgggagc caacaccaaa ccaggactct gtcgctctaa acatgaccat cgatagagca    60
ggtgtgacgg at                                                       72

<210> SEQ ID NO 358
<211> LENGTH: 72
<212> TYPE: DNA
<213> ORGANISM: Artificial Sequence
<220> FEATURE:
<223> OTHER INFORMATION: chemically synthesized

<400> SEQUENCE: 358
atccgtcaca cctgctctat cgatggtcat gtttagagcg acagagtcct ggtttggtgt    60
tggctcccgt at                                                       72
```

<210> SEQ ID NO 359
<211> LENGTH: 71
<212> TYPE: DNA
<213> ORGANISM: Artificial Sequence
<220> FEATURE:
<223> OTHER INFORMATION: chemically synthesized

<400> SEQUENCE: 359
atacgggagc caacaccaca accactgtag gctcatgtaa ctacccgttg ttgagagcag    60
gtgtgacgga t                                                        71

<210> SEQ ID NO 360
<211> LENGTH: 71
<212> TYPE: DNA
<213> ORGANISM: Artificial Sequence
<220> FEATURE:
<223> OTHER INFORMATION: chemically synthesized

<400> SEQUENCE: 360
atccgtcaca cctgctctca acaacgggta gttacatgag cctacagtgg ttgtggtgtt    60
ggctcccgta t                                                        71

<210> SEQ ID NO 361
<211> LENGTH: 72
<212> TYPE: DNA
<213> ORGANISM: Artificial Sequence
<220> FEATURE:
<223> OTHER INFORMATION: chemically synthesized

<400> SEQUENCE: 361
atacgggagc caacaccagg ggacaagcag aaccgaacag attgcaacgt atccagagca    60
ggtgtgacgg at                                                       72

<210> SEQ ID NO 362
<211> LENGTH: 72
<212> TYPE: DNA
<213> ORGANISM: Artificial Sequence
<220> FEATURE:
<223> OTHER INFORMATION: chemically synthesized

<400> SEQUENCE: 362
atccgtcaca cctgctctgg atacgttgca atctgttcgg ttctgcttgt ccctggtgt     60 tggctcccgt at                                                       72

<210> SEQ ID NO 363
<211> LENGTH: 72
<212> TYPE: DNA
<213> ORGANISM: Artificial Sequence
<220> FEATURE:
<223> OTHER INFORMATION: chemically synthesized

<400> SEQUENCE: 363
atacgggagc caacaccagc gcttgaacaa cataatgccg cccaagacct tgacagagca    60
ggtgtgacgg at                                                       72

<210> SEQ ID NO 364
<211> LENGTH: 72
<212> TYPE: DNA
<213> ORGANISM: Artificial Sequence
<220> FEATURE:
<223> OTHER INFORMATION: chemically synthesized

<400> SEQUENCE: 364
atccgtcaca cctgctctgt caaggtcttg ggcggcatta tgttgttcaa gcgctggtgt    60
tggctcccgt at                                                       72

<210> SEQ ID NO 365
<211> LENGTH: 72
<212> TYPE: DNA
<213> ORGANISM: Artificial Sequence
<220> FEATURE:
<223> OTHER INFORMATION: chemically synthesized

<400> SEQUENCE: 365
atacgggagc caacaccaca gtgcctagac ttttacaatg aaccaattgc tggaagagca    60
ggtgtgacgg at                                                       72

<210> SEQ ID NO 366
<211> LENGTH: 72
<212> TYPE: DNA
<213> ORGANISM: Artificial Sequence
<220> FEATURE:
<223> OTHER INFORMATION: chemically synthesized

<400> SEQUENCE: 366
atccgtcaca cctgctcttc cagcaattgg ttcattgtaa aagtctaggc actgtggtgt    60
tggctcccgt at                                                       72

<210> SEQ ID NO 367
<211> LENGTH: 72
<212> TYPE: DNA
<213> ORGANISM: Artificial Sequence
<220> FEATURE:
<223> OTHER INFORMATION: chemically synthesized

<400> SEQUENCE: 367
atacgggagc caacaccacc cactctcccc ccgctcccgc tcccccgctc cgcgagagca    60
ggtgtgacgg at                                                       72

<210> SEQ ID NO 368
<211> LENGTH: 72
<212> TYPE: DNA
<213> ORGANISM: Artificial Sequence
<220> FEATURE:
<223> OTHER INFORMATION: chemically synthesized

<400> SEQUENCE: 368
atccgtcaca cctgctctcg cggagcgggg gagcgggagc ggggggagag tgggtggtgt    60
tggctcccgt at                                                       72

<210> SEQ ID NO 369
<211> LENGTH: 72
<212> TYPE: DNA
<213> ORGANISM: Artificial Sequence
<220> FEATURE:
<223> OTHER INFORMATION: chemically synthesized

<400> SEQUENCE: 369
atacgggagc caacaccatc taacaatcat acacttggaa ggtgactgtc ctggagagca    60
ggtgtgacgg at                                                       72

<210> SEQ ID NO 370
<211> LENGTH: 72

```
<212> TYPE: DNA
<213> ORGANISM: Artificial Sequence
<220> FEATURE:
<223> OTHER INFORMATION: chemically synthesized

<400> SEQUENCE: 370
atccgtcaca cctgctctcc aggacagtca ccttccaagt gtatgattgt tagatggtgt    60
tggctcccgt at                                                        72

<210> SEQ ID NO 371
<211> LENGTH: 72
<212> TYPE: DNA
<213> ORGANISM: Artificial Sequence
<220> FEATURE:
<223> OTHER INFORMATION: chemically synthesized

<400> SEQUENCE: 371
atacgggagc caacaccatg tcaggacctc catcgcccgg gcccgccgcc gctgagagca    60
ggtgtgacgg at                                                        72

<210> SEQ ID NO 372
<211> LENGTH: 72
<212> TYPE: DNA
<213> ORGANISM: Artificial Sequence
<220> FEATURE:
<223> OTHER INFORMATION: chemically synthesized

<400> SEQUENCE: 372
atccgtcaca cctgctctca gcggcggcgg gcccgggcga tggaggtcct gacatggtgt    60
tggctcccgt at                                                        72

<210> SEQ ID NO 373
<211> LENGTH: 72
<212> TYPE: DNA
<213> ORGANISM: Artificial Sequence
<220> FEATURE:
<223> OTHER INFORMATION: chemically synthesized

<400> SEQUENCE: 373
atacgggagc caacaccagg cgacagcctg tgcgagtaag attgaatggt aggtagagca    60
ggtgtgacgg at                                                        72

<210> SEQ ID NO 374
<211> LENGTH: 72
<212> TYPE: DNA
<213> ORGANISM: Artificial Sequence
<220> FEATURE:
<223> OTHER INFORMATION: chemically synthesized

<400> SEQUENCE: 374
atccgtcaca cctgctctac ctaccattca atcttactcg cacaggctgt cgcctggtgt    60
tggctcccgt at                                                        72

<210> SEQ ID NO 375
<211> LENGTH: 72
<212> TYPE: DNA
<213> ORGANISM: Artificial Sequence
<220> FEATURE:
<223> OTHER INFORMATION: chemically synthesized

<400> SEQUENCE: 375
atacgggagc caacaccatc tgtgtcagtc tggcctgttt tttattctcc gcggagagca    60
```
ggtgtgacgg at                                                          72

<210> SEQ ID NO 376
<211> LENGTH: 72
<212> TYPE: DNA
<213> ORGANISM: Artificial Sequence
<220> FEATURE:
<223> OTHER INFORMATION: chemically synthesized

<400> SEQUENCE: 376
atccgtcaca cctgctctcc gcggagaata aaaaacaggc cagactgaca cagatggtgt     60
tggctcccgt at                                                          72

<210> SEQ ID NO 377
<211> LENGTH: 72
<212> TYPE: DNA
<213> ORGANISM: Artificial Sequence
<220> FEATURE:
<223> OTHER INFORMATION: chemically synthesized

<400> SEQUENCE: 377
atacgggagc caacaccagc caggaaaact atgaggcaaa aacacgatcc gggtagagca     60
ggtgtgacgg at                                                          72

<210> SEQ ID NO 378
<211> LENGTH: 72
<212> TYPE: DNA
<213> ORGANISM: Artificial Sequence
<220> FEATURE:
<223> OTHER INFORMATION: chemically synthesized

<400> SEQUENCE: 378
atccgtcaca cctgctctac ccggatcgtg tttttgcctc atagttttcc tggctggtgt     60
tggctcccgt at                                                          72

<210> SEQ ID NO 379
<211> LENGTH: 72
<212> TYPE: DNA
<213> ORGANISM: Artificial Sequence
<220> FEATURE:
<223> OTHER INFORMATION: chemically synthesized

<400> SEQUENCE: 379
atacgggagc caacaccata gaagtatgtt gttattctat ggaaataaaa cgacagagca     60
ggtgtgacgg at                                                          72

<210> SEQ ID NO 380
<211> LENGTH: 72
<212> TYPE: DNA
<213> ORGANISM: Artificial Sequence
<220> FEATURE:
<223> OTHER INFORMATION: chemically synthesized

<400> SEQUENCE: 380
atccgtcaca cctgctctgt cgttttattt ccatagaata acaacatact tctatggtgt     60
tggctcccgt at                                                          72

<210> SEQ ID NO 381
<211> LENGTH: 72
<212> TYPE: DNA
<213> ORGANISM: Artificial Sequence
<220> FEATURE:
<223> OTHER INFORMATION: chemically synthesized

```
<400> SEQUENCE: 381
atacgggagc caacaccatc ccgttgtgat cagagagcat gaaatgatgt tttgagagca      60
ggtgtgacgg at                                                          72

<210> SEQ ID NO 382
<211> LENGTH: 72
<212> TYPE: DNA
<213> ORGANISM: Artificial Sequence
<220> FEATURE:
<223> OTHER INFORMATION: chemically synthesized

<400> SEQUENCE: 382
atccgtcaca cctgctctca aaacatcatt tcatgctctc tgatcacaac gggatggtgt      60
tggctcccgt at                                                          72

<210> SEQ ID NO 383
<211> LENGTH: 72
<212> TYPE: DNA
<213> ORGANISM: Artificial Sequence
<220> FEATURE:
<223> OTHER INFORMATION: chemically synthesized

<400> SEQUENCE: 383
atacgggagc caacaccatg catgggacct gttatcctaa caagctgtca aggcagagca      60
ggtgtgacgg at                                                          72

<210> SEQ ID NO 384
<211> LENGTH: 72
<212> TYPE: DNA
<213> ORGANISM: Artificial Sequence
<220> FEATURE:
<223> OTHER INFORMATION: chemically synthesized

<400> SEQUENCE: 384
atccgtcaca cctgctctgc cttgacagct tgttaggata acaggtccca tgcatggtgt      60
tggctcccgt at                                                          72

<210> SEQ ID NO 385
<211> LENGTH: 71
<212> TYPE: DNA
<213> ORGANISM: Artificial Sequence
<220> FEATURE:
<223> OTHER INFORMATION: chemically synthesized

<400> SEQUENCE: 385
atacgggagc caacaccaca aaacgttccg agggagtaag cacttaataa tgtagagcag      60
gtgtgacgga t                                                           71

<210> SEQ ID NO 386
<211> LENGTH: 71
<212> TYPE: DNA
<213> ORGANISM: Artificial Sequence
<220> FEATURE:
<223> OTHER INFORMATION: chemically synthesized

<400> SEQUENCE: 386
atccgtcaca cctgctctac attattaagt gcttactccc tcggaacgtt ttgtggtgtt      60
ggctcccgta t                                                           71

<210> SEQ ID NO 387
```

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 387
atacgggagc caacaccacg tcttatagat gtctgtattg tttatcgctc gcccagagca     60
ggtgtgacgg at                                                        72

<210> SEQ ID NO 388
<211> LENGTH: 72
<212> TYPE: DNA
<213> ORGANISM: Artificial Sequence
<220> FEATURE:
<223> OTHER INFORMATION: chemically synthesized

<400> SEQUENCE: 388
atccgtcaca cctgctctgg gcgagcgata acaatacag acatctataa gacgtggtgt      60
tggctcccgt at                                                        72

<210> SEQ ID NO 389
<211> LENGTH: 72
<212> TYPE: DNA
<213> ORGANISM: Artificial Sequence
<220> FEATURE:
<223> OTHER INFORMATION: chemically synthesized

<400> SEQUENCE: 389
atacgggagc caacaccacc atctctggtg ataaccagtg atcttaacta tagcagagca     60
ggtgtgacgg at                                                        72

<210> SEQ ID NO 390
<211> LENGTH: 72
<212> TYPE: DNA
<213> ORGANISM: Artificial Sequence
<220> FEATURE:
<223> OTHER INFORMATION: chemically synthesized

<400> SEQUENCE: 390
atccgtcaca cctgctctgc tatagttaag atcactggtt atcaccagag atggtggtgt     60
tggctcccgt at                                                        72

<210> SEQ ID NO 391
<211> LENGTH: 72
<212> TYPE: DNA
<213> ORGANISM: Artificial Sequence
<220> FEATURE:
<223> OTHER INFORMATION: chemically synthesized

<400> SEQUENCE: 391
atacgggagc caacaccacc acctcactac agtgatcttt tgctctgaat agccagagca    60
ggtgtgacgg at                                                        72

<210> SEQ ID NO 392
<211> LENGTH: 72
<212> TYPE: DNA
<213> ORGANISM: Artificial Sequence
<220> FEATURE:
<223> OTHER INFORMATION: chemically synthesized

<400> SEQUENCE: 392
atccgtcaca cctgctctgg ctattcagag caaaagatca ctgtagtgag gtggtggtgt    60
```
tggctcccgt at                                                          72

<210> SEQ ID NO 393
<211> LENGTH: 72
<212> TYPE: DNA
<213> ORGANISM: Artificial Sequence
<220> FEATURE:
<223> OTHER INFORMATION: chemically synthesized

<400> SEQUENCE: 393
atacgggagc caacaccatg tctcttagga tacaaagcca aactgagccc gtgcagagca      60
ggtgtgacgg at                                                          72

<210> SEQ ID NO 394
<211> LENGTH: 72
<212> TYPE: DNA
<213> ORGANISM: Artificial Sequence
<220> FEATURE:
<223> OTHER INFORMATION: chemically synthesized

<400> SEQUENCE: 394
atccgtcaca cctgctctgc acgggctcag tttggctttg tatcctaaga gacatggtgt      60
tggctcccgt at                                                          72

<210> SEQ ID NO 395
<211> LENGTH: 72
<212> TYPE: DNA
<213> ORGANISM: Artificial Sequence
<220> FEATURE:
<223> OTHER INFORMATION: chemically synthesized

<400> SEQUENCE: 395
atacgggagc caacaccacc tccaatagcc aaaagaaatc gccaactaac ggcaagagca      60
ggtgtgacgg at                                                          72

<210> SEQ ID NO 396
<211> LENGTH: 72
<212> TYPE: DNA
<213> ORGANISM: Artificial Sequence
<220> FEATURE:
<223> OTHER INFORMATION: chemically synthesized

<400> SEQUENCE: 396
atccgtcaca cctgctcttg ccgttagttg gcgatttctt ttggctattg gaggtggtgt      60
tggctcccgt at                                                          72

<210> SEQ ID NO 397
<211> LENGTH: 72
<212> TYPE: DNA
<213> ORGANISM: Artificial Sequence
<220> FEATURE:
<223> OTHER INFORMATION: chemically synthesized

<400> SEQUENCE: 397
atacgggagc caacaccatc actacttta taatttcatt cttctggcgt ccctagagca       60
ggtgtgacgg at                                                          72

<210> SEQ ID NO 398
<211> LENGTH: 72
<212> TYPE: DNA
<213> ORGANISM: Artificial Sequence
<220> FEATURE:

<223> OTHER INFORMATION: chemically synthesized

<400> SEQUENCE: 398
atccgtcaca cctgctctag ggacgccaga agaatgaaat tataaaagta gtgatggtgt    60
tggctcccgt at    72

<210> SEQ ID NO 399
<211> LENGTH: 72
<212> TYPE: DNA
<213> ORGANISM: Artificial Sequence
<220> FEATURE:
<223> OTHER INFORMATION: chemically synthesized

<400> SEQUENCE: 399
atacgggagc caacaccaac tgcccacgcc gcgaccccgc ggcgcaccca accaagagca    60
ggtgtgacgg at    72

<210> SEQ ID NO 400
<211> LENGTH: 72
<212> TYPE: DNA
<213> ORGANISM: Artificial Sequence
<220> FEATURE:
<223> OTHER INFORMATION: chemically synthesized

<400> SEQUENCE: 400
atccgtcaca cctgctcttg gttgggtgcg ccgcggggtc gcggcgtggg cagttggtgt    60
tggctcccgt at    72

<210> SEQ ID NO 401
<211> LENGTH: 72
<212> TYPE: DNA
<213> ORGANISM: Artificial Sequence
<220> FEATURE:
<223> OTHER INFORMATION: chemically synthesized

<400> SEQUENCE: 401
atacgggagc caacaccaac ggttaccagg cgtgttaagg atatatgctg aaccagagca    60
ggtgtgacgg at    72

<210> SEQ ID NO 402
<211> LENGTH: 72
<212> TYPE: DNA
<213> ORGANISM: Artificial Sequence
<220> FEATURE:
<223> OTHER INFORMATION: chemically synthesized

<400> SEQUENCE: 402
atccgtcaca cctgctctgg ttcagcatat atccttaaca cgcctggtaa ccgttggtgt    60
tggctcccgt at    72

<210> SEQ ID NO 403
<211> LENGTH: 58
<212> TYPE: DNA
<213> ORGANISM: Artificial Sequence
<220> FEATURE:
<223> OTHER INFORMATION: chemically synthesized

<400> SEQUENCE: 403
atccgtcaca cctgctctgt ccaaaggcta cgcgttaacg tggtgttggc tcccgtat    58

<210> SEQ ID NO 404
<211> LENGTH: 58

```
<212> TYPE: DNA
<213> ORGANISM: Artificial Sequence
<220> FEATURE:
<223> OTHER INFORMATION: chemically synthesized

<400> SEQUENCE: 404
atccgtcaca cctgctctgg agcaatatgg tggagaaacg tggtgttggc tcccgtat      58

<210> SEQ ID NO 405
<211> LENGTH: 59
<212> TYPE: DNA
<213> ORGANISM: Artificial Sequence
<220> FEATURE:
<223> OTHER INFORMATION: chemically synthesized

<400> SEQUENCE: 405
atccgtcaca cctgctctgc cggaccatcc aatatcagct gtggtgttgg ctcccgtat     59

<210> SEQ ID NO 406
<211> LENGTH: 72
<212> TYPE: DNA
<213> ORGANISM: Artificial Sequence
<220> FEATURE:
<223> OTHER INFORMATION: chemically synthesized

<400> SEQUENCE: 406
atccgtcaca cctgctctga acaggatagg gattagcgag tcaactaagc agcatggtgt    60
tggctcccgt at                                                        72

<210> SEQ ID NO 407
<211> LENGTH: 72
<212> TYPE: DNA
<213> ORGANISM: Artificial Sequence
<220> FEATURE:
<223> OTHER INFORMATION: chemically synthesized

<400> SEQUENCE: 407
atccgtcaca cctgctctgg cggacaggaa ataagaatga acgcaaaatt tatctggtgt    60
tggctcccgt at                                                        72

<210> SEQ ID NO 408
<211> LENGTH: 72
<212> TYPE: DNA
<213> ORGANISM: Artificial Sequence
<220> FEATURE:
<223> OTHER INFORMATION: chemically synthesized

<400> SEQUENCE: 408
atccgtcaca cctgctctac gcaacgcgac aggaacattc attatagaat gtgttggtgt    60
tggctcccgt at                                                        72

<210> SEQ ID NO 409
<211> LENGTH: 72
<212> TYPE: DNA
<213> ORGANISM: Artificial Sequence
<220> FEATURE:
<223> OTHER INFORMATION: chemically synthesized

<400> SEQUENCE: 409
atccgtcaca cctgctctcg gctgcaatgc gggagagtag gggggaacca aacctggtgt    60
tggctcccgt at                                                        72

<210> SEQ ID NO 410
```

<211> LENGTH: 72
<212> TYPE: DNA
<213> ORGANISM: Artificial Sequence
<220> FEATURE:
<223> OTHER INFORMATION: chemically synthesized

<400> SEQUENCE: 410
atccgtcaca cctgctctat gactggaaca cgggtatcga tgattagatg tccttggtgt     60
tggctcccgt at     72

<210> SEQ ID NO 411
<211> LENGTH: 58
<212> TYPE: DNA
<213> ORGANISM: Artificial Sequence
<220> FEATURE:
<223> OTHER INFORMATION: chemically synthesized

<400> SEQUENCE: 411
atacgggagc caacaccacg ttaacgcgta gcctttggac agagcaggtg tgacggat     58

<210> SEQ ID NO 412
<211> LENGTH: 58
<212> TYPE: DNA
<213> ORGANISM: Artificial Sequence
<220> FEATURE:
<223> OTHER INFORMATION: chemically synthesized

<400> SEQUENCE: 412
atacgggagc caacaccacg tttctccacc atattgctcc agagcaggtg tgacggat     58

<210> SEQ ID NO 413
<211> LENGTH: 59
<212> TYPE: DNA
<213> ORGANISM: Artificial Sequence
<220> FEATURE:
<223> OTHER INFORMATION: chemically synthesized

<400> SEQUENCE: 413
atacgggagc caacaccaca gctgatattg gatggtccgg cagagcaggt gtgacggat     59

<210> SEQ ID NO 414
<211> LENGTH: 72
<212> TYPE: DNA
<213> ORGANISM: Artificial Sequence
<220> FEATURE:
<223> OTHER INFORMATION: chemically synthesized

<400> SEQUENCE: 414
atacgggagc caacaccatg ctgcttagtt gactcgctaa tccctatcct gttcagagca     60
ggtgtgacgg at     72

<210> SEQ ID NO 415
<211> LENGTH: 72
<212> TYPE: DNA
<213> ORGANISM: Artificial Sequence
<220> FEATURE:
<223> OTHER INFORMATION: chemically synthesized

<400> SEQUENCE: 415
atacgggagc caacaccaga taaattttgc gttcattctt atttcctgtc cgccagagca     60
ggtgtgacgg at     72

<210> SEQ ID NO 416
<211> LENGTH: 72

```
<212> TYPE: DNA
<213> ORGANISM: Artificial Sequence
<220> FEATURE:
<223> OTHER INFORMATION: chemically synthesized

<400> SEQUENCE: 416
atacgggagc caacaccaac acattctata atgaatgttc ctgtcgcgtt gcgtagagca    60
ggtgtgacgg at                                                        72

<210> SEQ ID NO 417
<211> LENGTH: 72
<212> TYPE: DNA
<213> ORGANISM: Artificial Sequence
<220> FEATURE:
<223> OTHER INFORMATION: chemically synthesized

<400> SEQUENCE: 417
atacgggagc caacaccagg tttggttccc ccctactctc ccgcattgca gccgagagca    60
ggtgtgacgg at                                                        72

<210> SEQ ID NO 418
<211> LENGTH: 72
<212> TYPE: DNA
<213> ORGANISM: Artificial Sequence
<220> FEATURE:
<223> OTHER INFORMATION: chemically synthesized

<400> SEQUENCE: 418
atacgggagc caacaccaag gacatctaat catcgatacc cgtgttccag tcatagagca    60
ggtgtgacgg at                                                        72

<210> SEQ ID NO 419
<211> LENGTH: 72
<212> TYPE: DNA
<213> ORGANISM: Artificial Sequence
<220> FEATURE:
<223> OTHER INFORMATION: chemically synthesized

<400> SEQUENCE: 419
atacgggagc caacaccaga taaattttgc gttcattctt atttcctgtc cgccagagca    60
ggtgtgacgg at                                                        72

<210> SEQ ID NO 420
<211> LENGTH: 72
<212> TYPE: DNA
<213> ORGANISM: Artificial Sequence
<220> FEATURE:
<223> OTHER INFORMATION: chemically synthesized

<400> SEQUENCE: 420
atccgtcaca cctgctctgg cggacaggaa ataagaatga acgcaaaatt tatctggtgt    60
tggctcccgt at                                                        72

<210> SEQ ID NO 421
<211> LENGTH: 71
<212> TYPE: DNA
<213> ORGANISM: Artificial Sequence
<220> FEATURE:
<223> OTHER INFORMATION: chemically synthesized

<400> SEQUENCE: 421
atacgggagc caacaccaga taaattttgg ttcattctta tttcctgtcc gccagagcag    60
```

```
gtgtgacgga t                                                          71

<210> SEQ ID NO 422
<211> LENGTH: 71
<212> TYPE: DNA
<213> ORGANISM: Artificial Sequence
<220> FEATURE:
<223> OTHER INFORMATION: chemically synthesized

<400> SEQUENCE: 422
atccgtcaca cctgctctgg cggacaggaa ataagaatga accaaaattt atctggtgtt    60
ggctcccgta t                                                          71

<210> SEQ ID NO 423
<211> LENGTH: 72
<212> TYPE: DNA
<213> ORGANISM: Artificial Sequence
<220> FEATURE:
<223> OTHER INFORMATION: chemically synthesized

<400> SEQUENCE: 423
atacgggagc aacaccacg gggctaccag caccgtcacc cctcattctg ccacagagca     60
ggtgtgacgg at                                                         72

<210> SEQ ID NO 424
<211> LENGTH: 72
<212> TYPE: DNA
<213> ORGANISM: Artificial Sequence
<220> FEATURE:
<223> OTHER INFORMATION: chemically synthesized

<400> SEQUENCE: 424
atccgtcaca cctgctctgt ggcagaatga ggggtgacgg tgctggtagc cccgtggtgt    60
tggctcccgt at                                                         72

<210> SEQ ID NO 425
<211> LENGTH: 69
<212> TYPE: DNA
<213> ORGANISM: Artificial Sequence
<220> FEATURE:
<223> OTHER INFORMATION: chemically synthesized

<400> SEQUENCE: 425
atacgggagc aacaccaaa agatggaaaa cactggaagg aaaatgcggt cagagcaggt     60
gtgacggat                                                             69

<210> SEQ ID NO 426
<211> LENGTH: 69
<212> TYPE: DNA
<213> ORGANISM: Artificial Sequence
<220> FEATURE:
<223> OTHER INFORMATION: chemically synthesized

<400> SEQUENCE: 426
atccgtcaca cctgctctga ccgcattttc cttccagtgt tttccatctt ttggtgttgg    60
ctcccgtat                                                             69

<210> SEQ ID NO 427
<211> LENGTH: 72
<212> TYPE: DNA
<213> ORGANISM: Artificial Sequence
<220> FEATURE:
<223> OTHER INFORMATION: chemically synthesized
```

<400> SEQUENCE: 427
atacgggagc caacaccacc gggccgatgg gcaccaggaa ctctcggacg agtgagagca    60
ggtgtgacgg at    72

<210> SEQ ID NO 428
<211> LENGTH: 72
<212> TYPE: DNA
<213> ORGANISM: Artificial Sequence
<220> FEATURE:
<223> OTHER INFORMATION: chemically synthesized

<400> SEQUENCE: 428
atccgtcaca cctgctctca ctcgtccgag agttcctggt gcccatcggc ccggtggtgt    60
tggctcccgt at    72

<210> SEQ ID NO 429
<211> LENGTH: 59
<212> TYPE: DNA
<213> ORGANISM: Artificial Sequence
<220> FEATURE:
<223> OTHER INFORMATION: chemically synthesized

<400> SEQUENCE: 429
atacgggagc caacaccaca gctgatattg gatggtccgg cagagcaggt gtgacggat    59

<210> SEQ ID NO 430
<211> LENGTH: 59
<212> TYPE: DNA
<213> ORGANISM: Artificial Sequence
<220> FEATURE:
<223> OTHER INFORMATION: chemically synthesized

<400> SEQUENCE: 430
atccgtcaca cctgctctgc cggaccatcc aatatcagct gtggtgttgg ctcccgtat    59

<210> SEQ ID NO 431
<211> LENGTH: 72
<212> TYPE: DNA
<213> ORGANISM: Artificial Sequence
<220> FEATURE:
<223> OTHER INFORMATION: chemically synthesized

<400> SEQUENCE: 431
atacgggagc caacaccagt cgaaaggcgg ccgtccagtc gagtgatttg acctagagca    60
ggtgtgacgg at    72

<210> SEQ ID NO 432
<211> LENGTH: 72
<212> TYPE: DNA
<213> ORGANISM: Artificial Sequence
<220> FEATURE:
<223> OTHER INFORMATION: chemically synthesized

<400> SEQUENCE: 432
atccgtcaca cctgctctag gtcaaatcac tcgactggac ggccgccttt cgactggtgt    60
tggctcccgt at    72

<210> SEQ ID NO 433
<211> LENGTH: 72
<212> TYPE: DNA
<213> ORGANISM: Artificial Sequence
<220> FEATURE:

-continued

<223> OTHER INFORMATION: chemically synthesized

<400> SEQUENCE: 433
atacgggagc caacaccacg gggcgtgccg tcaaaagacc gagatgtggc tgcgagagca    60
ggtgtgacgg at    72

<210> SEQ ID NO 434
<211> LENGTH: 72
<212> TYPE: DNA
<213> ORGANISM: Artificial Sequence
<220> FEATURE:
<223> OTHER INFORMATION: chemically synthesized

<400> SEQUENCE: 434
atccgtcaca cctgctctcg cagccacatc tcggtctttt gacggcacgc cccgtggtgt    60
tggctcccgt at    72

<210> SEQ ID NO 435
<211> LENGTH: 59
<212> TYPE: DNA
<213> ORGANISM: Artificial Sequence
<220> FEATURE:
<223> OTHER INFORMATION: chemically synthesized

<400> SEQUENCE: 435
atacgggagc caacaccact aacttgttgc tgatcttatc cagagcaggt gtgacggat    59

<210> SEQ ID NO 436
<211> LENGTH: 59
<212> TYPE: DNA
<213> ORGANISM: Artificial Sequence
<220> FEATURE:
<223> OTHER INFORMATION: chemically synthesized

<400> SEQUENCE: 436
atccgtcaca cctgctctgg ataagatcag caacaagtta gtggtgttgg ctcccgtat    59

<210> SEQ ID NO 437
<211> LENGTH: 72
<212> TYPE: DNA
<213> ORGANISM: Artificial Sequence
<220> FEATURE:
<223> OTHER INFORMATION: chemically synthesized

<400> SEQUENCE: 437
atacgggagc caacaccatt tagcgtaggg ctcgcttatc atttctcatt ccctagagca    60
ggtgtgacgg at    72

<210> SEQ ID NO 438
<211> LENGTH: 72
<212> TYPE: DNA
<213> ORGANISM: Artificial Sequence
<220> FEATURE:
<223> OTHER INFORMATION: chemically synthesized

<400> SEQUENCE: 438
atccgtcaca cctgctctag ggaatgagaa atgataagcg agccctacgc taaatggtgt    60
tggctcccgt at    72

<210> SEQ ID NO 439
<211> LENGTH: 72
<212> TYPE: DNA
<213> ORGANISM: Artificial Sequence

```
<220> FEATURE:
<223> OTHER INFORMATION: chemically synthesized

<400> SEQUENCE: 439
atacgggagc caacaccacc gcaacccaaa tctctacacg gattatcgtc gagcagagca    60
ggtgtgacgg at                                                       72

<210> SEQ ID NO 440
<211> LENGTH: 72
<212> TYPE: DNA
<213> ORGANISM: Artificial Sequence
<220> FEATURE:
<223> OTHER INFORMATION: chemically synthesized

<400> SEQUENCE: 440
atccgtcaca cctgctctgc tcgacgataa tccgtgtaga gatttgggtt gcggtggtgt    60
tggctcccgt at                                                       72

<210> SEQ ID NO 441
<211> LENGTH: 72
<212> TYPE: DNA
<213> ORGANISM: Artificial Sequence
<220> FEATURE:
<223> OTHER INFORMATION: chemically synthesized

<400> SEQUENCE: 441
atacgggagc caacaccaac acattctata atgaatgttc ctgtcgcgtt gcgtagagca    60
ggtgtgacgg at                                                       72

<210> SEQ ID NO 442
<211> LENGTH: 72
<212> TYPE: DNA
<213> ORGANISM: Artificial Sequence
<220> FEATURE:
<223> OTHER INFORMATION: chemically synthesized

<400> SEQUENCE: 442
atccgtcaca cctgctctac gcaacgcgac aggaacattc attatagaat gtgttggtgt    60
tggctcccgt at                                                       72

<210> SEQ ID NO 443
<211> LENGTH: 72
<212> TYPE: DNA
<213> ORGANISM: Artificial Sequence
<220> FEATURE:
<223> OTHER INFORMATION: chemically synthesized

<400> SEQUENCE: 443
atacgggagc caacaccagc ctacccccc tgtacgaggg ccgcaaccac gtagagagca    60
ggtgtgacgg at                                                       72

<210> SEQ ID NO 444
<211> LENGTH: 72
<212> TYPE: DNA
<213> ORGANISM: Artificial Sequence
<220> FEATURE:
<223> OTHER INFORMATION: chemically synthesized

<400> SEQUENCE: 444
atccgtcaca cctgctctct acgtggttgc ggccctcgta caggggggt aggctggtgt     60 tggctcccgt at                                                       72
```

<210> SEQ ID NO 445
<211> LENGTH: 59
<212> TYPE: DNA
<213> ORGANISM: Artificial Sequence
<220> FEATURE:
<223> OTHER INFORMATION: chemically synthesized

<400> SEQUENCE: 445
atacgggagc caacaccaca tctagcacga gacccctatcc cagagcaggt gtgacggat        59

<210> SEQ ID NO 446
<211> LENGTH: 59
<212> TYPE: DNA
<213> ORGANISM: Artificial Sequence
<220> FEATURE:
<223> OTHER INFORMATION: chemically synthesized

<400> SEQUENCE: 446
atccgtcaca cctgctctgg gatagggtct cgtgctagat gtggtgttgg ctcccgtat        59

<210> SEQ ID NO 447
<211> LENGTH: 72
<212> TYPE: DNA
<213> ORGANISM: Artificial Sequence
<220> FEATURE:
<223> OTHER INFORMATION: chemically synthesized

<400> SEQUENCE: 447
atacgggagc caacaccaac agcgactcga gtctgacgac tcgcggggca aatgagagca        60
ggtgtgacgg at                                                           72

<210> SEQ ID NO 448
<211> LENGTH: 72
<212> TYPE: DNA
<213> ORGANISM: Artificial Sequence
<220> FEATURE:
<223> OTHER INFORMATION: chemically synthesized

<400> SEQUENCE: 448
atccgtcaca cctgctctca tttgccccgc gagtcgtcag actcgagtcg ctgttggtgt        60
tggctcccgt at                                                           72

<210> SEQ ID NO 449
<211> LENGTH: 69
<212> TYPE: DNA
<213> ORGANISM: Artificial Sequence
<220> FEATURE:
<223> OTHER INFORMATION: chemically synthesized

<400> SEQUENCE: 449
atacgggagc caacaccata gtgttgggcc aatacggtaa cgtgtccttg gagagcaggt        60
gtgacggat                                                               69

<210> SEQ ID NO 450
<211> LENGTH: 69
<212> TYPE: DNA
<213> ORGANISM: Artificial Sequence
<220> FEATURE:
<223> OTHER INFORMATION: chemically synthesized

<400> SEQUENCE: 450
atccgtcaca cctgctctcc aaggacacgt taccgtattg gcccaacact atggtgttgg        60
ctcccgtat                                                               69

<210> SEQ ID NO 451
<211> LENGTH: 72
<212> TYPE: DNA
<213> ORGANISM: Artificial Sequence
<220> FEATURE:
<223> OTHER INFORMATION: chemically synthesized

<400> SEQUENCE: 451
atacgggagc caacaccact aaggagaggt cgcgacagac tcttctggtc aaggagagca    60
ggtgtgacgg at    72

<210> SEQ ID NO 452
<211> LENGTH: 73
<212> TYPE: DNA
<213> ORGANISM: Artificial Sequence
<220> FEATURE:
<223> OTHER INFORMATION: chemically synthesized

<400> SEQUENCE: 452
atccgtcaca cctgctctcc ttgaccagaa gagtctgtcg cgacctctcc ttagtggtgt    60
tggctcccgt atg    73

<210> SEQ ID NO 453
<211> LENGTH: 72
<212> TYPE: DNA
<213> ORGANISM: Artificial Sequence
<220> FEATURE:
<223> OTHER INFORMATION: chemically synthesized

<400> SEQUENCE: 453
atacgggagc caacaccaac ttcgactcaa agaagtccac gtgagactgg tggaagagca    60
ggtgtgacgg at    72

<210> SEQ ID NO 454
<211> LENGTH: 72
<212> TYPE: DNA
<213> ORGANISM: Artificial Sequence
<220> FEATURE:
<223> OTHER INFORMATION: chemically synthesized

<400> SEQUENCE: 454
atccgtcaca cctgctcttc caccagtctc acgtggactt ctttgagtcg aagttggtgt    60
tggctcccgt at    72

<210> SEQ ID NO 455
<211> LENGTH: 72
<212> TYPE: DNA
<213> ORGANISM: Artificial Sequence
<220> FEATURE:
<223> OTHER INFORMATION: chemically synthesized

<400> SEQUENCE: 455
atacgggagc caacaccacc cggggagacc cgcacgggcg cacaatcctt gtcgagagca    60
ggtgtgacgg at    72

<210> SEQ ID NO 456
<211> LENGTH: 72
<212> TYPE: DNA
<213> ORGANISM: Artificial Sequence
<220> FEATURE:
<223> OTHER INFORMATION: chemically synthesized

<400> SEQUENCE: 456
atccgtcaca cctgctctcg acaaggattg tgcgcccgtg cgggtctccc cgggtggtgt    60
tggctcccgt at    72

<210> SEQ ID NO 457
<211> LENGTH: 72
<212> TYPE: DNA
<213> ORGANISM: Artificial Sequence
<220> FEATURE:
<223> OTHER INFORMATION: chemically synthesized

<400> SEQUENCE: 457
atacgggagc caacaccagc tggaccaaac tacgcccatt gtggggtcc ccggagagca    60 ggtgtgacgg at    72

<210> SEQ ID NO 458
<211> LENGTH: 72
<212> TYPE: DNA
<213> ORGANISM: Artificial Sequence
<220> FEATURE:
<223> OTHER INFORMATION: chemically synthesized

<400> SEQUENCE: 458
atccgtcaca cctgctctcc ggggacccc acaatgggcg tagtttggtc cagctggtgt    60
tggctcccgt at    72

<210> SEQ ID NO 459
<211> LENGTH: 69
<212> TYPE: DNA
<213> ORGANISM: Artificial Sequence
<220> FEATURE:
<223> OTHER INFORMATION: chemically synthesized

<400> SEQUENCE: 459
atacgggagc caacaccata gtgttgggcc aatacggtaa cgtgtccttg gagagcaggt    60
gtgacggat    69

<210> SEQ ID NO 460
<211> LENGTH: 69
<212> TYPE: DNA
<213> ORGANISM: Artificial Sequence
<220> FEATURE:
<223> OTHER INFORMATION: chemically synthesized

<400> SEQUENCE: 460
atccgtcaca cctgctctcc aaggacacgt taccgtattg gcccaacact atggtgttgg    60
ctcccgtat    69

<210> SEQ ID NO 461
<211> LENGTH: 72
<212> TYPE: DNA
<213> ORGANISM: Artificial Sequence
<220> FEATURE:
<223> OTHER INFORMATION: chemically synthesized

<400> SEQUENCE: 461
atacgggagc caacaccagt gggacctacg gcctttggcc cgctgttaca acgtagagca    60
ggtgtgacgg at    72

<210> SEQ ID NO 462
<211> LENGTH: 72

```
<212> TYPE: DNA
<213> ORGANISM: Artificial Sequence
<220> FEATURE:
<223> OTHER INFORMATION: chemically synthesized

<400> SEQUENCE: 462
atccgtcaca cctgctctac gttgtaacag cgggccaaag gccgtaggtc ccactggtgt    60
tggctcccgt at                                                        72

<210> SEQ ID NO 463
<211> LENGTH: 72
<212> TYPE: DNA
<213> ORGANISM: Artificial Sequence
<220> FEATURE:
<223> OTHER INFORMATION: chemically synthesized

<400> SEQUENCE: 463
atacgggagc caacaccact tacgcatcag ccactcgaga gacggcgtta tgcagagca     60 ggtgtgacgg at                                                        72

<210> SEQ ID NO 464
<211> LENGTH: 72
<212> TYPE: DNA
<213> ORGANISM: Artificial Sequence
<220> FEATURE:
<223> OTHER INFORMATION: chemically synthesized

<400> SEQUENCE: 464
atccgtcaca cctgctctgc cataacgccg tctctcgagt ggctgatgcg taagtggtgt    60
tggctcccgt at                                                        72

<210> SEQ ID NO 465
<211> LENGTH: 72
<212> TYPE: DNA
<213> ORGANISM: Artificial Sequence
<220> FEATURE:
<223> OTHER INFORMATION: chemically synthesized

<400> SEQUENCE: 465
atacgggagc caacaccact atagggtgta gctgatccgc tcccttctcc caggagagca    60
ggtgtgacgg at                                                        72

<210> SEQ ID NO 466
<211> LENGTH: 72
<212> TYPE: DNA
<213> ORGANISM: Artificial Sequence
<220> FEATURE:
<223> OTHER INFORMATION: chemically synthesized

<400> SEQUENCE: 466
atccgtcaca cctgctctcc tgggagaagg gagcggatca gctacaccct atagtggtgt    60
tggctcccgt at                                                        72

<210> SEQ ID NO 467
<211> LENGTH: 72
<212> TYPE: DNA
<213> ORGANISM: Artificial Sequence
<220> FEATURE:
<223> OTHER INFORMATION: chemically synthesized

<400> SEQUENCE: 467
atacgggagc caacaccaga acacctagag actagttcgt gtcggcccag cgtgagagca    60
```
ggtgtgacgg at 72

<210> SEQ ID NO 468
<211> LENGTH: 72
<212> TYPE: DNA
<213> ORGANISM: Artificial Sequence
<220> FEATURE:
<223> OTHER INFORMATION: chemically synthesized

<400> SEQUENCE: 468
atccgtcaca cctgctctca cgctgggccg acacgaacta gtctctaggt gttctggtgt    60
tggctcccgt at                                                        72

<210> SEQ ID NO 469
<211> LENGTH: 72
<212> TYPE: DNA
<213> ORGANISM: Artificial Sequence
<220> FEATURE:
<223> OTHER INFORMATION: chemically synthesized

<400> SEQUENCE: 469
atacgggagc caacaccata agaaccacca ttccgcgttc gcctcccgag gtgtagagca    60
ggtgtgacgg at                                                        72

<210> SEQ ID NO 470
<211> LENGTH: 72
<212> TYPE: DNA
<213> ORGANISM: Artificial Sequence
<220> FEATURE:
<223> OTHER INFORMATION: chemically synthesized

<400> SEQUENCE: 470
atccgtcaca cctgctctac acctcgggag gcgaacgcgg aatggtggtt cttatggtgt    60
tggctcccgt at                                                        72

<210> SEQ ID NO 471
<211> LENGTH: 72
<212> TYPE: DNA
<213> ORGANISM: Artificial Sequence
<220> FEATURE:
<223> OTHER INFORMATION: chemically synthesized

<400> SEQUENCE: 471
atacgggagc caacaccagg ccataggcaa tttcatatag caactggtga gcgtagagca    60
ggtgtgacgg at                                                        72

<210> SEQ ID NO 472
<211> LENGTH: 72
<212> TYPE: DNA
<213> ORGANISM: Artificial Sequence
<220> FEATURE:
<223> OTHER INFORMATION: chemically synthesized

<400> SEQUENCE: 472
atccgtcaca cctgctctac gctcaccagt tgctatatga aattgcctat ggcctggtgt    60
tggctcccgt at                                                        72

<210> SEQ ID NO 473
<211> LENGTH: 72
<212> TYPE: DNA
<213> ORGANISM: Artificial Sequence
<220> FEATURE:
<223> OTHER INFORMATION: chemically synthesized

<400> SEQUENCE: 473
atacgggagc caacaccaac agaagtcgac cctggtaatc atgctctctc acggagagca    60
ggtgtgacgg at    72

<210> SEQ ID NO 474
<211> LENGTH: 72
<212> TYPE: DNA
<213> ORGANISM: Artificial Sequence
<220> FEATURE:
<223> OTHER INFORMATION: chemically synthesized

<400> SEQUENCE: 474
atccgtcaca cctgctctcc gtgagagagc atgattacca gggtcgactt ctgttggtgt    60
tggctcccgt at    72

<210> SEQ ID NO 475
<211> LENGTH: 72
<212> TYPE: DNA
<213> ORGANISM: Artificial Sequence
<220> FEATURE:
<223> OTHER INFORMATION: chemically synthesized

<400> SEQUENCE: 475
atacgggagc caacaccacc aacacctgga gaacttgaaa cgcagatggt ccccagagca    60
ggtgtgacgg at    72

<210> SEQ ID NO 476
<211> LENGTH: 72
<212> TYPE: DNA
<213> ORGANISM: Artificial Sequence
<220> FEATURE:
<223> OTHER INFORMATION: chemically synthesized

<400> SEQUENCE: 476
atccgtcaca cctgctctgg ggaccatctg cgtttcaagt tctccaggtg ttggtggtgt    60
tggctcccgt at    72

<210> SEQ ID NO 477
<211> LENGTH: 72
<212> TYPE: DNA
<213> ORGANISM: Artificial Sequence
<220> FEATURE:
<223> OTHER INFORMATION: chemically synthesized

<400> SEQUENCE: 477
atacgggagc caacaccagg tagcgacatg acagtaccac ttacaggacg tgccagagca    60
ggtgtgacgg at    72

<210> SEQ ID NO 478
<211> LENGTH: 72
<212> TYPE: DNA
<213> ORGANISM: Artificial Sequence
<220> FEATURE:
<223> OTHER INFORMATION: chemically synthesized

<400> SEQUENCE: 478
atccgtcaca cctgctctgg cacgtcctgt aagtggtact gtcatgtcgc tacctggtgt    60
tggctcccgt at    72

<210> SEQ ID NO 479

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 479
atacgggagc caacaccaat gacgtaaaca caaacggcgg acccaatcgt gttcagagca      60
ggtgtgacgg at                                                          72

<210> SEQ ID NO 480
<211> LENGTH: 72
<212> TYPE: DNA
<213> ORGANISM: Artificial Sequence
<220> FEATURE:
<223> OTHER INFORMATION: chemically synthesized

<400> SEQUENCE: 480
atccgtcaca cctgctctga acacgattgg gtccgccgtt tgtgtttacg tcattggtgt      60
tggctcccgt at                                                          72

<210> SEQ ID NO 481
<211> LENGTH: 72
<212> TYPE: DNA
<213> ORGANISM: Artificial Sequence
<220> FEATURE:
<223> OTHER INFORMATION: chemically synthesized

<400> SEQUENCE: 481
atacgggagc caacaccatg ctccagcata ttgattaatg ccaagagttg gaacagagca      60
ggtgtgacgg at                                                          72

<210> SEQ ID NO 482
<211> LENGTH: 72
<212> TYPE: DNA
<213> ORGANISM: Artificial Sequence
<220> FEATURE:
<223> OTHER INFORMATION: chemically synthesized

<400> SEQUENCE: 482
atccgtcaca cctgctctgt tccaactctt ggcattaatc aatatgctgg agcatggtgt      60
tggctcccgt at                                                          72

<210> SEQ ID NO 483
<211> LENGTH: 72
<212> TYPE: DNA
<213> ORGANISM: Artificial Sequence
<220> FEATURE:
<223> OTHER INFORMATION: chemically synthesized

<400> SEQUENCE: 483
atacgggagc caacaccatg tggttcagat gcgccatatc tagacggtct ctgtagagca      60
ggtgtgacgg at                                                          72

<210> SEQ ID NO 484
<211> LENGTH: 72
<212> TYPE: DNA
<213> ORGANISM: Artificial Sequence
<220> FEATURE:
<223> OTHER INFORMATION: chemically synthesized

<400> SEQUENCE: 484
atccgtcaca cctgctctac agagaccgtc tagatatggc gcatctgaac cacatggtgt      60
```
tggctcccgt at                                                           72

<210> SEQ ID NO 485
<211> LENGTH: 72
<212> TYPE: DNA
<213> ORGANISM: Artificial Sequence
<220> FEATURE:
<223> OTHER INFORMATION: chemically synthesized

<400> SEQUENCE: 485
atacgggagc caacaccaaa ccccattctg tcacagcgcc acccaacgag tgttagagca      60
ggtgtgacgg at                                                           72

<210> SEQ ID NO 486
<211> LENGTH: 72
<212> TYPE: DNA
<213> ORGANISM: Artificial Sequence
<220> FEATURE:
<223> OTHER INFORMATION: chemically synthesized

<400> SEQUENCE: 486
atccgtcaca cctgctctaa cactcgttgg gtggcgctgt gacagaatgg ggtttggtgt      60
tggctcccgt at                                                           72

<210> SEQ ID NO 487
<211> LENGTH: 72
<212> TYPE: DNA
<213> ORGANISM: Artificial Sequence
<220> FEATURE:
<223> OTHER INFORMATION: chemically synthesized

<400> SEQUENCE: 487
atacgggagc caacaccagc cggtatcggt gctgagggcc ttggcttggc tctgagagca      60
ggtgtgacgg at                                                           72

<210> SEQ ID NO 488
<211> LENGTH: 72
<212> TYPE: DNA
<213> ORGANISM: Artificial Sequence
<220> FEATURE:
<223> OTHER INFORMATION: chemically synthesized

<400> SEQUENCE: 488
atccgtcaca cctgctctca gagccaagcc aaggccctca gcaccgatac cggctggtgt      60
tggctcccgt at                                                           72

<210> SEQ ID NO 489
<211> LENGTH: 72
<212> TYPE: DNA
<213> ORGANISM: Artificial Sequence
<220> FEATURE:
<223> OTHER INFORMATION: chemically synthesized

<400> SEQUENCE: 489
atacgggagc caacaccatg gcgacctaat cagccggaca gtgctcctca acgtagagca      60
ggtgtgacgg at                                                           72

<210> SEQ ID NO 490
<211> LENGTH: 72
<212> TYPE: DNA
<213> ORGANISM: Artificial Sequence
<220> FEATURE:

<223> OTHER INFORMATION: chemically synthesized

<400> SEQUENCE: 490
atccgtcaca cctgctctac gttgaggagc actgtccggc tgattaggtc gccatggtgt    60
tggctcccgt at    72

<210> SEQ ID NO 491
<211> LENGTH: 71
<212> TYPE: DNA
<213> ORGANISM: Artificial Sequence
<220> FEATURE:
<223> OTHER INFORMATION: chemically synthesized

<400> SEQUENCE: 491
atacgggagc caacaccatg gagacagggg gaacgacagc ggcggttgcg gggcagagca    60
ggtgtgacgg a    71

<210> SEQ ID NO 492
<211> LENGTH: 72
<212> TYPE: DNA
<213> ORGANISM: Artificial Sequence
<220> FEATURE:
<223> OTHER INFORMATION: chemically synthesized

<400> SEQUENCE: 492
atccgtcaca cctgctctgc cccgcaaccg ccgctgtcgt tcccccctgtc tccatggtgt    60 tggctcccgt at    72

<210> SEQ ID NO 493
<211> LENGTH: 72
<212> TYPE: DNA
<213> ORGANISM: Artificial Sequence
<220> FEATURE:
<223> OTHER INFORMATION: chemically synthesized

<400> SEQUENCE: 493
atacgggagc caacaccaat agccggccga aatccctttg ggatggtcat accgagagca    60
ggtgtgacgg at    72

<210> SEQ ID NO 494
<211> LENGTH: 72
<212> TYPE: DNA
<213> ORGANISM: Artificial Sequence
<220> FEATURE:
<223> OTHER INFORMATION: chemically synthesized

<400> SEQUENCE: 494
atccgtcaca cctgctctcg gtatgaccat cccaaaggga tttcggccgg ctattggtgt    60
tggctcccgt at    72

<210> SEQ ID NO 495
<211> LENGTH: 72
<212> TYPE: DNA
<213> ORGANISM: Artificial Sequence
<220> FEATURE:
<223> OTHER INFORMATION: chemically synthesized

<400> SEQUENCE: 495
atacgggagc caacaccacc gaatgtgctg caagactaat ctggatggcc atgcagagca    60
ggtgtgacgg at    72

-continued

<210> SEQ ID NO 496
<211> LENGTH: 72
<212> TYPE: DNA
<213> ORGANISM: Artificial Sequence
<220> FEATURE:
<223> OTHER INFORMATION: chemically synthesized

<400> SEQUENCE: 496
atccgtcaca cctgctctgc atggccatcc agattagtct tgcagcacat tcggtggtgt    60
tggctcccgt at                                                        72

<210> SEQ ID NO 497
<211> LENGTH: 72
<212> TYPE: DNA
<213> ORGANISM: Artificial Sequence
<220> FEATURE:
<223> OTHER INFORMATION: chemically synthesized

<400> SEQUENCE: 497
atacgggagc caacaccaaa tcgagttcgt gacagttggg cagataccga gtccagagca    60
ggtgtgacgg at                                                        72

<210> SEQ ID NO 498
<211> LENGTH: 72
<212> TYPE: DNA
<213> ORGANISM: Artificial Sequence
<220> FEATURE:
<223> OTHER INFORMATION: chemically synthesized

<400> SEQUENCE: 498
atccgtcaca cctgctctgg actcggtatc tgcccaactg tcacgaactc gatttggtgt    60
tggctcccgt at                                                        72

<210> SEQ ID NO 499
<211> LENGTH: 72
<212> TYPE: DNA
<213> ORGANISM: Artificial Sequence
<220> FEATURE:
<223> OTHER INFORMATION: chemically synthesized

<400> SEQUENCE: 499
atacgggagc caacaccagg gtccacgcta cacggatcaa gtctagctgg ttgtagagca    60
ggtgtgacgg at                                                        72

<210> SEQ ID NO 500
<211> LENGTH: 72
<212> TYPE: DNA
<213> ORGANISM: Artificial Sequence
<220> FEATURE:
<223> OTHER INFORMATION: chemically synthesized

<400> SEQUENCE: 500
atccgtcaca cctgctctac aaccagctag acttgatccg tgtagcgtgg accctggtgt    60
tggctcccgt at                                                        72

<210> SEQ ID NO 501
<211> LENGTH: 72
<212> TYPE: DNA
<213> ORGANISM: Artificial Sequence
<220> FEATURE:
<223> OTHER INFORMATION: chemically synthesized

<400> SEQUENCE: 501

```
atacgggagc caacaccatc ccacaaggct cgtgttaggc ctccaatgct ctcgagagca      60
ggtgtgacgg at                                                          72

<210> SEQ ID NO 502
<211> LENGTH: 72
<212> TYPE: DNA
<213> ORGANISM: Artificial Sequence
<220> FEATURE:
<223> OTHER INFORMATION: chemically synthesized

<400> SEQUENCE: 502
atccgtcaca cctgctctcg agagcattgg aggcctaaca cgagccttgt gggatggtgt      60
tggctcccgt at                                                          72

<210> SEQ ID NO 503
<211> LENGTH: 72
<212> TYPE: DNA
<213> ORGANISM: Artificial Sequence
<220> FEATURE:
<223> OTHER INFORMATION: chemically synthesized

<400> SEQUENCE: 503
atacgggagc caacaccagg ccccgagaaa ttatcgatag tggtttctcg ccctagagca      60
ggtgtgacgg at                                                          72

<210> SEQ ID NO 504
<211> LENGTH: 72
<212> TYPE: DNA
<213> ORGANISM: Artificial Sequence
<220> FEATURE:
<223> OTHER INFORMATION: chemically synthesized

<400> SEQUENCE: 504
atccgtcaca cctgctctag ggcgagaaac cactatcgat aatttctcgg ggcctggtgt      60
tggctcccgt at                                                          72

<210> SEQ ID NO 505
<211> LENGTH: 72
<212> TYPE: DNA
<213> ORGANISM: Artificial Sequence
<220> FEATURE:
<223> OTHER INFORMATION: chemically synthesized

<400> SEQUENCE: 505
atacgggagc caacaccaca cccggatgcg attaagaagt tactgccttg cgggagagca      60
ggtgtgacgg at                                                          72

<210> SEQ ID NO 506
<211> LENGTH: 72
<212> TYPE: DNA
<213> ORGANISM: Artificial Sequence
<220> FEATURE:
<223> OTHER INFORMATION: chemically synthesized

<400> SEQUENCE: 506
atccgtcaca cctgctctcc cgcaaggcag taacttctta atcgcatccg ggtgtggtgt      60
tggctcccgt at                                                          72

<210> SEQ ID NO 507
<211> LENGTH: 72
<212> TYPE: DNA
<213> ORGANISM: Artificial Sequence
```

```
<220> FEATURE:
<223> OTHER INFORMATION: chemically synthesized

<400> SEQUENCE: 507
atacgggagc caacaccatg ccatgcactt ggttccgaac gttcgcgtca ttgcagagca      60
ggtgtgacgg at                                                         72

<210> SEQ ID NO 508
<211> LENGTH: 72
<212> TYPE: DNA
<213> ORGANISM: Artificial Sequence
<220> FEATURE:
<223> OTHER INFORMATION: chemically synthesized

<400> SEQUENCE: 508
atccgtcaca cctgctctgc aatgacgcga acgttcggaa ccaagtgcat ggcatggtgt      60
tggctcccgt at                                                         72

<210> SEQ ID NO 509
<211> LENGTH: 72
<212> TYPE: DNA
<213> ORGANISM: Artificial Sequence
<220> FEATURE:
<223> OTHER INFORMATION: chemically synthesized

<400> SEQUENCE: 509
atacgggagc caacaccacc aaaaaaagct gtgaccggaa ggtgctgctg acgtagagca      60
ggtgtgacgg at                                                         72

<210> SEQ ID NO 510
<211> LENGTH: 72
<212> TYPE: DNA
<213> ORGANISM: Artificial Sequence
<220> FEATURE:
<223> OTHER INFORMATION: chemically synthesized

<400> SEQUENCE: 510
atccgtcaca cctgctctac gtcagcagca ccttccggtc acagcttttt ttggtggtgt      60
tggctcccgt at                                                         72

<210> SEQ ID NO 511
<211> LENGTH: 72
<212> TYPE: DNA
<213> ORGANISM: Artificial Sequence
<220> FEATURE:
<223> OTHER INFORMATION: chemically synthesized

<400> SEQUENCE: 511
atacgggagc caacaccaag ctaccatcca cctaacagga ctacgcgaat tgcaagagca      60
ggtgtgacgg at                                                         72

<210> SEQ ID NO 512
<211> LENGTH: 72
<212> TYPE: DNA
<213> ORGANISM: Artificial Sequence
<220> FEATURE:
<223> OTHER INFORMATION: chemically synthesized

<400> SEQUENCE: 512
atccgtcaca cctgctcttg caattcgcgt agtcctgtta ggtggatggt agcttggtgt      60
tggctcccgt at                                                         72
```

```
<210> SEQ ID NO 513
<211> LENGTH: 59
<212> TYPE: DNA
<213> ORGANISM: Artificial Sequence
<220> FEATURE:
<223> OTHER INFORMATION: chemically synthesized

<400> SEQUENCE: 513
atacgggagc caacaccaca agcaggaata agcgccggtc cagagcaggt gtgacggat      59

<210> SEQ ID NO 514
<211> LENGTH: 59
<212> TYPE: DNA
<213> ORGANISM: Artificial Sequence
<220> FEATURE:
<223> OTHER INFORMATION: chemically synthesized

<400> SEQUENCE: 514
atccgtcaca cctgctctgg accggcgctt attcctgctt gtggtgttgg ctcccgtat      59

<210> SEQ ID NO 515
<211> LENGTH: 72
<212> TYPE: DNA
<213> ORGANISM: Artificial Sequence
<220> FEATURE:
<223> OTHER INFORMATION: chemically synthesized

<400> SEQUENCE: 515
atacgggagc caacaccaca tggaccggca acctcagaag tagcaaacca ccatagagca     60
ggtgtgacgg at                                                        72

<210> SEQ ID NO 516
<211> LENGTH: 72
<212> TYPE: DNA
<213> ORGANISM: Artificial Sequence
<220> FEATURE:
<223> OTHER INFORMATION: chemically synthesized

<400> SEQUENCE: 516
atccgtcaca cctgctctat ggtggtttgc tacttctgag gttgccggtc catgtggtgt     60
tggctcccgt at                                                        72

<210> SEQ ID NO 517
<211> LENGTH: 72
<212> TYPE: DNA
<213> ORGANISM: Artificial Sequence
<220> FEATURE:
<223> OTHER INFORMATION: chemically synthesized

<400> SEQUENCE: 517
atacgggagc caacaccatg tccaaaccat tctcggacct ccctcagtgg cggcagagca     60
ggtgtgacgg at                                                        72

<210> SEQ ID NO 518
<211> LENGTH: 72
<212> TYPE: DNA
<213> ORGANISM: Artificial Sequence
<220> FEATURE:
<223> OTHER INFORMATION: chemically synthesized

<400> SEQUENCE: 518
atccgtcaca cctgctctgc cgccactgag ggaggtccga gaatggtttg gacatggtgt     60
tggctcccgt at                                                        72
```

<210> SEQ ID NO 519
<211> LENGTH: 72
<212> TYPE: DNA
<213> ORGANISM: Artificial Sequence
<220> FEATURE:
<223> OTHER INFORMATION: chemically synthesized

<400> SEQUENCE: 519
atacgggagc caacaccagt ccgttatgac atgtccggac ccgtacgcgt gtcaagagca    60
ggtgtgacgg at    72

<210> SEQ ID NO 520
<211> LENGTH: 72
<212> TYPE: DNA
<213> ORGANISM: Artificial Sequence
<220> FEATURE:
<223> OTHER INFORMATION: chemically synthesized

<400> SEQUENCE: 520
atccgtcaca cctgctcttg acacgcgtac gggtccggac atgtcataac ggactggtgt    60
tggctcccgt at    72

<210> SEQ ID NO 521
<211> LENGTH: 72
<212> TYPE: DNA
<213> ORGANISM: Artificial Sequence
<220> FEATURE:
<223> OTHER INFORMATION: chemically synthesized

<400> SEQUENCE: 521
atacgggagc caacaccatc cgctcacatg atgctgtacg atggccgcgt gcaaagagca    60
ggtgtgacgg at    72

<210> SEQ ID NO 522
<211> LENGTH: 72
<212> TYPE: DNA
<213> ORGANISM: Artificial Sequence
<220> FEATURE:
<223> OTHER INFORMATION: chemically synthesized

<400> SEQUENCE: 522
atccgtcaca cctgctcttt gcacgcggcc atcgtacagc atcatgtgag cggatggtgt    60
tggctcccgt at    72

<210> SEQ ID NO 523
<211> LENGTH: 71
<212> TYPE: DNA
<213> ORGANISM: Artificial Sequence
<220> FEATURE:
<223> OTHER INFORMATION: chemically synthesized

<400> SEQUENCE: 523
atacgggagc caacaccacg tcgcatatac cccgagaagg tagatcgtgg actagagcag    60
gtgtgacgga t    71

<210> SEQ ID NO 524
<211> LENGTH: 71
<212> TYPE: DNA
<213> ORGANISM: Artificial Sequence
<220> FEATURE:
<223> OTHER INFORMATION: chemically synthesized

```
<400> SEQUENCE: 524
atccgtcaca cctgctctag tccacgatct accttctcgg ggtatatgcg acgtggtgtt    60
ggctcccgta t                                                         71

<210> SEQ ID NO 525
<211> LENGTH: 71
<212> TYPE: DNA
<213> ORGANISM: Artificial Sequence
<220> FEATURE:
<223> OTHER INFORMATION: chemically synthesized

<400> SEQUENCE: 525
atacgggagc caacaccacg aggacctaga cttgtccgac atcacagtgt gcgagagcag    60
gtgtgacgga t                                                         71

<210> SEQ ID NO 526
<211> LENGTH: 71
<212> TYPE: DNA
<213> ORGANISM: Artificial Sequence
<220> FEATURE:
<223> OTHER INFORMATION: chemically synthesized

<400> SEQUENCE: 526
atccgtcaca cctgctctcg cacactgtga tgtcggacaa gtctaggtcc tcgtggtgtt    60
ggctcccgta t                                                         71

<210> SEQ ID NO 527
<211> LENGTH: 59
<212> TYPE: DNA
<213> ORGANISM: Artificial Sequence
<220> FEATURE:
<223> OTHER INFORMATION: chemically synthesized

<400> SEQUENCE: 527
atacgggagc caacaccaca gctgatattg gatggtccgg cagagcaggt gtgacggat     59

<210> SEQ ID NO 528
<211> LENGTH: 59
<212> TYPE: DNA
<213> ORGANISM: Artificial Sequence
<220> FEATURE:
<223> OTHER INFORMATION: chemically synthesized

<400> SEQUENCE: 528
atccgtcaca cctgctctgc cggaccatcc aatatcagct gtggtgttgg ctcccgtat     59

<210> SEQ ID NO 529
<211> LENGTH: 72
<212> TYPE: DNA
<213> ORGANISM: Artificial Sequence
<220> FEATURE:
<223> OTHER INFORMATION: chemically synthesized

<400> SEQUENCE: 529
atacgggagc caacaccacg ggaccatcag cctcaacttc ctacaaggcc tactagagca    60
ggtgtgacgg at                                                        72

<210> SEQ ID NO 530
<211> LENGTH: 72
<212> TYPE: DNA
<213> ORGANISM: Artificial Sequence
<220> FEATURE:
<223> OTHER INFORMATION: chemically synthesized
```

<400> SEQUENCE: 530
atccgtcaca cctgctctag taggccttgt aggaagttga ggctgatggt cccgtggtgt    60
tggctcccgt at                                                        72

<210> SEQ ID NO 531
<211> LENGTH: 72
<212> TYPE: DNA
<213> ORGANISM: Artificial Sequence
<220> FEATURE:
<223> OTHER INFORMATION: chemically synthesized

<400> SEQUENCE: 531
atacgggagc caacaccaat ggacaaaggc aatagcgtca attgaagtca gaccagagca    60
ggtgtgacgg at                                                        72

<210> SEQ ID NO 532
<211> LENGTH: 72
<212> TYPE: DNA
<213> ORGANISM: Artificial Sequence
<220> FEATURE:
<223> OTHER INFORMATION: chemically synthesized

<400> SEQUENCE: 532
atccgtcaca cctgctctgg tctgacttca attgacgcta ttgcctttgt ccattggtgt    60
tggctcccgt at                                                        72

<210> SEQ ID NO 533
<211> LENGTH: 72
<212> TYPE: DNA
<213> ORGANISM: Artificial Sequence
<220> FEATURE:
<223> OTHER INFORMATION: chemically synthesized

<400> SEQUENCE: 533
atacgggagc caacaccaac tgaactcatg aagcacgatt gttgccccac gtgcagagca    60
ggtgtgacgg at                                                        72

<210> SEQ ID NO 534
<211> LENGTH: 72
<212> TYPE: DNA
<213> ORGANISM: Artificial Sequence
<220> FEATURE:
<223> OTHER INFORMATION: chemically synthesized

<400> SEQUENCE: 534
atccgtcaca cctgctctgc acgtggggca acaatcgtgc ttcatgagtt cagttggtgt    60
tggctcccgt at                                                        72

<210> SEQ ID NO 535
<211> LENGTH: 72
<212> TYPE: DNA
<213> ORGANISM: Artificial Sequence
<220> FEATURE:
<223> OTHER INFORMATION: chemically synthesized

<400> SEQUENCE: 535
atacgggagc caacaccaat ccctagcaag taagctggtg gagctagtac acgtagagca    60
ggtgtgacgg at                                                        72

<210> SEQ ID NO 536

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 536
atccgtcaca cctgctctac gtgtactagc tccaccagct tacttgctag ggattggtgt    60
tggctcccgt at                                                       72

<210> SEQ ID NO 537
<211> LENGTH: 72
<212> TYPE: DNA
<213> ORGANISM: Artificial Sequence
<220> FEATURE:
<223> OTHER INFORMATION: chemically synthesized

<400> SEQUENCE: 537
atacgggagc caacaccaca ccgaaagccg aacgatagg gtacagctgg gtgtagagca    60
ggtgtgacgg at                                                       72

<210> SEQ ID NO 538
<211> LENGTH: 72
<212> TYPE: DNA
<213> ORGANISM: Artificial Sequence
<220> FEATURE:
<223> OTHER INFORMATION: chemically synthesized

<400> SEQUENCE: 538
atccgtcaca cctgctctac acccagctgt accctatcgt tccggctttc ggtgtggtgt    60
tggctcccgt at                                                       72

<210> SEQ ID NO 539
<211> LENGTH: 72
<212> TYPE: DNA
<213> ORGANISM: Artificial Sequence
<220> FEATURE:
<223> OTHER INFORMATION: chemically synthesized

<400> SEQUENCE: 539
atacgggagc caacaccaag ggcgaactag catcacctcg gtcgctcata ggccagagca    60
ggtgtgacgg at                                                       72

<210> SEQ ID NO 540
<211> LENGTH: 72
<212> TYPE: DNA
<213> ORGANISM: Artificial Sequence
<220> FEATURE:
<223> OTHER INFORMATION: chemically synthesized

<400> SEQUENCE: 540
atccgtcaca cctgctctgg cctatgagcg accgaggtga tgctagttcg cccttggtgt    60
tggctcccgt at                                                       72

<210> SEQ ID NO 541
<211> LENGTH: 71
<212> TYPE: DNA
<213> ORGANISM: Artificial Sequence
<220> FEATURE:
<223> OTHER INFORMATION: chemically synthesized

<400> SEQUENCE: 541
atacgggagc caacaccaca gggcgacgta agctccgtcc agaggatgtc agtagagcag    60
```

-continued gtgtgacgga t                                                             71

<210> SEQ ID NO 542
<211> LENGTH: 71
<212> TYPE: DNA
<213> ORGANISM: Artificial Sequence
<220> FEATURE:
<223> OTHER INFORMATION: chemically synthesized

<400> SEQUENCE: 542
atccgtcaca cctgctctac tgacatcctc tggacggagc ttacgtcgcc ctgtggtgtt       60
ggctcccgta t                                                             71

<210> SEQ ID NO 543
<211> LENGTH: 72
<212> TYPE: DNA
<213> ORGANISM: Artificial Sequence
<220> FEATURE:
<223> OTHER INFORMATION: chemically synthesized

<400> SEQUENCE: 543
atccgtcaca cctgctctgg agacattaaa aaccggagtt tatttatacc tttctggtgt       60
tggctcccgt at                                                            72

<210> SEQ ID NO 544
<211> LENGTH: 72
<212> TYPE: DNA
<213> ORGANISM: Artificial Sequence
<220> FEATURE:
<223> OTHER INFORMATION: chemically synthesized

<400> SEQUENCE: 544
atacgggagc caacaccaga aaggtataaa taaactccgg tttttaatgt ctccagagca       60
ggtgtgacgg at                                                            72

<210> SEQ ID NO 545
<211> LENGTH: 59
<212> TYPE: DNA
<213> ORGANISM: Artificial Sequence
<220> FEATURE:
<223> OTHER INFORMATION: chemically synthesized

<400> SEQUENCE: 545
atacgggagc caacaccact aacttgttgc tgatcttatc cagagcaggt gtgacggat        59

<210> SEQ ID NO 546
<211> LENGTH: 59
<212> TYPE: DNA
<213> ORGANISM: Artificial Sequence
<220> FEATURE:
<223> OTHER INFORMATION: chemically synthesized

<400> SEQUENCE: 546
atccgtcaca cctgctctgg ataagatcag caacaagtta gtggtgttgg ctcccgtat        59

<210> SEQ ID NO 547
<211> LENGTH: 58
<212> TYPE: DNA
<213> ORGANISM: Artificial Sequence
<220> FEATURE:
<223> OTHER INFORMATION: chemically synthesized

<400> SEQUENCE: 547
atccgtcaca cctgctctgc atggagagtt ttttggtcag tggtgttggc tcccgtat    58

<210> SEQ ID NO 548
<211> LENGTH: 58
<212> TYPE: DNA
<213> ORGANISM: Artificial Sequence
<220> FEATURE:
<223> OTHER INFORMATION: chemically synthesized

<400> SEQUENCE: 548
atacgggagc caacaccact gaccaaaaaa ctctccatgc agagcaggtg tgacggat    58

<210> SEQ ID NO 549
<211> LENGTH: 58
<212> TYPE: DNA
<213> ORGANISM: Artificial Sequence
<220> FEATURE:
<223> OTHER INFORMATION: chemically synthesized

<400> SEQUENCE: 549
atacgggagc caacaccacg ttaacgcgta gcctttggac agagcaggtg tgacggat    58

<210> SEQ ID NO 550
<211> LENGTH: 58
<212> TYPE: DNA
<213> ORGANISM: Artificial Sequence
<220> FEATURE:
<223> OTHER INFORMATION: chemically synthesized

<400> SEQUENCE: 550
atccgtcaca cctgctctgt ccaaaggcta cgcgttaacg tggtgttggc tcccgtat    58

<210> SEQ ID NO 551
<211> LENGTH: 59
<212> TYPE: DNA
<213> ORGANISM: Artificial Sequence
<220> FEATURE:
<223> OTHER INFORMATION: chemically synthesized

<400> SEQUENCE: 551
atccgtcaca cctgctctgc cggaccatcc aatatcagct gtggtgttgg ctcccgtat    59

<210> SEQ ID NO 552
<211> LENGTH: 59
<212> TYPE: DNA
<213> ORGANISM: Artificial Sequence
<220> FEATURE:
<223> OTHER INFORMATION: chemically synthesized

<400> SEQUENCE: 552
atacgggagc caacaccaca gctgatattg gatggtccgg cagagcaggt gtgacggat    59

<210> SEQ ID NO 553
<211> LENGTH: 72
<212> TYPE: DNA
<213> ORGANISM: Artificial Sequence
<220> FEATURE:
<223> OTHER INFORMATION: chemically synthesized

<400> SEQUENCE: 553
atccgtcaca cctgctctcg tccgtcatta agttcggagg ctggcgggtt gcgttggtgt    60
tggctcccgt at    72

<210> SEQ ID NO 554
<211> LENGTH: 72

```
<212> TYPE: DNA
<213> ORGANISM: Artificial Sequence
<220> FEATURE:
<223> OTHER INFORMATION: chemically synthesized

<400> SEQUENCE: 554
atacgggagc caacaccaac gcaacccgcc agcctccgaa cttaatgacg gacgagagca    60
ggtgtgacgg at                                                       72

<210> SEQ ID NO 555
<211> LENGTH: 72
<212> TYPE: DNA
<213> ORGANISM: Artificial Sequence
<220> FEATURE:
<223> OTHER INFORMATION: chemically synthesized

<400> SEQUENCE: 555
atacgggagc caacaccatt ctatcgttcc ggacgcttat gccttgccat ctacagagca    60
ggtgtgacgg at                                                       72

<210> SEQ ID NO 556
<211> LENGTH: 72
<212> TYPE: DNA
<213> ORGANISM: Artificial Sequence
<220> FEATURE:
<223> OTHER INFORMATION: chemically synthesized

<400> SEQUENCE: 556
atccgtcaca cctgctctgt agatggcaag gcataagcgt ccggaacgat agaatggtgt    60
tggctcccgt at                                                       72

<210> SEQ ID NO 557
<211> LENGTH: 72
<212> TYPE: DNA
<213> ORGANISM: Artificial Sequence
<220> FEATURE:
<223> OTHER INFORMATION: chemically synthesized

<400> SEQUENCE: 557
atccgtcaca cctgctctaa ctcttactac tttgttgcta tcacattcaa ctgttggtgt    60
tggctcccgt at                                                       72

<210> SEQ ID NO 558
<211> LENGTH: 72
<212> TYPE: DNA
<213> ORGANISM: Artificial Sequence
<220> FEATURE:
<223> OTHER INFORMATION: chemically synthesized

<400> SEQUENCE: 558
atacgggagc caacaccaac agttgaatgt gatagcaaca aagtagtaag agttagagca    60
ggtgtgacgg at                                                       72

<210> SEQ ID NO 559
<211> LENGTH: 58
<212> TYPE: DNA
<213> ORGANISM: Artificial Sequence
<220> FEATURE:
<223> OTHER INFORMATION: chemically synthesized

<400> SEQUENCE: 559
atccgtcaca cctgctctgg cctttcacca agcgtccttg tggtgttggc tcccgtat     58
```

```
<210> SEQ ID NO 560
<211> LENGTH: 58
<212> TYPE: DNA
<213> ORGANISM: Artificial Sequence
<220> FEATURE:
<223> OTHER INFORMATION: chemically synthesized

<400> SEQUENCE: 560
atacgggagc caacaccaca aggacgcttg gtgaaaggcc agagcaggtg tgacggat        58

<210> SEQ ID NO 561
<211> LENGTH: 58
<212> TYPE: DNA
<213> ORGANISM: Artificial Sequence
<220> FEATURE:
<223> OTHER INFORMATION: chemically synthesized

<400> SEQUENCE: 561
atccgtcaca cctgctctgg caccgagcac gggaacccag tggtgttggc tcccgtat        58

<210> SEQ ID NO 562
<211> LENGTH: 58
<212> TYPE: DNA
<213> ORGANISM: Artificial Sequence
<220> FEATURE:
<223> OTHER INFORMATION: chemically synthesized

<400> SEQUENCE: 562
atacgggagc caacaccact gggttcccgt gctcggtgcc agagcaggtg tgacggat        58

<210> SEQ ID NO 563
<211> LENGTH: 69
<212> TYPE: DNA
<213> ORGANISM: Artificial Sequence
<220> FEATURE:
<223> OTHER INFORMATION: chemically synthesized

<400> SEQUENCE: 563
atacgggagc caacaccata gtgttgggcc aatacggtaa cgtgtccttg gagagcaggt      60
gtgacggat                                                             69

<210> SEQ ID NO 564
<211> LENGTH: 69
<212> TYPE: DNA
<213> ORGANISM: Artificial Sequence
<220> FEATURE:
<223> OTHER INFORMATION: chemically synthesized

<400> SEQUENCE: 564
atccgtcaca cctgctctcc aaggacacgt taccgtattg gcccaacact atggtgttgg      60
ctcccgtat                                                             69

<210> SEQ ID NO 565
<211> LENGTH: 72
<212> TYPE: DNA
<213> ORGANISM: Artificial Sequence
<220> FEATURE:
<223> OTHER INFORMATION: chemically synthesized

<400> SEQUENCE: 565
atccgtcaca cctgctctac ccgatgccgc cccgggattg ttgtatgacc atcttggtgt      60
tggctcccgt at                                                         72
```

<210> SEQ ID NO 566
<211> LENGTH: 72
<212> TYPE: DNA
<213> ORGANISM: Artificial Sequence
<220> FEATURE:
<223> OTHER INFORMATION: chemically synthesized

<400> SEQUENCE: 566
atacgggagc caacaccaag atggtcatac aacaatcccg gggcggcatc gggtagagca    60
ggtgtgacgg at    72

<210> SEQ ID NO 567
<211> LENGTH: 72
<212> TYPE: DNA
<213> ORGANISM: Artificial Sequence
<220> FEATURE:
<223> OTHER INFORMATION: chemically synthesized

<400> SEQUENCE: 567
atacgggagc caacaccacc ccatgagtac acgtgaacgg acacagcctc cggcagagca    60
ggtgtgacgg at    72

<210> SEQ ID NO 568
<211> LENGTH: 72
<212> TYPE: DNA
<213> ORGANISM: Artificial Sequence
<220> FEATURE:
<223> OTHER INFORMATION: chemically synthesized

<400> SEQUENCE: 568
atccgtcaca cctgctctgc cggaggctgt gtccgttcac gtgtactcat ggggtggtgt    60
tggctcccgt at    72

<210> SEQ ID NO 569
<211> LENGTH: 72
<212> TYPE: DNA
<213> ORGANISM: Artificial Sequence
<220> FEATURE:
<223> OTHER INFORMATION: chemically synthesized

<400> SEQUENCE: 569
atccgtcaca cctgctctta accattcatt tcttttgtgg tatgaccgtt cgcctggtgt    60
tggctcccgt at    72

<210> SEQ ID NO 570
<211> LENGTH: 72
<212> TYPE: DNA
<213> ORGANISM: Artificial Sequence
<220> FEATURE:
<223> OTHER INFORMATION: chemically synthesized

<400> SEQUENCE: 570
atacgggagc caacaccagg cgaacggtca taccacaaaa gaaatgaatg gttaagagca    60
ggtgtgacgg at    72

<210> SEQ ID NO 571
<211> LENGTH: 58
<212> TYPE: DNA
<213> ORGANISM: Artificial Sequence
<220> FEATURE:
<223> OTHER INFORMATION: chemically synthesized

<400> SEQUENCE: 571

```
atccgtcaca cctgctctgg ggctctttttc gttaaccagg tggtgttggc tcccgtat       58
```

<210> SEQ ID NO 572
<211> LENGTH: 58
<212> TYPE: DNA
<213> ORGANISM: Artificial Sequence
<220> FEATURE:
<223> OTHER INFORMATION: chemically synthesized

<400> SEQUENCE: 572

```
atacgggagc caacaccacc tggttaacga aaagagcccc agagcaggtg tgacggat        58
```

<210> SEQ ID NO 573
<211> LENGTH: 72
<212> TYPE: DNA
<213> ORGANISM: Artificial Sequence
<220> FEATURE:
<223> OTHER INFORMATION: chemically synthesized

<400> SEQUENCE: 573

```
atacgggagc caacaccagg cgaccaagtt tgaatcacca caatcgtgac ggtgagagca      60
ggtgtgacgg at                                                         72
```

<210> SEQ ID NO 574
<211> LENGTH: 72
<212> TYPE: DNA
<213> ORGANISM: Artificial Sequence
<220> FEATURE:
<223> OTHER INFORMATION: chemically synthesized

<400> SEQUENCE: 574

```
atccgtcaca cctgctctca ccgtcacgat tgtggtgatt caaacttggt cgcctggtgt      60
tggctcccgt at                                                         72
```

<210> SEQ ID NO 575
<211> LENGTH: 72
<212> TYPE: DNA
<213> ORGANISM: Artificial Sequence
<220> FEATURE:
<223> OTHER INFORMATION: chemically synthesized

<400> SEQUENCE: 575

```
atacgggagc caacaccacc atcacatctt ggcccggtac cctggatact agccagagca      60
ggtgtgacgg at                                                         72
```

<210> SEQ ID NO 576
<211> LENGTH: 72
<212> TYPE: DNA
<213> ORGANISM: Artificial Sequence
<220> FEATURE:
<223> OTHER INFORMATION: chemically synthesized

<400> SEQUENCE: 576

```
atccgtcaca cctgctctgg ctagtatcca gggtaccggg ccaagatgtg atggtggtgt      60
tggctcccgt at                                                         72
```

<210> SEQ ID NO 577
<211> LENGTH: 72
<212> TYPE: DNA
<213> ORGANISM: Artificial Sequence
<220> FEATURE:
<223> OTHER INFORMATION: chemically synthesized

<400> SEQUENCE: 577

```
atacgggagc caacaccagc actagctcgg gtaacgggga cattagagtt tgccagagca    60
ggtgtgacgg at                                                       72

<210> SEQ ID NO 578
<211> LENGTH: 72
<212> TYPE: DNA
<213> ORGANISM: Artificial Sequence
<220> FEATURE:
<223> OTHER INFORMATION: chemically synthesized

<400> SEQUENCE: 578
atccgtcaca cctgctctgg caaactctaa tgtccccgtt acccgagcta gtgctggtgt    60
tggctcccgt at                                                       72

<210> SEQ ID NO 579
<211> LENGTH: 72
<212> TYPE: DNA
<213> ORGANISM: Artificial Sequence
<220> FEATURE:
<223> OTHER INFORMATION: chemically synthesized

<400> SEQUENCE: 579
atacgggagc caacaccaaa gcccaccgcg cccagatcta caagacttcc aactagagca    60
ggtgtgacgg at                                                       72

<210> SEQ ID NO 580
<211> LENGTH: 72
<212> TYPE: DNA
<213> ORGANISM: Artificial Sequence
<220> FEATURE:
<223> OTHER INFORMATION: chemically synthesized

<400> SEQUENCE: 580
atccgtcaca cctgctctag ttggaagtct tgtagatctg ggcgcggtgg gctttggtgt    60
tggctcccgt at                                                       72

<210> SEQ ID NO 581
<211> LENGTH: 72
<212> TYPE: DNA
<213> ORGANISM: Artificial Sequence
<220> FEATURE:
<223> OTHER INFORMATION: chemically synthesized

<400> SEQUENCE: 581
atacgggagc caacaccatc tttgtcactc tggattaggt taatccactg aaacagagca    60
ggtgtgacgg at                                                       72

<210> SEQ ID NO 582
<211> LENGTH: 72
<212> TYPE: DNA
<213> ORGANISM: Artificial Sequence
<220> FEATURE:
<223> OTHER INFORMATION: chemically synthesized

<400> SEQUENCE: 582
atccgtcaca cctgctctgt ttcagtggat taacctaatc cagagtgaca aagatggtgt    60
tggctcccgt at                                                       72

<210> SEQ ID NO 583
<211> LENGTH: 72
<212> TYPE: DNA
```

<213> ORGANISM: Artificial Sequence
<220> FEATURE:
<223> OTHER INFORMATION: chemically synthesized

<400> SEQUENCE: 583
atacgggagc caacaccacg aacccgggat tctagcaatt gtcccctcg agcgagagca      60 ggtgtgacgg at                                                         72

<210> SEQ ID NO 584
<211> LENGTH: 72
<212> TYPE: DNA
<213> ORGANISM: Artificial Sequence
<220> FEATURE:
<223> OTHER INFORMATION: chemically synthesized

<400> SEQUENCE: 584
atccgtcaca cctgctctcg ctcgagggg acaattgcta gaatcccggg ttcgtggtgt       60
tggctcccgt at                                                         72

<210> SEQ ID NO 585
<211> LENGTH: 72
<212> TYPE: DNA
<213> ORGANISM: Artificial Sequence
<220> FEATURE:
<223> OTHER INFORMATION: chemically synthesized

<400> SEQUENCE: 585
atacgggagc caacaccaat gattaataga acccctatg acctggccgc tgggagagca      60
ggtgtgacgg at                                                         72

<210> SEQ ID NO 586
<211> LENGTH: 72
<212> TYPE: DNA
<213> ORGANISM: Artificial Sequence
<220> FEATURE:
<223> OTHER INFORMATION: chemically synthesized

<400> SEQUENCE: 586
atccgtcaca cctgctctcc cagcggccag gtcatagggg gttctattaa tcattggtgt      60
tggctcccgt at                                                         72

<210> SEQ ID NO 587
<211> LENGTH: 72
<212> TYPE: DNA
<213> ORGANISM: Artificial Sequence
<220> FEATURE:
<223> OTHER INFORMATION: chemically synthesized

<400> SEQUENCE: 587
atacgggagc caacaccatg gtcggatagc atgtccatgt tgtcgggttt aacaagagca      60
ggtgtgacgg at                                                         72

<210> SEQ ID NO 588
<211> LENGTH: 72
<212> TYPE: DNA
<213> ORGANISM: Artificial Sequence
<220> FEATURE:
<223> OTHER INFORMATION: chemically synthesized

<400> SEQUENCE: 588
atccgtcaca cctgctcttg ttaaacccga caacatggac atgctatccg accatggtgt      60
tggctcccgt at                                                         72

<210> SEQ ID NO 589
<211> LENGTH: 72
<212> TYPE: DNA
<213> ORGANISM: Artificial Sequence
<220> FEATURE:
<223> OTHER INFORMATION: chemically synthesized

<400> SEQUENCE: 589
atacgggagc caacaccagg ggaatcttgc ttgcgtagcg acgcataatg acgtagagca    60
ggtgtgacgg at    72

<210> SEQ ID NO 590
<211> LENGTH: 72
<212> TYPE: DNA
<213> ORGANISM: Artificial Sequence
<220> FEATURE:
<223> OTHER INFORMATION: chemically synthesized

<400> SEQUENCE: 590
atccgtcaca cctgctctac gtcattatgc gtcgctacgc aagcaagatt cccctggtgt    60
tggctcccgt at    72

<210> SEQ ID NO 591
<211> LENGTH: 72
<212> TYPE: DNA
<213> ORGANISM: Artificial Sequence
<220> FEATURE:
<223> OTHER INFORMATION: chemically synthesized

<400> SEQUENCE: 591
atacgggagc caacaccatg aagtggacaa atgtgcgttc ccctgacgta ccggagagca    60
ggtgtgacgg at    72

<210> SEQ ID NO 592
<211> LENGTH: 71
<212> TYPE: DNA
<213> ORGANISM: Artificial Sequence
<220> FEATURE:
<223> OTHER INFORMATION: chemically synthesized

<400> SEQUENCE: 592
atccgtcaca cctgctctcc ggtacgtcag gggaacgcac atttgtccac ttcatggtgt    60
tggctcccgt a    71

<210> SEQ ID NO 593
<211> LENGTH: 72
<212> TYPE: DNA
<213> ORGANISM: Artificial Sequence
<220> FEATURE:
<223> OTHER INFORMATION: chemically synthesized

<400> SEQUENCE: 593
atacgggagc caacaccacc atttagtgtt agactaagtg atatcgagtc gaggagagca    60
ggtgtgacgg at    72

<210> SEQ ID NO 594
<211> LENGTH: 72
<212> TYPE: DNA
<213> ORGANISM: Artificial Sequence
<220> FEATURE:
<223> OTHER INFORMATION: chemically synthesized

<400> SEQUENCE: 594
atccgtcaca cctgctctcc tcgactcgat atcacttagt ctaacactaa atggtggtgt    60
tggctcccgt at    72

<210> SEQ ID NO 595
<211> LENGTH: 72
<212> TYPE: DNA
<213> ORGANISM: Artificial Sequence
<220> FEATURE:
<223> OTHER INFORMATION: chemically synthesized

<400> SEQUENCE: 595
atacgggagc caacaccact tccactttt cgcctaattg cctgttgcat ggtaagagca    60
ggtgtgacgg at    72

<210> SEQ ID NO 596
<211> LENGTH: 72
<212> TYPE: DNA
<213> ORGANISM: Artificial Sequence
<220> FEATURE:
<223> OTHER INFORMATION: chemically synthesized

<400> SEQUENCE: 596
atccgtcaca cctgctctta ccatgcaaca ggcaattagg cgaaaaagtg aagtggtgt    60 tggctcccgt at    72

<210> SEQ ID NO 597
<211> LENGTH: 72
<212> TYPE: DNA
<213> ORGANISM: Artificial Sequence
<220> FEATURE:
<223> OTHER INFORMATION: chemically synthesized

<400> SEQUENCE: 597
atacgggagc caacaccagg cgatgtccta aagtctttaa ggcgaatata gttgagagca    60
ggtgtgacgg at    72

<210> SEQ ID NO 598
<211> LENGTH: 72
<212> TYPE: DNA
<213> ORGANISM: Artificial Sequence
<220> FEATURE:
<223> OTHER INFORMATION: chemically synthesized

<400> SEQUENCE: 598
atccgtcaca cctgctctca actatattcg ccttaaagac tttaggacat cgcctggtgt    60
tggctcccgt at    72

<210> SEQ ID NO 599
<211> LENGTH: 72
<212> TYPE: DNA
<213> ORGANISM: Artificial Sequence
<220> FEATURE:
<223> OTHER INFORMATION: chemically synthesized

<400> SEQUENCE: 599
atacgggagc caacaccacc cccccctccg tgggccgctc ccctcggccg ggccagagca    60
ggtgtgacgg at    72

<210> SEQ ID NO 600
<211> LENGTH: 72

```
<212> TYPE: DNA
<213> ORGANISM: Artificial Sequence
<220> FEATURE:
<223> OTHER INFORMATION: chemically synthesized

<400> SEQUENCE: 600
atccgtcaca cctgctctgg cccggccgag gggagcggcc cacggagggg ggggtggtgt    60
tggctcccgt at                                                        72

<210> SEQ ID NO 601
<211> LENGTH: 72
<212> TYPE: DNA
<213> ORGANISM: Artificial Sequence
<220> FEATURE:
<223> OTHER INFORMATION: chemically synthesized

<400> SEQUENCE: 601
atacgggagc caacaccatc ccgtgaagca acgacaatac aagacgagcg aaggagagca    60
ggtgtgacgg at                                                        72

<210> SEQ ID NO 602
<211> LENGTH: 72
<212> TYPE: DNA
<213> ORGANISM: Artificial Sequence
<220> FEATURE:
<223> OTHER INFORMATION: chemically synthesized

<400> SEQUENCE: 602
atccgtcaca cctgctctcc ttcgctcgtc ttgtattgtc gttgcttcac gggatggtgt    60
tggctcccgt at                                                        72

<210> SEQ ID NO 603
<211> LENGTH: 72
<212> TYPE: DNA
<213> ORGANISM: Artificial Sequence
<220> FEATURE:
<223> OTHER INFORMATION: chemically synthesized

<400> SEQUENCE: 603
atacgggagc caacaccacg cgacttcttc aacagataca gagcgcttgg ggccagagca    60
ggtgtgacgg at                                                        72

<210> SEQ ID NO 604
<211> LENGTH: 72
<212> TYPE: DNA
<213> ORGANISM: Artificial Sequence
<220> FEATURE:
<223> OTHER INFORMATION: chemically synthesized

<400> SEQUENCE: 604
atccgtcaca cctgctctgg ccccaagcgc tctgtatctg ttgaagaagt cgcgtggtgt    60
tggctcccgt at                                                        72

<210> SEQ ID NO 605
<211> LENGTH: 72
<212> TYPE: DNA
<213> ORGANISM: Artificial Sequence
<220> FEATURE:
<223> OTHER INFORMATION: chemically synthesized

<400> SEQUENCE: 605
atacgggagc caacaccagg aaatggtacc taagaaatga gaactttgac gcacagagca    60
```

```
ggtgtgacgg at                                                       72

<210> SEQ ID NO 606
<211> LENGTH: 72
<212> TYPE: DNA
<213> ORGANISM: Artificial Sequence
<220> FEATURE:
<223> OTHER INFORMATION: chemically synthesized

<400> SEQUENCE: 606
atccgtcaca cctgctctgt gcgtcaaagt tctcatttct taggtaccat ttcctggtgt   60
tggctcccgt at                                                       72

<210> SEQ ID NO 607
<211> LENGTH: 72
<212> TYPE: DNA
<213> ORGANISM: Artificial Sequence
<220> FEATURE:
<223> OTHER INFORMATION: chemically synthesized

<400> SEQUENCE: 607
atacgggagc caacaccatt aaagttaatc ttacacgttt ccgacttcca tttgagagca   60
ggtgtgacgg at                                                       72

<210> SEQ ID NO 608
<211> LENGTH: 72
<212> TYPE: DNA
<213> ORGANISM: Artificial Sequence
<220> FEATURE:
<223> OTHER INFORMATION: chemically synthesized

<400> SEQUENCE: 608
atccgtcaca cctgctctca aatggaagtc ggaaacgtgt aagattaact ttaatggtgt   60
tggctcccgt at                                                       72

<210> SEQ ID NO 609
<211> LENGTH: 72
<212> TYPE: DNA
<213> ORGANISM: Artificial Sequence
<220> FEATURE:
<223> OTHER INFORMATION: chemically synthesized

<400> SEQUENCE: 609
atacgggagc caacaccaag gagtccgtct acgttttacg agctaaggcc tttgagagca   60
ggtgtgacgg at                                                       72

<210> SEQ ID NO 610
<211> LENGTH: 72
<212> TYPE: DNA
<213> ORGANISM: Artificial Sequence
<220> FEATURE:
<223> OTHER INFORMATION: chemically synthesized

<400> SEQUENCE: 610
atccgtcaca cctgctctca aaggccttag ctcgtaaaac gtagacggac tccttggtgt   60
tggctcccgt at                                                       72

<210> SEQ ID NO 611
<211> LENGTH: 72
<212> TYPE: DNA
<213> ORGANISM: Artificial Sequence
<220> FEATURE:
<223> OTHER INFORMATION: chemically synthesized
```

<400> SEQUENCE: 611
atacgggagc caacaccata atgaagcgat gtagcgagtt tttgaaaggg acacagagca    60
ggtgtgacgg at    72

<210> SEQ ID NO 612
<211> LENGTH: 72
<212> TYPE: DNA
<213> ORGANISM: Artificial Sequence
<220> FEATURE:
<223> OTHER INFORMATION: chemically synthesized

<400> SEQUENCE: 612
atccgtcaca cctgctctgt gtccctttca aaaactcgct acatcgcttc attatggtgt    60
tggctcccgt at    72

<210> SEQ ID NO 613
<211> LENGTH: 72
<212> TYPE: DNA
<213> ORGANISM: Artificial Sequence
<220> FEATURE:
<223> OTHER INFORMATION: chemically synthesized

<400> SEQUENCE: 613
atacgggagc caacaccatt tagtccatag cttcagcgct tccacctcct taacagagca    60
ggtgtgacgg at    72

<210> SEQ ID NO 614
<211> LENGTH: 72
<212> TYPE: DNA
<213> ORGANISM: Artificial Sequence
<220> FEATURE:
<223> OTHER INFORMATION: chemically synthesized

<400> SEQUENCE: 614
atccgtcaca cctgctctgt taaggaggtg gaagcgctga agctatggac taaatggtgt    60
tggctcccgt at    72

<210> SEQ ID NO 615
<211> LENGTH: 72
<212> TYPE: DNA
<213> ORGANISM: Artificial Sequence
<220> FEATURE:
<223> OTHER INFORMATION: chemically synthesized

<400> SEQUENCE: 615
atacgggagc caacaccacc cgtttttgat ctaatgagga tacaatattc gtctagagca    60
ggtgtgacgg at    72

<210> SEQ ID NO 616
<211> LENGTH: 72
<212> TYPE: DNA
<213> ORGANISM: Artificial Sequence
<220> FEATURE:
<223> OTHER INFORMATION: chemically synthesized

<400> SEQUENCE: 616
atccgtcaca cctgctctag acgaatattg tatcctcatt agatcaaaaa cgggtggtgt    60
tggctcccgt at    72

<210> SEQ ID NO 617

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 617
atacgggagc caacaccacc gggtccccgt gatctaggac aacacggcgg ttggagagca      60
ggtgtgacgg at                                                         72

<210> SEQ ID NO 618
<211> LENGTH: 72
<212> TYPE: DNA
<213> ORGANISM: Artificial Sequence
<220> FEATURE:
<223> OTHER INFORMATION: chemically synthesized

<400> SEQUENCE: 618
atccgtcaca cctgctctcc aaccgccgtg ttgtcctaga tcacggggac ccggtggtgt      60
tggctcccgt at                                                         72

<210> SEQ ID NO 619
<211> LENGTH: 72
<212> TYPE: DNA
<213> ORGANISM: Artificial Sequence
<220> FEATURE:
<223> OTHER INFORMATION: chemically synthesized

<400> SEQUENCE: 619
atacgggagc caacaccagt tcaggcatac atgatgtggg ttcttattcc gtgcagagca      60
ggtgtgacgg at                                                         72

<210> SEQ ID NO 620
<211> LENGTH: 72
<212> TYPE: DNA
<213> ORGANISM: Artificial Sequence
<220> FEATURE:
<223> OTHER INFORMATION: chemically synthesized

<400> SEQUENCE: 620
atccgtcaca cctgctctgc acggaataag aacccacatc atgtatgcct gaactggtgt      60
tggctcccgt at                                                         72

<210> SEQ ID NO 621
<211> LENGTH: 72
<212> TYPE: DNA
<213> ORGANISM: Artificial Sequence
<220> FEATURE:
<223> OTHER INFORMATION: chemically synthesized

<400> SEQUENCE: 621
atacgggagc caacaccagg cagcccggtc ccggactaac aaccgcggta cccaagagca      60
ggtgtgacgg at                                                         72

<210> SEQ ID NO 622
<211> LENGTH: 72
<212> TYPE: DNA
<213> ORGANISM: Artificial Sequence
<220> FEATURE:
<223> OTHER INFORMATION: chemically synthesized

<400> SEQUENCE: 622
atccgtcaca cctgctcttg ggtaccgcgg ttgttagtcc gggaccgggc tgcctggtgt      60
```
tggctcccgt at                                                          72

<210> SEQ ID NO 623
<211> LENGTH: 72
<212> TYPE: DNA
<213> ORGANISM: Artificial Sequence
<220> FEATURE:
<223> OTHER INFORMATION: chemically synthesized

<400> SEQUENCE: 623
atacgggagc caacaccatt cagggctttt gtgtatgcac tccagctatc agacagagca      60
ggtgtgacgg at                                                          72

<210> SEQ ID NO 624
<211> LENGTH: 72
<212> TYPE: DNA
<213> ORGANISM: Artificial Sequence
<220> FEATURE:
<223> OTHER INFORMATION: chemically synthesized

<400> SEQUENCE: 624
atccgtcaca cctgctctgt ctgatagctg gagtgcatac acaaaagccc tgaatggtgt      60
tggctcccgt at                                                          72

<210> SEQ ID NO 625
<211> LENGTH: 72
<212> TYPE: DNA
<213> ORGANISM: Artificial Sequence
<220> FEATURE:
<223> OTHER INFORMATION: chemically synthesized

<400> SEQUENCE: 625
atacgggagc caacaccaag ggacggcagg ttcgcagctg cgtcatcttt cttcagagca      60
ggtgtgacgg at                                                          72

<210> SEQ ID NO 626
<211> LENGTH: 72
<212> TYPE: DNA
<213> ORGANISM: Artificial Sequence
<220> FEATURE:
<223> OTHER INFORMATION: chemically synthesized

<400> SEQUENCE: 626
atccgtcaca cctgctctga agaaagatga cgcagctgcg aacctgccgt cccttggtgt      60
tggctcccgt at                                                          72

<210> SEQ ID NO 627
<211> LENGTH: 71
<212> TYPE: DNA
<213> ORGANISM: Artificial Sequence
<220> FEATURE:
<223> OTHER INFORMATION: chemically synthesized

<400> SEQUENCE: 627
atacgggagc caacaccacg aggacttaga cttgtccgac atcacagtgt gcgagagcag      60
gtgtgacgga t                                                           71

<210> SEQ ID NO 628
<211> LENGTH: 71
<212> TYPE: DNA
<213> ORGANISM: Artificial Sequence
<220> FEATURE:

<223> OTHER INFORMATION: chemically synthesized

<400> SEQUENCE: 628
atccgtcaca cctgctctcg cacactgtga tgtcggacaa gtctaagtcc tcgtggtgtt    60
ggctcccgta t    71

<210> SEQ ID NO 629
<211> LENGTH: 72
<212> TYPE: DNA
<213> ORGANISM: Artificial Sequence
<220> FEATURE:
<223> OTHER INFORMATION: chemically synthesized

<400> SEQUENCE: 629
atacgggagc caacaccact tccctgtcct tccctcagtg aggcctgtct cctcagagca    60
ggtgtgacgg at    72

<210> SEQ ID NO 630
<211> LENGTH: 72
<212> TYPE: DNA
<213> ORGANISM: Artificial Sequence
<220> FEATURE:
<223> OTHER INFORMATION: chemically synthesized

<400> SEQUENCE: 630
atccgtcaca cctgctctga ggagacaggc ctcactgagg aaggacagg gaagtggtgt    60 tggctcccgt at    72

<210> SEQ ID NO 631
<211> LENGTH: 72
<212> TYPE: DNA
<213> ORGANISM: Artificial Sequence
<220> FEATURE:
<223> OTHER INFORMATION: chemically synthesized

<400> SEQUENCE: 631
atacgggagc caacaccagg agatgttcgt gtaatagggg gttacacccg gtcgagagca    60
ggtgtgacgg at    72

<210> SEQ ID NO 632
<211> LENGTH: 72
<212> TYPE: DNA
<213> ORGANISM: Artificial Sequence
<220> FEATURE:
<223> OTHER INFORMATION: chemically synthesized

<400> SEQUENCE: 632
atccgtcaca cctgctctcg accgggtgta accccctatt acacgaacat ctcctggtgt    60
tggctcccgt at    72

<210> SEQ ID NO 633
<211> LENGTH: 72
<212> TYPE: DNA
<213> ORGANISM: Artificial Sequence
<220> FEATURE:
<223> OTHER INFORMATION: chemically synthesized

<400> SEQUENCE: 633
atacgggagc caacaccatc gctcaagttc ttcattactc ctatcgcttc cgctagagca    60
ggtgtgacgg at    72

<210> SEQ ID NO 634
<211> LENGTH: 72
<212> TYPE: DNA
<213> ORGANISM: Artificial Sequence
<220> FEATURE:
<223> OTHER INFORMATION: chemically synthesized

<400> SEQUENCE: 634
atccgtcaca cctgctctag cggaagcgat aggagtaatg aagaacttga gcgatggtgt    60
tggctcccgt at                                                        72

<210> SEQ ID NO 635
<211> LENGTH: 72
<212> TYPE: DNA
<213> ORGANISM: Artificial Sequence
<220> FEATURE:
<223> OTHER INFORMATION: chemically synthesized

<400> SEQUENCE: 635
atacgggagc caacaccatt ctactcccag gtatgtctct gggccccccc ggccagagca    60
ggtgtgacgg at                                                        72

<210> SEQ ID NO 636
<211> LENGTH: 72
<212> TYPE: DNA
<213> ORGANISM: Artificial Sequence
<220> FEATURE:
<223> OTHER INFORMATION: chemically synthesized

<400> SEQUENCE: 636
atccgtcaca cctgctctgg ccggggggc ccagagacat acctgggagt agaatggtgt     60
tggctcccgt at                                                        72

<210> SEQ ID NO 637
<211> LENGTH: 72
<212> TYPE: DNA
<213> ORGANISM: Artificial Sequence
<220> FEATURE:
<223> OTHER INFORMATION: chemically synthesized

<400> SEQUENCE: 637
atacgggagc caacaccaac aacatagccc tggcacgaca gtggcatacc aggcagagca    60
ggtgtgacgg at                                                        72

<210> SEQ ID NO 638
<211> LENGTH: 72
<212> TYPE: DNA
<213> ORGANISM: Artificial Sequence
<220> FEATURE:
<223> OTHER INFORMATION: chemically synthesized

<400> SEQUENCE: 638
atccgtcaca cctgctctgc ctggtatgcc actgtcgtgc cagggctatg ttgttggtgt    60
tggctcccgt at                                                        72

<210> SEQ ID NO 639
<211> LENGTH: 72
<212> TYPE: DNA
<213> ORGANISM: Artificial Sequence
<220> FEATURE:
<223> OTHER INFORMATION: chemically synthesized

<400> SEQUENCE: 639

```
atacgggagc caacaccacg taatgatgtg cacctctctc cgactgtttc tcgtagagca    60
ggtgtgacgg at                                                        72

<210> SEQ ID NO 640
<211> LENGTH: 72
<212> TYPE: DNA
<213> ORGANISM: Artificial Sequence
<220> FEATURE:
<223> OTHER INFORMATION: chemically synthesized

<400> SEQUENCE: 640
atccgtcaca cctgctctac gagaaacagt cggagagagg tgcacatcat tacgtggtgt    60
tggctcccgt at                                                        72

<210> SEQ ID NO 641
<211> LENGTH: 72
<212> TYPE: DNA
<213> ORGANISM: Artificial Sequence
<220> FEATURE:
<223> OTHER INFORMATION: chemically synthesized

<400> SEQUENCE: 641
atacgggagc caacaccaca tcttattcgt ccccagtcct ttggtctcct gctcagagca    60
ggtgtgacgg at                                                        72

<210> SEQ ID NO 642
<211> LENGTH: 72
<212> TYPE: DNA
<213> ORGANISM: Artificial Sequence
<220> FEATURE:
<223> OTHER INFORMATION: chemically synthesized

<400> SEQUENCE: 642
atccgtcaca cctgctctga gcaggagacc aaaggactgg ggacgaataa gatgtggtgt    60
tggctcccgt at                                                        72

<210> SEQ ID NO 643
<211> LENGTH: 72
<212> TYPE: DNA
<213> ORGANISM: Artificial Sequence
<220> FEATURE:
<223> OTHER INFORMATION: chemically synthesized

<400> SEQUENCE: 643
atacgggagc caacaccacc tgctgatttc ctataatccg gcccatacct taggagagca    60
ggtgtgacgg at                                                        72

<210> SEQ ID NO 644
<211> LENGTH: 72
<212> TYPE: DNA
<213> ORGANISM: Artificial Sequence
<220> FEATURE:
<223> OTHER INFORMATION: chemically synthesized

<400> SEQUENCE: 644
atccgtcaca cctgctctcc taaggtatgg gccggattat aggaaatcag caggtggtgt    60
tggctcccgt at                                                        72

<210> SEQ ID NO 645
<211> LENGTH: 72
<212> TYPE: DNA
<213> ORGANISM: Artificial Sequence
```

<220> FEATURE:
<223> OTHER INFORMATION: chemically synthesized

<400> SEQUENCE: 645

```
atacgggagc caacaccata agagtcctct aaggtcgctt atttttaacc cctaagagca    60
ggtgtgacgg at                                                        72
```

<210> SEQ ID NO 646
<211> LENGTH: 72
<212> TYPE: DNA
<213> ORGANISM: Artificial Sequence
<220> FEATURE:
<223> OTHER INFORMATION: chemically synthesized

<400> SEQUENCE: 646

```
atccgtcaca cctgctctta ggggttaaaa ataagcgacc ttagaggact cttatggtgt    60
tggctcccgt at                                                        72
```

<210> SEQ ID NO 647
<211> LENGTH: 72
<212> TYPE: DNA
<213> ORGANISM: Artificial Sequence
<220> FEATURE:
<223> OTHER INFORMATION: chemically synthesized

<400> SEQUENCE: 647

```
atacgggagc caacaccatc cccacaccct cgttccgacc gctagaatcc ccgaagagca    60
ggtgtgacgg at                                                        72
```

<210> SEQ ID NO 648
<211> LENGTH: 72
<212> TYPE: DNA
<213> ORGANISM: Artificial Sequence
<220> FEATURE:
<223> OTHER INFORMATION: chemically synthesized

<400> SEQUENCE: 648

```
atccgtcaca cctgctcttc ggggattcta gcggtcggaa cgagggtgtg gggatggtgt    60
tggctcccgt at                                                        72
```

<210> SEQ ID NO 649
<211> LENGTH: 72
<212> TYPE: DNA
<213> ORGANISM: Artificial Sequence
<220> FEATURE:
<223> OTHER INFORMATION: chemically synthesized

<400> SEQUENCE: 649

```
atacgggagc caacaccaca ggataatgcg tgaaattagg actaaaatgt ttgcagagca    60
ggtgtgacgg at                                                        72
```

<210> SEQ ID NO 650
<211> LENGTH: 72
<212> TYPE: DNA
<213> ORGANISM: Artificial Sequence
<220> FEATURE:
<223> OTHER INFORMATION: chemically synthesized

<400> SEQUENCE: 650

```
atccgtcaca cctgctctgc aaacatttta gtcctaattt cacgcattat cctgtggtgt    60
tggctcccgt at                                                        72
```

<210> SEQ ID NO 651
<211> LENGTH: 72
<212> TYPE: DNA
<213> ORGANISM: Artificial Sequence
<220> FEATURE:
<223> OTHER INFORMATION: chemically synthesized

<400> SEQUENCE: 651
atacgggagc caacaccatc tctcttagga tacaaagcca aactgagccc gtgcagagca    60
ggtgtgacgg at                                                       72

<210> SEQ ID NO 652
<211> LENGTH: 72
<212> TYPE: DNA
<213> ORGANISM: Artificial Sequence
<220> FEATURE:
<223> OTHER INFORMATION: chemically synthesized

<400> SEQUENCE: 652
atccgtcaca cctgctctgc acgggctcag tttggctttg tatcctaaga gagatggtgt    60
tggctcccgt at                                                       72

<210> SEQ ID NO 653
<211> LENGTH: 72
<212> TYPE: DNA
<213> ORGANISM: Artificial Sequence
<220> FEATURE:
<223> OTHER INFORMATION: chemically synthesized

<400> SEQUENCE: 653
atacgggagc caacaccact atctagctaa cagacttgag ataaagctac tggcagagca    60
ggtgtgacgg at                                                       72

<210> SEQ ID NO 654
<211> LENGTH: 72
<212> TYPE: DNA
<213> ORGANISM: Artificial Sequence
<220> FEATURE:
<223> OTHER INFORMATION: chemically synthesized

<400> SEQUENCE: 654
atccgtcaca cctgctctgc cagtagcttt atctcaagtc tgttagctag atagtggtgt    60
tggctcccgt at                                                       72

<210> SEQ ID NO 655
<211> LENGTH: 72
<212> TYPE: DNA
<213> ORGANISM: Artificial Sequence
<220> FEATURE:
<223> OTHER INFORMATION: chemically synthesized

<400> SEQUENCE: 655
atacgggagc caacaccaca attctacgca cataaacgca tagttctcat taccagagca    60
ggtgtgacgg at                                                       72

<210> SEQ ID NO 656
<211> LENGTH: 72
<212> TYPE: DNA
<213> ORGANISM: Artificial Sequence
<220> FEATURE:
<223> OTHER INFORMATION: chemically synthesized

<400> SEQUENCE: 656

```
atccgtcaca cctgctctgg taatgagaac tatgcgttta tgtgcgtaga attgtggtgt    60
tggctcccgt at                                                       72

<210> SEQ ID NO 657
<211> LENGTH: 72
<212> TYPE: DNA
<213> ORGANISM: Artificial Sequence
<220> FEATURE:
<223> OTHER INFORMATION: chemically synthesized

<400> SEQUENCE: 657
atacgggagc caacaccata aggccatgga aagtaacatc aaacaggtgg gggtagagca    60
ggtgtgacgg at                                                       72

<210> SEQ ID NO 658
<211> LENGTH: 72
<212> TYPE: DNA
<213> ORGANISM: Artificial Sequence
<220> FEATURE:
<223> OTHER INFORMATION: chemically synthesized

<400> SEQUENCE: 658
atccgtcaca cctgctctac ccccacctgt ttgatgttac tttccatggc cttatggtgt    60
tggctcccgt at                                                       72

<210> SEQ ID NO 659
<211> LENGTH: 72
<212> TYPE: DNA
<213> ORGANISM: Artificial Sequence
<220> FEATURE:
<223> OTHER INFORMATION: chemically synthesized

<400> SEQUENCE: 659
atacgggagc caacaccact acatcggcca actatgtcca cctataccat atccagagca    60
ggtgtgacgg at                                                       72

<210> SEQ ID NO 660
<211> LENGTH: 72
<212> TYPE: DNA
<213> ORGANISM: Artificial Sequence
<220> FEATURE:
<223> OTHER INFORMATION: chemically synthesized

<400> SEQUENCE: 660
atccgtcaca cctgctctgg atatggtata ggtggacata gttggccgat gtagtggtgt    60
tggctcccgt at                                                       72

<210> SEQ ID NO 661
<211> LENGTH: 72
<212> TYPE: DNA
<213> ORGANISM: Artificial Sequence
<220> FEATURE:
<223> OTHER INFORMATION: chemically synthesized

<400> SEQUENCE: 661
atacgggagc caacaccaca gaacagcccc agcgcgtgag acgattttac ctccagagca    60
ggtgtgacgg at                                                       72

<210> SEQ ID NO 662
<211> LENGTH: 72
<212> TYPE: DNA
```

```
<213> ORGANISM: Artificial Sequence
<220> FEATURE:
<223> OTHER INFORMATION: chemically synthesized

<400> SEQUENCE: 662
atccgtcaca cctgctctgg aggtaaaatc gtctcacgcg ctggggctgt tctgtggtgt     60
tggctcccgt at                                                         72

<210> SEQ ID NO 663
<211> LENGTH: 72
<212> TYPE: DNA
<213> ORGANISM: Artificial Sequence
<220> FEATURE:
<223> OTHER INFORMATION: chemically synthesized

<400> SEQUENCE: 663
atacgggagc caacaccata tcatacgatc cttgggcggg gtgagccgct gtgcagagca     60
ggtgtgacgg at                                                         72

<210> SEQ ID NO 664
<211> LENGTH: 72
<212> TYPE: DNA
<213> ORGANISM: Artificial Sequence
<220> FEATURE:
<223> OTHER INFORMATION: chemically synthesized

<400> SEQUENCE: 664
atccgtcaca cctgctctgc acagcggctc accccgccca aggatcgtat gatatggtgt     60
tggctcccgt at                                                         72

<210> SEQ ID NO 665
<211> LENGTH: 72
<212> TYPE: DNA
<213> ORGANISM: Artificial Sequence
<220> FEATURE:
<223> OTHER INFORMATION: chemically synthesized

<400> SEQUENCE: 665
atacgggagc caacaccatg agcactgcac ttccggtccc cccctgtcc acccagagca      60 ggtgtgacgg at                                                         72

<210> SEQ ID NO 666
<211> LENGTH: 72
<212> TYPE: DNA
<213> ORGANISM: Artificial Sequence
<220> FEATURE:
<223> OTHER INFORMATION: chemically synthesized

<400> SEQUENCE: 666
atccgtcaca cctgctctgg gtggacaggg gggggaccgg aagtgcagtg ctcatggtgt     60
tggctcccgt at                                                         72

<210> SEQ ID NO 667
<211> LENGTH: 72
<212> TYPE: DNA
<213> ORGANISM: Artificial Sequence
<220> FEATURE:
<223> OTHER INFORMATION: chemically synthesized

<400> SEQUENCE: 667
atacgggagc caacaccaag tatggcggag tgcgcggacg attaaactca gtgtagagca     60
ggtgtgacgg at                                                         72
```

<210> SEQ ID NO 668
<211> LENGTH: 72
<212> TYPE: DNA
<213> ORGANISM: Artificial Sequence
<220> FEATURE:
<223> OTHER INFORMATION: chemically synthesized

<400> SEQUENCE: 668
atccgtcaca cctgctctac actgagttta atcgtccgcg cactccgcca tacttggtgt    60
tggctcccgt at    72

<210> SEQ ID NO 669
<211> LENGTH: 72
<212> TYPE: DNA
<213> ORGANISM: Artificial Sequence
<220> FEATURE:
<223> OTHER INFORMATION: chemically synthesized

<400> SEQUENCE: 669
atacgggagc caacaccagg agagcacata tagttgacac gaaaacatac aggtagagca    60
ggtgtgacgg at    72

<210> SEQ ID NO 670
<211> LENGTH: 72
<212> TYPE: DNA
<213> ORGANISM: Artificial Sequence
<220> FEATURE:
<223> OTHER INFORMATION: chemically synthesized

<400> SEQUENCE: 670
atccgtcaca cctgctctac ctgtatgttt tcgtgtcaac tatatgtgct ctcctggtgt    60
tggctcccgt at    72

<210> SEQ ID NO 671
<211> LENGTH: 72
<212> TYPE: DNA
<213> ORGANISM: Artificial Sequence
<220> FEATURE:
<223> OTHER INFORMATION: chemically synthesized

<400> SEQUENCE: 671
atacgggagc caacaccata acacacgggg ccagcccatc ctctacagca taccagagca    60
ggtgtgacgg at    72

<210> SEQ ID NO 672
<211> LENGTH: 72
<212> TYPE: DNA
<213> ORGANISM: Artificial Sequence
<220> FEATURE:
<223> OTHER INFORMATION: chemically synthesized

<400> SEQUENCE: 672
atccgtcaca cctgctctgg tatgctgtag aggatgggct ggccccgtgt gttatggtgt    60
tggctcccgt at    72

<210> SEQ ID NO 673
<211> LENGTH: 72
<212> TYPE: DNA
<213> ORGANISM: Artificial Sequence
<220> FEATURE:
<223> OTHER INFORMATION: chemically synthesized

<400> SEQUENCE: 673
atacgggagc caacaccata gggaagcttc aacaaggttg caaacgtagg gtccagagca    60
ggtgtgacgg at    72

<210> SEQ ID NO 674
<211> LENGTH: 72
<212> TYPE: DNA
<213> ORGANISM: Artificial Sequence
<220> FEATURE:
<223> OTHER INFORMATION: chemically synthesized

<400> SEQUENCE: 674
atccgtcaca cctgctctgg accctacgtt tgcaaccttg ttgaagcttc cctatggtgt    60
tggctcccgt at    72

<210> SEQ ID NO 675
<211> LENGTH: 72
<212> TYPE: DNA
<213> ORGANISM: Artificial Sequence
<220> FEATURE:
<223> OTHER INFORMATION: chemically synthesized

<400> SEQUENCE: 675
atacgggagc caacaccact accaacataa tccggtccca accccgcgca ccccagagca    60
ggtgtgacgg at    72

<210> SEQ ID NO 676
<211> LENGTH: 72
<212> TYPE: DNA
<213> ORGANISM: Artificial Sequence
<220> FEATURE:
<223> OTHER INFORMATION: chemically synthesized

<400> SEQUENCE: 676
atccgtcaca cctgctctgg ggtgcgcggg gttgggaccg gattatgttg gtagtggtgt    60
tggctcccgt at    72

<210> SEQ ID NO 677
<211> LENGTH: 72
<212> TYPE: DNA
<213> ORGANISM: Artificial Sequence
<220> FEATURE:
<223> OTHER INFORMATION: chemically synthesized

<400> SEQUENCE: 677
atacgggagc caacaccact aagcgttaaa tgattaagca gcccgttttg ctgtagagca    60
ggtgtgacgg at    72

<210> SEQ ID NO 678
<211> LENGTH: 72
<212> TYPE: DNA
<213> ORGANISM: Artificial Sequence
<220> FEATURE:
<223> OTHER INFORMATION: chemically synthesized

<400> SEQUENCE: 678
atccgtcaca cctgctctac agcaaaacgg gctgcttaat catttaacgc ttagtggtgt    60
tggctcccgt at    72

<210> SEQ ID NO 679
<211> LENGTH: 72

```
<212> TYPE: DNA
<213> ORGANISM: Artificial Sequence
<220> FEATURE:
<223> OTHER INFORMATION: chemically synthesized

<400> SEQUENCE: 679
atacgggagc caacaccaca tagcccgaaa tattagcacc tctagggggg ggccagagca    60
ggtgtgacgg at                                                       72

<210> SEQ ID NO 680
<211> LENGTH: 72
<212> TYPE: DNA
<213> ORGANISM: Artificial Sequence
<220> FEATURE:
<223> OTHER INFORMATION: chemically synthesized

<400> SEQUENCE: 680
atccgtcaca cctgctctgg ccccccccta gaggtgctaa tatttcgggc tatgtggtgt    60
tggctcccgt at                                                       72

<210> SEQ ID NO 681
<211> LENGTH: 72
<212> TYPE: DNA
<213> ORGANISM: Artificial Sequence
<220> FEATURE:
<223> OTHER INFORMATION: chemically synthesized

<400> SEQUENCE: 681
atacgggagc caacaccacg aaaaaacgat taatatcaca agccatatgc aggtagagca    60
ggtgtgacgg at                                                       72

<210> SEQ ID NO 682
<211> LENGTH: 72
<212> TYPE: DNA
<213> ORGANISM: Artificial Sequence
<220> FEATURE:
<223> OTHER INFORMATION: chemically synthesized

<400> SEQUENCE: 682
atccgtcaca cctgctctac ctgcatatgg cttgtgatat taatcgtttt ttcgtggtgt    60
tggctcccgt at                                                       72

<210> SEQ ID NO 683
<211> LENGTH: 72
<212> TYPE: DNA
<213> ORGANISM: Artificial Sequence
<220> FEATURE:
<223> OTHER INFORMATION: chemically synthesized

<400> SEQUENCE: 683
atacgggagc caacaccagg ggacgtggag actatacaaa tgcaacttgt gggcagagca    60
ggtgtgacgg at                                                       72

<210> SEQ ID NO 684
<211> LENGTH: 72
<212> TYPE: DNA
<213> ORGANISM: Artificial Sequence
<220> FEATURE:
<223> OTHER INFORMATION: chemically synthesized

<400> SEQUENCE: 684
atccgtcaca cctgctctgc ccacaagttg catttgtata gtctccacgt cccctggtgt    60
```

```
tggctcccgt at                                                          72

<210> SEQ ID NO 685
<211> LENGTH: 72
<212> TYPE: DNA
<213> ORGANISM: Artificial Sequence
<220> FEATURE:
<223> OTHER INFORMATION: chemically synthesized

<400> SEQUENCE: 685
atacgggagc caacaccaca cactcctttt aataactgct tagataccgg tgccagagca      60
ggtgtgacgg at                                                          72

<210> SEQ ID NO 686
<211> LENGTH: 72
<212> TYPE: DNA
<213> ORGANISM: Artificial Sequence
<220> FEATURE:
<223> OTHER INFORMATION: chemically synthesized

<400> SEQUENCE: 686
atccgtcaca cctgctctgg caccggtatc taagcagtta ttaaaaggag tgtgtggtgt      60
tggctcccgt at                                                          72

<210> SEQ ID NO 687
<211> LENGTH: 72
<212> TYPE: DNA
<213> ORGANISM: Artificial Sequence
<220> FEATURE:
<223> OTHER INFORMATION: chemically synthesized

<400> SEQUENCE: 687
atacgggagc caacaccaag agacatccag atcgaattag gtttatgaca gtgcagagca      60
ggtgtgacgg at                                                          72

<210> SEQ ID NO 688
<211> LENGTH: 72
<212> TYPE: DNA
<213> ORGANISM: Artificial Sequence
<220> FEATURE:
<223> OTHER INFORMATION: chemically synthesized

<400> SEQUENCE: 688
atccgtcaca cctgctctgc actgtcataa acctaattcg atctggatgt ctcttggtgt      60
tggctcccgt at                                                          72

<210> SEQ ID NO 689
<211> LENGTH: 72
<212> TYPE: DNA
<213> ORGANISM: Artificial Sequence
<220> FEATURE:
<223> OTHER INFORMATION: chemically synthesized

<400> SEQUENCE: 689
atacgggagc caacaccagg taaaacaatt agtacaacct gtaatcgacg tggcagagca      60
ggtgtgacgg at                                                          72

<210> SEQ ID NO 690
<211> LENGTH: 72
<212> TYPE: DNA
<213> ORGANISM: Artificial Sequence
<220> FEATURE:
<223> OTHER INFORMATION: chemically synthesized
```

<400> SEQUENCE: 690
atccgtcaca cctgctctgc cacgtcgatt acaggttgta ctaattgttt tacctggtgt    60
tggctcccgt at    72

<210> SEQ ID NO 691
<211> LENGTH: 72
<212> TYPE: DNA
<213> ORGANISM: Artificial Sequence
<220> FEATURE:
<223> OTHER INFORMATION: chemically synthesized

<400> SEQUENCE: 691
atacgggagc caacaccacg gtccttaccc cacactcccg gttatgttgc ccccagagca    60
ggtgtgacgg at    72

<210> SEQ ID NO 692
<211> LENGTH: 72
<212> TYPE: DNA
<213> ORGANISM: Artificial Sequence
<220> FEATURE:
<223> OTHER INFORMATION: chemically synthesized

<400> SEQUENCE: 692
atccgtcaca cctgctctgg gggcaacata accgggagtg tggggtaagg accgtggtgt    60
tggctcccgt at    72

<210> SEQ ID NO 693
<211> LENGTH: 72
<212> TYPE: DNA
<213> ORGANISM: Artificial Sequence
<220> FEATURE:
<223> OTHER INFORMATION: chemically synthesized

<400> SEQUENCE: 693
atacgggagc caacaccatg ccggacttcg cgaaaacaca atctttgcac acccagagca    60
ggtgtgacgg at    72

<210> SEQ ID NO 694
<211> LENGTH: 72
<212> TYPE: DNA
<213> ORGANISM: Artificial Sequence
<220> FEATURE:
<223> OTHER INFORMATION: chemically synthesized

<400> SEQUENCE: 694
atccgtcaca cctgctctgg gtgtgcaaag attgtgtttt cgcgaagtcc ggcatggtgt    60
tggctcccgt at    72

<210> SEQ ID NO 695
<211> LENGTH: 72
<212> TYPE: DNA
<213> ORGANISM: Artificial Sequence
<220> FEATURE:
<223> OTHER INFORMATION: chemically synthesized

<400> SEQUENCE: 695
atacgggagc caacaccact ccacgcgact tgcccgaacc atgtaccctc gtccagagca    60
ggtgtgacgg at    72

<210> SEQ ID NO 696

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 696
atccgtcaca cctgctctgg acgagggtac atggttcggg caagtcgcgt ggagtggtgt    60
tggctcccgt at                                                       72

<210> SEQ ID NO 697
<211> LENGTH: 72
<212> TYPE: DNA
<213> ORGANISM: Artificial Sequence
<220> FEATURE:
<223> OTHER INFORMATION: chemically synthesized

<400> SEQUENCE: 697
atacgggagc caacaccact taaatataca gcgtagcagt gaacaaacat tgccagagca    60
ggtgtgacgg at                                                       72

<210> SEQ ID NO 698
<211> LENGTH: 72
<212> TYPE: DNA
<213> ORGANISM: Artificial Sequence
<220> FEATURE:
<223> OTHER INFORMATION: chemically synthesized

<400> SEQUENCE: 698
atccgtcaca cctgctctgg caatgtttgt tcactgctac gctgtatatt taagtggtgt    60
tggctcccgt at                                                       72

<210> SEQ ID NO 699
<211> LENGTH: 72
<212> TYPE: DNA
<213> ORGANISM: Artificial Sequence
<220> FEATURE:
<223> OTHER INFORMATION: chemically synthesized

<400> SEQUENCE: 699
atacgggagc caacaccacc tctacacccc gaactttgcg tttgctacga tcccagagca    60
ggtgtgacgg at                                                       72

<210> SEQ ID NO 700
<211> LENGTH: 72
<212> TYPE: DNA
<213> ORGANISM: Artificial Sequence
<220> FEATURE:
<223> OTHER INFORMATION: chemically synthesized

<400> SEQUENCE: 700
atccgtcaca cctgctctgg gatcgtagca aacgcaaagt tcggggtgta gaggtggtgt    60
tggctcccgt at                                                       72

<210> SEQ ID NO 701
<211> LENGTH: 72
<212> TYPE: DNA
<213> ORGANISM: Artificial Sequence
<220> FEATURE:
<223> OTHER INFORMATION: chemically synthesized

<400> SEQUENCE: 701
atacgggagc caacaccata cgcgcacgcg gattgaaagg taacgactac atagagagca    60
```
ggtgtgacgg at                                                           72

<210> SEQ ID NO 702
<211> LENGTH: 72
<212> TYPE: DNA
<213> ORGANISM: Artificial Sequence
<220> FEATURE:
<223> OTHER INFORMATION: chemically synthesized

<400> SEQUENCE: 702
atccgtcaca cctgctctct atgtagtcgt tacctttcaa tccgcgtgcg cgtatggtgt      60
tggctcccgt at                                                           72

<210> SEQ ID NO 703
<211> LENGTH: 72
<212> TYPE: DNA
<213> ORGANISM: Artificial Sequence
<220> FEATURE:
<223> OTHER INFORMATION: chemically synthesized

<400> SEQUENCE: 703
atacgggagc caacaccaga caacctatga agccgcttct gtcattgatt atgcagagca      60
ggtgtgacgg at                                                           72

<210> SEQ ID NO 704
<211> LENGTH: 72
<212> TYPE: DNA
<213> ORGANISM: Artificial Sequence
<220> FEATURE:
<223> OTHER INFORMATION: chemically synthesized

<400> SEQUENCE: 704
atccgtcaca cctgctctgc ataatcaatg acagaagcgg cttcataggt tgtctggtgt      60
tggctcccgt at                                                           72

<210> SEQ ID NO 705
<211> LENGTH: 72
<212> TYPE: DNA
<213> ORGANISM: Artificial Sequence
<220> FEATURE:
<223> OTHER INFORMATION: chemically synthesized

<400> SEQUENCE: 705
atacgggagc caacaccata atcaataagg gatgcaaagg gatgatagcc acgcagagca      60
ggtgtgacgg at                                                           72

<210> SEQ ID NO 706
<211> LENGTH: 72
<212> TYPE: DNA
<213> ORGANISM: Artificial Sequence
<220> FEATURE:
<223> OTHER INFORMATION: chemically synthesized

<400> SEQUENCE: 706
atccgtcaca cctgctctgc gtggctatca tccctttgca tcccttattg attatggtgt      60
tggctcccgt at                                                           72

<210> SEQ ID NO 707
<211> LENGTH: 72
<212> TYPE: DNA
<213> ORGANISM: Artificial Sequence
<220> FEATURE:

```
<223> OTHER INFORMATION: chemically synthesized

<400> SEQUENCE: 707
atacgggagc caacaccagg accaaccaat agagtcaaga tgacagcgac gccgagagca      60
ggtgtgacgg at                                                         72

<210> SEQ ID NO 708
<211> LENGTH: 72
<212> TYPE: DNA
<213> ORGANISM: Artificial Sequence
<220> FEATURE:
<223> OTHER INFORMATION: chemically synthesized

<400> SEQUENCE: 708
atccgtcaca cctgctctcg gcgtcgctgt catcttgact ctattggttg gtcctggtgt      60
tggctcccgt at                                                         72

<210> SEQ ID NO 709
<211> LENGTH: 72
<212> TYPE: DNA
<213> ORGANISM: Artificial Sequence
<220> FEATURE:
<223> OTHER INFORMATION: chemically synthesized

<400> SEQUENCE: 709
atacgggagc caacaccata gataattata tcactggaag agcaatcgtg gtccagagca      60
ggtgtgacgg at                                                         72

<210> SEQ ID NO 710
<211> LENGTH: 72
<212> TYPE: DNA
<213> ORGANISM: Artificial Sequence
<220> FEATURE:
<223> OTHER INFORMATION: chemically synthesized

<400> SEQUENCE: 710
atccgtcaca cctgctctgg accacgattg ctcttccagt gatataatta tctatggtgt      60
tggctcccgt at                                                         72

<210> SEQ ID NO 711
<211> LENGTH: 72
<212> TYPE: DNA
<213> ORGANISM: Artificial Sequence
<220> FEATURE:
<223> OTHER INFORMATION: chemically synthesized

<400> SEQUENCE: 711
atacgggagc caacaccacg acactagtac gactacccac gcacgtgcgc ccccagagca      60
ggtgtgacgg at                                                         72

<210> SEQ ID NO 712
<211> LENGTH: 72
<212> TYPE: DNA
<213> ORGANISM: Artificial Sequence
<220> FEATURE:
<223> OTHER INFORMATION: chemically synthesized

<400> SEQUENCE: 712
atccgtcaca cctgctctgg gggcgcacgt gcgtgggtag tcgtactagt gtcgtggtgt      60
tggctcccgt at                                                         72
```

<210> SEQ ID NO 713
<211> LENGTH: 72
<212> TYPE: DNA
<213> ORGANISM: Artificial Sequence
<220> FEATURE:
<223> OTHER INFORMATION: chemically synthesized

<400> SEQUENCE: 713
atacgggagc caacaccagg ccaaaaccta attttagtgg cgaagatcta tgggagagca    60
ggtgtgacgg at    72

<210> SEQ ID NO 714
<211> LENGTH: 72
<212> TYPE: DNA
<213> ORGANISM: Artificial Sequence
<220> FEATURE:
<223> OTHER INFORMATION: chemically synthesized

<400> SEQUENCE: 714
atccgtcaca cctgctctcc catagatctt cgccactaaa attaggtttt ggcctggtgt    60
tggctcccgt at    72

<210> SEQ ID NO 715
<211> LENGTH: 72
<212> TYPE: DNA
<213> ORGANISM: Artificial Sequence
<220> FEATURE:
<223> OTHER INFORMATION: chemically synthesized

<400> SEQUENCE: 715
atacgggagc caacaccagc gccaaacgcc ctcaccccgc accaacttcc gcccagagca    60
ggtgtgacgg at    72

<210> SEQ ID NO 716
<211> LENGTH: 72
<212> TYPE: DNA
<213> ORGANISM: Artificial Sequence
<220> FEATURE:
<223> OTHER INFORMATION: chemically synthesized

<400> SEQUENCE: 716
atccgtcaca cctgctctgg gcggaagttg gtgcggggtg agggcgtttg gcgctggtgt    60
tggctcccgt at    72

<210> SEQ ID NO 717
<211> LENGTH: 72
<212> TYPE: DNA
<213> ORGANISM: Artificial Sequence
<220> FEATURE:
<223> OTHER INFORMATION: chemically synthesized

<400> SEQUENCE: 717
atacgggagc caacaccata cacagccata agctgccatt cgatatagtg ccccagagca    60
ggtgtgacgg at    72

<210> SEQ ID NO 718
<211> LENGTH: 72
<212> TYPE: DNA
<213> ORGANISM: Artificial Sequence
<220> FEATURE:
<223> OTHER INFORMATION: chemically synthesized

<400> SEQUENCE: 718
atccgtcaca cctgctctgg ggcactatat cgaatggcag cttatggctg tgtatggtgt    60
tggctcccgt at                                                        72

<210> SEQ ID NO 719
<211> LENGTH: 72
<212> TYPE: DNA
<213> ORGANISM: Artificial Sequence
<220> FEATURE:
<223> OTHER INFORMATION: chemically synthesized

<400> SEQUENCE: 719
atacgggagc caacaccaca acagcaaaat gattgtatgg acttgctaat caccagagca    60
ggtgtgacgg at                                                        72

<210> SEQ ID NO 720
<211> LENGTH: 72
<212> TYPE: DNA
<213> ORGANISM: Artificial Sequence
<220> FEATURE:
<223> OTHER INFORMATION: chemically synthesized

<400> SEQUENCE: 720
atccgtcaca cctgctctgg tgattagcaa gtccatacaa tcattttgct gttgtggtgt    60
tggctcccgt at                                                        72

<210> SEQ ID NO 721
<211> LENGTH: 72
<212> TYPE: DNA
<213> ORGANISM: Artificial Sequence
<220> FEATURE:
<223> OTHER INFORMATION: chemically synthesized

<400> SEQUENCE: 721
atacgggagc caacaccacc acttttgaa aataaattca atctgctaga tgggagagca     60
ggtgtgacgg at                                                        72

<210> SEQ ID NO 722
<211> LENGTH: 72
<212> TYPE: DNA
<213> ORGANISM: Artificial Sequence
<220> FEATURE:
<223> OTHER INFORMATION: chemically synthesized

<400> SEQUENCE: 722
atccgtcaca cctgctctcc catctagcag attgaattta ttttcaaaaa gtggtggtgt    60
tggctcccgt at                                                        72

<210> SEQ ID NO 723
<211> LENGTH: 72
<212> TYPE: DNA
<213> ORGANISM: Artificial Sequence
<220> FEATURE:
<223> OTHER INFORMATION: chemically synthesized

<400> SEQUENCE: 723
atacgggagc caacaccata cgcctaatat tttaaatgcg cacgtacagg ttcgagagca    60
ggtgtgacgg at                                                        72

<210> SEQ ID NO 724
<211> LENGTH: 72
<212> TYPE: DNA
<213> ORGANISM: Artificial Sequence

```
<220> FEATURE:
<223> OTHER INFORMATION: chemically synthesized

<400> SEQUENCE: 724
atccgtcaca cctgctctcg aacctgtacg tgcgcattta aaatattagg cgtatggtgt     60
tggctcccgt at                                                        72

<210> SEQ ID NO 725
<211> LENGTH: 70
<212> TYPE: DNA
<213> ORGANISM: Artificial Sequence
<220> FEATURE:
<223> OTHER INFORMATION: chemically synthesized

<400> SEQUENCE: 725
atacgggagc caaccccagc cagaaactct gtgaactgcc ccccccccg ccagagcagg       60 tgtgacggat                                                           70

<210> SEQ ID NO 726
<211> LENGTH: 70
<212> TYPE: DNA
<213> ORGANISM: Artificial Sequence
<220> FEATURE:
<223> OTHER INFORMATION: chemically synthesized

<400> SEQUENCE: 726
atccgtcaca cctgctctgg cggggggggg ggcagttcac agagtttctg gctggggttg     60
gctcccgtat                                                           70

<210> SEQ ID NO 727
<211> LENGTH: 72
<212> TYPE: DNA
<213> ORGANISM: Artificial Sequence
<220> FEATURE:
<223> OTHER INFORMATION: chemically synthesized

<400> SEQUENCE: 727
atacgggagc caacaccaca tcctagccac taacagaaac tatatcccct ttgcagagca     60
ggtgtgacgg at                                                        72

<210> SEQ ID NO 728
<211> LENGTH: 72
<212> TYPE: DNA
<213> ORGANISM: Artificial Sequence
<220> FEATURE:
<223> OTHER INFORMATION: chemically synthesized

<400> SEQUENCE: 728
atccgtcaca cctgctctgc aaagggata tagtttctgt tagtggctag gatgtggtgt      60
tggctcccgt at                                                        72

<210> SEQ ID NO 729
<211> LENGTH: 72
<212> TYPE: DNA
<213> ORGANISM: Artificial Sequence
<220> FEATURE:
<223> OTHER INFORMATION: chemically synthesized

<400> SEQUENCE: 729
atacgggagc caaccccatc acatactatg cctgaaccca ttaagtttgt cgcgagagca     60
ggtgtgacgg at                                                        72
```

```
<210> SEQ ID NO 730
<211> LENGTH: 72
<212> TYPE: DNA
<213> ORGANISM: Artificial Sequence
<220> FEATURE:
<223> OTHER INFORMATION: chemically synthesized

<400> SEQUENCE: 730
atccgtcaca cctgctctcg cgacaaactt aatgggttca ggcatagtat gtgatggtgt    60
tggctcccgt at                                                        72

<210> SEQ ID NO 731
<211> LENGTH: 72
<212> TYPE: DNA
<213> ORGANISM: Artificial Sequence
<220> FEATURE:
<223> OTHER INFORMATION: chemically synthesized

<400> SEQUENCE: 731
atacgggagc caacaccatg aaatttatct agttgtcatt atatgaggga tcccagagca    60
ggtgtgacgg at                                                        72

<210> SEQ ID NO 732
<211> LENGTH: 72
<212> TYPE: DNA
<213> ORGANISM: Artificial Sequence
<220> FEATURE:
<223> OTHER INFORMATION: chemically synthesized

<400> SEQUENCE: 732
atccgtcaca cctgctctgg gatccctcat ataatgacaa ctagataaat ttcatggtgt    60
tggctcccgt at                                                        72

<210> SEQ ID NO 733
<211> LENGTH: 72
<212> TYPE: DNA
<213> ORGANISM: Artificial Sequence
<220> FEATURE:
<223> OTHER INFORMATION: chemically synthesized

<400> SEQUENCE: 733
atacgggagc caacaccagg ccggccccgc ggggcgactt gtactgtaaa gcttagagca    60
ggtgtgacgg at                                                        72

<210> SEQ ID NO 734
<211> LENGTH: 72
<212> TYPE: DNA
<213> ORGANISM: Artificial Sequence
<220> FEATURE:
<223> OTHER INFORMATION: chemically synthesized

<400> SEQUENCE: 734
atccgtcaca cctgctctaa gctttacagt acaagtcgcc ccgcggggcc ggcctggtgt    60
tggctcccgt at                                                        72

<210> SEQ ID NO 735
<211> LENGTH: 72
<212> TYPE: DNA
<213> ORGANISM: Artificial Sequence
<220> FEATURE:
<223> OTHER INFORMATION: chemically synthesized

<400> SEQUENCE: 735
```

```
atacgggagc caacaccacc ccttgccata ttggctgcgg ctccacggcg gtcgagagca    60
ggtgtgacgg at                                                        72

<210> SEQ ID NO 736
<211> LENGTH: 72
<212> TYPE: DNA
<213> ORGANISM: Artificial Sequence
<220> FEATURE:
<223> OTHER INFORMATION: chemically synthesized

<400> SEQUENCE: 736
atccgtcaca cctgctctcg accgccgtgg agccgcagcc aatatggcaa ggggtggtgt    60
tggctcccgt at                                                        72

<210> SEQ ID NO 737
<211> LENGTH: 71
<212> TYPE: DNA
<213> ORGANISM: Artificial Sequence
<220> FEATURE:
<223> OTHER INFORMATION: chemically synthesized

<400> SEQUENCE: 737
atacgggagc caacaccagc ccactcacaa ccctcctctt tcatttgcct accagagcag    60
gtgtgacgga t                                                         71

<210> SEQ ID NO 738
<211> LENGTH: 71
<212> TYPE: DNA
<213> ORGANISM: Artificial Sequence
<220> FEATURE:
<223> OTHER INFORMATION: chemically synthesized

<400> SEQUENCE: 738
atccgtcaca cctgctctgg taggcaaatg aaagaggagg ttgtgagtg ggctggtgtt     60 ggctcccgta t                                                         71

<210> SEQ ID NO 739
<211> LENGTH: 72
<212> TYPE: DNA
<213> ORGANISM: Artificial Sequence
<220> FEATURE:
<223> OTHER INFORMATION: chemically synthesized

<400> SEQUENCE: 739
atacgggagc caacaccacg ctacggggcg gctaaaggcc gacgaataaa ctctagagca    60
ggtgtgacgg at                                                        72

<210> SEQ ID NO 740
<211> LENGTH: 72
<212> TYPE: DNA
<213> ORGANISM: Artificial Sequence
<220> FEATURE:
<223> OTHER INFORMATION: chemically synthesized

<400> SEQUENCE: 740
atccgtcaca cctgctctag agtttattcg tcggccttta gccgccccgt agcgtggtgt    60
tggctcccgt at                                                        72

<210> SEQ ID NO 741
<211> LENGTH: 72
<212> TYPE: DNA
```

```
<213> ORGANISM: Artificial Sequence
<220> FEATURE:
<223> OTHER INFORMATION: chemically synthesized

<400> SEQUENCE: 741
atacgggagc caacaccatc atagaccgta ataattgaat ctaagaaacc gtgtagagca    60
ggtgtgacgg at                                                        72

<210> SEQ ID NO 742
<211> LENGTH: 72
<212> TYPE: DNA
<213> ORGANISM: Artificial Sequence
<220> FEATURE:
<223> OTHER INFORMATION: chemically synthesized

<400> SEQUENCE: 742
atccgtcaca cctgctctac acggtttctt agattcaatt attacggtct atgatggtgt    60
tggctcccgt at                                                        72

<210> SEQ ID NO 743
<211> LENGTH: 72
<212> TYPE: DNA
<213> ORGANISM: Artificial Sequence
<220> FEATURE:
<223> OTHER INFORMATION: chemically synthesized

<400> SEQUENCE: 743
atacgggagc caacaccata cctataaatg gaaaatatgg gatcctagta acgcagagca    60
ggtgtgacgg at                                                        72

<210> SEQ ID NO 744
<211> LENGTH: 72
<212> TYPE: DNA
<213> ORGANISM: Artificial Sequence
<220> FEATURE:
<223> OTHER INFORMATION: chemically synthesized

<400> SEQUENCE: 744
atccgtcaca cctgctctgc gttactagga tcccatattt tccatttata ggtatggtgt    60
tggctcccgt at                                                        72

<210> SEQ ID NO 745
<211> LENGTH: 72
<212> TYPE: DNA
<213> ORGANISM: Artificial Sequence
<220> FEATURE:
<223> OTHER INFORMATION: chemically synthesized

<400> SEQUENCE: 745
atacgggagc caacaccacc cactctcccc ccgctcccgc tcccccgctc cgcgagagca    60
ggtgtgacgg at                                                        72

<210> SEQ ID NO 746
<211> LENGTH: 72
<212> TYPE: DNA
<213> ORGANISM: Artificial Sequence
<220> FEATURE:
<223> OTHER INFORMATION: chemically synthesized

<400> SEQUENCE: 746
atccgtcaca cctgctctcg cggagcgggg gagcgggagc gggggagag tgggtggtgt     60 tggctcccgt at                                                        72
```

<210> SEQ ID NO 747
<211> LENGTH: 72
<212> TYPE: DNA
<213> ORGANISM: Artificial Sequence
<220> FEATURE:
<223> OTHER INFORMATION: chemically synthesized

<400> SEQUENCE: 747
atacgggagc caacaccata cctgaccccc cgccgcaatc ctagtctacc tccgagagca    60
ggtgtgacgg at    72

<210> SEQ ID NO 748
<211> LENGTH: 72
<212> TYPE: DNA
<213> ORGANISM: Artificial Sequence
<220> FEATURE:
<223> OTHER INFORMATION: chemically synthesized

<400> SEQUENCE: 748
atccgtcaca cctgctctcg gaggtagact aggattgcgg cggggggtca ggtatggtgt    60
tggctcccgt at    72

<210> SEQ ID NO 749
<211> LENGTH: 72
<212> TYPE: DNA
<213> ORGANISM: Artificial Sequence
<220> FEATURE:
<223> OTHER INFORMATION: chemically synthesized

<400> SEQUENCE: 749
atacgggagc caacaccacc cgtggccttc acccagccag ggaccccgtc tctgagagca    60
ggtgtgacgg at    72

<210> SEQ ID NO 750
<211> LENGTH: 72
<212> TYPE: DNA
<213> ORGANISM: Artificial Sequence
<220> FEATURE:
<223> OTHER INFORMATION: chemically synthesized

<400> SEQUENCE: 750
atccgtcaca cctgctctca gagacggggt ccctggctgg gtgaaggcca cggtggtgt    60 tggctcccgt at    72

<210> SEQ ID NO 751
<211> LENGTH: 72
<212> TYPE: DNA
<213> ORGANISM: Artificial Sequence
<220> FEATURE:
<223> OTHER INFORMATION: chemically synthesized

<400> SEQUENCE: 751
atacgggagc caacaccaca cacagagcgc catggactca gtcagatgtg atgtagagca    60
ggtgtgacgg at    72

<210> SEQ ID NO 752
<211> LENGTH: 72
<212> TYPE: DNA
<213> ORGANISM: Artificial Sequence
<220> FEATURE:
<223> OTHER INFORMATION: chemically synthesized

```
<400> SEQUENCE: 752
atccgtcaca cctgctctac atcacatctg actgagtcca tggcgctctg tgtgtggtgt    60
tggctcccgt at                                                        72

<210> SEQ ID NO 753
<211> LENGTH: 72
<212> TYPE: DNA
<213> ORGANISM: Artificial Sequence
<220> FEATURE:
<223> OTHER INFORMATION: chemically synthesized

<400> SEQUENCE: 753
atacgggagc caacaccatc cctcttagga tacaaagcca aactgagccc gtgcagagca    60
ggtgtgacgg at                                                        72

<210> SEQ ID NO 754
<211> LENGTH: 72
<212> TYPE: DNA
<213> ORGANISM: Artificial Sequence
<220> FEATURE:
<223> OTHER INFORMATION: chemically synthesized

<400> SEQUENCE: 754
atccgtcaca cctgctctgc acgggctcag tttggctttg tatcctaaga gggatggtgt    60
tggctcccgt at                                                        72

<210> SEQ ID NO 755
<211> LENGTH: 72
<212> TYPE: DNA
<213> ORGANISM: Artificial Sequence
<220> FEATURE:
<223> OTHER INFORMATION: chemically synthesized

<400> SEQUENCE: 755
atacgggagc caacaccatc agcagctctg cttacaggcg cccgtaatcc ggacagagca    60
ggtgtgacgg at                                                        72

<210> SEQ ID NO 756
<211> LENGTH: 72
<212> TYPE: DNA
<213> ORGANISM: Artificial Sequence
<220> FEATURE:
<223> OTHER INFORMATION: chemically synthesized

<400> SEQUENCE: 756
atccgtcaca cctgctctgt ccggattacg ggcgcctgta agcagagctg ctgatggtgt    60
tggctcccgt at                                                        72

<210> SEQ ID NO 757
<211> LENGTH: 73
<212> TYPE: DNA
<213> ORGANISM: Artificial Sequence
<220> FEATURE:
<223> OTHER INFORMATION: chemically synthesized

<400> SEQUENCE: 757
atacgggagc caacaccatg tgccaggtag agcccgataa tccttacagt acgctagagc    60
aggtgtgacg gat                                                       73

<210> SEQ ID NO 758
<211> LENGTH: 73
```

```
<212> TYPE: DNA
<213> ORGANISM: Artificial Sequence
<220> FEATURE:
<223> OTHER INFORMATION: chemically synthesized

<400> SEQUENCE: 758
atccgtcaca cctgctctag cgtactgtaa ggattatcgg gctctacctg gcacatggtg    60
ttggctcccg tat                                                       73

<210> SEQ ID NO 759
<211> LENGTH: 72
<212> TYPE: DNA
<213> ORGANISM: Artificial Sequence
<220> FEATURE:
<223> OTHER INFORMATION: chemically synthesized

<400> SEQUENCE: 759
atacgggagc caacaccacg tacataccct ccatctaacc gccgtcccca gtcaagagca    60
ggtgtgacgg at                                                        72

<210> SEQ ID NO 760
<211> LENGTH: 72
<212> TYPE: DNA
<213> ORGANISM: Artificial Sequence
<220> FEATURE:
<223> OTHER INFORMATION: chemically synthesized

<400> SEQUENCE: 760
atccgtcaca cctgctcttg actggggacg gcggttagat ggagggtatg tacgtggtgt    60
tggctcccgt at                                                        72

<210> SEQ ID NO 761
<211> LENGTH: 71
<212> TYPE: DNA
<213> ORGANISM: Artificial Sequence
<220> FEATURE:
<223> OTHER INFORMATION: chemically synthesized

<400> SEQUENCE: 761
atacgggagc caacaccacg aggacctaga cttgtccgac atcacagtgt gcgagagcag    60
gtgtgacgga t                                                         71

<210> SEQ ID NO 762
<211> LENGTH: 71
<212> TYPE: DNA
<213> ORGANISM: Artificial Sequence
<220> FEATURE:
<223> OTHER INFORMATION: chemically synthesized

<400> SEQUENCE: 762
atccgtcaca cctgctctcg cacactgtga tgtcggacaa gtctaggtcc tcgtggtgtt    60
ggctcccgta t                                                         71

<210> SEQ ID NO 763
<211> LENGTH: 72
<212> TYPE: DNA
<213> ORGANISM: Artificial Sequence
<220> FEATURE:
<223> OTHER INFORMATION: chemically synthesized

<400> SEQUENCE: 763
atacgggagc caacaccacg tattgcgcga tccgttgcca actcttatcg ggccagagca    60
```

```
ggtgtgacgg at                                                             72

<210> SEQ ID NO 764
<211> LENGTH: 72
<212> TYPE: DNA
<213> ORGANISM: Artificial Sequence
<220> FEATURE:
<223> OTHER INFORMATION: chemically synthesized

<400> SEQUENCE: 764
atccgtcaca cctgctctgg cccgataaga gttggcaacg gatcgcgcaa tacgtggtgt         60
tggctcccgt at                                                             72

<210> SEQ ID NO 765
<211> LENGTH: 72
<212> TYPE: DNA
<213> ORGANISM: Artificial Sequence
<220> FEATURE:
<223> OTHER INFORMATION: chemically synthesized

<400> SEQUENCE: 765
atacgggagc caacaccacc cgcaccctga tcccttccac ccgtcccctc ccgcagagca         60
ggtgtgacgg at                                                             72

<210> SEQ ID NO 766
<211> LENGTH: 72
<212> TYPE: DNA
<213> ORGANISM: Artificial Sequence
<220> FEATURE:
<223> OTHER INFORMATION: chemically synthesized

<400> SEQUENCE: 766
atccgtcaca cctgctctgc gggaggggac gggtggaagg gatcagggtg cgggtggtgt         60
tggctcccgt at                                                             72

<210> SEQ ID NO 767
<211> LENGTH: 72
<212> TYPE: DNA
<213> ORGANISM: Artificial Sequence
<220> FEATURE:
<223> OTHER INFORMATION: chemically synthesized

<400> SEQUENCE: 767
atacgggagc caacaccatg aaatggtccg atgctgtatt atccctccgc agcgagagca         60
ggtgtgacgg at                                                             72

<210> SEQ ID NO 768
<211> LENGTH: 72
<212> TYPE: DNA
<213> ORGANISM: Artificial Sequence
<220> FEATURE:
<223> OTHER INFORMATION: chemically synthesized

<400> SEQUENCE: 768
atccgtcaca cctgctctcg ctgcggaggg ataatacagc atcggaccat ttcatggtgt         60
tggctcccgt at                                                             72

<210> SEQ ID NO 769
<211> LENGTH: 72
<212> TYPE: DNA
<213> ORGANISM: Artificial Sequence
<220> FEATURE:
<223> OTHER INFORMATION: chemically synthesized
```

<400> SEQUENCE: 769
atacgggagc caacaccata cgggatagcg ggtaggatcc cgtgccatca cgtcagagca    60
ggtgtgacgg at    72

<210> SEQ ID NO 770
<211> LENGTH: 72
<212> TYPE: DNA
<213> ORGANISM: Artificial Sequence
<220> FEATURE:
<223> OTHER INFORMATION: chemically synthesized

<400> SEQUENCE: 770
atccgtcaca cctgctctga cgtgatggca cgggatccta cccgctatcc cgtatggtgt    60
tggctcccgt at    72

<210> SEQ ID NO 771
<211> LENGTH: 72
<212> TYPE: DNA
<213> ORGANISM: Artificial Sequence
<220> FEATURE:
<223> OTHER INFORMATION: chemically synthesized

<400> SEQUENCE: 771
atacgggagc caacaccagg ttgacatctg taaagttccg tactggtggc taggagagca    60
ggtgtgacgg at    72

<210> SEQ ID NO 772
<211> LENGTH: 72
<212> TYPE: DNA
<213> ORGANISM: Artificial Sequence
<220> FEATURE:
<223> OTHER INFORMATION: chemically synthesized

<400> SEQUENCE: 772
atccgtcaca cctgctctcc tagccaccag tacggaactt tacagatgtc aacctggtgt    60
tggctcccgt at    72

<210> SEQ ID NO 773
<211> LENGTH: 72
<212> TYPE: DNA
<213> ORGANISM: Artificial Sequence
<220> FEATURE:
<223> OTHER INFORMATION: chemically synthesized

<400> SEQUENCE: 773
atacgggagc caacaccacc cccataccgt acactgtcca tcccgccttt ctccagagca    60
ggtgtgacgg at    72

<210> SEQ ID NO 774
<211> LENGTH: 72
<212> TYPE: DNA
<213> ORGANISM: Artificial Sequence
<220> FEATURE:
<223> OTHER INFORMATION: chemically synthesized

<400> SEQUENCE: 774
atccgtcaca cctgctctgg agaaaggcgg gatggacagt gtacggtatg ggggtggtgt    60
tggctcccgt at    72

<210> SEQ ID NO 775

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 775
atacgggagc caacaccacg gagtgcccag tgcaagttta cgccagatgt gcgcagagca     60
ggtgtgacgg at                                                         72

<210> SEQ ID NO 776
<211> LENGTH: 72
<212> TYPE: DNA
<213> ORGANISM: Artificial Sequence
<220> FEATURE:
<223> OTHER INFORMATION: chemically synthesized

<400> SEQUENCE: 776
atccgtcaca cctgctctgc gcacatctgg cgtaaacttg cactgggcac tccgtggtgt     60
tggctcccgt at                                                         72

<210> SEQ ID NO 777
<211> LENGTH: 72
<212> TYPE: DNA
<213> ORGANISM: Artificial Sequence
<220> FEATURE:
<223> OTHER INFORMATION: chemically synthesized

<400> SEQUENCE: 777
atacgggagc caacaccacc tgtcatccat gctccgcttc tcccggtacc gtccagagca     60
ggtgtgacgg at                                                         72

<210> SEQ ID NO 778
<211> LENGTH: 72
<212> TYPE: DNA
<213> ORGANISM: Artificial Sequence
<220> FEATURE:
<223> OTHER INFORMATION: chemically synthesized

<400> SEQUENCE: 778
atccgtcaca cctgctctgg acggtaccgg agaagcgga gcatggatga caggtggtgt      60
tggctcccgt at                                                         72

<210> SEQ ID NO 779
<211> LENGTH: 72
<212> TYPE: DNA
<213> ORGANISM: Artificial Sequence
<220> FEATURE:
<223> OTHER INFORMATION: chemically synthesized

<400> SEQUENCE: 779
atacgggagc caacaccacc cgtggccttc acccagccag gggccccgtc tctgagagca     60
ggtgtgacgg at                                                         72

<210> SEQ ID NO 780
<211> LENGTH: 72
<212> TYPE: DNA
<213> ORGANISM: Artificial Sequence
<220> FEATURE:
<223> OTHER INFORMATION: chemically synthesized

<400> SEQUENCE: 780
atccgtcaca cctgctctca gagacgggc ccctggctgg gtgaaggcca cgggtggtgt      60
```
tggctcccgt at                                                          72

<210> SEQ ID NO 781
<211> LENGTH: 72
<212> TYPE: DNA
<213> ORGANISM: Artificial Sequence
<220> FEATURE:
<223> OTHER INFORMATION: chemically synthesized

<400> SEQUENCE: 781
atacgggagc caacaccagg agcgtccccc gtcccccgca cccaacggcg agccagagca      60
ggtgtgacgg at                                                          72

<210> SEQ ID NO 782
<211> LENGTH: 72
<212> TYPE: DNA
<213> ORGANISM: Artificial Sequence
<220> FEATURE:
<223> OTHER INFORMATION: chemically synthesized

<400> SEQUENCE: 782
atccgtcaca cctgctctgg ctcgccgttg ggtgcggggg acggggacg ctcctggtgt       60 tggctcccgt at                                                          72

<210> SEQ ID NO 783
<211> LENGTH: 72
<212> TYPE: DNA
<213> ORGANISM: Artificial Sequence
<220> FEATURE:
<223> OTHER INFORMATION: chemically synthesized

<400> SEQUENCE: 783
atacgggagc caacaccaat agagcgtcta cccgtatccc gccttggatt ccacagagca      60
ggtgtgacgg at                                                          72

<210> SEQ ID NO 784
<211> LENGTH: 72
<212> TYPE: DNA
<213> ORGANISM: Artificial Sequence
<220> FEATURE:
<223> OTHER INFORMATION: chemically synthesized

<400> SEQUENCE: 784
atccgtcaca cctgctctgt ggaatccaag gcgggatacg ggtagacgct ctattggtgt      60
tggctcccgt at                                                          72

<210> SEQ ID NO 785
<211> LENGTH: 72
<212> TYPE: DNA
<213> ORGANISM: Artificial Sequence
<220> FEATURE:
<223> OTHER INFORMATION: chemically synthesized

<400> SEQUENCE: 785
atacgggagc caacaccact gtctacgtgg gtctcacagt ccgtgctatt tgccagagca      60
ggtgtgacgg at                                                          72

<210> SEQ ID NO 786
<211> LENGTH: 72
<212> TYPE: DNA
<213> ORGANISM: Artificial Sequence
<220> FEATURE:

<223> OTHER INFORMATION: chemically synthesized

<400> SEQUENCE: 786
atccgtcaca cctgctctgg caaatagcac ggactgtgag acccacgtag acagtggtgt    60
tggctcccgt at                                                        72

<210> SEQ ID NO 787
<211> LENGTH: 72
<212> TYPE: DNA
<213> ORGANISM: Artificial Sequence
<220> FEATURE:
<223> OTHER INFORMATION: chemically synthesized

<400> SEQUENCE: 787
atacgggagc caacaccata caccacagca cacaagattc aggctagaga cgggagagca    60
ggtgtgacgg at                                                        72

<210> SEQ ID NO 788
<211> LENGTH: 72
<212> TYPE: DNA
<213> ORGANISM: Artificial Sequence
<220> FEATURE:
<223> OTHER INFORMATION: chemically synthesized

<400> SEQUENCE: 788
atccgtcaca cctgctctcc cgtctctagc ctgaatcttg tgtgctgtgg tgtatggtgt    60
tggctcccgt at                                                        72

<210> SEQ ID NO 789
<211> LENGTH: 72
<212> TYPE: DNA
<213> ORGANISM: Artificial Sequence
<220> FEATURE:
<223> OTHER INFORMATION: chemically synthesized

<400> SEQUENCE: 789
atacgggagc caacaccaca tgcgcacctt tccctcctcc aactcgaatc cgccagagca    60
ggtgtgacgg at                                                        72

<210> SEQ ID NO 790
<211> LENGTH: 72
<212> TYPE: DNA
<213> ORGANISM: Artificial Sequence
<220> FEATURE:
<223> OTHER INFORMATION: chemically synthesized

<400> SEQUENCE: 790
atccgtcaca cctgctctgg cggattcgag ttggaggagg gaaaggtgcg catgtggtgt    60
tggctcccgt at                                                        72

<210> SEQ ID NO 791
<211> LENGTH: 72
<212> TYPE: DNA
<213> ORGANISM: Artificial Sequence
<220> FEATURE:
<223> OTHER INFORMATION: chemically synthesized

<400> SEQUENCE: 791
atacgggagc caacaccatg gggggtacgg agagtgatac ttggaggttg gccagagca    60 ggtgtgacgg at                                                        72

-continued

```
<210> SEQ ID NO 792
<211> LENGTH: 72
<212> TYPE: DNA
<213> ORGANISM: Artificial Sequence
<220> FEATURE:
<223> OTHER INFORMATION: chemically synthesized

<400> SEQUENCE: 792
atccgtcaca cctgctctgg cccaacctcc aagtatcact ctccgtaccc cccatggtgt      60
tggctcccgt at                                                         72

<210> SEQ ID NO 793
<211> LENGTH: 72
<212> TYPE: DNA
<213> ORGANISM: Artificial Sequence
<220> FEATURE:
<223> OTHER INFORMATION: chemically synthesized

<400> SEQUENCE: 793
atacgggagc caacaccact ggaattcaaa aatactacac tatattgctg tggcagagca      60
ggtgtgacgg at                                                         72

<210> SEQ ID NO 794
<211> LENGTH: 72
<212> TYPE: DNA
<213> ORGANISM: Artificial Sequence
<220> FEATURE:
<223> OTHER INFORMATION: chemically synthesized

<400> SEQUENCE: 794
atccgtcaca cctgctctgc cacagcaata tagtgtagta tttttgaatt ccagtggtgt      60
tggctcccgt at                                                         72

<210> SEQ ID NO 795
<211> LENGTH: 72
<212> TYPE: DNA
<213> ORGANISM: Artificial Sequence
<220> FEATURE:
<223> OTHER INFORMATION: chemically synthesized

<400> SEQUENCE: 795
atacgggagc caacaccagg ccagggtaac ttaaaacagc attatctatt gtacagagca      60
ggtgtgacgg at                                                         72

<210> SEQ ID NO 796
<211> LENGTH: 72
<212> TYPE: DNA
<213> ORGANISM: Artificial Sequence
<220> FEATURE:
<223> OTHER INFORMATION: chemically synthesized

<400> SEQUENCE: 796
atccgtcaca cctgctctgt acaatagata atgctgtttt aagttaccct ggcctggtgt      60
tggctcccgt at                                                         72

<210> SEQ ID NO 797
<211> LENGTH: 72
<212> TYPE: DNA
<213> ORGANISM: Artificial Sequence
<220> FEATURE:
<223> OTHER INFORMATION: chemically synthesized

<400> SEQUENCE: 797
```

```
atacgggagc caacaccacc acattccggc cgaacgactt ataagtaaca attcagagca      60
ggtgtgacgg at                                                         72

<210> SEQ ID NO 798
<211> LENGTH: 72
<212> TYPE: DNA
<213> ORGANISM: Artificial Sequence
<220> FEATURE:
<223> OTHER INFORMATION: chemically synthesized

<400> SEQUENCE: 798
atccgtcaca cctgctctga attgttactt ataagtcgtt cggccggaat gtggtggtgt      60
tggctcccgt at                                                         72

<210> SEQ ID NO 799
<211> LENGTH: 72
<212> TYPE: DNA
<213> ORGANISM: Artificial Sequence
<220> FEATURE:
<223> OTHER INFORMATION: chemically synthesized

<400> SEQUENCE: 799
atacgggagc caacaccaca caaagaagta gaatgtatgg gaatgaattg acatagagca      60
ggtgtgacgg at                                                         72

<210> SEQ ID NO 800
<211> LENGTH: 71
<212> TYPE: DNA
<213> ORGANISM: Artificial Sequence
<220> FEATURE:
<223> OTHER INFORMATION: chemically synthesized

<400> SEQUENCE: 800
atccgtcaca cctgctctat gtcaattcat tcccatacat tctacttctt tgtgtggtgt      60
tggctcccgt a                                                          71

<210> SEQ ID NO 801
<211> LENGTH: 72
<212> TYPE: DNA
<213> ORGANISM: Artificial Sequence
<220> FEATURE:
<223> OTHER INFORMATION: chemically synthesized

<400> SEQUENCE: 801
atacgggagc caacaccact gggacacttc aacctgtaac atactcattc ggtgagagca      60
ggtgtgacgg at                                                         72

<210> SEQ ID NO 802
<211> LENGTH: 72
<212> TYPE: DNA
<213> ORGANISM: Artificial Sequence
<220> FEATURE:
<223> OTHER INFORMATION: chemically synthesized

<400> SEQUENCE: 802
atccgtcaca cctgctctca ccgaatgagt atgttacagg ttgaagtgtc ccagtggtgt      60
tggctcccgt at                                                         72

<210> SEQ ID NO 803
<211> LENGTH: 72
<212> TYPE: DNA
<213> ORGANISM: Artificial Sequence
```

```
<220> FEATURE:
<223> OTHER INFORMATION: chemically synthesized

<400> SEQUENCE: 803
atacgggagc caacaccacc cctctctcgt acgccgcccg gggtccacct acccagagca    60
ggtgtgacgg at                                                        72

<210> SEQ ID NO 804
<211> LENGTH: 72
<212> TYPE: DNA
<213> ORGANISM: Artificial Sequence
<220> FEATURE:
<223> OTHER INFORMATION: chemically synthesized

<400> SEQUENCE: 804
atccgtcaca cctgctctgg gtaggtggac cccgggcggc gtacgagaga ggggtggtgt    60
tggctcccgt at                                                        72

<210> SEQ ID NO 805
<211> LENGTH: 72
<212> TYPE: DNA
<213> ORGANISM: Artificial Sequence
<220> FEATURE:
<223> OTHER INFORMATION: chemically synthesized

<400> SEQUENCE: 805
atacgggagc caacaccatg ggggatgtga tgatgagcag gctatggtct ctccagagca    60
ggtgtgacgg at                                                        72

<210> SEQ ID NO 806
<211> LENGTH: 72
<212> TYPE: DNA
<213> ORGANISM: Artificial Sequence
<220> FEATURE:
<223> OTHER INFORMATION: chemically synthesized

<400> SEQUENCE: 806
atccgtcaca cctgctctgg agagaccata gcctgctcat catcacatcc cccatggtgt    60
tggctcccgt at                                                        72

<210> SEQ ID NO 807
<211> LENGTH: 72
<212> TYPE: DNA
<213> ORGANISM: Artificial Sequence
<220> FEATURE:
<223> OTHER INFORMATION: chemically synthesized

<400> SEQUENCE: 807
atacgggagc caacaccacg gcatgcaact atttaataac attgttgctt gggtagagca    60
ggtgtgacgg at                                                        72

<210> SEQ ID NO 808
<211> LENGTH: 72
<212> TYPE: DNA
<213> ORGANISM: Artificial Sequence
<220> FEATURE:
<223> OTHER INFORMATION: chemically synthesized

<400> SEQUENCE: 808
atccgtcaca cctgctctac ccaagcaaca atgttattaa atagttgcat gccgtggtgt    60
tggctcccgt at                                                        72
```

<210> SEQ ID NO 809
<211> LENGTH: 72
<212> TYPE: DNA
<213> ORGANISM: Artificial Sequence
<220> FEATURE:
<223> OTHER INFORMATION: chemically synthesized

<400> SEQUENCE: 809
atacgggagc caacaccatt agaaacatca gtagacaaac taaggtttta cgggagagca    60
ggtgtgacgg at    72

<210> SEQ ID NO 810
<211> LENGTH: 72
<212> TYPE: DNA
<213> ORGANISM: Artificial Sequence
<220> FEATURE:
<223> OTHER INFORMATION: chemically synthesized

<400> SEQUENCE: 810
atccgtcaca cctgctctcc cgtaaaacct tagtttgtct actgatgttt ctaatggtgt    60
tggctcccgt at    72

<210> SEQ ID NO 811
<211> LENGTH: 72
<212> TYPE: DNA
<213> ORGANISM: Artificial Sequence
<220> FEATURE:
<223> OTHER INFORMATION: chemically synthesized

<400> SEQUENCE: 811
atacgggagc caacaccata cctatattgt taactagaag tggggtcagg ggagagagca    60
ggtgtgacgg at    72

<210> SEQ ID NO 812
<211> LENGTH: 72
<212> TYPE: DNA
<213> ORGANISM: Artificial Sequence
<220> FEATURE:
<223> OTHER INFORMATION: chemically synthesized

<400> SEQUENCE: 812
atccgtcaca cctgctctct cccctgaccc cacttctagt taacaatata ggtatggtgt    60
tggctcccgt at    72

<210> SEQ ID NO 813
<211> LENGTH: 72
<212> TYPE: DNA
<213> ORGANISM: Artificial Sequence
<220> FEATURE:
<223> OTHER INFORMATION: chemically synthesized

<400> SEQUENCE: 813
atacgggagc caacaccatg gtcgaccctc cttgaggact aatctctaca ctcgagagca    60
ggtgtgacgg at    72

<210> SEQ ID NO 814
<211> LENGTH: 72
<212> TYPE: DNA
<213> ORGANISM: Artificial Sequence
<220> FEATURE:
<223> OTHER INFORMATION: chemically synthesized

<400> SEQUENCE: 814

```
atccgtcaca cctgctctcg agtgtagaga ttagtcctca aggagggtcg accatggtgt    60
tggctcccgt at                                                        72

<210> SEQ ID NO 815
<211> LENGTH: 72
<212> TYPE: DNA
<213> ORGANISM: Artificial Sequence
<220> FEATURE:
<223> OTHER INFORMATION: chemically synthesized

<400> SEQUENCE: 815
atacgggagc caacaccata cgaagaccgt taggatgcca cccaagttaa ttacagagca    60
ggtgtgacgg at                                                        72

<210> SEQ ID NO 816
<211> LENGTH: 72
<212> TYPE: DNA
<213> ORGANISM: Artificial Sequence
<220> FEATURE:
<223> OTHER INFORMATION: chemically synthesized

<400> SEQUENCE: 816
atccgtcaca cctgctctgt aattaacttg ggtggcatcc taacggtctt cgtatggtgt    60
tggctcccgt at                                                        72

<210> SEQ ID NO 817
<211> LENGTH: 72
<212> TYPE: DNA
<213> ORGANISM: Artificial Sequence
<220> FEATURE:
<223> OTHER INFORMATION: chemically synthesized

<400> SEQUENCE: 817
atacgggagc caacaccatg ctaatataaa catctatcca tattaaccat gtccagagca    60
ggtgtgacgg at                                                        72

<210> SEQ ID NO 818
<211> LENGTH: 72
<212> TYPE: DNA
<213> ORGANISM: Artificial Sequence
<220> FEATURE:
<223> OTHER INFORMATION: chemically synthesized

<400> SEQUENCE: 818
atccgtcaca cctgctctgg acatggttaa tatggataga tgtttatatt agcatggtgt    60
tggctcccgt at                                                        72

<210> SEQ ID NO 819
<211> LENGTH: 72
<212> TYPE: DNA
<213> ORGANISM: Artificial Sequence
<220> FEATURE:
<223> OTHER INFORMATION: chemically synthesized

<400> SEQUENCE: 819
atacgggagc caacaccaga gtgaataaag acccttcggc gaccagccgc ccccagagca    60
ggtgtgacgg at                                                        72

<210> SEQ ID NO 820
<211> LENGTH: 72
<212> TYPE: DNA
```

```
<213> ORGANISM: Artificial Sequence
<220> FEATURE:
<223> OTHER INFORMATION: chemically synthesized

<400> SEQUENCE: 820
atccgtcaca cctgctctgg gggcggctgg tcgccgaagg gtctttattc actctggtgt    60
tggctcccgt at                                                       72

<210> SEQ ID NO 821
<211> LENGTH: 72
<212> TYPE: DNA
<213> ORGANISM: Artificial Sequence
<220> FEATURE:
<223> OTHER INFORMATION: chemically synthesized

<400> SEQUENCE: 821
atacgggagc caacaccatg agaccgcgcc cgtgacatag aatcccttc ccgtagagca     60 ggtgtgacgg at                                                       72

<210> SEQ ID NO 822
<211> LENGTH: 72
<212> TYPE: DNA
<213> ORGANISM: Artificial Sequence
<220> FEATURE:
<223> OTHER INFORMATION: chemically synthesized

<400> SEQUENCE: 822
atccgtcaca cctgctctac gggaagggga ttctatgtca cgggcgcggt ctcatggtgt    60
tggctcccgt at                                                       72

<210> SEQ ID NO 823
<211> LENGTH: 72
<212> TYPE: DNA
<213> ORGANISM: Artificial Sequence
<220> FEATURE:
<223> OTHER INFORMATION: chemically synthesized

<400> SEQUENCE: 823
atacgggagc caacaccaac aggatgttaa gaggtgagag ggcaggcgag gtccagagca    60
ggtgtgacgg at                                                       72

<210> SEQ ID NO 824
<211> LENGTH: 72
<212> TYPE: DNA
<213> ORGANISM: Artificial Sequence
<220> FEATURE:
<223> OTHER INFORMATION: chemically synthesized

<400> SEQUENCE: 824
atccgtcaca cctgctctgg acctcgcctg ccctctcacc tcttaacatc ctgttggtgt    60
tggctcccgt at                                                       72

<210> SEQ ID NO 825
<211> LENGTH: 72
<212> TYPE: DNA
<213> ORGANISM: Artificial Sequence
<220> FEATURE:
<223> OTHER INFORMATION: chemically synthesized

<400> SEQUENCE: 825
atacgggagc caacaccagc catcgttcag tacattacga acccatctta ccccagagca    60
ggtgtgacgg at                                                       72
```

<210> SEQ ID NO 826
<211> LENGTH: 72
<212> TYPE: DNA
<213> ORGANISM: Artificial Sequence
<220> FEATURE:
<223> OTHER INFORMATION: chemically synthesized

<400> SEQUENCE: 826
atccgtcaca cctgctctgg ggtaagatgg gttcgtaatg tactgaacga tggctggtgt     60
tggctcccgt at                                                         72

<210> SEQ ID NO 827
<211> LENGTH: 76
<212> TYPE: DNA
<213> ORGANISM: Artificial Sequence
<220> FEATURE:
<223> OTHER INFORMATION: chemically synthesized

<400> SEQUENCE: 827
atacgggagc caacaccaca gcaggtgtga cggatgaggt cgaattccag cacactggcg     60
gccgttacta atggat                                                     76

<210> SEQ ID NO 828
<211> LENGTH: 76
<212> TYPE: DNA
<213> ORGANISM: Artificial Sequence
<220> FEATURE:
<223> OTHER INFORMATION: chemically synthesized

<400> SEQUENCE: 828
atccattagt aacggccgcc agtgtgctgg aattcgacct catccgtcac acctgctgtg     60
gtgttggctc ccgtat                                                     76

<210> SEQ ID NO 829
<211> LENGTH: 72
<212> TYPE: DNA
<213> ORGANISM: Artificial Sequence
<220> FEATURE:
<223> OTHER INFORMATION: chemically synthesized

<400> SEQUENCE: 829
atacgggagc caacaccatg ataagccaag atgttcaata tttataagtc tcccagagca     60
ggtgtgacgg at                                                         72

<210> SEQ ID NO 830
<211> LENGTH: 72
<212> TYPE: DNA
<213> ORGANISM: Artificial Sequence
<220> FEATURE:
<223> OTHER INFORMATION: chemically synthesized

<400> SEQUENCE: 830
atccgtcaca cctgctctgg gagacttata aatattgaac atcttggctt atcatggtgt     60
tggctcccgt at                                                         72

<210> SEQ ID NO 831
<211> LENGTH: 72
<212> TYPE: DNA
<213> ORGANISM: Artificial Sequence
<220> FEATURE:
<223> OTHER INFORMATION: chemically synthesized

```
<400> SEQUENCE: 831
atacgggagc caacaccagc actacccgct tattgaaatg tggtgtatta ttggagagca    60
ggtgtgacgg at                                                        72

<210> SEQ ID NO 832
<211> LENGTH: 72
<212> TYPE: DNA
<213> ORGANISM: Artificial Sequence
<220> FEATURE:
<223> OTHER INFORMATION: chemically synthesized

<400> SEQUENCE: 832
atccgtcaca cctgctctcc aataatacac cacatttcaa taagcgggta gtgctggtgt    60
tggctcccgt at                                                        72

<210> SEQ ID NO 833
<211> LENGTH: 72
<212> TYPE: DNA
<213> ORGANISM: Artificial Sequence
<220> FEATURE:
<223> OTHER INFORMATION: chemically synthesized

<400> SEQUENCE: 833
atacgggagc caacaccaag acgcgcaaaa aaaacacgga aagattactc ggacagagca    60
ggtgtgacgg at                                                        72

<210> SEQ ID NO 834
<211> LENGTH: 72
<212> TYPE: DNA
<213> ORGANISM: Artificial Sequence
<220> FEATURE:
<223> OTHER INFORMATION: chemically synthesized

<400> SEQUENCE: 834
atccgtcaca cctgctctgt ccgagtaatc tttccgtgtt ttttttgcgc gtcttggtgt    60
tggctcccgt at                                                        72

<210> SEQ ID NO 835
<211> LENGTH: 72
<212> TYPE: DNA
<213> ORGANISM: Artificial Sequence
<220> FEATURE:
<223> OTHER INFORMATION: chemically synthesized

<400> SEQUENCE: 835
atacgggagc caacaccaca ttgtactcca ccctaccgaa aagcccattt cagcagagca    60
ggtgtgacgg at                                                        72

<210> SEQ ID NO 836
<211> LENGTH: 72
<212> TYPE: DNA
<213> ORGANISM: Artificial Sequence
<220> FEATURE:
<223> OTHER INFORMATION: chemically synthesized

<400> SEQUENCE: 836
atccgtcaca cctgctctgc tgaaatgggc ttttcggtag ggtggagtac aatgtggtgt    60
tggctcccgt at                                                        72

<210> SEQ ID NO 837
<211> LENGTH: 72
```

```
<212> TYPE: DNA
<213> ORGANISM: Artificial Sequence
<220> FEATURE:
<223> OTHER INFORMATION: chemically synthesized

<400> SEQUENCE: 837
atacgggagc caacaccaga aacaaggtgg cccaaataca agcactagct ttagagagca      60
ggtgtgacgg at                                                         72

<210> SEQ ID NO 838
<211> LENGTH: 72
<212> TYPE: DNA
<213> ORGANISM: Artificial Sequence
<220> FEATURE:
<223> OTHER INFORMATION: chemically synthesized

<400> SEQUENCE: 838
atccgtcaca cctgctctct aaagctagtg cttgtatttg ggccaccttg tttctggtgt      60
tggctcccgt at                                                         72

<210> SEQ ID NO 839
<211> LENGTH: 72
<212> TYPE: DNA
<213> ORGANISM: Artificial Sequence
<220> FEATURE:
<223> OTHER INFORMATION: chemically synthesized

<400> SEQUENCE: 839
atacgggagc caacaccaaa ggctgtaggg gggaggaaat attgggatcc tggcagagca      60
ggtgtgacgg at                                                         72

<210> SEQ ID NO 840
<211> LENGTH: 72
<212> TYPE: DNA
<213> ORGANISM: Artificial Sequence
<220> FEATURE:
<223> OTHER INFORMATION: chemically synthesized

<400> SEQUENCE: 840
atccgtcaca cctgctctgc caggatccca atatttcctc cccctacag cctttggtgt       60 tggctcccgt at                                                         72

<210> SEQ ID NO 841
<211> LENGTH: 72
<212> TYPE: DNA
<213> ORGANISM: Artificial Sequence
<220> FEATURE:
<223> OTHER INFORMATION: chemically synthesized

<400> SEQUENCE: 841
atacgggagc caacaccaca ggatatcaac gcactaaaaa tctaggatct ttggagagca      60
ggtgtgacgg at                                                         72

<210> SEQ ID NO 842
<211> LENGTH: 72
<212> TYPE: DNA
<213> ORGANISM: Artificial Sequence
<220> FEATURE:
<223> OTHER INFORMATION: chemically synthesized

<400> SEQUENCE: 842
atccgtcaca cctgctctcc aaagatccta gattttagt gcgttgatat cctgtggtgt       60
```

```
tggctcccgt at                                                          72
```

<210> SEQ ID NO 843
<211> LENGTH: 72
<212> TYPE: DNA
<213> ORGANISM: Artificial Sequence
<220> FEATURE:
<223> OTHER INFORMATION: chemically synthesized

<400> SEQUENCE: 843

```
atacgggagc caacaccagt gagtcgatag accgacatgt gtctggtaat ctgtagagca      60
ggtgtgacgg at                                                          72
```

<210> SEQ ID NO 844
<211> LENGTH: 72
<212> TYPE: DNA
<213> ORGANISM: Artificial Sequence
<220> FEATURE:
<223> OTHER INFORMATION: chemically synthesized

<400> SEQUENCE: 844

```
atccgtcaca cctgctctac agattaccag acacatgtcg gtctatcgac tcactggtgt      60
tggctcccgt at                                                          72
```

<210> SEQ ID NO 845
<211> LENGTH: 72
<212> TYPE: DNA
<213> ORGANISM: Artificial Sequence
<220> FEATURE:
<223> OTHER INFORMATION: chemically synthesized

<400> SEQUENCE: 845

```
atacgggagc caacaccaat aggttccagg gcgtagctat tagcgctaac cagaagagca      60
ggtgtgacgg at                                                          72
```

<210> SEQ ID NO 846
<211> LENGTH: 72
<212> TYPE: DNA
<213> ORGANISM: Artificial Sequence
<220> FEATURE:
<223> OTHER INFORMATION: chemically synthesized

<400> SEQUENCE: 846

```
atccgtcaca cctgctcttc tggttagcgc taatagctac gccctggaac ctattggtgt      60
tggctcccgt at                                                          72
```

<210> SEQ ID NO 847
<211> LENGTH: 72
<212> TYPE: DNA
<213> ORGANISM: Artificial Sequence
<220> FEATURE:
<223> OTHER INFORMATION: chemically synthesized

<400> SEQUENCE: 847

```
atacgggagc caacaccagc gcctctaccg ccgcccaccg catccacgca catcagagca      60
ggtgtgacgg at                                                          72
```

<210> SEQ ID NO 848
<211> LENGTH: 72
<212> TYPE: DNA
<213> ORGANISM: Artificial Sequence
<220> FEATURE:
<223> OTHER INFORMATION: chemically synthesized

```
<400> SEQUENCE: 848
atccgtcaca cctgctctga tgtgcgtgga tgcggtgggc ggcggtagag gcgctggtgt    60
tggctcccgt at                                                       72

<210> SEQ ID NO 849
<211> LENGTH: 72
<212> TYPE: DNA
<213> ORGANISM: Artificial Sequence
<220> FEATURE:
<223> OTHER INFORMATION: chemically synthesized

<400> SEQUENCE: 849
atacgggagc caacaccact ttatagaaac atgcaccgat ctattgttgt gaggagagca    60
ggtgtgacgg at                                                       72

<210> SEQ ID NO 850
<211> LENGTH: 72
<212> TYPE: DNA
<213> ORGANISM: Artificial Sequence
<220> FEATURE:
<223> OTHER INFORMATION: chemically synthesized

<400> SEQUENCE: 850
atccgtcaca cctgctctcc tcacaacaat agatcggtgc atgtttctat aaagtggtgt    60
tggctcccgt at                                                       72

<210> SEQ ID NO 851
<211> LENGTH: 72
<212> TYPE: DNA
<213> ORGANISM: Artificial Sequence
<220> FEATURE:
<223> OTHER INFORMATION: chemically synthesized

<400> SEQUENCE: 851
atacgggagc caacaccaaa aactgacgag gtgagtatta tatttaaggc atatagagca    60
ggtgtgacgg at                                                       72

<210> SEQ ID NO 852
<211> LENGTH: 72
<212> TYPE: DNA
<213> ORGANISM: Artificial Sequence
<220> FEATURE:
<223> OTHER INFORMATION: chemically synthesized

<400> SEQUENCE: 852
atccgtcaca cctgctctat atgccttaaa tataatactc acctcgtcag tttttggtgt    60
tggctcccgt at                                                       72

<210> SEQ ID NO 853
<211> LENGTH: 72
<212> TYPE: DNA
<213> ORGANISM: Artificial Sequence
<220> FEATURE:
<223> OTHER INFORMATION: chemically synthesized

<400> SEQUENCE: 853
atacgggagc caacaccagc agtgtgatct ggttacactg tggatacgat acggagagca    60
ggtgtgacgg at                                                       72

<210> SEQ ID NO 854
```

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 854
atccgtcaca cctgctctcc gtatcgtatc cacagtgtaa ccagatcaca ctgctggtgt     60
tggctcccgt at                                                         72

<210> SEQ ID NO 855
<211> LENGTH: 72
<212> TYPE: DNA
<213> ORGANISM: Artificial Sequence
<220> FEATURE:
<223> OTHER INFORMATION: chemically synthesized

<400> SEQUENCE: 855
atacgggagc caacaccaca cgataatcgg tagaaactta aatactaccc gtccagagca     60
ggtgtgacgg at                                                         72

<210> SEQ ID NO 856
<211> LENGTH: 72
<212> TYPE: DNA
<213> ORGANISM: Artificial Sequence
<220> FEATURE:
<223> OTHER INFORMATION: chemically synthesized

<400> SEQUENCE: 856
atccgtcaca cctgctctgg acgggtagta tttaagtttc taccgattat cgtgtggtgt     60
tggctcccgt at                                                         72

<210> SEQ ID NO 857
<211> LENGTH: 72
<212> TYPE: DNA
<213> ORGANISM: Artificial Sequence
<220> FEATURE:
<223> OTHER INFORMATION: chemically synthesized

<400> SEQUENCE: 857
atacgggagc caacaccata tgtcagagaa agaagtctca tcctttagac ccccagagca     60
ggtgtgacgg at                                                         72

<210> SEQ ID NO 858
<211> LENGTH: 72
<212> TYPE: DNA
<213> ORGANISM: Artificial Sequence
<220> FEATURE:
<223> OTHER INFORMATION: chemically synthesized

<400> SEQUENCE: 858
atccgtcaca cctgctctgg gggtctaaag gatgagactt ctttctctga catatggtgt     60
tggctcccgt at                                                         72

<210> SEQ ID NO 859
<211> LENGTH: 72
<212> TYPE: DNA
<213> ORGANISM: Artificial Sequence
<220> FEATURE:
<223> OTHER INFORMATION: chemically synthesized

<400> SEQUENCE: 859
atacgggagc caacaccacc taaccatccg atgccttctg tcatgaaagc atctagagca     60
```
ggtgtgacgg at 72

<210> SEQ ID NO 860
<211> LENGTH: 72
<212> TYPE: DNA
<213> ORGANISM: Artificial Sequence
<220> FEATURE:
<223> OTHER INFORMATION: chemically synthesized

<400> SEQUENCE: 860
atccgtcaca cctgctctag atgctttcat gacagaaggc atcggatggt taggtggtgt    60
tggctcccgt at    72

<210> SEQ ID NO 861
<211> LENGTH: 72
<212> TYPE: DNA
<213> ORGANISM: Artificial Sequence
<220> FEATURE:
<223> OTHER INFORMATION: chemically synthesized

<400> SEQUENCE: 861
atacgggagc caacaccagc ccaagtaggc agaaagtgaa caatgcttct gaccagagca    60
ggtgtgacgg at    72

<210> SEQ ID NO 862
<211> LENGTH: 72
<212> TYPE: DNA
<213> ORGANISM: Artificial Sequence
<220> FEATURE:
<223> OTHER INFORMATION: chemically synthesized

<400> SEQUENCE: 862
atccgtcaca cctgctctgg tcagaagcat tgttcactttt ctgcctactt gggctggtgt    60
tggctcccgt at    72

<210> SEQ ID NO 863
<211> LENGTH: 72
<212> TYPE: DNA
<213> ORGANISM: Artificial Sequence
<220> FEATURE:
<223> OTHER INFORMATION: chemically synthesized

<400> SEQUENCE: 863
atacgggagc caacaccaag gcacgcgcac cagctggaaa gcccatggta cctcagagca    60
ggtgtgacgg at    72

<210> SEQ ID NO 864
<211> LENGTH: 72
<212> TYPE: DNA
<213> ORGANISM: Artificial Sequence
<220> FEATURE:
<223> OTHER INFORMATION: chemically synthesized

<400> SEQUENCE: 864
atccgtcaca cctgctctga ggtaccatgg gctttccagc tggtgcgcgt gccttggtgt    60
tggctcccgt at    72

<210> SEQ ID NO 865
<211> LENGTH: 72
<212> TYPE: DNA
<213> ORGANISM: Artificial Sequence
<220> FEATURE:

<223> OTHER INFORMATION: chemically synthesized

<400> SEQUENCE: 865
atacgggagc caacaccaca accttttctc tcaagcccct ctgccccac tcagagagca    60 ggtgtgacgg at    72

<210> SEQ ID NO 866
<211> LENGTH: 72
<212> TYPE: DNA
<213> ORGANISM: Artificial Sequence
<220> FEATURE:
<223> OTHER INFORMATION: chemically synthesized

<400> SEQUENCE: 866
atccgtcaca cctgctctct gagtgggggc agaggggctt gagagaaaag gttgtggtgt    60
tggctcccgt at    72

<210> SEQ ID NO 867
<211> LENGTH: 72
<212> TYPE: DNA
<213> ORGANISM: Artificial Sequence
<220> FEATURE:
<223> OTHER INFORMATION: chemically synthesized

<400> SEQUENCE: 867
atacgggagc caacaccaca caataaaacg aacaccaaca gacaatacat tcacagagca    60
ggtgtgacgg at    72

<210> SEQ ID NO 868
<211> LENGTH: 72
<212> TYPE: DNA
<213> ORGANISM: Artificial Sequence
<220> FEATURE:
<223> OTHER INFORMATION: chemically synthesized

<400> SEQUENCE: 868
atccgtcaca cctgctctgt gaatgtattg tctgttggtg ttcgttttat tgtgtggtgt    60
tggctcccgt at    72

<210> SEQ ID NO 869
<211> LENGTH: 72
<212> TYPE: DNA
<213> ORGANISM: Artificial Sequence
<220> FEATURE:
<223> OTHER INFORMATION: chemically synthesized

<400> SEQUENCE: 869
atacgggagc caacaccagt gcctggccaa gccctctcac ttggcaatga tggcagagca    60
ggtgtgacgg at    72

<210> SEQ ID NO 870
<211> LENGTH: 72
<212> TYPE: DNA
<213> ORGANISM: Artificial Sequence
<220> FEATURE:
<223> OTHER INFORMATION: chemically synthesized

<400> SEQUENCE: 870
atccgtcaca cctgctctgc catcattgcc aagtgagagg gcttggccag gcactggtgt    60
tggctcccgt at    72

<210> SEQ ID NO 871
<211> LENGTH: 71
<212> TYPE: DNA
<213> ORGANISM: Artificial Sequence
<220> FEATURE:
<223> OTHER INFORMATION: chemically synthesized

<400> SEQUENCE: 871
atacgggagc caacaccaag caactaagaa caagttataa ctatattacg gggagagcag    60
gtgtgacgga t                                                        71

<210> SEQ ID NO 872
<211> LENGTH: 71
<212> TYPE: DNA
<213> ORGANISM: Artificial Sequence
<220> FEATURE:
<223> OTHER INFORMATION: chemically synthesized

<400> SEQUENCE: 872
atccgtcaca cctgctctcc ccgtaatata gttataactt gttcttagtt gcttggtgtt    60
ggctcccgta t                                                        71

<210> SEQ ID NO 873
<211> LENGTH: 72
<212> TYPE: DNA
<213> ORGANISM: Artificial Sequence
<220> FEATURE:
<223> OTHER INFORMATION: chemically synthesized

<400> SEQUENCE: 873
atacgggagc caacaccaat gaaacatgcc gattgcttaa cagtgtattc tgatagagca    60
ggtgtgacgg at                                                       72

<210> SEQ ID NO 874
<211> LENGTH: 72
<212> TYPE: DNA
<213> ORGANISM: Artificial Sequence
<220> FEATURE:
<223> OTHER INFORMATION: chemically synthesized

<400> SEQUENCE: 874
atccgtcaca cctgctctat cagaatacac tgttaagcaa tcggcatgtt tcattggtgt    60
tggctcccgt at                                                       72

<210> SEQ ID NO 875
<211> LENGTH: 72
<212> TYPE: DNA
<213> ORGANISM: Artificial Sequence
<220> FEATURE:
<223> OTHER INFORMATION: chemically synthesized

<400> SEQUENCE: 875
atacgggagc caacaccata caccaactac tgagattcga gttaccgaaa tcgtagagca    60
ggtgtgacgg at                                                       72

<210> SEQ ID NO 876
<211> LENGTH: 72
<212> TYPE: DNA
<213> ORGANISM: Artificial Sequence
<220> FEATURE:
<223> OTHER INFORMATION: chemically synthesized

<400> SEQUENCE: 876

```
atccgtcaca cctgctctac gatttcggta actcgaatct cagtagttgg tgtatggtgt    60
tggctcccgt at                                                         72
```

<210> SEQ ID NO 877
<211> LENGTH: 72
<212> TYPE: DNA
<213> ORGANISM: Artificial Sequence
<220> FEATURE:
<223> OTHER INFORMATION: chemically synthesized

<400> SEQUENCE: 877

```
atacgggagc caacaccaat gatgcgccaa gggttgccgg cggctcgatt tgcgagagca    60
ggtgtgacgg at                                                         72
```

<210> SEQ ID NO 878
<211> LENGTH: 72
<212> TYPE: DNA
<213> ORGANISM: Artificial Sequence
<220> FEATURE:
<223> OTHER INFORMATION: chemically synthesized

<400> SEQUENCE: 878

```
atccgtcaca cctgctctcg caaatcgagc cgccggcaac ccttggcgca tcattggtgt    60
tggctcccgt at                                                         72
```

<210> SEQ ID NO 879
<211> LENGTH: 71
<212> TYPE: DNA
<213> ORGANISM: Artificial Sequence
<220> FEATURE:
<223> OTHER INFORMATION: chemically synthesized

<400> SEQUENCE: 879

```
atacgggagc caacaccagc cggtgtatag aatgatggag atgtagtttt ggaagagcag    60
gtgtgacgga t                                                          71
```

<210> SEQ ID NO 880
<211> LENGTH: 71
<212> TYPE: DNA
<213> ORGANISM: Artificial Sequence
<220> FEATURE:
<223> OTHER INFORMATION: chemically synthesized

<400> SEQUENCE: 880

```
atccgtcaca cctgctcttc caaaactaca tctccatcat tctatacacc ggctggtgtt    60
ggctcccgta t                                                          71
```

<210> SEQ ID NO 881
<211> LENGTH: 72
<212> TYPE: DNA
<213> ORGANISM: Artificial Sequence
<220> FEATURE:
<223> OTHER INFORMATION: chemically synthesized

<400> SEQUENCE: 881

```
atacgggagc caacaccaag cggaggtaac acaataatgt gagagactgg tgaaagagca    60
ggtgtgacgg at                                                         72
```

<210> SEQ ID NO 882
<211> LENGTH: 72
<212> TYPE: DNA
<213> ORGANISM: Artificial Sequence
<220> FEATURE:
<223> OTHER INFORMATION: chemically synthesized

<400> SEQUENCE: 882
atccgtcaca cctgctcttt caccagtctc tcacattatt gtgttacctc cgcttggtgt    60
tggctcccgt at    72

<210> SEQ ID NO 883
<211> LENGTH: 72
<212> TYPE: DNA
<213> ORGANISM: Artificial Sequence
<220> FEATURE:
<223> OTHER INFORMATION: chemically synthesized

<400> SEQUENCE: 883
atacgggagc caacaccatt cacatctatc cctcacagcg cctgagctgt cacgagagca    60
ggtgtgacgg at    72

<210> SEQ ID NO 884
<211> LENGTH: 72
<212> TYPE: DNA
<213> ORGANISM: Artificial Sequence
<220> FEATURE:
<223> OTHER INFORMATION: chemically synthesized

<400> SEQUENCE: 884
atccgtcaca cctgctctcg tgacagctca ggcgctgtga gggatagatg tgaatggtgt    60
tggctcccgt at    72

<210> SEQ ID NO 885
<211> LENGTH: 72
<212> TYPE: DNA
<213> ORGANISM: Artificial Sequence
<220> FEATURE:
<223> OTHER INFORMATION: chemically synthesized

<400> SEQUENCE: 885
atacgggagc caacaccagg tcccgcctgc ttaagttcgt ctatcttgcc ttcaagagca    60
ggtgtgacgg at    72

<210> SEQ ID NO 886
<211> LENGTH: 72
<212> TYPE: DNA
<213> ORGANISM: Artificial Sequence
<220> FEATURE:
<223> OTHER INFORMATION: chemically synthesized

<400> SEQUENCE: 886
atccgtcaca cctgctcttg aaggcaagat agacgaactt aagcaggcgg gacctggtgt    60
tggctcccgt at    72

<210> SEQ ID NO 887
<211> LENGTH: 72
<212> TYPE: DNA
<213> ORGANISM: Artificial Sequence
<220> FEATURE:
<223> OTHER INFORMATION: chemically synthesized

<400> SEQUENCE: 887
atacgggagc caacaccagc tcctgttaac gaatctttaa gccatgctgt gcggagagca    60
ggtgtgacgg at    72

<210> SEQ ID NO 888
<211> LENGTH: 72
<212> TYPE: DNA
<213> ORGANISM: Artificial Sequence
<220> FEATURE:
<223> OTHER INFORMATION: chemically synthesized

<400> SEQUENCE: 888
atccgtcaca cctgctctcc gcacagcatg gcttaaagat tcgttaacag gagctggtgt    60
tggctcccgt at                                                        72

<210> SEQ ID NO 889
<211> LENGTH: 72
<212> TYPE: DNA
<213> ORGANISM: Artificial Sequence
<220> FEATURE:
<223> OTHER INFORMATION: chemically synthesized

<400> SEQUENCE: 889
atacgggagc caacaccagt aaccgataca tagacgaaaa gttggctacg aatgagagca    60
ggtgtgacgg at                                                        72

<210> SEQ ID NO 890
<211> LENGTH: 72
<212> TYPE: DNA
<213> ORGANISM: Artificial Sequence
<220> FEATURE:
<223> OTHER INFORMATION: chemically synthesized

<400> SEQUENCE: 890
atccgtcaca cctgctctca ttcgtagcca acttttcgtc tatgtatcgg ttactggtgt    60
tggctcccgt at                                                        72

<210> SEQ ID NO 891
<211> LENGTH: 72
<212> TYPE: DNA
<213> ORGANISM: Artificial Sequence
<220> FEATURE:
<223> OTHER INFORMATION: chemically synthesized

<400> SEQUENCE: 891
atacgggagc caacaccagc ttgcggcggg atcggagtaa acttaatgtc gtggagagca    60
ggtgtgacgg at                                                        72

<210> SEQ ID NO 892
<211> LENGTH: 72
<212> TYPE: DNA
<213> ORGANISM: Artificial Sequence
<220> FEATURE:
<223> OTHER INFORMATION: chemically synthesized

<400> SEQUENCE: 892
atccgtcaca cctgctctcc acgacattaa gtttactccg atcccgccgc aagctggtgt    60
tggctcccgt at                                                        72

<210> SEQ ID NO 893
<211> LENGTH: 72
<212> TYPE: DNA
<213> ORGANISM: Artificial Sequence
<220> FEATURE:
<223> OTHER INFORMATION: chemically synthesized

<400> SEQUENCE: 893

```
atacgggagc caacaccaga caattttgat gtgagcgaaa aacaggtccc gcccagagca      60
ggtgtgacgg at                                                         72

<210> SEQ ID NO 894
<211> LENGTH: 72
<212> TYPE: DNA
<213> ORGANISM: Artificial Sequence
<220> FEATURE:
<223> OTHER INFORMATION: chemically synthesized

<400> SEQUENCE: 894
atccgtcaca cctgctctgg gcgggacctg ttttttcgctc acatcaaaat tgtctggtgt     60
tggctcccgt at                                                         72

<210> SEQ ID NO 895
<211> LENGTH: 72
<212> TYPE: DNA
<213> ORGANISM: Artificial Sequence
<220> FEATURE:
<223> OTHER INFORMATION: chemically synthesized

<400> SEQUENCE: 895
atacgggagc caacaccacg agtgggttca atgagactgc ataatgacac ccgtagagca     60
ggtgtgacgg at                                                         72

<210> SEQ ID NO 896
<211> LENGTH: 72
<212> TYPE: DNA
<213> ORGANISM: Artificial Sequence
<220> FEATURE:
<223> OTHER INFORMATION: chemically synthesized

<400> SEQUENCE: 896
atccgtcaca cctgctctac gggtgtcatt atgcagtctc attgaaccca ctcgtggtgt     60
tggctcccgt at                                                         72

<210> SEQ ID NO 897
<211> LENGTH: 72
<212> TYPE: DNA
<213> ORGANISM: Artificial Sequence
<220> FEATURE:
<223> OTHER INFORMATION: chemically synthesized

<400> SEQUENCE: 897
atacgggagc caacaccata gtcctgaaac gatcagatga aaataaatag ttgtagagca     60
ggtgtgacgg at                                                         72

<210> SEQ ID NO 898
<211> LENGTH: 72
<212> TYPE: DNA
<213> ORGANISM: Artificial Sequence
<220> FEATURE:
<223> OTHER INFORMATION: chemically synthesized

<400> SEQUENCE: 898
atccgtcaca cctgctctac aactatttat tttcatctga tcgtttcagg actatggtgt     60
tggctcccgt at                                                         72

<210> SEQ ID NO 899
<211> LENGTH: 72
<212> TYPE: DNA
```

```
<213> ORGANISM: Artificial Sequence
<220> FEATURE:
<223> OTHER INFORMATION: chemically synthesized

<400> SEQUENCE: 899
atacgggagc caacaccatg gtacacaagg tatggtctgg atgttcgagc ctaaagagca      60
ggtgtgacgg at                                                         72

<210> SEQ ID NO 900
<211> LENGTH: 72
<212> TYPE: DNA
<213> ORGANISM: Artificial Sequence
<220> FEATURE:
<223> OTHER INFORMATION: chemically synthesized

<400> SEQUENCE: 900
atccgtcaca cctgctcttt aggctcgaac atccagacca taccttgtgt accatggtgt      60
tggctcccgt at                                                         72

<210> SEQ ID NO 901
<211> LENGTH: 72
<212> TYPE: DNA
<213> ORGANISM: Artificial Sequence
<220> FEATURE:
<223> OTHER INFORMATION: chemically synthesized

<400> SEQUENCE: 901
atacgggagc caacaccagg gctgaccaat taacctgtta acataaatcc ctcaagagca      60
ggtgtgacgg at                                                         72

<210> SEQ ID NO 902
<211> LENGTH: 72
<212> TYPE: DNA
<213> ORGANISM: Artificial Sequence
<220> FEATURE:
<223> OTHER INFORMATION: chemically synthesized

<400> SEQUENCE: 902
atccgtcaca cctgctcttg agggatttat gttaacaggt taattggtca gccctggtgt      60
tggctcccgt at                                                         72

<210> SEQ ID NO 903
<211> LENGTH: 72
<212> TYPE: DNA
<213> ORGANISM: Artificial Sequence
<220> FEATURE:
<223> OTHER INFORMATION: chemically synthesized

<400> SEQUENCE: 903
atacgggagc caacaccata ggcaaaacca gaataagatg cagtgttggg aagtagagca      60
ggtgtgacgg at                                                         72

<210> SEQ ID NO 904
<211> LENGTH: 72
<212> TYPE: DNA
<213> ORGANISM: Artificial Sequence
<220> FEATURE:
<223> OTHER INFORMATION: chemically synthesized

<400> SEQUENCE: 904
atccgtcaca cctgctctac ttcccaacac tgcatcttat tctggttttg cctatggtgt      60
tggctcccgt at                                                         72
```

<210> SEQ ID NO 905
<211> LENGTH: 72
<212> TYPE: DNA
<213> ORGANISM: Artificial Sequence
<220> FEATURE:
<223> OTHER INFORMATION: chemically synthesized

<400> SEQUENCE: 905
atacgggagc caacaccata tttaggggt aaaatgtatg ggatgtttct ttacagagca    60
ggtgtgacgg at    72

<210> SEQ ID NO 906
<211> LENGTH: 72
<212> TYPE: DNA
<213> ORGANISM: Artificial Sequence
<220> FEATURE:
<223> OTHER INFORMATION: chemically synthesized

<400> SEQUENCE: 906
atccgtcaca cctgctctgt aaagaaacat cccatacatt ttaccccta aatatggtgt    60 tggctcccgt at    72

<210> SEQ ID NO 907
<211> LENGTH: 72
<212> TYPE: DNA
<213> ORGANISM: Artificial Sequence
<220> FEATURE:
<223> OTHER INFORMATION: chemically synthesized

<400> SEQUENCE: 907
atacgggagc caacaccagg gccggatccg ctctaatagc taacatgttg gatcagagca    60
ggtgtgacgg at    72

<210> SEQ ID NO 908
<211> LENGTH: 72
<212> TYPE: DNA
<213> ORGANISM: Artificial Sequence
<220> FEATURE:
<223> OTHER INFORMATION: chemically synthesized

<400> SEQUENCE: 908
atccgtcaca cctgctctga tccaacatgt tagctattag agcggatccg gccctggtgt    60
tggctcccgt at    72

<210> SEQ ID NO 909
<211> LENGTH: 72
<212> TYPE: DNA
<213> ORGANISM: Artificial Sequence
<220> FEATURE:
<223> OTHER INFORMATION: chemically synthesized

<400> SEQUENCE: 909
atacgggagc caacaccacc accctcgagc cgaacatctc cccgccgatt cttcagagca    60
ggtgtgacgg at    72

<210> SEQ ID NO 910
<211> LENGTH: 72
<212> TYPE: DNA
<213> ORGANISM: Artificial Sequence
<220> FEATURE:
<223> OTHER INFORMATION: chemically synthesized

<400> SEQUENCE: 910
atccgtcaca cctgctctga agaatcggcg gggagatgtt cggctcgagg gtggtggtgt  60
tggctcccgt at  72

<210> SEQ ID NO 911
<211> LENGTH: 72
<212> TYPE: DNA
<213> ORGANISM: Artificial Sequence
<220> FEATURE:
<223> OTHER INFORMATION: chemically synthesized

<400> SEQUENCE: 911
atacgggagc caacaccatc caatgaggcc atggaccggt aaactcggac gcgcagagca  60
ggtgtgacgg at  72

<210> SEQ ID NO 912
<211> LENGTH: 72
<212> TYPE: DNA
<213> ORGANISM: Artificial Sequence
<220> FEATURE:
<223> OTHER INFORMATION: chemically synthesized

<400> SEQUENCE: 912
atccgtcaca cctgctctgc gcgtccgagt ttaccggtcc atggcctcat tggatggtgt  60
tggctcccgt at  72

<210> SEQ ID NO 913
<211> LENGTH: 73
<212> TYPE: DNA
<213> ORGANISM: Artificial Sequence
<220> FEATURE:
<223> OTHER INFORMATION: chemically synthesized

<400> SEQUENCE: 913
atacgggagc caacaccact atgaccgtgc cccgtttgga tcatcgagct ggctcagagc  60
aggtgtgacg gat  73

<210> SEQ ID NO 914
<211> LENGTH: 73
<212> TYPE: DNA
<213> ORGANISM: Artificial Sequence
<220> FEATURE:
<223> OTHER INFORMATION: chemically synthesized

<400> SEQUENCE: 914
atccgtcaca cctgctctga gccagctcga tgatccaaac ggggcacggt catagtggtg  60
ttggctcccg tat  73

<210> SEQ ID NO 915
<211> LENGTH: 72
<212> TYPE: DNA
<213> ORGANISM: Artificial Sequence
<220> FEATURE:
<223> OTHER INFORMATION: chemically synthesized

<400> SEQUENCE: 915
atacgggagc caacaccact atcccccgat tcagcgcatt ctcagcatat ccccagagca  60
ggtgtgacgg at  72

<210> SEQ ID NO 916
<211> LENGTH: 72

```
<212> TYPE: DNA
<213> ORGANISM: Artificial Sequence
<220> FEATURE:
<223> OTHER INFORMATION: chemically synthesized

<400> SEQUENCE: 916
atccgtcaca cctgctctgg ggatatgctg agaatgcgct gaatcggggg atagtggtgt      60
tggctcccgt at                                                         72

<210> SEQ ID NO 917
<211> LENGTH: 72
<212> TYPE: DNA
<213> ORGANISM: Artificial Sequence
<220> FEATURE:
<223> OTHER INFORMATION: chemically synthesized

<400> SEQUENCE: 917
atacgggagc caacaccata gaagagagag agaatgacag tcaggtgtag caccagagca      60
ggtgtgacgg at                                                         72

<210> SEQ ID NO 918
<211> LENGTH: 72
<212> TYPE: DNA
<213> ORGANISM: Artificial Sequence
<220> FEATURE:
<223> OTHER INFORMATION: chemically synthesized

<400> SEQUENCE: 918
atccgtcaca cctgctctgg tgctacacct gactgtcatt ctctctctct tctatggtgt      60
tggctcccgt at                                                         72

<210> SEQ ID NO 919
<211> LENGTH: 72
<212> TYPE: DNA
<213> ORGANISM: Artificial Sequence
<220> FEATURE:
<223> OTHER INFORMATION: chemically synthesized

<400> SEQUENCE: 919
atacgggagc caacaccaaa cattacaacg atgtgggtga atattccgcg ttccagagca      60
ggtgtgacgg at                                                         72

<210> SEQ ID NO 920
<211> LENGTH: 72
<212> TYPE: DNA
<213> ORGANISM: Artificial Sequence
<220> FEATURE:
<223> OTHER INFORMATION: chemically synthesized

<400> SEQUENCE: 920
atccgtcaca cctgctctgg aacgcggaat attcacccac atcgttgtaa tgtttggtgt      60
tggctcccgt at                                                         72

<210> SEQ ID NO 921
<211> LENGTH: 72
<212> TYPE: DNA
<213> ORGANISM: Artificial Sequence
<220> FEATURE:
<223> OTHER INFORMATION: chemically synthesized

<400> SEQUENCE: 921
atacgggagc caacaccagc gaatcttata aacaacacc actaacctta tgacagagca       60
```
ggtgtgacgg at                                                              72

<210> SEQ ID NO 922
<211> LENGTH: 72
<212> TYPE: DNA
<213> ORGANISM: Artificial Sequence
<220> FEATURE:
<223> OTHER INFORMATION: chemically synthesized

<400> SEQUENCE: 922
atccgtcaca cctgctctgt cataaggtta gtggtgttgt tttataagat tcgctggtgt         60
tggctcccgt at                                                              72

<210> SEQ ID NO 923
<211> LENGTH: 72
<212> TYPE: DNA
<213> ORGANISM: Artificial Sequence
<220> FEATURE:
<223> OTHER INFORMATION: chemically synthesized

<400> SEQUENCE: 923
atacgggagc caacaccacc gaatgtgctg caagactaat ctggatggcc atgcagagca         60
ggtgtgacgg at                                                              72

<210> SEQ ID NO 924
<211> LENGTH: 72
<212> TYPE: DNA
<213> ORGANISM: Artificial Sequence
<220> FEATURE:
<223> OTHER INFORMATION: chemically synthesized

<400> SEQUENCE: 924
atccgtcaca cctgctctgc atggccatcc agattagtct tgcagcacat tcggtggtgt         60
tggctcccgt at                                                              72

<210> SEQ ID NO 925
<211> LENGTH: 72
<212> TYPE: DNA
<213> ORGANISM: Artificial Sequence
<220> FEATURE:
<223> OTHER INFORMATION: chemically synthesized

<400> SEQUENCE: 925
atacgggagc caacaccacc gcgcacatgg gcggagccgc tactctcccc cgctagagca         60
ggtgtgacgg at                                                              72

<210> SEQ ID NO 926
<211> LENGTH: 72
<212> TYPE: DNA
<213> ORGANISM: Artificial Sequence
<220> FEATURE:
<223> OTHER INFORMATION: chemically synthesized

<400> SEQUENCE: 926
atccgtcaca cctgctctag cgggggagag tagcggctcc gcccatgtgc gcggtggtgt         60
tggctcccgt at                                                              72

<210> SEQ ID NO 927
<211> LENGTH: 72
<212> TYPE: DNA
<213> ORGANISM: Artificial Sequence
<220> FEATURE:
<223> OTHER INFORMATION: chemically synthesized

<400> SEQUENCE: 927
atacgggagc caacaccacg ataagtgcga cttctctaca tccttaaccc ccccagagca    60
ggtgtgacgg at    72

<210> SEQ ID NO 928
<211> LENGTH: 72
<212> TYPE: DNA
<213> ORGANISM: Artificial Sequence
<220> FEATURE:
<223> OTHER INFORMATION: chemically synthesized

<400> SEQUENCE: 928
atccgtcaca cctgctctgg gggggttaag gatgtagaga agtcgcactt atcgtggtgt    60
tggctcccgt at    72

<210> SEQ ID NO 929
<211> LENGTH: 71
<212> TYPE: DNA
<213> ORGANISM: Artificial Sequence
<220> FEATURE:
<223> OTHER INFORMATION: chemically synthesized

<400> SEQUENCE: 929
atacgggagc caacaccaga atagttgtgc tgataaggaa atcattcggg gccaaaacaa    60
gggtgacgga t    71

<210> SEQ ID NO 930
<211> LENGTH: 71
<212> TYPE: DNA
<213> ORGANISM: Artificial Sequence
<220> FEATURE:
<223> OTHER INFORMATION: chemically synthesized

<400> SEQUENCE: 930
atccgtcacc cttgttttgg ccccgaatga tttccttatc agcacaacta ttctggtgtt    60
ggctcccgta t    71

<210> SEQ ID NO 931
<211> LENGTH: 72
<212> TYPE: DNA
<213> ORGANISM: Artificial Sequence
<220> FEATURE:
<223> OTHER INFORMATION: chemically synthesized

<400> SEQUENCE: 931
atacgggagc caacaccatt tcgactctgg tccgaatgct tatcgatgtg cctgagagca    60
ggtgtgacgg at    72

<210> SEQ ID NO 932
<211> LENGTH: 72
<212> TYPE: DNA
<213> ORGANISM: Artificial Sequence
<220> FEATURE:
<223> OTHER INFORMATION: chemically synthesized

<400> SEQUENCE: 932
atccgtcaca cctgctctca ggcacatcga taagcattcg gaccagagtc gaaatggtgt    60
tggctcccgt at    72

<210> SEQ ID NO 933

-continued

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 933
atacgggagc caacaccatc tagtctgatt accggtgata agtgatcgaa gcggagagca      60
ggtgtgacgg at                                                         72

<210> SEQ ID NO 934
<211> LENGTH: 72
<212> TYPE: DNA
<213> ORGANISM: Artificial Sequence
<220> FEATURE:
<223> OTHER INFORMATION: chemically synthesized

<400> SEQUENCE: 934
atccgtcaca cctgctctcc gcttcgatca cttatcaccg gtaatcagac tagatggtgt      60
tggctcccgt at                                                         72

<210> SEQ ID NO 935
<211> LENGTH: 72
<212> TYPE: DNA
<213> ORGANISM: Artificial Sequence
<220> FEATURE:
<223> OTHER INFORMATION: chemically synthesized

<400> SEQUENCE: 935
atacgggagc caacaccact cgagccaatg ctcatgagta agcgatctat ctccagagca      60
ggtgtgacgg at                                                         72

<210> SEQ ID NO 936
<211> LENGTH: 72
<212> TYPE: DNA
<213> ORGANISM: Artificial Sequence
<220> FEATURE:
<223> OTHER INFORMATION: chemically synthesized

<400> SEQUENCE: 936
atccgtcaca cctgctctgg agatagatcg cttactcatg agcattggct cgagtggtgt      60
tggctcccgt at                                                         72

<210> SEQ ID NO 937
<211> LENGTH: 72
<212> TYPE: DNA
<213> ORGANISM: Artificial Sequence
<220> FEATURE:
<223> OTHER INFORMATION: chemically synthesized

<400> SEQUENCE: 937
atacgggagc caacaccatt tcttcggtgt cctactgcac aattcccttc tttaagagca      60
ggtgtgacgg at                                                         72

<210> SEQ ID NO 938
<211> LENGTH: 72
<212> TYPE: DNA
<213> ORGANISM: Artificial Sequence
<220> FEATURE:
<223> OTHER INFORMATION: chemically synthesized

<400> SEQUENCE: 938
atccgtcaca cctgctctta agaagggaa ttgtgcagta ggacaccgaa gaaatggtgt       60
```
tggctcccgt at                                                          72

<210> SEQ ID NO 939
<211> LENGTH: 72
<212> TYPE: DNA
<213> ORGANISM: Artificial Sequence
<220> FEATURE:
<223> OTHER INFORMATION: chemically synthesized

<400> SEQUENCE: 939
atacgggagc caacaccagg gtgtgagaga tagggtaaat ggtgtggcag ttagagagca      60
ggtgtgacgg at                                                          72

<210> SEQ ID NO 940
<211> LENGTH: 72
<212> TYPE: DNA
<213> ORGANISM: Artificial Sequence
<220> FEATURE:
<223> OTHER INFORMATION: chemically synthesized

<400> SEQUENCE: 940
atccgtcaca cctgctctct aactgccaca ccatttaccc tatctctcac accctggtgt      60
tggctcccgt at                                                          72

<210> SEQ ID NO 941
<211> LENGTH: 72
<212> TYPE: DNA
<213> ORGANISM: Artificial Sequence
<220> FEATURE:
<223> OTHER INFORMATION: chemically synthesized

<400> SEQUENCE: 941
atacgggagc caacaccaca catttgacgg ttttctctct gagattggca ttacagagca      60
ggtgtgacgg at                                                          72

<210> SEQ ID NO 942
<211> LENGTH: 72
<212> TYPE: DNA
<213> ORGANISM: Artificial Sequence
<220> FEATURE:
<223> OTHER INFORMATION: chemically synthesized

<400> SEQUENCE: 942
atccgtcaca cctgctctgt aatgccaatc tcagagagaa aaccgtcaaa tgtgtggtgt      60
tggctcccgt at                                                          72

<210> SEQ ID NO 943
<211> LENGTH: 71
<212> TYPE: DNA
<213> ORGANISM: Artificial Sequence
<220> FEATURE:
<223> OTHER INFORMATION: chemically synthesized

<400> SEQUENCE: 943
atacgggagc caacaccact acatgtctgt cacgtcccaa acgtgattgc gcaagagcag      60
gtgtgacgga t                                                           71

<210> SEQ ID NO 944
<211> LENGTH: 71
<212> TYPE: DNA
<213> ORGANISM: Artificial Sequence
<220> FEATURE:

<223> OTHER INFORMATION: chemically synthesized

<400> SEQUENCE: 944
atccgtcaca cctgctcttg cgcaatcacg tttgggacgt gacagacatg tagtggtgtt    60
ggctcccgta t    71

<210> SEQ ID NO 945
<211> LENGTH: 72
<212> TYPE: DNA
<213> ORGANISM: Artificial Sequence
<220> FEATURE:
<223> OTHER INFORMATION: chemically synthesized

<400> SEQUENCE: 945
atacgggagc caacaccaac aggcagagtg gtgtagtgaa aatataattt gagtagagca    60
ggtgtgacgg at    72

<210> SEQ ID NO 946
<211> LENGTH: 72
<212> TYPE: DNA
<213> ORGANISM: Artificial Sequence
<220> FEATURE:
<223> OTHER INFORMATION: chemically synthesized

<400> SEQUENCE: 946
atccgtcaca cctgctctac tcaaattata ttttcactac accactctgc ctgttggtgt    60
tggctcccgt at    72

<210> SEQ ID NO 947
<211> LENGTH: 72
<212> TYPE: DNA
<213> ORGANISM: Artificial Sequence
<220> FEATURE:
<223> OTHER INFORMATION: chemically synthesized

<400> SEQUENCE: 947
atacgggagc caacaccagt tctaggcagt cgtcgctagt gagaaaaata cttcagagca    60
ggtgtgacgg at    72

<210> SEQ ID NO 948
<211> LENGTH: 72
<212> TYPE: DNA
<213> ORGANISM: Artificial Sequence
<220> FEATURE:
<223> OTHER INFORMATION: chemically synthesized

<400> SEQUENCE: 948
atccgtcaca cctgctctga agtattttc tcactagcga cgactgccta gaactggtgt    60
tggctcccgt at    72

<210> SEQ ID NO 949
<211> LENGTH: 72
<212> TYPE: DNA
<213> ORGANISM: Artificial Sequence
<220> FEATURE:
<223> OTHER INFORMATION: chemically synthesized

<400> SEQUENCE: 949
atacgggagc caacaccatc cacaacgaac ttacatactc ccatcatact ctacagagca    60
ggtgtgacgg at    72

```
<210> SEQ ID NO 950
<211> LENGTH: 72
<212> TYPE: DNA
<213> ORGANISM: Artificial Sequence
<220> FEATURE:
<223> OTHER INFORMATION: chemically synthesized

<400> SEQUENCE: 950
atccgtcaca cctgctctgt agagtatgat gggagtatgt aagttcgttg tggatggtgt     60
tggctcccgt at                                                         72

<210> SEQ ID NO 951
<211> LENGTH: 72
<212> TYPE: DNA
<213> ORGANISM: Artificial Sequence
<220> FEATURE:
<223> OTHER INFORMATION: chemically synthesized

<400> SEQUENCE: 951
atacgggagc caacaccatg tttaataatt tgcattgtac gacaggacgg agacagagca     60
ggtgtgacgg at                                                         72

<210> SEQ ID NO 952
<211> LENGTH: 72
<212> TYPE: DNA
<213> ORGANISM: Artificial Sequence
<220> FEATURE:
<223> OTHER INFORMATION: chemically synthesized

<400> SEQUENCE: 952
atccgtcaca cctgctctgt ctccgtcctg tcgtacaatg caaattatta aacatggtgt     60
tggctcccgt at                                                         72

<210> SEQ ID NO 953
<211> LENGTH: 71
<212> TYPE: DNA
<213> ORGANISM: Artificial Sequence
<220> FEATURE:
<223> OTHER INFORMATION: chemically synthesized

<400> SEQUENCE: 953
atacgggagc caacaccaca tggttttgt aggataagga atagcttctt tccagagcag      60
gtgtgacgga t                                                          71

<210> SEQ ID NO 954
<211> LENGTH: 71
<212> TYPE: DNA
<213> ORGANISM: Artificial Sequence
<220> FEATURE:
<223> OTHER INFORMATION: chemically synthesized

<400> SEQUENCE: 954
atccgtcaca cctgctctgg aaagaagcta ttccttatcc tacaaaaacc atgtggtgtt     60
ggctcccgta t                                                          71

<210> SEQ ID NO 955
<211> LENGTH: 71
<212> TYPE: DNA
<213> ORGANISM: Artificial Sequence
<220> FEATURE:
<223> OTHER INFORMATION: chemically synthesized

<400> SEQUENCE: 955
```

```
atacgggagc caacaccagc aaccatcacc cacacgcacc ccccctccacc tacagagcag    60 gtgtgacgga t                                                          71

<210> SEQ ID NO 956
<211> LENGTH: 71
<212> TYPE: DNA
<213> ORGANISM: Artificial Sequence
<220> FEATURE:
<223> OTHER INFORMATION: chemically synthesized

<400> SEQUENCE: 956
atccgtcaca cctgctctgt aggtggaggg gggtgcgtgt gggtgatggt tgctggtgtt    60
ggctcccgta t                                                          71

<210> SEQ ID NO 957
<211> LENGTH: 72
<212> TYPE: DNA
<213> ORGANISM: Artificial Sequence
<220> FEATURE:
<223> OTHER INFORMATION: chemically synthesized

<400> SEQUENCE: 957
atacgggagc caacaccaag tcaaacaacc ggaatgatca aataagtgtt atccagagca    60
ggtgtgacgg at                                                         72

<210> SEQ ID NO 958
<211> LENGTH: 72
<212> TYPE: DNA
<213> ORGANISM: Artificial Sequence
<220> FEATURE:
<223> OTHER INFORMATION: chemically synthesized

<400> SEQUENCE: 958
atccgtcaca cctgctctgg ataacactta tttgatcatt ccggttgttt gacttggtgt    60
tggctcccgt at                                                         72

<210> SEQ ID NO 959
<211> LENGTH: 72
<212> TYPE: DNA
<213> ORGANISM: Artificial Sequence
<220> FEATURE:
<223> OTHER INFORMATION: chemically synthesized

<400> SEQUENCE: 959
atacgggagc caacaccacc gttcattgat cataagagtg agaccgtata catgagagca    60
ggtgtgacgg at                                                         72

<210> SEQ ID NO 960
<211> LENGTH: 72
<212> TYPE: DNA
<213> ORGANISM: Artificial Sequence
<220> FEATURE:
<223> OTHER INFORMATION: chemically synthesized

<400> SEQUENCE: 960
atccgtcaca cctgctctca tgtatacggt ctcactctta tgatcaatga acggtggtgt    60
tggctcccgt at                                                         72

<210> SEQ ID NO 961
<211> LENGTH: 72
<212> TYPE: DNA
<213> ORGANISM: Artificial Sequence
```

```
<220> FEATURE:
<223> OTHER INFORMATION: chemically synthesized

<400> SEQUENCE: 961
atacgggagc caacaccaag agattagagg acacaaagga ggctatgtca aggtagagca    60
ggtgtgacgg at                                                        72

<210> SEQ ID NO 962
<211> LENGTH: 72
<212> TYPE: DNA
<213> ORGANISM: Artificial Sequence
<220> FEATURE:
<223> OTHER INFORMATION: chemically synthesized

<400> SEQUENCE: 962
atccgtcaca cctgctctac cttgacatag cctcctttgt gtcctctaat ctcttggtgt    60
tggctcccgt at                                                        72

<210> SEQ ID NO 963
<211> LENGTH: 72
<212> TYPE: DNA
<213> ORGANISM: Artificial Sequence
<220> FEATURE:
<223> OTHER INFORMATION: chemically synthesized

<400> SEQUENCE: 963
atacgggagc caacaccaca ctgcctacgt cgcccgcctt tccagccatc ctccagagca    60
ggtgtgacgg at                                                        72

<210> SEQ ID NO 964
<211> LENGTH: 72
<212> TYPE: DNA
<213> ORGANISM: Artificial Sequence
<220> FEATURE:
<223> OTHER INFORMATION: chemically synthesized

<400> SEQUENCE: 964
atccgtcaca cctgctctgg aggatggctg gaaaggcggg cgacgtaggc agtgtggtgt    60
tggctcccgt at                                                        72

<210> SEQ ID NO 965
<211> LENGTH: 72
<212> TYPE: DNA
<213> ORGANISM: Artificial Sequence
<220> FEATURE:
<223> OTHER INFORMATION: chemically synthesized

<400> SEQUENCE: 965
atacgggagc caacaccatg gagaatgggc caatcttgtt atacatgcat gagcagagca    60
ggtgtgacgg at                                                        72

<210> SEQ ID NO 966
<211> LENGTH: 72
<212> TYPE: DNA
<213> ORGANISM: Artificial Sequence
<220> FEATURE:
<223> OTHER INFORMATION: chemically synthesized

<400> SEQUENCE: 966
atccgtcaca cctgctctgc tcatgcatgt ataacaagat tgcccattc tccatggtgt     60 tggctcccgt at                                                        72
```

<210> SEQ ID NO 967
<211> LENGTH: 72
<212> TYPE: DNA
<213> ORGANISM: Artificial Sequence
<220> FEATURE:
<223> OTHER INFORMATION: chemically synthesized

<400> SEQUENCE: 967
atacgggagc caacaccata ttgtgacaat atatatatat ttagatagcg acgcagagca    60
ggtgtgacgg at                                                       72

<210> SEQ ID NO 968
<211> LENGTH: 72
<212> TYPE: DNA
<213> ORGANISM: Artificial Sequence
<220> FEATURE:
<223> OTHER INFORMATION: chemically synthesized

<400> SEQUENCE: 968
atccgtcaca cctgctctgc gtcgctatct aaatatatat atattgtcac aatatggtgt    60
tggctcccgt at                                                       72

<210> SEQ ID NO 969
<211> LENGTH: 72
<212> TYPE: DNA
<213> ORGANISM: Artificial Sequence
<220> FEATURE:
<223> OTHER INFORMATION: chemically synthesized

<400> SEQUENCE: 969
atacgggagc caacaccatg ggcaattgtt atttagaagg atgataataa ctggagagca    60
ggtgtgacgg at                                                       72

<210> SEQ ID NO 970
<211> LENGTH: 72
<212> TYPE: DNA
<213> ORGANISM: Artificial Sequence
<220> FEATURE:
<223> OTHER INFORMATION: chemically synthesized

<400> SEQUENCE: 970
atccgtcaca cctgctctcc agttattatc atccttctaa ataacaattg cccatggtgt    60
tggctcccgt at                                                       72

<210> SEQ ID NO 971
<211> LENGTH: 72
<212> TYPE: DNA
<213> ORGANISM: Artificial Sequence
<220> FEATURE:
<223> OTHER INFORMATION: chemically synthesized

<400> SEQUENCE: 971
atacgggagc caacaccacc cttgggacac aaattgttta ctgtaaaagt ccggagagca    60
ggtgtgacgg at                                                       72

<210> SEQ ID NO 972
<211> LENGTH: 72
<212> TYPE: DNA
<213> ORGANISM: Artificial Sequence
<220> FEATURE:
<223> OTHER INFORMATION: chemically synthesized

<400> SEQUENCE: 972

```
atccgtcaca cctgctctcc ggacttttac agtaaacaat ttgtgtccca agggtggtgt    60
tggctcccgt at                                                       72
```

<210> SEQ ID NO 973
<211> LENGTH: 71
<212> TYPE: DNA
<213> ORGANISM: Artificial Sequence
<220> FEATURE:
<223> OTHER INFORMATION: chemically synthesized

<400> SEQUENCE: 973

```
atacgggagc caacaccaca accgaacccc atgacccggc ccccataccc ggtgagagca    60
ggtgtgacgg a                                                        71
```

<210> SEQ ID NO 974
<211> LENGTH: 72
<212> TYPE: DNA
<213> ORGANISM: Artificial Sequence
<220> FEATURE:
<223> OTHER INFORMATION: chemically synthesized

<400> SEQUENCE: 974

```
atccgtcaca cctgctctca ccgggtatgg gggccgggtc atggggttcg gttgtggtgt    60
tggctcccgt at                                                       72
```

<210> SEQ ID NO 975
<211> LENGTH: 72
<212> TYPE: DNA
<213> ORGANISM: Artificial Sequence
<220> FEATURE:
<223> OTHER INFORMATION: chemically synthesized

<400> SEQUENCE: 975

```
atacgggagc caacaccagc aaacgaagat gttgattctc gagtgatagg aaggagagca    60
ggtgtgacgg at                                                       72
```

<210> SEQ ID NO 976
<211> LENGTH: 72
<212> TYPE: DNA
<213> ORGANISM: Artificial Sequence
<220> FEATURE:
<223> OTHER INFORMATION: chemically synthesized

<400> SEQUENCE: 976

```
atccgtcaca cctgctctcc ttcctatcac tcgagaatca acatcttcgt ttgctggtgt    60
tggctcccgt at                                                       72
```

<210> SEQ ID NO 977
<211> LENGTH: 72
<212> TYPE: DNA
<213> ORGANISM: Artificial Sequence
<220> FEATURE:
<223> OTHER INFORMATION: chemically synthesized

<400> SEQUENCE: 977

```
atacgggagc caacaccact tattgattag ttttcttata ataatacgag ggctagagca    60
ggtgtgacgg at                                                       72
```

<210> SEQ ID NO 978
<211> LENGTH: 72
<212> TYPE: DNA

<213> ORGANISM: Artificial Sequence
<220> FEATURE:
<223> OTHER INFORMATION: chemically synthesized

<400> SEQUENCE: 978
atccgtcaca cctgctctag ccctcgtatt attataagaa aactaatcaa taagtggtgt    60
tggctcccgt at    72

<210> SEQ ID NO 979
<211> LENGTH: 72
<212> TYPE: DNA
<213> ORGANISM: Artificial Sequence
<220> FEATURE:
<223> OTHER INFORMATION: chemically synthesized

<400> SEQUENCE: 979
atacgggagc caacaccagg gaaggcaagt tgtgaaaata ttggtaggta tggcagagca    60
ggtgtgacgg at    72

<210> SEQ ID NO 980
<211> LENGTH: 72
<212> TYPE: DNA
<213> ORGANISM: Artificial Sequence
<220> FEATURE:
<223> OTHER INFORMATION: chemically synthesized

<400> SEQUENCE: 980
atccgtcaca cctgctctgc catacctacc aatattttca caacttgcct tccctggtgt    60
tggctcccgt at    72

<210> SEQ ID NO 981
<211> LENGTH: 72
<212> TYPE: DNA
<213> ORGANISM: Artificial Sequence
<220> FEATURE:
<223> OTHER INFORMATION: chemically synthesized

<400> SEQUENCE: 981
atacgggagc caacaccata gtggacggaa tgacaagtcg acgggggtg tgtgagagca    60 ggtgtgacgg at    72

<210> SEQ ID NO 982
<211> LENGTH: 72
<212> TYPE: DNA
<213> ORGANISM: Artificial Sequence
<220> FEATURE:
<223> OTHER INFORMATION: chemically synthesized

<400> SEQUENCE: 982
atccgtcaca cctgctctca cacaccccc gtcgacttgt cattccgtcc actatggtgt    60
tggctcccgt at    72

<210> SEQ ID NO 983
<211> LENGTH: 72
<212> TYPE: DNA
<213> ORGANISM: Artificial Sequence
<220> FEATURE:
<223> OTHER INFORMATION: chemically synthesized

<400> SEQUENCE: 983
atacgggagc caacaccaac agagttacaa agaaaaacgg taccaaccag ccccagagca    60
ggtgtgacgg at    72

<210> SEQ ID NO 984
<211> LENGTH: 72
<212> TYPE: DNA
<213> ORGANISM: Artificial Sequence
<220> FEATURE:
<223> OTHER INFORMATION: chemically synthesized

<400> SEQUENCE: 984
atccgtcaca cctgctctgg ggctggttgg taccgttttt ctttgtaact ctgttggtgt    60
tggctcccgt at    72

<210> SEQ ID NO 985
<211> LENGTH: 72
<212> TYPE: DNA
<213> ORGANISM: Artificial Sequence
<220> FEATURE:
<223> OTHER INFORMATION: chemically synthesized

<400> SEQUENCE: 985
atacgggagc caacaccatc ccggccctac agactgacta aagactgata atacagagca    60
ggtgtgacgg at    72

<210> SEQ ID NO 986
<211> LENGTH: 72
<212> TYPE: DNA
<213> ORGANISM: Artificial Sequence
<220> FEATURE:
<223> OTHER INFORMATION: chemically synthesized

<400> SEQUENCE: 986
atccgtcaca cctgctctgt attatcagtc tttagtcagt ctgtagggcc gggatggtgt    60
tggctcccgt at    72

<210> SEQ ID NO 987
<211> LENGTH: 72
<212> TYPE: DNA
<213> ORGANISM: Artificial Sequence
<220> FEATURE:
<223> OTHER INFORMATION: chemically synthesized

<400> SEQUENCE: 987
atacgggagc caacaccact ccatgaataa ctatgactcg ccctcaaccc tgtaagagca    60
ggtgtgacgg at    72

<210> SEQ ID NO 988
<211> LENGTH: 72
<212> TYPE: DNA
<213> ORGANISM: Artificial Sequence
<220> FEATURE:
<223> OTHER INFORMATION: chemically synthesized

<400> SEQUENCE: 988
atccgtcaca cctgctctta cagggttgag ggcgagtcat agttattcat ggagtggtgt    60
tggctcccgt at    72

<210> SEQ ID NO 989
<211> LENGTH: 72
<212> TYPE: DNA
<213> ORGANISM: Artificial Sequence
<220> FEATURE:
<223> OTHER INFORMATION: chemically synthesized

```
<400> SEQUENCE: 989
atacgggagc caacaccaaa caagattaaa gaattcatcg ccaacgtatc atgtagagca      60
ggtgtgacgg at                                                         72

<210> SEQ ID NO 990
<211> LENGTH: 72
<212> TYPE: DNA
<213> ORGANISM: Artificial Sequence
<220> FEATURE:
<223> OTHER INFORMATION: chemically synthesized

<400> SEQUENCE: 990
atccgtcaca cctgctctac atgatacgtt ggcgatgaat tctttaatct tgtttggtgt      60
tggctcccgt at                                                         72

<210> SEQ ID NO 991
<211> LENGTH: 72
<212> TYPE: DNA
<213> ORGANISM: Artificial Sequence
<220> FEATURE:
<223> OTHER INFORMATION: chemically synthesized

<400> SEQUENCE: 991
atacgggagc caacaccaca tagttatgaa acagaagcag taaccgggaa caatagagca      60
ggtgtgacgg at                                                         72

<210> SEQ ID NO 992
<211> LENGTH: 72
<212> TYPE: DNA
<213> ORGANISM: Artificial Sequence
<220> FEATURE:
<223> OTHER INFORMATION: chemically synthesized

<400> SEQUENCE: 992
atccgtcaca cctgctctat tgttcccggt tactgcttct gtttcataac tatgtggtgt      60
tggctcccgt at                                                         72

<210> SEQ ID NO 993
<211> LENGTH: 72
<212> TYPE: DNA
<213> ORGANISM: Artificial Sequence
<220> FEATURE:
<223> OTHER INFORMATION: chemically synthesized

<400> SEQUENCE: 993
atacgggagc caacaccaac acgctcactc ttcctacaca aactacaaca ccctagagca      60
ggtgtgacgg at                                                         72

<210> SEQ ID NO 994
<211> LENGTH: 72
<212> TYPE: DNA
<213> ORGANISM: Artificial Sequence
<220> FEATURE:
<223> OTHER INFORMATION: chemically synthesized

<400> SEQUENCE: 994
atccgtcaca cctgctctag ggtgttgtag tttgtgtagg aagagtgagc gtgttggtgt      60
tggctcccgt at                                                         72

<210> SEQ ID NO 995
<211> LENGTH: 72
```

```
<212> TYPE: DNA
<213> ORGANISM: Artificial Sequence
<220> FEATURE:
<223> OTHER INFORMATION: chemically synthesized

<400> SEQUENCE: 995
atacgggagc caacaccaag agctaagatt acacagcagt ctcaccacca ttacagagca      60
ggtgtgacgg at                                                         72

<210> SEQ ID NO 996
<211> LENGTH: 72
<212> TYPE: DNA
<213> ORGANISM: Artificial Sequence
<220> FEATURE:
<223> OTHER INFORMATION: chemically synthesized

<400> SEQUENCE: 996
atccgtcaca cctgctctcg ccccgatctc tagaatatta gtttcgagat aagatggtgt      60
tggctcccgt at                                                         72

<210> SEQ ID NO 997
<211> LENGTH: 72
<212> TYPE: DNA
<213> ORGANISM: Artificial Sequence
<220> FEATURE:
<223> OTHER INFORMATION: chemically synthesized

<400> SEQUENCE: 997
atacgggagc caacaccagg acaatagtgt tcaggaagga acggtccata cacgagagca      60
ggtgtgacgg at                                                         72

<210> SEQ ID NO 998
<211> LENGTH: 72
<212> TYPE: DNA
<213> ORGANISM: Artificial Sequence
<220> FEATURE:
<223> OTHER INFORMATION: chemically synthesized

<400> SEQUENCE: 998
atccgtcaca cctgctctcg tgtatggacc gttccttcct gaacactatt gtcctggtgt      60
tggctcccgt at                                                         72

<210> SEQ ID NO 999
<211> LENGTH: 71
<212> TYPE: DNA
<213> ORGANISM: Artificial Sequence
<220> FEATURE:
<223> OTHER INFORMATION: chemically synthesized

<400> SEQUENCE: 999
atacgggagc caacaccaca cagcacaacg gcttaaccac atctccgtac atgagagcag      60
gtgtgacgga t                                                          71

<210> SEQ ID NO 1000
<211> LENGTH: 71
<212> TYPE: DNA
<213> ORGANISM: Artificial Sequence
<220> FEATURE:
<223> OTHER INFORMATION: chemically synthesized

<400> SEQUENCE: 1000
atccgtcaca cctgctctca tgtacggaga tgtggttaag ccgttgtgct gtgtggtgtt      60
```

-continued

```
ggctcccgta t                                                          71

<210> SEQ ID NO 1001
<211> LENGTH: 72
<212> TYPE: DNA
<213> ORGANISM: Artificial Sequence
<220> FEATURE:
<223> OTHER INFORMATION: chemically synthesized

<400> SEQUENCE: 1001
atacgggagc caacaccaag acagaggtaa ttggtgaaat aaactaaatc atggagagca    60
ggtgtgacgg at                                                        72

<210> SEQ ID NO 1002
<211> LENGTH: 72
<212> TYPE: DNA
<213> ORGANISM: Artificial Sequence
<220> FEATURE:
<223> OTHER INFORMATION: chemically synthesized

<400> SEQUENCE: 1002
atccgtcaca cctgctctcc atgatttagt ttatttcacc aattacctct gtcttggtgt    60
tggctcccgt at                                                        72

<210> SEQ ID NO 1003
<211> LENGTH: 72
<212> TYPE: DNA
<213> ORGANISM: Artificial Sequence
<220> FEATURE:
<223> OTHER INFORMATION: chemically synthesized

<400> SEQUENCE: 1003
atacgggagc caacaccata gtctctactc gaattgcacc caacatgtct cagtagagca    60
ggtgtgacgg at                                                        72

<210> SEQ ID NO 1004
<211> LENGTH: 72
<212> TYPE: DNA
<213> ORGANISM: Artificial Sequence
<220> FEATURE:
<223> OTHER INFORMATION: chemically synthesized

<400> SEQUENCE: 1004
atccgtcaca cctgctctac tgagacatgt tgggtgcaat tcgagtagag actatggtgt    60
tggctcccgt at                                                        72

<210> SEQ ID NO 1005
<211> LENGTH: 72
<212> TYPE: DNA
<213> ORGANISM: Artificial Sequence
<220> FEATURE:
<223> OTHER INFORMATION: chemically synthesized

<400> SEQUENCE: 1005
atacgggagc caacaccatg ggataaacca taaagtctct gtgtaaactg cgcaagagca    60
ggtgtgacgg at                                                        72

<210> SEQ ID NO 1006
<211> LENGTH: 72
<212> TYPE: DNA
<213> ORGANISM: Artificial Sequence
<220> FEATURE:
<223> OTHER INFORMATION: chemically synthesized
```

```
<400> SEQUENCE: 1006
atccgtcaca cctgctcttg cgcagtttac acagagactt tatggtttat cccatggtgt    60
tggctcccgt at                                                        72

<210> SEQ ID NO 1007
<211> LENGTH: 72
<212> TYPE: DNA
<213> ORGANISM: Artificial Sequence
<220> FEATURE:
<223> OTHER INFORMATION: chemically synthesized

<400> SEQUENCE: 1007
atacgggagc caacaccact agttaggtct actgggtctg aaaaggtggt agtgagagca    60
ggtgtgacgg at                                                        72

<210> SEQ ID NO 1008
<211> LENGTH: 72
<212> TYPE: DNA
<213> ORGANISM: Artificial Sequence
<220> FEATURE:
<223> OTHER INFORMATION: chemically synthesized

<400> SEQUENCE: 1008
atccgtcaca cctgctctca ctaccacctt ttcagaccca gtagacctaa ctagtggtgt    60
tggctcccgt at                                                        72

<210> SEQ ID NO 1009
<211> LENGTH: 72
<212> TYPE: DNA
<213> ORGANISM: Artificial Sequence
<220> FEATURE:
<223> OTHER INFORMATION: chemically synthesized

<400> SEQUENCE: 1009
atacgggagc caacaccact aaactatact cagtgataaa gtcagaatgt gccgagagca    60
ggtgtgacgg at                                                        72

<210> SEQ ID NO 1010
<211> LENGTH: 72
<212> TYPE: DNA
<213> ORGANISM: Artificial Sequence
<220> FEATURE:
<223> OTHER INFORMATION: chemically synthesized

<400> SEQUENCE: 1010
atccgtcaca cctgctctcg gcacattctg actttatcac tgagtatagt ttagtggtgt    60
tggctcccgt at                                                        72

<210> SEQ ID NO 1011
<211> LENGTH: 72
<212> TYPE: DNA
<213> ORGANISM: Artificial Sequence
<220> FEATURE:
<223> OTHER INFORMATION: chemically synthesized

<400> SEQUENCE: 1011
atacgggagc caacaccacc acggactagt acattagaaa tcgcatacaa cagcagagca    60
ggtgtgacgg at                                                        72

<210> SEQ ID NO 1012
```

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 1012
atccgtcaca cctgctctgc tgttgtatgc gatttctaat gtactagtcc gtggtggtgt    60
tggctcccgt at                                                       72

<210> SEQ ID NO 1013
<211> LENGTH: 72
<212> TYPE: DNA
<213> ORGANISM: Artificial Sequence
<220> FEATURE:
<223> OTHER INFORMATION: chemically synthesized

<400> SEQUENCE: 1013
atacgggagc caacaccaaa aaatctgagg ggaaaatttg accaagctga ctagagagca    60
ggtgtgacgg at                                                       72

<210> SEQ ID NO 1014
<211> LENGTH: 72
<212> TYPE: DNA
<213> ORGANISM: Artificial Sequence
<220> FEATURE:
<223> OTHER INFORMATION: chemically synthesized

<400> SEQUENCE: 1014
atccgtcaca cctgctctct agtcagcttg gtcaaatttt cccctcagat tttttggtgt    60
tggctcccgt at                                                       72

<210> SEQ ID NO 1015
<211> LENGTH: 71
<212> TYPE: DNA
<213> ORGANISM: Artificial Sequence
<220> FEATURE:
<223> OTHER INFORMATION: chemically synthesized

<400> SEQUENCE: 1015
atacgggagc caacaccacg tatgtggaag tcgaatcaaa aggcgacgac ctcagagcag    60
gtgtgacgga t                                                        71

<210> SEQ ID NO 1016
<211> LENGTH: 71
<212> TYPE: DNA
<213> ORGANISM: Artificial Sequence
<220> FEATURE:
<223> OTHER INFORMATION: chemically synthesized

<400> SEQUENCE: 1016
atccgtcaca cctgctctga ggtcgtcgcc ttttgattcg acttccacat acgtggtgtt    60
ggctcccgta t                                                        71

<210> SEQ ID NO 1017
<211> LENGTH: 72
<212> TYPE: DNA
<213> ORGANISM: Artificial Sequence
<220> FEATURE:
<223> OTHER INFORMATION: chemically synthesized

<400> SEQUENCE: 1017
atacgggagc caacaccagg gacatagtag ataggattga aaagtcgacc gttgagagca    60
```
ggtgtgacgg at                                                          72

<210> SEQ ID NO 1018
<211> LENGTH: 72
<212> TYPE: DNA
<213> ORGANISM: Artificial Sequence
<220> FEATURE:
<223> OTHER INFORMATION: chemically synthesized

<400> SEQUENCE: 1018
atccgtcaca cctgctctca acggtcgact tttcaatcct atctactatg tccctggtgt     60
tggctcccgt at                                                          72

<210> SEQ ID NO 1019
<211> LENGTH: 72
<212> TYPE: DNA
<213> ORGANISM: Artificial Sequence
<220> FEATURE:
<223> OTHER INFORMATION: chemically synthesized

<400> SEQUENCE: 1019
atacgggagc caacaccaat cccggacttc tcaacagaga tccctatctt accgagagca     60
ggtgtgacgg at                                                          72

<210> SEQ ID NO 1020
<211> LENGTH: 72
<212> TYPE: DNA
<213> ORGANISM: Artificial Sequence
<220> FEATURE:
<223> OTHER INFORMATION: chemically synthesized

<400> SEQUENCE: 1020
atccgtcaca cctgctctcg gtaagatagg gatctctgtt gagaagtccg ggattggtgt     60
tggctcccgt at                                                          72

<210> SEQ ID NO 1021
<211> LENGTH: 72
<212> TYPE: DNA
<213> ORGANISM: Artificial Sequence
<220> FEATURE:
<223> OTHER INFORMATION: chemically synthesized

<400> SEQUENCE: 1021
atacgggagc caacaccact gacggacccc cgggatggga caacctcatc taccagagca     60
ggtgtgacgg at                                                          72

<210> SEQ ID NO 1022
<211> LENGTH: 72
<212> TYPE: DNA
<213> ORGANISM: Artificial Sequence
<220> FEATURE:
<223> OTHER INFORMATION: chemically synthesized

<400> SEQUENCE: 1022
atccgtcaca cctgctctgg tagatgaggt tgtcccatcc cggggtccg tcagtggtgt      60 tggctcccgt at                                                          72

<210> SEQ ID NO 1023
<211> LENGTH: 72
<212> TYPE: DNA
<213> ORGANISM: Artificial Sequence
<220> FEATURE:

<223> OTHER INFORMATION: chemically synthesized

<400> SEQUENCE: 1023
atacgggagc caacaccacg tcctgtgaaa ttgcgcggct atactagtgt ggtcagagca    60
ggtgtgacgg at    72

<210> SEQ ID NO 1024
<211> LENGTH: 72
<212> TYPE: DNA
<213> ORGANISM: Artificial Sequence
<220> FEATURE:
<223> OTHER INFORMATION: chemically synthesized

<400> SEQUENCE: 1024
atccgtcaca cctgctctga ccacactagt atagccgcgc aatttcacag gacgtggtgt    60
tggctcccgt at    72

<210> SEQ ID NO 1025
<211> LENGTH: 72
<212> TYPE: DNA
<213> ORGANISM: Artificial Sequence
<220> FEATURE:
<223> OTHER INFORMATION: chemically synthesized

<400> SEQUENCE: 1025
atacgggagc caacaccaca atggcgacac tcctgacctg ttgagtggtt ttatagagca    60
ggtgtgacgg at    72

<210> SEQ ID NO 1026
<211> LENGTH: 72
<212> TYPE: DNA
<213> ORGANISM: Artificial Sequence
<220> FEATURE:
<223> OTHER INFORMATION: chemically synthesized

<400> SEQUENCE: 1026
atccgtcaca cctgctctat aaaaccactc aacaggtcag gagtgtcgcc attgtggtgt    60
tggctcccgt at    72

<210> SEQ ID NO 1027
<211> LENGTH: 72
<212> TYPE: DNA
<213> ORGANISM: Artificial Sequence
<220> FEATURE:
<223> OTHER INFORMATION: chemically synthesized

<400> SEQUENCE: 1027
atacgggagc caacaccaac cataaaacca caaaatataa attccaaacc ccagagagca    60
ggtgtgacgg at    72

<210> SEQ ID NO 1028
<211> LENGTH: 72
<212> TYPE: DNA
<213> ORGANISM: Artificial Sequence
<220> FEATURE:
<223> OTHER INFORMATION: chemically synthesized

<400> SEQUENCE: 1028
atccgtcaca cctgctctct ggggtttgga atttatattt tgtggtttta tggttggtgt    60
tggctcccgt at    72

```
<210> SEQ ID NO 1029
<211> LENGTH: 72
<212> TYPE: DNA
<213> ORGANISM: Artificial Sequence
<220> FEATURE:
<223> OTHER INFORMATION: chemically synthesized

<400> SEQUENCE: 1029
atacgggagc caacaccatc tctcttagga tacaaagcca aactgagccc gtgcagagca    60
ggtgtgacgg at                                                       72

<210> SEQ ID NO 1030
<211> LENGTH: 72
<212> TYPE: DNA
<213> ORGANISM: Artificial Sequence
<220> FEATURE:
<223> OTHER INFORMATION: chemically synthesized

<400> SEQUENCE: 1030
atccgtcaca cctgctctgc acgggctcag tttggctttg tatcctaaga gagatggtgt    60
tggctcccgt at                                                       72

<210> SEQ ID NO 1031
<211> LENGTH: 72
<212> TYPE: DNA
<213> ORGANISM: Artificial Sequence
<220> FEATURE:
<223> OTHER INFORMATION: chemically synthesized

<400> SEQUENCE: 1031
atacgggagc caacaccact taagcggtgt actataactg agataggagt gagcagagca    60
ggtgtgacgg at                                                       72

<210> SEQ ID NO 1032
<211> LENGTH: 72
<212> TYPE: DNA
<213> ORGANISM: Artificial Sequence
<220> FEATURE:
<223> OTHER INFORMATION: chemically synthesized

<400> SEQUENCE: 1032
atccgtcaca cctgctctgc tcactcctat ctcagttata gtacaccgct taagtggtgt    60
tggctcccgt at                                                       72

<210> SEQ ID NO 1033
<211> LENGTH: 72
<212> TYPE: DNA
<213> ORGANISM: Artificial Sequence
<220> FEATURE:
<223> OTHER INFORMATION: chemically synthesized

<400> SEQUENCE: 1033
atacgggagc caacaccaac tctcccttcc ttcttcccac cctccctctc gtccagagca    60
ggtgtgacgg at                                                       72

<210> SEQ ID NO 1034
<211> LENGTH: 72
<212> TYPE: DNA
<213> ORGANISM: Artificial Sequence
<220> FEATURE:
<223> OTHER INFORMATION: chemically synthesized

<400> SEQUENCE: 1034
```
atccgtcaca cctgctctgg acgagaggga gggtgggaag aaggaaggga gagttggtgt    60
tggctcccgt at    72

<210> SEQ ID NO 1035
<211> LENGTH: 72
<212> TYPE: DNA
<213> ORGANISM: Artificial Sequence
<220> FEATURE:
<223> OTHER INFORMATION: chemically synthesized

<400> SEQUENCE: 1035
atacgggagc caacaccact tgaacgatgc cgcggccttt ggatctgtgg tgggagagca    60
ggtgtgacgg at    72

<210> SEQ ID NO 1036
<211> LENGTH: 72
<212> TYPE: DNA
<213> ORGANISM: Artificial Sequence
<220> FEATURE:
<223> OTHER INFORMATION: chemically synthesized

<400> SEQUENCE: 1036
atccgtcaca cctgctctcc caccacagat ccaaaggccg cggcatcgtt caagtggtgt    60
tggctcccgt at    72

<210> SEQ ID NO 1037
<211> LENGTH: 72
<212> TYPE: DNA
<213> ORGANISM: Artificial Sequence
<220> FEATURE:
<223> OTHER INFORMATION: chemically synthesized

<400> SEQUENCE: 1037
atacgggagc caacaccact aacggctaca ctattcctta gacctcccct ctgtagagca    60
ggtgtgacgg at    72

<210> SEQ ID NO 1038
<211> LENGTH: 72
<212> TYPE: DNA
<213> ORGANISM: Artificial Sequence
<220> FEATURE:
<223> OTHER INFORMATION: chemically synthesized

<400> SEQUENCE: 1038
atccgtcaca cctgctctac agagggagg tctaaggaat agtgtagccg ttagtggtgt    60
tggctcccgt at    72

<210> SEQ ID NO 1039
<211> LENGTH: 72
<212> TYPE: DNA
<213> ORGANISM: Artificial Sequence
<220> FEATURE:
<223> OTHER INFORMATION: chemically synthesized

<400> SEQUENCE: 1039
atacgggagc caacaccaac tagtaacggt tctgattcct aaatattttt ccacagagca    60
ggtgtgacgg at    72

<210> SEQ ID NO 1040
<211> LENGTH: 72
<212> TYPE: DNA
<213> ORGANISM: Artificial Sequence
<220> FEATURE:
<223> OTHER INFORMATION: chemically synthesized

<400> SEQUENCE: 1040
atccgtcaca cctgctctgt ggaaaaatat ttaggaatca gaaccgttac tagttggtgt    60
tggctcccgt at    72

<210> SEQ ID NO 1041
<211> LENGTH: 72
<212> TYPE: DNA
<213> ORGANISM: Artificial Sequence
<220> FEATURE:
<223> OTHER INFORMATION: chemically synthesized

<400> SEQUENCE: 1041
atacgggagc caacaccata tagtgttata taaacaaagg aatagaaatt ggtgagagca    60
ggtgtgacgg at    72

<210> SEQ ID NO 1042
<211> LENGTH: 72
<212> TYPE: DNA
<213> ORGANISM: Artificial Sequence
<220> FEATURE:
<223> OTHER INFORMATION: chemically synthesized

<400> SEQUENCE: 1042
atccgtcaca cctgctctca ccaatttcta ttcctttgtt tatataacac tatatggtgt    60
tggctcccgt at    72

<210> SEQ ID NO 1043
<211> LENGTH: 72
<212> TYPE: DNA
<213> ORGANISM: Artificial Sequence
<220> FEATURE:
<223> OTHER INFORMATION: chemically synthesized

<400> SEQUENCE: 1043
atacgggagc caacaccacc atatatcaac attcaaccgc ttttctacg acccagagca    60 ggtgtgacgg at    72

<210> SEQ ID NO 1044
<211> LENGTH: 72
<212> TYPE: DNA
<213> ORGANISM: Artificial Sequence
<220> FEATURE:
<223> OTHER INFORMATION: chemically synthesized

<400> SEQUENCE: 1044
atccgtcaca cctgctctgg gtcgtagaaa aagcggttga atgttgatat atggtggtgt    60
tggctcccgt at    72

<210> SEQ ID NO 1045
<211> LENGTH: 72
<212> TYPE: DNA
<213> ORGANISM: Artificial Sequence
<220> FEATURE:
<223> OTHER INFORMATION: chemically synthesized

<400> SEQUENCE: 1045
atacgggagc caacaccata tttatagtac aagaaaaaca ccatggacgt gtacagagca    60
ggtgtgacgg at    72

<210> SEQ ID NO 1046
<211> LENGTH: 72
<212> TYPE: DNA
<213> ORGANISM: Artificial Sequence
<220> FEATURE:
<223> OTHER INFORMATION: chemically synthesized

<400> SEQUENCE: 1046
atccgtcaca cctgctctgt acacgtccat ggtgttttc ttgtactata aatatggtgt    60
tggctcccgt at                                                       72

<210> SEQ ID NO 1047
<211> LENGTH: 72
<212> TYPE: DNA
<213> ORGANISM: Artificial Sequence
<220> FEATURE:
<223> OTHER INFORMATION: chemically synthesized

<400> SEQUENCE: 1047
atacgggagc caacaccatt gttactatta acatatcagt ggcggatgtt cacgagagca    60
ggtgtgacgg at                                                       72

<210> SEQ ID NO 1048
<211> LENGTH: 72
<212> TYPE: DNA
<213> ORGANISM: Artificial Sequence
<220> FEATURE:
<223> OTHER INFORMATION: chemically synthesized

<400> SEQUENCE: 1048
atccgtcaca cctgctctcg tgaacatccg ccactgatat gttaatagta acaatggtgt    60
tggctcccgt at                                                       72

<210> SEQ ID NO 1049
<211> LENGTH: 72
<212> TYPE: DNA
<213> ORGANISM: Artificial Sequence
<220> FEATURE:
<223> OTHER INFORMATION: chemically synthesized

<400> SEQUENCE: 1049
atacgggagc caacaccaga atgaatttat gaataaggaa ggctggagag ccctagagca    60
ggtgtgacgg at                                                       72

<210> SEQ ID NO 1050
<211> LENGTH: 72
<212> TYPE: DNA
<213> ORGANISM: Artificial Sequence
<220> FEATURE:
<223> OTHER INFORMATION: chemically synthesized

<400> SEQUENCE: 1050
atccgtcaca cctgctctag ggctctccag ccttccttat tcataaattc attctggtgt    60
tggctcccgt at                                                       72

<210> SEQ ID NO 1051
<211> LENGTH: 72
<212> TYPE: DNA
<213> ORGANISM: Artificial Sequence
<220> FEATURE:
<223> OTHER INFORMATION: chemically synthesized

<400> SEQUENCE: 1051

```
atacgggagc caacaccata agataaaggt agacgtaata tagtaactat atacagagca    60
ggtgtgacgg at                                                        72

<210> SEQ ID NO 1052
<211> LENGTH: 72
<212> TYPE: DNA
<213> ORGANISM: Artificial Sequence
<220> FEATURE:
<223> OTHER INFORMATION: chemically synthesized

<400> SEQUENCE: 1052
atccgtcaca cctgctctgt atatagttac tatattacgt ctacctttat cttatggtgt    60
tggctcccgt at                                                        72

<210> SEQ ID NO 1053
<211> LENGTH: 72
<212> TYPE: DNA
<213> ORGANISM: Artificial Sequence
<220> FEATURE:
<223> OTHER INFORMATION: chemically synthesized

<400> SEQUENCE: 1053
atacgggagc caacaccata cgtgtttata attacactga atgaataaga tagtagagca    60
ggtgtgacgg at                                                        72

<210> SEQ ID NO 1054
<211> LENGTH: 72
<212> TYPE: DNA
<213> ORGANISM: Artificial Sequence
<220> FEATURE:
<223> OTHER INFORMATION: chemically synthesized

<400> SEQUENCE: 1054
atccgtcaca cctgctctac tatcttattc attcagtgta attataaaca cgtatggtgt    60
tggctcccgt at                                                        72

<210> SEQ ID NO 1055
<211> LENGTH: 71
<212> TYPE: DNA
<213> ORGANISM: Artificial Sequence
<220> FEATURE:
<223> OTHER INFORMATION: chemically synthesized

<400> SEQUENCE: 1055
atacgggagc caacaccaca tcaaaattat tattgtcctg tatggagtta gacagagcag    60
gtgtgacgga t                                                         71

<210> SEQ ID NO 1056
<211> LENGTH: 71
<212> TYPE: DNA
<213> ORGANISM: Artificial Sequence
<220> FEATURE:
<223> OTHER INFORMATION: chemically synthesized

<400> SEQUENCE: 1056
atccgtcaca cctgctctgt ctaactccat acaggacaat aataattttg atgtggtgtt    60
ggctcccgta t                                                         71

<210> SEQ ID NO 1057
<211> LENGTH: 72
<212> TYPE: DNA
```

```
<213> ORGANISM: Artificial Sequence
<220> FEATURE:
<223> OTHER INFORMATION: chemically synthesized

<400> SEQUENCE: 1057
atacgggagc caacaccata acccaaaagg gcgggggatg tattacttag caccagagca      60
ggtgtgacgg at                                                         72

<210> SEQ ID NO 1058
<211> LENGTH: 72
<212> TYPE: DNA
<213> ORGANISM: Artificial Sequence
<220> FEATURE:
<223> OTHER INFORMATION: chemically synthesized

<400> SEQUENCE: 1058
atccgtcaca cctgctctgg tgctaagtaa tacatccccc gcccttttgg gttatggtgt      60
tggctcccgt at                                                         72

<210> SEQ ID NO 1059
<211> LENGTH: 72
<212> TYPE: DNA
<213> ORGANISM: Artificial Sequence
<220> FEATURE:
<223> OTHER INFORMATION: chemically synthesized

<400> SEQUENCE: 1059
atacgggagc caacaccata tgatttacta ctttacagag gaagctcgtg ttgcagagca      60
ggtgtgacgg at                                                         72

<210> SEQ ID NO 1060
<211> LENGTH: 72
<212> TYPE: DNA
<213> ORGANISM: Artificial Sequence
<220> FEATURE:
<223> OTHER INFORMATION: chemically synthesized

<400> SEQUENCE: 1060
atccgtcaca cctgctctgc aacacgagct tcctctgtaa agtagtaaat catatggtgt      60
tggctcccgt at                                                         72

<210> SEQ ID NO 1061
<211> LENGTH: 72
<212> TYPE: DNA
<213> ORGANISM: Artificial Sequence
<220> FEATURE:
<223> OTHER INFORMATION: chemically synthesized

<400> SEQUENCE: 1061
atacgggagc caacaccacc acctatcgac ttttgcactg gaccctagct ccccagagca      60
ggtgtgacgg at                                                         72

<210> SEQ ID NO 1062
<211> LENGTH: 72
<212> TYPE: DNA
<213> ORGANISM: Artificial Sequence
<220> FEATURE:
<223> OTHER INFORMATION: chemically synthesized

<400> SEQUENCE: 1062
atccgtcaca cctgctctgg ggagctaggg tccagtgcaa aagtcgatag gtggtggtgt      60
tggctcccgt at                                                         72
```

<210> SEQ ID NO 1063
<211> LENGTH: 72
<212> TYPE: DNA
<213> ORGANISM: Artificial Sequence
<220> FEATURE:
<223> OTHER INFORMATION: chemically synthesized

<400> SEQUENCE: 1063
atacgggagc caacaccact aatcaaatct taggacgttc aaggtaagat cggcagagca    60
ggtgtgacgg at    72

<210> SEQ ID NO 1064
<211> LENGTH: 72
<212> TYPE: DNA
<213> ORGANISM: Artificial Sequence
<220> FEATURE:
<223> OTHER INFORMATION: chemically synthesized

<400> SEQUENCE: 1064
atccgtcaca cctgctctgc cgatcttacc ttgaacgtcc taagatttga ttagtggtgt    60
tggctcccgt at    72

<210> SEQ ID NO 1065
<211> LENGTH: 68
<212> TYPE: DNA
<213> ORGANISM: Artificial Sequence
<220> FEATURE:
<223> OTHER INFORMATION: chemically synthesized

<400> SEQUENCE: 1065
atacgggagc caacaccatc tagaaaaagg aacgagcctt ccacatgtcc agagcaggtg    60
tgacggat    68

<210> SEQ ID NO 1066
<211> LENGTH: 68
<212> TYPE: DNA
<213> ORGANISM: Artificial Sequence
<220> FEATURE:
<223> OTHER INFORMATION: chemically synthesized

<400> SEQUENCE: 1066
atccgtcaca cctgctctgg acatgtggaa ggctcgttcc tttttctaga tggtgttggc    60
tcccgtat    68

<210> SEQ ID NO 1067
<211> LENGTH: 71
<212> TYPE: DNA
<213> ORGANISM: Artificial Sequence
<220> FEATURE:
<223> OTHER INFORMATION: chemically synthesized

<400> SEQUENCE: 1067
atacgggagc caacaccact actctcccgc gccccgttgc cccccataa ccaagagcag    60 gtgtgacgga t    71

<210> SEQ ID NO 1068
<211> LENGTH: 71
<212> TYPE: DNA
<213> ORGANISM: Artificial Sequence
<220> FEATURE:
<223> OTHER INFORMATION: chemically synthesized

<400> SEQUENCE: 1068
atccgtcaca cctgctcttg gttatggggg ggcaacgggg cgcgggagag tagtggtgtt    60
ggctcccgta t                                                         71

<210> SEQ ID NO 1069
<211> LENGTH: 72
<212> TYPE: DNA
<213> ORGANISM: Artificial Sequence
<220> FEATURE:
<223> OTHER INFORMATION: chemically synthesized

<400> SEQUENCE: 1069
atacgggagc caacaccatt tgtatagaat aacagcaatt acattccaca acccagagca    60
ggtgtgacgg at                                                        72

<210> SEQ ID NO 1070
<211> LENGTH: 72
<212> TYPE: DNA
<213> ORGANISM: Artificial Sequence
<220> FEATURE:
<223> OTHER INFORMATION: chemically synthesized

<400> SEQUENCE: 1070
atccgtcaca cctgctctgg gttgtggaat gtaattgctg ttattctata caaatggtgt    60
tggctcccgt at                                                        72

<210> SEQ ID NO 1071
<211> LENGTH: 72
<212> TYPE: DNA
<213> ORGANISM: Artificial Sequence
<220> FEATURE:
<223> OTHER INFORMATION: chemically synthesized

<400> SEQUENCE: 1071
atacgggagc caacaccagc ataaattgta tatagtggta ccctttttc atggagagca     60 ggtgtgacgg at                                                        72

<210> SEQ ID NO 1072
<211> LENGTH: 72
<212> TYPE: DNA
<213> ORGANISM: Artificial Sequence
<220> FEATURE:
<223> OTHER INFORMATION: chemically synthesized

<400> SEQUENCE: 1072
atccgtcaca cctgctctcc atgaaaaaag ggtaccacta tatacaattt atgctggtgt    60
tggctcccgt at                                                        72

<210> SEQ ID NO 1073
<211> LENGTH: 72
<212> TYPE: DNA
<213> ORGANISM: Artificial Sequence
<220> FEATURE:
<223> OTHER INFORMATION: chemically synthesized

<400> SEQUENCE: 1073
atacgggagc caacaccaca tcttctcgcc ctccccccgc cgccccggaa cccgagagca    60
ggtgtgacgg at                                                        72

<210> SEQ ID NO 1074
<211> LENGTH: 72

```
<212> TYPE: DNA
<213> ORGANISM: Artificial Sequence
<220> FEATURE:
<223> OTHER INFORMATION: chemically synthesized

<400> SEQUENCE: 1074
atccgtcaca cctgctctcg ggttccgggg cggcgggggg agggcgagaa gatgtggtgt      60
tggctcccgt at                                                         72

<210> SEQ ID NO 1075
<211> LENGTH: 72
<212> TYPE: DNA
<213> ORGANISM: Artificial Sequence
<220> FEATURE:
<223> OTHER INFORMATION: chemically synthesized

<400> SEQUENCE: 1075
atacgggagc caacaccaga cgaacatata taacaattcg ttaatggatg cgtcagagca      60
ggtgtgacgg at                                                         72

<210> SEQ ID NO 1076
<211> LENGTH: 72
<212> TYPE: DNA
<213> ORGANISM: Artificial Sequence
<220> FEATURE:
<223> OTHER INFORMATION: chemically synthesized

<400> SEQUENCE: 1076
atccgtcaca cctgctctga cgcatccatt aacgaattgt tatatatgtt cgtctggtgt      60
tggctcccgt at                                                         72

<210> SEQ ID NO 1077
<211> LENGTH: 72
<212> TYPE: DNA
<213> ORGANISM: Artificial Sequence
<220> FEATURE:
<223> OTHER INFORMATION: chemically synthesized

<400> SEQUENCE: 1077
atacgggagc caacaccacg actgccaccg aattacttaa actcatttag agcgagagca      60
ggtgtgacgg at                                                         72

<210> SEQ ID NO 1078
<211> LENGTH: 72
<212> TYPE: DNA
<213> ORGANISM: Artificial Sequence
<220> FEATURE:
<223> OTHER INFORMATION: chemically synthesized

<400> SEQUENCE: 1078
atccgtcaca cctgctctcg ctctaaatga gtttaagtaa ttcggtggca gtcgtggtgt      60
tggctcccgt at                                                         72

<210> SEQ ID NO 1079
<211> LENGTH: 72
<212> TYPE: DNA
<213> ORGANISM: Artificial Sequence
<220> FEATURE:
<223> OTHER INFORMATION: chemically synthesized

<400> SEQUENCE: 1079
atacgggagc caacaccacc caacaaacta ctcacccatc ctaatcaacc ttcgagagca      60
```

```
ggtgtgacgg at                                                         72
```

<210> SEQ ID NO 1080
<211> LENGTH: 72
<212> TYPE: DNA
<213> ORGANISM: Artificial Sequence
<220> FEATURE:
<223> OTHER INFORMATION: chemically synthesized

<400> SEQUENCE: 1080

```
atccgtcaca cctgctctcg aaggttgatt aggatgggtg agtagtttgt tgggtggtgt     60
tggctcccgt at                                                         72
```

<210> SEQ ID NO 1081
<211> LENGTH: 72
<212> TYPE: DNA
<213> ORGANISM: Artificial Sequence
<220> FEATURE:
<223> OTHER INFORMATION: chemically synthesized

<400> SEQUENCE: 1081

```
atacgggagc caacaccagg gagagagaac gtacccgaac ttttcttac tgagagagca      60 ggtgtgacgg at                                                         72
```

<210> SEQ ID NO 1082
<211> LENGTH: 72
<212> TYPE: DNA
<213> ORGANISM: Artificial Sequence
<220> FEATURE:
<223> OTHER INFORMATION: chemically synthesized

<400> SEQUENCE: 1082

```
atccgtcaca cctgctctct cagtaagaaa aagttcgggt acgttctctc tccctggtgt     60
tggctcccgt at                                                         72
```

<210> SEQ ID NO 1083
<211> LENGTH: 72
<212> TYPE: DNA
<213> ORGANISM: Artificial Sequence
<220> FEATURE:
<223> OTHER INFORMATION: chemically synthesized

<400> SEQUENCE: 1083

```
atacgggagc caacaccacg cacacttcac caatacgatc cagcccggaa tgatagagca     60
ggtgtgacgg at                                                         72
```

<210> SEQ ID NO 1084
<211> LENGTH: 72
<212> TYPE: DNA
<213> ORGANISM: Artificial Sequence
<220> FEATURE:
<223> OTHER INFORMATION: chemically synthesized

<400> SEQUENCE: 1084

```
atccgtcaca cctgctctat cattccgggc tggatcgtat tggtgaagtg tgcgtggtgt     60
tggctcccgt at                                                         72
```

<210> SEQ ID NO 1085
<211> LENGTH: 72
<212> TYPE: DNA
<213> ORGANISM: Artificial Sequence
<220> FEATURE:
<223> OTHER INFORMATION: chemically synthesized

```
<400> SEQUENCE: 1085
atacgggagc caacaccatc gcagcaatct attcttagat ctcctatttc gtcaagagca    60
ggtgtgacgg at                                                        72

<210> SEQ ID NO 1086
<211> LENGTH: 72
<212> TYPE: DNA
<213> ORGANISM: Artificial Sequence
<220> FEATURE:
<223> OTHER INFORMATION: chemically synthesized

<400> SEQUENCE: 1086
atccgtcaca cctgctcttg acgaaatagg agatctaaga atagattgct gcgatggtgt    60
tggctcccgt at                                                        72

<210> SEQ ID NO 1087
<211> LENGTH: 72
<212> TYPE: DNA
<213> ORGANISM: Artificial Sequence
<220> FEATURE:
<223> OTHER INFORMATION: chemically synthesized

<400> SEQUENCE: 1087
atacgggagc caacaccagt aaatatcaaa tccctatcct cctccttcga taggagagca    60
ggtgtgacgg at                                                        72

<210> SEQ ID NO 1088
<211> LENGTH: 72
<212> TYPE: DNA
<213> ORGANISM: Artificial Sequence
<220> FEATURE:
<223> OTHER INFORMATION: chemically synthesized

<400> SEQUENCE: 1088
atccgtcaca cctgctctcc tatcgaagga ggaggatagg gatttgatat ttactggtgt    60
tggctcccgt at                                                        72

<210> SEQ ID NO 1089
<211> LENGTH: 72
<212> TYPE: DNA
<213> ORGANISM: Artificial Sequence
<220> FEATURE:
<223> OTHER INFORMATION: chemically synthesized

<400> SEQUENCE: 1089
atacgggagc caacaccacc ccaggtttgc ccgcctatat cgcattcgtc ctctagagca    60
ggtgtgacgg at                                                        72

<210> SEQ ID NO 1090
<211> LENGTH: 72
<212> TYPE: DNA
<213> ORGANISM: Artificial Sequence
<220> FEATURE:
<223> OTHER INFORMATION: chemically synthesized

<400> SEQUENCE: 1090
atccgtcaca cctgctctag aggacgaatg cgatataggc gggcaaacct ggggtggtgt    60
tggctcccgt at                                                        72

<210> SEQ ID NO 1091
```

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 1091
atacgggagc caacaccatc gtgtactatt cctgtgggtg gacactacag ggccagagca      60
ggtgtgacgg at                                                         72

<210> SEQ ID NO 1092
<211> LENGTH: 72
<212> TYPE: DNA
<213> ORGANISM: Artificial Sequence
<220> FEATURE:
<223> OTHER INFORMATION: chemically synthesized

<400> SEQUENCE: 1092
atccgtcaca cctgctctgg ccctgtagtg tccacccaca ggaatagtac acgatggtgt      60
tggctcccgt at                                                         72

<210> SEQ ID NO 1093
<211> LENGTH: 72
<212> TYPE: DNA
<213> ORGANISM: Artificial Sequence
<220> FEATURE:
<223> OTHER INFORMATION: chemically synthesized

<400> SEQUENCE: 1093
atacgggagc caacaccacc tctcccacac cagcccagcc cccgcgccat tccaagagca      60
ggtgtgacgg at                                                         72

<210> SEQ ID NO 1094
<211> LENGTH: 72
<212> TYPE: DNA
<213> ORGANISM: Artificial Sequence
<220> FEATURE:
<223> OTHER INFORMATION: chemically synthesized

<400> SEQUENCE: 1094
atccgtcaca cctgctcttg aatggcgcg ggggctgggc tggtgtggga gaggtggtgt       60
tggctcccgt at                                                         72

<210> SEQ ID NO 1095
<211> LENGTH: 72
<212> TYPE: DNA
<213> ORGANISM: Artificial Sequence
<220> FEATURE:
<223> OTHER INFORMATION: chemically synthesized

<400> SEQUENCE: 1095
atacgggagc caacaccagt gtaagtgttg attgtctttt ttgtgaatta gcggagagca      60
ggtgtgacgg at                                                         72

<210> SEQ ID NO 1096
<211> LENGTH: 72
<212> TYPE: DNA
<213> ORGANISM: Artificial Sequence
<220> FEATURE:
<223> OTHER INFORMATION: chemically synthesized

<400> SEQUENCE: 1096
atccgtcaca cctgctctcc gctaattcac aaaaaagaca atcaacactt acactggtgt      60
```
tggctcccgt at                                                         72

<210> SEQ ID NO 1097
<211> LENGTH: 72
<212> TYPE: DNA
<213> ORGANISM: Artificial Sequence
<220> FEATURE:
<223> OTHER INFORMATION: chemically synthesized

<400> SEQUENCE: 1097
atacgggagc caacaccacg tgacaattat ccatacgccg cgcaatccgc tgttagagca     60
ggtgtgacgg at                                                         72

<210> SEQ ID NO 1098
<211> LENGTH: 72
<212> TYPE: DNA
<213> ORGANISM: Artificial Sequence
<220> FEATURE:
<223> OTHER INFORMATION: chemically synthesized

<400> SEQUENCE: 1098
atccgtcaca cctgctctaa cagcggattg cgcggcgtat ggataattgt cacgtggtgt     60
tggctcccgt at                                                         72

<210> SEQ ID NO 1099
<211> LENGTH: 72
<212> TYPE: DNA
<213> ORGANISM: Artificial Sequence
<220> FEATURE:
<223> OTHER INFORMATION: chemically synthesized

<400> SEQUENCE: 1099
atacgggagc caacaccacc cctaagttcg ttgcaacata ccccaggcac tcttagagca     60
ggtgtgacgg at                                                         72

<210> SEQ ID NO 1100
<211> LENGTH: 72
<212> TYPE: DNA
<213> ORGANISM: Artificial Sequence
<220> FEATURE:
<223> OTHER INFORMATION: chemically synthesized

<400> SEQUENCE: 1100
atccgtcaca cctgctctaa gagtgcctgg ggtatgttgc aacgaactta ggggtggtgt     60
tggctcccgt at                                                         72

<210> SEQ ID NO 1101
<211> LENGTH: 72
<212> TYPE: DNA
<213> ORGANISM: Artificial Sequence
<220> FEATURE:
<223> OTHER INFORMATION: chemically synthesized

<400> SEQUENCE: 1101
atacgggagc caacaccagc cagcgacgag gtgtatagag gtgaggttac tttgagagca     60
ggtgtgacgg at                                                         72

<210> SEQ ID NO 1102
<211> LENGTH: 72
<212> TYPE: DNA
<213> ORGANISM: Artificial Sequence
<220> FEATURE:

<223> OTHER INFORMATION: chemically synthesized

<400> SEQUENCE: 1102
atccgtcaca cctgctctca aagtaacctc acctctatac acctcgtcgc tggctggtgt    60
tggctcccgt at    72

<210> SEQ ID NO 1103
<211> LENGTH: 72
<212> TYPE: DNA
<213> ORGANISM: Artificial Sequence
<220> FEATURE:
<223> OTHER INFORMATION: chemically synthesized

<400> SEQUENCE: 1103
atacgggagc caacaccaat cgttagttat aacagcacga cgactggata gtggagagca    60
ggtgtgacgg at    72

<210> SEQ ID NO 1104
<211> LENGTH: 72
<212> TYPE: DNA
<213> ORGANISM: Artificial Sequence
<220> FEATURE:
<223> OTHER INFORMATION: chemically synthesized

<400> SEQUENCE: 1104
atccgtcaca cctgctctcc actatccagt cgtcgtgctg ttataactaa cgattggtgt    60
tggctcccgt at    72

<210> SEQ ID NO 1105
<211> LENGTH: 72
<212> TYPE: DNA
<213> ORGANISM: Artificial Sequence
<220> FEATURE:
<223> OTHER INFORMATION: chemically synthesized

<400> SEQUENCE: 1105
atacgggagc caacaccagt ccgttatgac atgtccggac ccgtacgcgt gtcaagagca    60
ggtgtgacgg at    72

<210> SEQ ID NO 1106
<211> LENGTH: 72
<212> TYPE: DNA
<213> ORGANISM: Artificial Sequence
<220> FEATURE:
<223> OTHER INFORMATION: chemically synthesized

<400> SEQUENCE: 1106
atccgtcaca cctgctcttg acacgcgtac gggtccggac atgtcataac ggactggtgt    60
tggctcccgt at    72

<210> SEQ ID NO 1107
<211> LENGTH: 72
<212> TYPE: DNA
<213> ORGANISM: Artificial Sequence
<220> FEATURE:
<223> OTHER INFORMATION: chemically synthesized

<400> SEQUENCE: 1107
atacgggagc caacaccata acgagatagg tgagcctgaa atagtgggtt atgcagagca    60
ggtgtgacgg at    72

-continued

<210> SEQ ID NO 1108
<211> LENGTH: 72
<212> TYPE: DNA
<213> ORGANISM: Artificial Sequence
<220> FEATURE:
<223> OTHER INFORMATION: chemically synthesized

<400> SEQUENCE: 1108
atccgtcaca cctgctctgc ataacccact atttcaggct cacctatctc gttatggtgt     60
tggctcccgt at                                                          72

<210> SEQ ID NO 1109
<211> LENGTH: 72
<212> TYPE: DNA
<213> ORGANISM: Artificial Sequence
<220> FEATURE:
<223> OTHER INFORMATION: chemically synthesized

<400> SEQUENCE: 1109
atacgggagc caacaccagg ttactggtca cgatcaaagc tggtaattaa tgtgagagca     60
ggtgtgacgg at                                                          72

<210> SEQ ID NO 1110
<211> LENGTH: 72
<212> TYPE: DNA
<213> ORGANISM: Artificial Sequence
<220> FEATURE:
<223> OTHER INFORMATION: chemically synthesized

<400> SEQUENCE: 1110
atccgtcaca cctgctctca cattaattac cagctttgat cgtgaccagt aacctggtgt     60
tggctcccgt at                                                          72

<210> SEQ ID NO 1111
<211> LENGTH: 72
<212> TYPE: DNA
<213> ORGANISM: Artificial Sequence
<220> FEATURE:
<223> OTHER INFORMATION: chemically synthesized

<400> SEQUENCE: 1111
atacgggagc caacaccagc gagataaata gccagcccaa aaccggcgaa gtacagagca     60
ggtgtgacgg at                                                          72

<210> SEQ ID NO 1112
<211> LENGTH: 72
<212> TYPE: DNA
<213> ORGANISM: Artificial Sequence
<220> FEATURE:
<223> OTHER INFORMATION: chemically synthesized

<400> SEQUENCE: 1112
atccgtcaca cctgctctgt acttcgccgg ttttgggctg gctatttatc tcgctggtgt     60
tggctcccgt at                                                          72

<210> SEQ ID NO 1113
<211> LENGTH: 72
<212> TYPE: DNA
<213> ORGANISM: Artificial Sequence
<220> FEATURE:
<223> OTHER INFORMATION: chemically synthesized

<400> SEQUENCE: 1113

```
atacgggagc caacaccatg acaccagcc tttccggcat gatatccacc ctcaagagca    60
ggtgtgacgg at                                                      72
```

<210> SEQ ID NO 1114
<211> LENGTH: 72
<212> TYPE: DNA
<213> ORGANISM: Artificial Sequence
<220> FEATURE:
<223> OTHER INFORMATION: chemically synthesized

<400> SEQUENCE: 1114

```
atccgtcaca cctgctcttg agggtggata tcatgccgga aaggctggtg tccatggtgt   60
tggctcccgt at                                                      72
```

<210> SEQ ID NO 1115
<211> LENGTH: 72
<212> TYPE: DNA
<213> ORGANISM: Artificial Sequence
<220> FEATURE:
<223> OTHER INFORMATION: chemically synthesized

<400> SEQUENCE: 1115

```
atacgggagc caacaccaca tatgtctggg cagacgatga agagagacaa caagagagca   60
ggtgtgacgg at                                                      72
```

<210> SEQ ID NO 1116
<211> LENGTH: 72
<212> TYPE: DNA
<213> ORGANISM: Artificial Sequence
<220> FEATURE:
<223> OTHER INFORMATION: chemically synthesized

<400> SEQUENCE: 1116

```
atccgtcaca cctgctctct tgttgtctct cttcatcgtc tgcccagaca tatgtggtgt   60
tggctcccgt at                                                      72
```

<210> SEQ ID NO 1117
<211> LENGTH: 72
<212> TYPE: DNA
<213> ORGANISM: Artificial Sequence
<220> FEATURE:
<223> OTHER INFORMATION: chemically synthesized

<400> SEQUENCE: 1117

```
atacgggagc caacaccacg ttaagtaacg acaggcaaat atgacactaa tgctagagca   60
ggtgtgacgg at                                                      72
```

<210> SEQ ID NO 1118
<211> LENGTH: 72
<212> TYPE: DNA
<213> ORGANISM: Artificial Sequence
<220> FEATURE:
<223> OTHER INFORMATION: chemically synthesized

<400> SEQUENCE: 1118

```
atccgtcaca cctgctctag cattagtgtc atatttgcct gtcgttactt aacgtggtgt   60
tggctcccgt at                                                      72
```

<210> SEQ ID NO 1119
<211> LENGTH: 72
<212> TYPE: DNA
<213> ORGANISM: Artificial Sequence

```
<220> FEATURE:
<223> OTHER INFORMATION: chemically synthesized

<400> SEQUENCE: 1119
atacgggagc caacaccatc gatgtatgca tccaccccgg acatcccgct cacgagagca    60
ggtgtgacgg at                                                         72

<210> SEQ ID NO 1120
<211> LENGTH: 72
<212> TYPE: DNA
<213> ORGANISM: Artificial Sequence
<220> FEATURE:
<223> OTHER INFORMATION: chemically synthesized

<400> SEQUENCE: 1120
atccgtcaca cctgctctcg tgagcgggat gtccggggtg gatgcataca tcgatggtgt    60
tggctcccgt at                                                         72

<210> SEQ ID NO 1121
<211> LENGTH: 72
<212> TYPE: DNA
<213> ORGANISM: Artificial Sequence
<220> FEATURE:
<223> OTHER INFORMATION: chemically synthesized

<400> SEQUENCE: 1121
atacgggagc caacaccagg atggaacgaa catacagatc gagttgtatt taccagagca    60
ggtgtgacgg at                                                         72

<210> SEQ ID NO 1122
<211> LENGTH: 72
<212> TYPE: DNA
<213> ORGANISM: Artificial Sequence
<220> FEATURE:
<223> OTHER INFORMATION: chemically synthesized

<400> SEQUENCE: 1122
atccgtcaca cctgctctgg taaatacaac tcgatctgta tgttcgttcc atcctggtgt    60
tggctcccgt at                                                         72

<210> SEQ ID NO 1123
<211> LENGTH: 72
<212> TYPE: DNA
<213> ORGANISM: Artificial Sequence
<220> FEATURE:
<223> OTHER INFORMATION: chemically synthesized

<400> SEQUENCE: 1123
atacgggagc caacaccacc ctgcccggca ccccagtggg ccgtcgaccc aacgagagca    60
ggtgtgacgg at                                                         72

<210> SEQ ID NO 1124
<211> LENGTH: 72
<212> TYPE: DNA
<213> ORGANISM: Artificial Sequence
<220> FEATURE:
<223> OTHER INFORMATION: chemically synthesized

<400> SEQUENCE: 1124
atccgtcaca cctgctctcg ttgggtcgac ggcccactgg ggtgccgggc agggtggtgt    60
tggctcccgt at                                                         72
```

<210> SEQ ID NO 1125
<211> LENGTH: 72
<212> TYPE: DNA
<213> ORGANISM: Artificial Sequence
<220> FEATURE:
<223> OTHER INFORMATION: chemically synthesized

<400> SEQUENCE: 1125
atacgggagc caacaccata tatgaataac tcgcctaagt aacgcaagca gtatagagca    60
ggtgtgacgg at    72

<210> SEQ ID NO 1126
<211> LENGTH: 72
<212> TYPE: DNA
<213> ORGANISM: Artificial Sequence
<220> FEATURE:
<223> OTHER INFORMATION: chemically synthesized

<400> SEQUENCE: 1126
atccgtcaca cctgctctat actgcttgcg ttacttaggc gagttattca tatatggtgt    60
tggctcccgt at    72

<210> SEQ ID NO 1127
<211> LENGTH: 68
<212> TYPE: DNA
<213> ORGANISM: Artificial Sequence
<220> FEATURE:
<223> OTHER INFORMATION: chemically synthesized

<400> SEQUENCE: 1127
atacgggagc caacaccaat tcaaatcttc acatcatcaa cgttgtgcac agagcaggtg    60
tgacggat    68

<210> SEQ ID NO 1128
<211> LENGTH: 68
<212> TYPE: DNA
<213> ORGANISM: Artificial Sequence
<220> FEATURE:
<223> OTHER INFORMATION: chemically synthesized

<400> SEQUENCE: 1128
atccgtcaca cctgctctgt gcacaacgtt gatgatgtga agatttgaat tggtgttggc    60
tcccgtat    68

<210> SEQ ID NO 1129
<211> LENGTH: 58
<212> TYPE: DNA
<213> ORGANISM: Artificial Sequence
<220> FEATURE:
<223> OTHER INFORMATION: chemically synthesized

<400> SEQUENCE: 1129
atacgggagc caacaccaca tgactgcgcc ctacacttgc agagcaggtg tgacggat    58

<210> SEQ ID NO 1130
<211> LENGTH: 58
<212> TYPE: DNA
<213> ORGANISM: Artificial Sequence
<220> FEATURE:
<223> OTHER INFORMATION: chemically synthesized

<400> SEQUENCE: 1130
atccgtcaca cctgctctgc aagtgtaggg cgcagtcatg tggtgttggc tcccgtat    58

<210> SEQ ID NO 1131
<211> LENGTH: 72
<212> TYPE: DNA
<213> ORGANISM: Artificial Sequence
<220> FEATURE:
<223> OTHER INFORMATION: chemically synthesized

<400> SEQUENCE: 1131
atacgggagc caacaccaac cactactcgt tttaggaagc gttccaaacg gagcagagca    60
ggtgtgacgg at                                                       72

<210> SEQ ID NO 1132
<211> LENGTH: 72
<212> TYPE: DNA
<213> ORGANISM: Artificial Sequence
<220> FEATURE:
<223> OTHER INFORMATION: chemically synthesized

<400> SEQUENCE: 1132
atccgtcaca cctgctctgc tccgtttgga acgcttccta aaacgagtag tggttggtgt    60
tggctcccgt at                                                       72

<210> SEQ ID NO 1133
<211> LENGTH: 72
<212> TYPE: DNA
<213> ORGANISM: Artificial Sequence
<220> FEATURE:
<223> OTHER INFORMATION: chemically synthesized

<400> SEQUENCE: 1133
atacgggagc caacaccagt ccgttatgac atgtccggac ccgtacgcgt gtcaagagca    60
ggtgtgacgg at                                                       72

<210> SEQ ID NO 1134
<211> LENGTH: 72
<212> TYPE: DNA
<213> ORGANISM: Artificial Sequence
<220> FEATURE:
<223> OTHER INFORMATION: chemically synthesized

<400> SEQUENCE: 1134
atccgtcaca cctgctcttg acacgcgtac gggtccggac atgtcataac ggactggtgt    60
tggctcccgt at                                                       72

<210> SEQ ID NO 1135
<211> LENGTH: 72
<212> TYPE: DNA
<213> ORGANISM: Artificial Sequence
<220> FEATURE:
<223> OTHER INFORMATION: chemically synthesized

<400> SEQUENCE: 1135
atacgggagc caacaccaca agacccaaag acgggtcgtg acccgatttt gctgagagca    60
ggtgtgacgg at                                                       72

<210> SEQ ID NO 1136
<211> LENGTH: 72
<212> TYPE: DNA
<213> ORGANISM: Artificial Sequence
<220> FEATURE:
<223> OTHER INFORMATION: chemically synthesized

```
-continued

<400> SEQUENCE: 1136
atccgtcaca cctgctctca gcaaatcggg gtcacgaccc gtctttgggt cttgtggtgt    60
tggctcccgt at                                                        72

<210> SEQ ID NO 1137
<211> LENGTH: 72
<212> TYPE: DNA
<213> ORGANISM: Artificial Sequence
<220> FEATURE:
<223> OTHER INFORMATION: chemically synthesized

<400> SEQUENCE: 1137
atacgggagc caacaccatg cattacagac ctaaaaagaa aagatcgccg aaaaagagca    60
ggtgtgacgg at                                                        72

<210> SEQ ID NO 1138
<211> LENGTH: 72
<212> TYPE: DNA
<213> ORGANISM: Artificial Sequence
<220> FEATURE:
<223> OTHER INFORMATION: chemically synthesized

<400> SEQUENCE: 1138
atccgtcaca cctgctcttt ttcggcgatc ttttcttttt aggtctgtaa tgcatggtgt    60
tggctcccgt at                                                        72

<210> SEQ ID NO 1139
<211> LENGTH: 71
<212> TYPE: DNA
<213> ORGANISM: Artificial Sequence
<220> FEATURE:
<223> OTHER INFORMATION: chemically synthesized

<400> SEQUENCE: 1139
atacgggagc caacaccagt ccgttatgac atgtcggacc cgtacgcgtg tcaagagcag    60
gtgtgacgga t                                                         71

<210> SEQ ID NO 1140
<211> LENGTH: 71
<212> TYPE: DNA
<213> ORGANISM: Artificial Sequence
<220> FEATURE:
<223> OTHER INFORMATION: chemically synthesized

<400> SEQUENCE: 1140
atccgtcaca cctgctcttg acacgcgtac gggtccgaca tgtcataacg gactggtgtt    60
ggctcccgta t                                                         71

<210> SEQ ID NO 1141
<211> LENGTH: 72
<212> TYPE: DNA
<213> ORGANISM: Artificial Sequence
<220> FEATURE:
<223> OTHER INFORMATION: chemically synthesized

<400> SEQUENCE: 1141
atacgggagc caacaccagg tgacattcat ctaggaaact tgaatgtgag atatagagca    60
ggtgtgacgg at                                                        72

<210> SEQ ID NO 1142
<211> LENGTH: 72
```

```
<212> TYPE: DNA
<213> ORGANISM: Artificial Sequence
<220> FEATURE:
<223> OTHER INFORMATION: chemically synthesized

<400> SEQUENCE: 1142
atccgtcaca cctgctctat atctcacatt caagtttcct agatgaatgt cacctggtgt    60
tggctcccgt at                                                        72

<210> SEQ ID NO 1143
<211> LENGTH: 72
<212> TYPE: DNA
<213> ORGANISM: Artificial Sequence
<220> FEATURE:
<223> OTHER INFORMATION: chemically synthesized

<400> SEQUENCE: 1143
atacgggagc caacaccaaa gcgtgttgct ggacagattc agacatagga acttagagca    60
ggtgtgacgg at                                                        72

<210> SEQ ID NO 1144
<211> LENGTH: 72
<212> TYPE: DNA
<213> ORGANISM: Artificial Sequence
<220> FEATURE:
<223> OTHER INFORMATION: chemically synthesized

<400> SEQUENCE: 1144
atccgtcaca cctgctctaa gttcctatgt ctgaatctgt ccagcaacac gctttggtgt    60
tggctcccgt at                                                        72

<210> SEQ ID NO 1145
<211> LENGTH: 72
<212> TYPE: DNA
<213> ORGANISM: Artificial Sequence
<220> FEATURE:
<223> OTHER INFORMATION: chemically synthesized

<400> SEQUENCE: 1145
atacgggagc caacaccatt aacaaatgat aagttaggat tctgaacact tggcagagca    60
ggtgtgacgg at                                                        72

<210> SEQ ID NO 1146
<211> LENGTH: 72
<212> TYPE: DNA
<213> ORGANISM: Artificial Sequence
<220> FEATURE:
<223> OTHER INFORMATION: chemically synthesized

<400> SEQUENCE: 1146
atccgtcaca cctgctctgc caagtgttca gaatcctaac ttatcatttg ttaatggtgt    60
tggctcccgt at                                                        72

<210> SEQ ID NO 1147
<211> LENGTH: 72
<212> TYPE: DNA
<213> ORGANISM: Artificial Sequence
<220> FEATURE:
<223> OTHER INFORMATION: chemically synthesized

<400> SEQUENCE: 1147
atacgggagc caacaccacg ggtgagttaa taaatgtggg tcactccgtc caacagagca    60
```

```
ggtgtgacgg at                                                         72
```

<210> SEQ ID NO 1148
<211> LENGTH: 72
<212> TYPE: DNA
<213> ORGANISM: Artificial Sequence
<220> FEATURE:
<223> OTHER INFORMATION: chemically synthesized

<400> SEQUENCE: 1148

```
atccgtcaca cctgctctgt tggacggagt gacccacatt tattaactca cccgtggtgt    60
tggctcccgt at                                                         72
```

<210> SEQ ID NO 1149
<211> LENGTH: 72
<212> TYPE: DNA
<213> ORGANISM: Artificial Sequence
<220> FEATURE:
<223> OTHER INFORMATION: chemically synthesized

<400> SEQUENCE: 1149

```
atacgggagc caacaccatg aatgcaatgt attagagcga tgaaatcatt atttagagca    60
ggtgtgacgg at                                                         72
```

<210> SEQ ID NO 1150
<211> LENGTH: 72
<212> TYPE: DNA
<213> ORGANISM: Artificial Sequence
<220> FEATURE:
<223> OTHER INFORMATION: chemically synthesized

<400> SEQUENCE: 1150

```
atccgtcaca cctgctctaa ataatgattt catcgctcta atacattgca ttcatggtgt    60
tggctcccgt at                                                         72
```

<210> SEQ ID NO 1151
<211> LENGTH: 72
<212> TYPE: DNA
<213> ORGANISM: Artificial Sequence
<220> FEATURE:
<223> OTHER INFORMATION: chemically synthesized

<400> SEQUENCE: 1151

```
atacgggagc caacaccaat agggttaaac gaactggaca aggcggtgct atcgagagca    60
ggtgtgacgg at                                                         72
```

<210> SEQ ID NO 1152
<211> LENGTH: 72
<212> TYPE: DNA
<213> ORGANISM: Artificial Sequence
<220> FEATURE:
<223> OTHER INFORMATION: chemically synthesized

<400> SEQUENCE: 1152

```
atccgtcaca cctgctctcg atagcaccgc cttgtccagt tcgtttaacc ctattggtgt    60
tggctcccgt at                                                         72
```

<210> SEQ ID NO 1153
<211> LENGTH: 72
<212> TYPE: DNA
<213> ORGANISM: Artificial Sequence
<220> FEATURE:
<223> OTHER INFORMATION: chemically synthesized

<400> SEQUENCE: 1153
atacgggagc caacaccaat atcgttagaa gtttgtaaag tatccttcga tataagagca    60
ggtgtgacgg at    72

<210> SEQ ID NO 1154
<211> LENGTH: 72
<212> TYPE: DNA
<213> ORGANISM: Artificial Sequence
<220> FEATURE:
<223> OTHER INFORMATION: chemically synthesized

<400> SEQUENCE: 1154
atccgtcaca cctgctctta tatcgaagga tactttacaa acttctaacg atattggtgt    60
tggctcccgt at    72

<210> SEQ ID NO 1155
<211> LENGTH: 72
<212> TYPE: DNA
<213> ORGANISM: Artificial Sequence
<220> FEATURE:
<223> OTHER INFORMATION: chemically synthesized

<400> SEQUENCE: 1155
atacgggagc caacaccata taagtaccac cataacgaag tgagtggaat gaacagagca    60
ggtgtgacgg at    72

<210> SEQ ID NO 1156
<211> LENGTH: 72
<212> TYPE: DNA
<213> ORGANISM: Artificial Sequence
<220> FEATURE:
<223> OTHER INFORMATION: chemically synthesized

<400> SEQUENCE: 1156
atccgtcaca cctgctctgt tcattccact cacttcgtta tggtggtact tatatggtgt    60
tggctcccgt at    72

<210> SEQ ID NO 1157
<211> LENGTH: 72
<212> TYPE: DNA
<213> ORGANISM: Artificial Sequence
<220> FEATURE:
<223> OTHER INFORMATION: chemically synthesized

<400> SEQUENCE: 1157
atacgggagc caacaccacc tcctacccccc aacccggtc cccgtaaatg tactagagca    60
ggtgtgacgg at    72

<210> SEQ ID NO 1158
<211> LENGTH: 72
<212> TYPE: DNA
<213> ORGANISM: Artificial Sequence
<220> FEATURE:
<223> OTHER INFORMATION: chemically synthesized

<400> SEQUENCE: 1158
atccgtcaca cctgctctag tacatttacg ggaccgggg ttgggggtag gaggtggtgt    60
tggctcccgt at    72

<210> SEQ ID NO 1159

```
<211> LENGTH: 72
<212> TYPE: DNA
<213> ORGANISM: Artificial Sequence
<220> FEATURE:
<223> OTHER INFORMATION: chemically synthesized

<400> SEQUENCE: 1159
atacgggagc caacaccatg attgaatagg tggaattagg taagtaaccg acctagagca      60
ggtgtgacgg at                                                         72

<210> SEQ ID NO 1160
<211> LENGTH: 72
<212> TYPE: DNA
<213> ORGANISM: Artificial Sequence
<220> FEATURE:
<223> OTHER INFORMATION: chemically synthesized

<400> SEQUENCE: 1160
atccgtcaca cctgctctag gtcggttact tacctaattc cacctattca atcatggtgt      60
tggctcccgt at                                                         72

<210> SEQ ID NO 1161
<211> LENGTH: 72
<212> TYPE: DNA
<213> ORGANISM: Artificial Sequence
<220> FEATURE:
<223> OTHER INFORMATION: chemically synthesized

<400> SEQUENCE: 1161
atacgggagc caacaccagc caagcccagc cctcccttct cctctctctc cctcagagca      60
ggtgtgacgg at                                                         72

<210> SEQ ID NO 1162
<211> LENGTH: 72
<212> TYPE: DNA
<213> ORGANISM: Artificial Sequence
<220> FEATURE:
<223> OTHER INFORMATION: chemically synthesized

<400> SEQUENCE: 1162
atccgtcaca cctgctctga gggagagaga ggagaaggga gggctgggct tggctggtgt      60
tggctcccgt at                                                         72

<210> SEQ ID NO 1163
<211> LENGTH: 72
<212> TYPE: DNA
<213> ORGANISM: Artificial Sequence
<220> FEATURE:
<223> OTHER INFORMATION: chemically synthesized

<400> SEQUENCE: 1163
atacgggagc caacaccatc tagcaagacg tacgtagata aggttattcc cacaagagca      60
ggtgtgacgg at                                                         72

<210> SEQ ID NO 1164
<211> LENGTH: 72
<212> TYPE: DNA
<213> ORGANISM: Artificial Sequence
<220> FEATURE:
<223> OTHER INFORMATION: chemically synthesized

<400> SEQUENCE: 1164
atccgtcaca cctgctcttg tgggaataac cttatctacg tacgtcttgc tagatggtgt      60
```
tggctcccgt at 72

<210> SEQ ID NO 1165
<211> LENGTH: 72
<212> TYPE: DNA
<213> ORGANISM: Artificial Sequence
<220> FEATURE:
<223> OTHER INFORMATION: chemically synthesized

<400> SEQUENCE: 1165
atacgggagc caacaccaga cgatatgacc gtagttcggc gacactctat ggggagagca 60
ggtgtgacgg at 72

<210> SEQ ID NO 1166
<211> LENGTH: 72
<212> TYPE: DNA
<213> ORGANISM: Artificial Sequence
<220> FEATURE:
<223> OTHER INFORMATION: chemically synthesized

<400> SEQUENCE: 1166
atccgtcaca cctgctctcc ccatagagtg tcgccgaact acggtcatat cgtctggtgt 60
tggctcccgt at 72

<210> SEQ ID NO 1167
<211> LENGTH: 72
<212> TYPE: DNA
<213> ORGANISM: Artificial Sequence
<220> FEATURE:
<223> OTHER INFORMATION: chemically synthesized

<400> SEQUENCE: 1167
atacgggagc caacaccaca gaccccctca tcccgccggc agcccccttt gccgagagca 60
ggtgtgacgg at 72

<210> SEQ ID NO 1168
<211> LENGTH: 72
<212> TYPE: DNA
<213> ORGANISM: Artificial Sequence
<220> FEATURE:
<223> OTHER INFORMATION: chemically synthesized

<400> SEQUENCE: 1168
atccgtcaca cctgctctcg gcaaaggggg ctgccggcgg gatgaggggg tctgtggtgt 60
tggctcccgt at 72

<210> SEQ ID NO 1169
<211> LENGTH: 72
<212> TYPE: DNA
<213> ORGANISM: Artificial Sequence
<220> FEATURE:
<223> OTHER INFORMATION: chemically synthesized

<400> SEQUENCE: 1169
atacgggagc caacaccaac cccactaagt cccctatcat ttaagatgcc ctaaagagca 60
ggtgtgacgg at 72

<210> SEQ ID NO 1170
<211> LENGTH: 72
<212> TYPE: DNA
<213> ORGANISM: Artificial Sequence
<220> FEATURE:

<223> OTHER INFORMATION: chemically synthesized

<400> SEQUENCE: 1170
atccgtcaca cctgctcttt agggcatctt aaatgatagg ggacttagtg gggttggtgt    60
tggctcccgt at                                                       72

<210> SEQ ID NO 1171
<211> LENGTH: 72
<212> TYPE: DNA
<213> ORGANISM: Artificial Sequence
<220> FEATURE:
<223> OTHER INFORMATION: chemically synthesized

<400> SEQUENCE: 1171
atacgggagc caacaccaga caaccettct accectcaag tcgccaataa cggtagagca    60
ggtgtgacgg at                                                       72

<210> SEQ ID NO 1172
<211> LENGTH: 72
<212> TYPE: DNA
<213> ORGANISM: Artificial Sequence
<220> FEATURE:
<223> OTHER INFORMATION: chemically synthesized

<400> SEQUENCE: 1172
atccgtcaca cctgctctac cgttattggc gacttgaggg gtagaagggt tgtctggtgt    60
tggctcccgt at                                                       72

<210> SEQ ID NO 1173
<211> LENGTH: 72
<212> TYPE: DNA
<213> ORGANISM: Artificial Sequence
<220> FEATURE:
<223> OTHER INFORMATION: chemically synthesized

<400> SEQUENCE: 1173
atacgggagc caacaccagg tttaaagatt cattcgcagc tcaaatatct ttggagagca    60
ggtgtgacgg at                                                       72

<210> SEQ ID NO 1174
<211> LENGTH: 72
<212> TYPE: DNA
<213> ORGANISM: Artificial Sequence
<220> FEATURE:
<223> OTHER INFORMATION: chemically synthesized

<400> SEQUENCE: 1174
atccgtcaca cctgctctcc aaagatattt gagctgcgaa tgaatcttta aacctggtgt    60
tggctcccgt at                                                       72

<210> SEQ ID NO 1175
<211> LENGTH: 72
<212> TYPE: DNA
<213> ORGANISM: Artificial Sequence
<220> FEATURE:
<223> OTHER INFORMATION: chemically synthesized

<400> SEQUENCE: 1175
atacgtgagc caacaccata aatagaaagc caagagaggt tagggttaat gagtagagca    60
ggtgtgacgg at                                                       72

```
<210> SEQ ID NO 1176
<211> LENGTH: 72
<212> TYPE: DNA
<213> ORGANISM: Artificial Sequence
<220> FEATURE:
<223> OTHER INFORMATION: chemically synthesized

<400> SEQUENCE: 1176
atccgtcaca cctgctctac tcattaaccc taacctctct tggctttcta tttatggtgt    60
tggctcacgt at                                                        72

<210> SEQ ID NO 1177
<211> LENGTH: 72
<212> TYPE: DNA
<213> ORGANISM: Artificial Sequence
<220> FEATURE:
<223> OTHER INFORMATION: chemically synthesized

<400> SEQUENCE: 1177
atacgggagc caacaccacc caccttccct cttcatacgc cacctcacac atccagagca    60
ggtgtgacgg at                                                        72

<210> SEQ ID NO 1178
<211> LENGTH: 72
<212> TYPE: DNA
<213> ORGANISM: Artificial Sequence
<220> FEATURE:
<223> OTHER INFORMATION: chemically synthesized

<400> SEQUENCE: 1178
atccgtcaca cctgctctgg atgtgtgagg tggcgtatga agagggaagg tgggtggtgt    60
tggctcccgt at                                                        72

<210> SEQ ID NO 1179
<211> LENGTH: 72
<212> TYPE: DNA
<213> ORGANISM: Artificial Sequence
<220> FEATURE:
<223> OTHER INFORMATION: chemically synthesized

<400> SEQUENCE: 1179
atacgggagc caacaccaag tccgaaagaa cttataacgc aatggaatcc tgggagagca    60
ggtgtgacgg at                                                        72

<210> SEQ ID NO 1180
<211> LENGTH: 72
<212> TYPE: DNA
<213> ORGANISM: Artificial Sequence
<220> FEATURE:
<223> OTHER INFORMATION: chemically synthesized

<400> SEQUENCE: 1180
atccgtcaca cctgctctcc caggattcca ttgcgttata agttctttcg gacttggtgt    60
tggctcccgt at                                                        72

<210> SEQ ID NO 1181
<211> LENGTH: 72
<212> TYPE: DNA
<213> ORGANISM: Artificial Sequence
<220> FEATURE:
<223> OTHER INFORMATION: chemically synthesized

<400> SEQUENCE: 1181
```

```
atacgggagc caacaccaga attacactct ggtggggtgg gggaagaggg atgtagagca      60
ggtgtgacgg at                                                         72
```

<210> SEQ ID NO 1182
<211> LENGTH: 72
<212> TYPE: DNA
<213> ORGANISM: Artificial Sequence
<220> FEATURE:
<223> OTHER INFORMATION: chemically synthesized

<400> SEQUENCE: 1182

```
atccgtcaca cctgctctac atccctcttc ccccacccca ccagagtgta attctggtgt      60
tggctcccgt at                                                         72
```

<210> SEQ ID NO 1183
<211> LENGTH: 72
<212> TYPE: DNA
<213> ORGANISM: Artificial Sequence
<220> FEATURE:
<223> OTHER INFORMATION: chemically synthesized

<400> SEQUENCE: 1183

```
atacgggagc caacaccaaa acaacacaat acgccctata gcgaaagaca acgtagagca      60
ggtgtgacgg at                                                         72
```

<210> SEQ ID NO 1184
<211> LENGTH: 72
<212> TYPE: DNA
<213> ORGANISM: Artificial Sequence
<220> FEATURE:
<223> OTHER INFORMATION: chemically synthesized

<400> SEQUENCE: 1184

```
atccgtcaca cctgctctac gttgtctttc gctatagggc gtattgtgtt gttttggtgt      60
tggctcccgt at                                                         72
```

<210> SEQ ID NO 1185
<211> LENGTH: 72
<212> TYPE: DNA
<213> ORGANISM: Artificial Sequence
<220> FEATURE:
<223> OTHER INFORMATION: chemically synthesized

<400> SEQUENCE: 1185

```
atacgggagc caacaccatc tttcttagga tacaaagcca aactgagccc gtgcagagca      60
ggtgtgacgg at                                                         72
```

<210> SEQ ID NO 1186
<211> LENGTH: 72
<212> TYPE: DNA
<213> ORGANISM: Artificial Sequence
<220> FEATURE:
<223> OTHER INFORMATION: chemically synthesized

<400> SEQUENCE: 1186

```
atccgtcaca cctgctctgc acgggctcag tttggctttg tatcctaaga aagatggtgt      60
tggctcccgt at                                                         72
```

<210> SEQ ID NO 1187
<211> LENGTH: 72
<212> TYPE: DNA
<213> ORGANISM: Artificial Sequence
<220> FEATURE:
<223> OTHER INFORMATION: chemically synthesized

<400> SEQUENCE: 1187
atacgggagc caacaccacg acattattat tgtatcatgt acggtagcct tttgagagca    60
ggtgtgacgg at    72

<210> SEQ ID NO 1188
<211> LENGTH: 72
<212> TYPE: DNA
<213> ORGANISM: Artificial Sequence
<220> FEATURE:
<223> OTHER INFORMATION: chemically synthesized

<400> SEQUENCE: 1188
atccgtcaca cctgctctca aaaggctacc gtacatgata caataataat gtcgtggtgt    60
tggctcccgt at    72

<210> SEQ ID NO 1189
<211> LENGTH: 72
<212> TYPE: DNA
<213> ORGANISM: Artificial Sequence
<220> FEATURE:
<223> OTHER INFORMATION: chemically synthesized

<400> SEQUENCE: 1189
atacgggagc caacaccaac gttccagctc aaagactctt ttctaaaacg gtgtagagca    60
ggtgtgacgg at    72

<210> SEQ ID NO 1190
<211> LENGTH: 72
<212> TYPE: DNA
<213> ORGANISM: Artificial Sequence
<220> FEATURE:
<223> OTHER INFORMATION: chemically synthesized

<400> SEQUENCE: 1190
atccgtcaca cctgctctac accgttttag aaaagagtct tgagctgga acgttggtgt    60 tggctcccgt at    72

<210> SEQ ID NO 1191
<211> LENGTH: 72
<212> TYPE: DNA
<213> ORGANISM: Artificial Sequence
<220> FEATURE:
<223> OTHER INFORMATION: chemically synthesized

<400> SEQUENCE: 1191
atacgggagc caacaccacc aaaaacccct accccacacc agacttcccc cgccagagca    60
ggtgtgacgg at    72

<210> SEQ ID NO 1192
<211> LENGTH: 72
<212> TYPE: DNA
<213> ORGANISM: Artificial Sequence
<220> FEATURE:
<223> OTHER INFORMATION: chemically synthesized

<400> SEQUENCE: 1192
atccgtcaca cctgctctgg cggggggaagt ctggtgtggg gtaggggttt tggtggtgt    60 tggctcccgt at    72

<210> SEQ ID NO 1193
<211> LENGTH: 72
<212> TYPE: DNA
<213> ORGANISM: Artificial Sequence
<220> FEATURE:
<223> OTHER INFORMATION: chemically synthesized

<400> SEQUENCE: 1193
atacgggagc caacaccaat aattaaaaat aagatagaaa gaacatgtca gtctagagca    60
ggtgtgacgg at    72

<210> SEQ ID NO 1194
<211> LENGTH: 72
<212> TYPE: DNA
<213> ORGANISM: Artificial Sequence
<220> FEATURE:
<223> OTHER INFORMATION: chemically synthesized

<400> SEQUENCE: 1194
atccgtcaca cctgctctag actgacatgt tctttctatc ttattttaa ttattggtgt    60 tggctcccgt at    72

<210> SEQ ID NO 1195
<211> LENGTH: 69
<212> TYPE: DNA
<213> ORGANISM: Artificial Sequence
<220> FEATURE:
<223> OTHER INFORMATION: chemically synthesized

<400> SEQUENCE: 1195
atacgggagc caacaccaga gcaggtgtga cggagagcag gtgtgacggg tagagcaggt    60
gtgacggat    69

<210> SEQ ID NO 1196
<211> LENGTH: 69
<212> TYPE: DNA
<213> ORGANISM: Artificial Sequence
<220> FEATURE:
<223> OTHER INFORMATION: chemically synthesized

<400> SEQUENCE: 1196
atccgtcaca cctgctctac ccgtcacacc tgctctccgt cacacctgct ctggtgttgg    60
ctcccgtat    69

<210> SEQ ID NO 1197
<211> LENGTH: 72
<212> TYPE: DNA
<213> ORGANISM: Artificial Sequence
<220> FEATURE:
<223> OTHER INFORMATION: chemically synthesized

<400> SEQUENCE: 1197
atacgggagc caacaccata ctgtttaggc gagttcgcta ttttcctcca tgatagagca    60
ggtgtgacgg at    72

<210> SEQ ID NO 1198
<211> LENGTH: 72
<212> TYPE: DNA
<213> ORGANISM: Artificial Sequence
<220> FEATURE:
<223> OTHER INFORMATION: chemically synthesized

<400> SEQUENCE: 1198

```
atccgtcaca cctgctctat catggaggaa aatagcgaac tcgcctaaac agtatggtgt      60
tggctcccgt at                                                         72

<210> SEQ ID NO 1199
<211> LENGTH: 72
<212> TYPE: DNA
<213> ORGANISM: Artificial Sequence
<220> FEATURE:
<223> OTHER INFORMATION: chemically synthesized

<400> SEQUENCE: 1199
atacgggagc caacaccacg tccgtctatt cccggtcttc ctcctccctt gaccagagca      60
ggtgtgacgg at                                                         72

<210> SEQ ID NO 1200
<211> LENGTH: 72
<212> TYPE: DNA
<213> ORGANISM: Artificial Sequence
<220> FEATURE:
<223> OTHER INFORMATION: chemically synthesized

<400> SEQUENCE: 1200
atccgtcaca cctgctctgg tcaagggagg aggaagaccg ggaatagacg gacgtggtgt      60
tggctcccgt at                                                         72

<210> SEQ ID NO 1201
<211> LENGTH: 72
<212> TYPE: DNA
<213> ORGANISM: Artificial Sequence
<220> FEATURE:
<223> OTHER INFORMATION: chemically synthesized

<400> SEQUENCE: 1201
atacgggagc caacaccatg ggggaaatgg ggatgcagta aattacatga gtgcagagca      60
ggtgtgacgg at                                                         72

<210> SEQ ID NO 1202
<211> LENGTH: 72
<212> TYPE: DNA
<213> ORGANISM: Artificial Sequence
<220> FEATURE:
<223> OTHER INFORMATION: chemically synthesized

<400> SEQUENCE: 1202
atccgtcaca cctgctctgc actcatgtaa tttactgcat ccccatttcc cccatggtgt      60
tggctcccgt at                                                         72

<210> SEQ ID NO 1203
<211> LENGTH: 72
<212> TYPE: DNA
<213> ORGANISM: Artificial Sequence
<220> FEATURE:
<223> OTHER INFORMATION: chemically synthesized

<400> SEQUENCE: 1203
atacgggagc caacaccatc tctcttagga tacaaagcca aactgagccc gtgcagagca      60
ggtgtgacgg at                                                         72

<210> SEQ ID NO 1204
<211> LENGTH: 72
<212> TYPE: DNA
```

```
<213> ORGANISM: Artificial Sequence
<220> FEATURE:
<223> OTHER INFORMATION: chemically synthesized

<400> SEQUENCE: 1204
atccgtcaca cctgctctgc acgggctcag tttggctttg tatcctaaga gagatggtgt    60
tggctcccgt at                                                        72

<210> SEQ ID NO 1205
<211> LENGTH: 72
<212> TYPE: DNA
<213> ORGANISM: Artificial Sequence
<220> FEATURE:
<223> OTHER INFORMATION: chemically synthesized

<400> SEQUENCE: 1205
atacgggagc caacaccacg tcaactaagc gagaattcag aaagctgttt gaccagagca    60
ggtgtgacgg at                                                        72

<210> SEQ ID NO 1206
<211> LENGTH: 72
<212> TYPE: DNA
<213> ORGANISM: Artificial Sequence
<220> FEATURE:
<223> OTHER INFORMATION: chemically synthesized

<400> SEQUENCE: 1206
atccgtcaca cctgctctgg tcaaacagct ttctgaattc tcgcttagtt gacgtggtgt    60
tggctcccgt at                                                        72

<210> SEQ ID NO 1207
<211> LENGTH: 72
<212> TYPE: DNA
<213> ORGANISM: Artificial Sequence
<220> FEATURE:
<223> OTHER INFORMATION: chemically synthesized

<400> SEQUENCE: 1207
atacgggagc caacaccacc ccctccgctt tactctccca cactgcccta tcacagagca    60
ggtgtgacgg at                                                        72

<210> SEQ ID NO 1208
<211> LENGTH: 72
<212> TYPE: DNA
<213> ORGANISM: Artificial Sequence
<220> FEATURE:
<223> OTHER INFORMATION: chemically synthesized

<400> SEQUENCE: 1208
atccgtcaca cctgctctgt gatagggcag tgtgggagag taaagcggag ggggtggtgt    60
tggctcccgt at                                                        72

<210> SEQ ID NO 1209
<211> LENGTH: 37
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (19)..(19)
<223> OTHER INFORMATION: n is a, c, g, or t

<400> SEQUENCE: 1209
```

-continued

```
atccgtcaca cctgctctnt ggtgttggct cccgtat                    37

<210> SEQ ID NO 1210
<211> LENGTH: 18
<212> TYPE: DNA
<213> ORGANISM: Artificial Sequence
<220> FEATURE:
<223> OTHER INFORMATION: chemically synthesized

<400> SEQUENCE: 1210
atacgggagc caacacca                                         18

<210> SEQ ID NO 1211
<211> LENGTH: 18
<212> TYPE: DNA
<213> ORGANISM: Artificial Sequence
<220> FEATURE:
<223> OTHER INFORMATION: chemically synthesized

<400> SEQUENCE: 1211
atccgtcaca cctgctct                                         18
```